US011408000B2

(12) United States Patent
Bermingham et al.

(10) Patent No.: US 11,408,000 B2
(45) Date of Patent: Aug. 9, 2022

(54) OLIGONUCLEOTIDES FOR THE TREATMENT OF NUCLEOTIDE REPEAT EXPANSION DISORDERS ASSOCIATED WITH MSH3 ACTIVITY

(71) Applicant: Triplet Therapeutics, Inc., Cambridge, MA (US)

(72) Inventors: Nessan Anthony Bermingham, Boston, MA (US); Brian R. Bettencourt, Groton, MA (US); Pei Ge, Arlington, MA (US)

(73) Assignee: Triplet Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/337,172

(22) Filed: Jun. 2, 2021

(65) Prior Publication Data

US 2021/0395740 A1 Dec. 23, 2021

Related U.S. Application Data

(60) Provisional application No. 63/034,319, filed on Jun. 3, 2020.

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/335* (2013.01); *C12N 2310/3341* (2013.01); *C12N 2310/346* (2013.01); *C12N 2320/35* (2013.01)

(58) Field of Classification Search
None
See application file for complete search history.

(56) References Cited

U.S. PATENT DOCUMENTS 3,687,808 A 8/1972 Thomas, Jr. et al.
4,469,863 A 9/1984 Ts'o et al.
4,476,301 A 10/1984 Imbach et al.
4,587,044 A 5/1986 Miller et al.
4,605,735 A 8/1986 Miyoshi et al.
4,667,025 A 5/1987 Miyoshi et al.
4,683,202 A 7/1987 Mullis
4,762,779 A 8/1988 Snitman
4,789,737 A 12/1988 Miyoshi et al.
4,824,941 A 4/1989 Gordon et al.
4,828,979 A 5/1989 Klevan et al.
4,835,263 A 5/1989 Nguyen et al.
4,837,028 A 6/1989 Allen
4,845,205 A 7/1989 Huynh Dinh et al.
4,876,335 A 10/1989 Yamane et al.
4,897,355 A 1/1990 Eppstein et al.
4,904,582 A 2/1990 Tullis
4,948,882 A 8/1990 Ruth
4,958,013 A 9/1990 Letsinger
4,981,957 A 1/1991 Lebleu et al.
5,023,243 A 6/1991 Tullis
5,034,506 A 7/1991 Summerton et al.
5,082,830 A 1/1992 Brakel et al.
5,109,124 A 4/1992 Ramachandran et al.
5,112,963 A 5/1992 Pieles et al.
5,118,800 A 6/1992 Smith et al.
5,118,802 A 6/1992 Smith et al.
5,130,302 A 7/1992 Spielvogel et al.
5,134,066 A 7/1992 Rogers et al.
5,138,045 A 8/1992 Cook et al.
5,166,315 A 11/1992 Summerton et al.
5,171,678 A 12/1992 Behr et al.
5,175,273 A 12/1992 Bischofberger et al.
5,177,195 A 1/1993 Gregory et al.
5,185,444 A 2/1993 Summerton et al.
5,188,897 A 2/1993 Suhadolnik et al.
5,214,134 A 5/1993 Weis et al.
5,214,136 A 5/1993 Lin et al.
5,216,141 A 6/1993 Benner
5,218,105 A 6/1993 Cook et al.
5,235,033 A 8/1993 Summerton et al.
5,245,022 A 9/1993 Weis et al.
5,254,469 A 10/1993 Warren, III et al.
5,258,506 A 11/1993 Urdea et al.
5,262,536 A 11/1993 Hobbs, Jr.
5,264,423 A 11/1993 Cohen et al.
(Continued)

FOREIGN PATENT DOCUMENTS

WO WO-8804924 A1 7/1988
WO WO-9116024 A1 10/1991
(Continued)

OTHER PUBLICATIONS

Akhtar, S., and Juliano, R. L., "Cellular uptake and intracellular fate of antisense oligonucleotides," Trends in Cell Biology 2(5):139-144, Elsevier Science Publishers Ltd., United Kingdom (May 1992).
Allen, T. M., and Chonn, A., "Large unilamellar liposomes with low uptake into the reticuloendothelial system," FEBS Letters 223(1):42-46, John Wiley & Sons Ltd., United Kingdom (Oct. 1987).
Al-Mahdawi, S., et al., "GAA repeat expansion mutation mouse models of Friedreich ataxia exhibit oxidative stress leading to progressive neuronal and cardiac pathology," Genomics 88(5):580-590, Academic Press, United States (Nov. 2006).
Arnold, A. S., et al., "Specific beta 1-adrenergic receptor silencing with small interfering RNA lowers high blood pressure and improves cardiac function in myocardial ischemia," Journal of Hypertension 25(1): 197-205, Lippincott Williams & Wilkins, United Kingdom (Jan. 2007).
Bangham, A. D., et al., "Diffusion of univalent ions across the lamellae of swollen phospholipids," Journal of Molecular Biology 13(1):238-252, Elsevier, Netherlands (1965).
(Continued)

*Primary Examiner* — Kimberly Chong
(74) *Attorney, Agent, or Firm* — Sterne, Kessler, Goldstein & Fox P.L.L.C.

(57) ABSTRACT

The present disclosure features useful compositions and methods to treat nucleotide repeat expansion disorders, e.g., in a subject in need thereof. In some aspects, the compositions and methods described herein are useful in the treatment of disorders associated with MSH3 activity.

10 Claims, No Drawings

Specification includes a Sequence Listing.

(56) References Cited

U.S. PATENT DOCUMENTS 5,264,562 A 11/1993 Matteucci
5,264,564 A 11/1993 Matteucci
5,272,250 A 12/1993 Spielvogel et al.
5,276,019 A 1/1994 Cohen et al.
5,278,302 A 1/1994 Caruthers et al.
5,283,185 A 2/1994 Epand et al.
5,286,717 A 2/1994 Cohen et al.
5,292,873 A 3/1994 Rokita et al.
5,317,098 A 5/1994 Shizuya et al.
5,319,080 A 6/1994 Leumann
5,321,131 A 6/1994 Agrawal et al.
5,359,044 A 10/1994 Cook et al.
5,367,066 A 11/1994 Urdea et al.
5,371,241 A 12/1994 Brush
5,391,723 A 2/1995 Priest
5,393,878 A 2/1995 Leumann
5,399,676 A 3/1995 Froehler
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,445,934 A 8/1995 Fodor et al.
5,446,137 A 8/1995 Maag et al.
5,451,463 A 9/1995 Nelson et al.
5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,466,786 A 11/1995 Buhr et al.
5,470,967 A 11/1995 Huie et al.
5,476,925 A 12/1995 Letsinger et al.
5,484,908 A 1/1996 Froehler et al.
5,486,603 A 1/1996 Buhr
5,489,677 A 2/1996 Sanghvi et al.
5,502,177 A 3/1996 Matteucci et al.
5,510,475 A 4/1996 Agrawal et al.
5,512,439 A 4/1996 Hornes et al.
5,512,667 A 4/1996 Reed et al.
5,514,785 A 5/1996 Van Ness et al.
5,519,126 A 5/1996 Hecht
5,519,134 A 5/1996 Acevedo et al.
5,525,465 A 6/1996 Haralambidis et al.
5,525,711 A 6/1996 Hawkins et al.
5,536,821 A 7/1996 Agrawal et al.
5,539,082 A 7/1996 Nielsen et al.
5,541,307 A 7/1996 Cook et al.
5,541,313 A 7/1996 Ruth
5,541,316 A 7/1996 Engelskirchen et al.
5,543,152 A 8/1996 Webb et al.
5,545,730 A 8/1996 Urdea et al.
5,550,111 A 8/1996 Suhadolnik et al.
5,552,538 A 9/1996 Urdea et al.
5,552,540 A 9/1996 Haralambidis
5,561,225 A 10/1996 Maddry et al.
5,563,253 A 10/1996 Agrawal et al.
5,565,552 A 10/1996 Magda et al.
5,567,810 A 10/1996 Weis et al.
5,567,811 A 10/1996 Misiura et al.
5,571,799 A 11/1996 Tkachuk et al.
5,574,142 A 11/1996 Meyer, Jr. et al.
5,576,427 A 11/1996 Cook et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,591,722 A 1/1997 Montgomery et al.
5,594,121 A 1/1997 Froehler et al.
5,595,726 A 1/1997 Magda et al.
5,596,086 A 1/1997 Matteucci et al.
5,596,091 A 1/1997 Switzer
5,597,696 A 1/1997 Linn et al.
5,597,909 A 1/1997 Urdea et al.
5,599,923 A 2/1997 Sessler et al.
5,599,928 A 2/1997 Hemmi et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,070 A 4/1997 Cook et al.
5,625,050 A 4/1997 Beaton et al.
5,627,053 A 5/1997 Usman et al.
5,633,360 A 5/1997 Bischofberger et al.
5,639,873 A 6/1997 Barascut et al.
5,646,265 A 7/1997 McGee
5,658,873 A 8/1997 Bertsch-Frank et al.
5,663,312 A 9/1997 Chaturvedula
5,670,633 A 9/1997 Cook et al.
5,677,195 A 10/1997 Winkler et al.
5,677,437 A 10/1997 Teng et al.
5,677,439 A 10/1997 Weis et al.
5,681,941 A 10/1997 Cook et al.
5,688,941 A 11/1997 Cook et al.
5,700,920 A 12/1997 Altmann et al.
5,714,331 A 2/1998 Buchardt et al.
5,719,262 A 2/1998 Buchardt et al.
5,744,305 A 4/1998 Fodor et al.
5,750,692 A 5/1998 Cook et al.
5,770,722 A 6/1998 Lockhart et al.
5,854,033 A 12/1998 Lizardi
5,874,219 A 2/1999 Rava et al.
5,976,567 A 11/1999 Wheeler et al.
5,981,501 A 11/1999 Wheeler et al.
6,015,886 A 1/2000 Dale et al.
6,028,188 A 2/2000 Arnold, Jr. et al.
6,124,445 A 9/2000 Imbach et al.
6,147,200 A 11/2000 Manoharan et al.
6,160,109 A 12/2000 Just et al.
6,166,197 A 12/2000 Cook et al.
6,169,170 B1 1/2001 Gryaznov et al.
6,172,209 B1 1/2001 Manoharan et al.
6,222,025 B1 4/2001 Cook et al.
6,235,887 B1 5/2001 Froehler et al.
6,239,265 B1 5/2001 Cook
6,268,490 B1 7/2001 Imanishi et al.
6,277,603 B1 8/2001 Cook
6,294,664 B1 9/2001 Ravikumar et al.
6,320,017 B1 11/2001 Ansell
6,326,199 B1 12/2001 Cook et al.
6,346,614 B1 2/2002 Metelev et al.
6,380,368 B1 4/2002 Froehler et al.
6,444,423 B1 9/2002 Meade et al.
6,525,191 B1 2/2003 Ramasamy
6,528,640 B1 3/2003 Beigelman et al.
6,531,590 B1 3/2003 Manoharan et al.
6,534,484 B1 3/2003 Wheeler et al.
6,534,639 B1 3/2003 Manoharan et al.
6,576,752 B1 6/2003 Manoharan et al.
6,586,410 B1 7/2003 Wheeler et al.
6,608,035 B1 8/2003 Agrawal et al.
6,617,438 B1 9/2003 Beigelman et al.
6,639,062 B2 10/2003 Manoharan et al.
6,670,461 B1 12/2003 Wengel et al.
6,683,167 B2 1/2004 Metelev et al.
6,770,748 B2 8/2004 Imanishi et al.
6,783,931 B1 8/2004 Cook et al.
6,794,499 B2 9/2004 Wengel et al.
6,815,432 B2 11/2004 Wheeler et al.
6,858,225 B2 2/2005 Semple et al.
6,858,715 B2 2/2005 Ravikumar et al.
6,867,294 B1 3/2005 Sanghvi et al.
6,878,805 B2 4/2005 Manoharan et al.
6,900,297 B1 5/2005 Cook et al.
6,998,484 B2 2/2006 Koch et al.
7,015,315 B1 3/2006 Cook et al.
7,034,133 B2 4/2006 Wengel et al.

(56) References Cited

U.S. PATENT DOCUMENTS 7,037,646 B1 5/2006 Cook et al.
7,041,816 B2 5/2006 Ravikumar et al.
7,045,610 B2 5/2006 Dempcy et al.
7,053,207 B2 5/2006 Wengel
7,084,125 B2 8/2006 Wengel
RE39,464 E 1/2007 Cook et al.
7,273,933 B1 9/2007 Krotz et al.
7,321,029 B2 1/2008 Gryaznov et al.
7,399,845 B2 7/2008 Swayze et al.
7,427,605 B2 9/2008 Davis et al.
7,427,672 B2 9/2008 Imanishi et al.
7,495,088 B1 2/2009 Brakel et al.
7,569,686 B1 8/2009 Bhat et al.
7,741,457 B2 6/2010 Seth et al.
8,022,193 B2 9/2011 Seth et al.
8,030,467 B2 10/2011 Seth et al.
8,058,069 B2 11/2011 Yaworski et al.
8,106,022 B2 1/2012 Manoharan et al.
8,158,601 B2 4/2012 Chen et al.
8,278,283 B2 10/2012 Seth et al.
8,278,425 B2 10/2012 Prakash et al.
8,278,426 B2 10/2012 Seth et al.
8,314,227 B2 11/2012 Wengel
9,006,198 B2 4/2015 Bennett et al.
10,669,542 B2 6/2020 Grabczyk et al.
2002/0068709 A1 6/2002 Orum et al.
2004/0171570 A1 9/2004 Allerson et al.
2006/0058255 A1 3/2006 Chen et al.
2007/0243546 A1* 10/2007 Cao ..................... C12Q 1/6837 435/6.12
2008/0039618 A1 2/2008 Allerson et al.
2008/0200409 A1 8/2008 Wilson et al.
2009/0012281 A1 1/2009 Swayze et al.
2010/0324120 A1 12/2010 Chen et al.
2011/0313020 A1 12/2011 Templin et al.
2012/0157511 A1 6/2012 Manoharan et al.
2013/0011922 A1 1/2013 Quay et al.
2013/0096289 A1 4/2013 Wengel
2013/0190383 A1 7/2013 Vaish et al.
2013/0317086 A1 11/2013 Guire et al.
2014/0135376 A1 5/2014 Engbersen et al.
2014/0342003 A1 11/2014 Saltzman et al.
2015/0174549 A1 6/2015 Lim et al.
2015/0307554 A1 10/2015 Castillo Rodriguez
2015/0335764 A1 11/2015 Martinez Fong
2016/0230189 A1 8/2016 Kotha et al.
2016/0251478 A1 9/2016 Saltzman et al.
2016/0279256 A1 9/2016 Wang et al.
2016/0369269 A1 12/2016 Shen et al.
2017/0044539 A1 2/2017 Oestergaard et al.
2017/0121454 A1 5/2017 Saltzman et al.
2017/0183655 A1 6/2017 Grabczyk et al.
2018/0216108 A1 8/2018 Vargeese et al.
2019/0309289 A1 10/2019 Konieczka et al.
2021/0062188 A1 3/2021 Grabczyk et al.

FOREIGN PATENT DOCUMENTS

WO WO-9324640 A2 12/1993
WO WO-9400569 A1 1/1994
WO WO-9402595 A1 2/1994
WO WO-9637194 A1 11/1996
WO WO-9640964 A2 12/1996
WO WO-9713499 A1 4/1997
WO WO-9839359 A1 9/1998
WO WO-9910369 A1 3/1999
WO WO-9914226 A2 3/1999
WO WO-0003683 A2 1/2000
WO WO-0123613 A1 4/2001
WO WO-2008042973 A2 4/2008
WO WO-2008157747 A1 12/2008
WO WO-2011005861 A1 1/2011
WO WO-2012177906 A1 12/2012
WO WO-2013036868 A1 3/2013
WO WO-2014076195 A1 5/2014
WO WO-2014179620 A1 11/2014
WO WO-2014179627 A2 11/2014
WO WO-2015171918 A2 11/2015
WO WO-2016073990 A2 5/2016
WO WO-2017192679 A1 11/2017
WO WO-2018195165 A1 10/2018
WO WO-2019241802 A2 12/2019
WO WO-2020117702 A1 6/2020
WO WO-2020117703 A1 6/2020

OTHER PUBLICATIONS

Barany, F., "Genetic disease detection and DNA amplification using cloned thermostable ligase," Proc Natl Acad Sci USA 88(1):189-193, National Academy of Sciences, United States (Jan. 1991).

Berge, S. M., et al., "Pharmaceutical salts," Journal of Pharmaceutical Sciences 66(1): 1-19, John Wiley & Sons, United States (Jan. 1977).

Bergstrom, D. E., "Unnatural nucleosides with unusual base pairing properties," Current Protocols in Nucleic Acid Chemistry 37(1):1.4.1-1.4.32, Wiley Interscience, United States (Jun. 2009).

Bettencourt, C., et al., "DNA repair pathways underlie a common genetic mechanism modulating onset in poly glutamine diseases," Annals of Neurology 79(6):983-990, Wiley Periodicals, United States (Jun. 2016).

Black, R. D., and Sang, C. N., "Advances and limitations in the evaluation of analgesic combination therapy," Neurology 65(12 Suppl 4):S3-S6, Lippincott Williams & Wilkins, United States (Dec. 2005).

Bonnet, M. E., et al., "Systemic delivery of DNA or siRNA mediated by linear polyethylenimine (L-PEI) does not induce an inflammatory response," Pharmaceutical Research 25(12):2972-2982, Kluwer Academic/Plenum Publishers, United States (Dec. 2008).

Bourn, R. L., et al., "Pms2 suppresses large expansions of the $(GAA{\bullet}TTC)_n$ sequence in neuronal tissues," PLoS One 7(10):e47085, Public Library of Science, United States (2012).

Carroll, J. B., et al., "Potent and selective antisense oligonucleotides targeting single-nucleotide polymorphisms in the Huntington disease gene / allele-specific silencing of mutant huntingtin," Molecular Therapy 19(12):2178-2185, Cell Press, United States (Dec. 2011).

Chatterjee, N., et al., "Mismatch repair enhances convergent transcription-induced cell death at trinucleotide repeats by activating ATR" DNA Repair 42:26-32, Elsevier, Netherlands. (Jun. 2016).

Chien, P., et al., "Novel cationic cardiolipin analogue-based liposome for efficient DNA and small interfering RNA delivery in vitro and in vivo," Cancer Gene Therapy 12(3):321-328, Nature Publishing Group, United Kingdom (Mar. 2005).

Coppede, F., et al., "The hOGG1 Ser326Cys polymorphism and Huntington's disease," Toxicology 278(2):199-203, Elsevier, Ireland (Dec. 2010).

Crooke, S. T., et al., "Pharmacokinetic properties of several novel oligonucleotide analogs in mice," The Journal of Pharmacology and Experimental Therapeutics 277(2):923-937, American Society for Pharmacology and Experimental Therapeutics, United States (May 1996).

Drouet, V., et al., "Allele-specific silencing of mutant huntingtin in rodent brain and human stem cells," PLoS One 9(6):e99341, Public Library of Science, United States (Jun. 2014).

Du Plessis, J., et al., "Topical delivery of liposomally encapsulated gamma-interferon," Antiviral Research 18(3-4):259-265, Elsevier, Netherlands (Jun. 1992).

Englisch, U., and Gauss, D. H., "Chemically Modified Oligonucleotides as Probes and Inhibitors," Angewandte Chemie International Edition 30(6):613-629, Germany Chemical Society, Germany (1991).

Felgner, J. H., et al., "Enhanced gene delivery and mechamsm studies with a novel series of cationic lipid formulations," The Journal of Biological Chemistry 269(4):2550-2561, Elsevier Inc., United States (Jan. 1994).

(56) References Cited

OTHER PUBLICATIONS

Felgner, P. L., et al., "Lipofection: a highly efficient, lipid-mediated DNA-transfection procedure," Proc Natl Acad Sci USA 84(21):7413-7417, National Academy of Sciences, United States (Nov. 1987).
Fluiter, K., et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Molecular BioSystems 5(8):838-843, Royal Society of Chemistry, United Kingdom (Aug. 2009).
Fukunaga, M., et al., "Liposome entrapment enhances the hypocalcemic action of parenterally administered calcitonin," Endocrinology 115(2):757-761, Oxford University Press, United Kingdom (Aug. 1984).
Gabizon, A., and Papahadjopoulos, D., "Liposome formulations with prolonged circulation time in blood and enhanced uptake by tumors," Proc Natl Acad Sci USA 85(18):6949-6953, National Academy of Sciences, United States (Sep. 1988).
Gao, X., and Huang, L., "A novel cationic liposome reagent for efficient transfection of mammalian cells," Biochemical and Biophysical Research Communications 179(1):280-285, Elsevier, United States (Aug. 1991).
Geary, R. S., et al., "Absolute bioavailability of 2'-O-(2-methoxyethyl)-modified antisense oligonucleotides following intraduodenal instillation in rats," Journal of Pharmacology and Experimental Therapeutics 296(3):898-904, American Society for Pharmacology and Experimental Therapeutics, United States (Mar. 2001).
GenBank, "*Homo sapiens* mutS homolog 3 (MSH3), mRNA," Accession No. NM_002439.4, accessed at URL:[https://www.ncbi.nlm.nih.gov/nuccore/NM_002439.4] on Oct. 18, 2021, 5 pages.
GenBank, "Mus musculus mutS homolog 3 (Msh3), transcript variant 1, mRNA," Accession No. NM_010829.2, accessed at URL: [https://www.ncbi.nlm.nih.gov/nuccore/NM_010829.2] on Oct. 18, 2021, 5 pages.
GenBank, "Predicied: Macaca fascicularis mutS homolog 3 (MSH3), transcript variant X1, mRNA," Accession No. XM_005557283.2, accessed at URL:[https://www.ncbi.nlm.nih.gov/nuccore/XM_005557283.2] on Oct. 18, 2021, 3 pages.
GenBank, "Rattus norvegicus mutS homolog 3 (Msh3), mRNA," Accession No. NM_001191957.1, accessed at URL: [https://www.ncbi.nlm.nih.gov/nuccore/NM_001191957.1] on Oct. 18, 2021, 4 pages.
GenPept, "DNA mismatch repair protein Msh3 [*Homo sapiens*]," Accession No. NP_002430.3, accessed at URL: [https://www.ncbi.nlm.nih.gov/protein/NP_002430.3] on Oct. 18, 2021, 4 pages.
Genetic Modifiers of Huntington's Disease (GeM-HD) Consortium, "Identification of genetic factors that modify clinical onset of Huntington's disease," Cell 162(3):516-526, Cell Press, United States (Jul. 2015).
Gershon, H., et al., "Mode of formation and structural features of DNA-cationic liposome complexes used for transfection," Biochemistry 32(28):7143-7151, American Chemical Society, United States (Jul. 1993).
Gomes-Pereira, M., and Monckton, D. G., "Ethidium bromide modifies the agarose electrophoretic mobility of CAG•CTG alternative DNA Structures Generated by PCR," Frontiers in Cellular Neuroscience 11:153, Frontiers Research Foundation, Switzerland (May 2017).
Goold, R., et al., "FAN1 modifies Huntington's disease progression by stabilizing the expanded HTT CAG repeat," Human Molecular Genetics 28(4):650-661, Oxford University Press, United Kingdom (Feb. 2019).
Grunweller, A., et al., "Comparison of different antisense strategies in mammalian cells using locked nucleic acids, 2'-O-methyl RNA, phosphorothioates and small interfering RNA," Nucleic Acids Research 31(12):3185-3193, Oxford University Press, United Kingdom (Jun. 2003).
Guatelli, J. C., et al., "Isothermal, in vitro amplification of nucleic acids by a multienzyme reaction modeled after retroviral replication," Proc Natl Acad Sci USA 87(5):1874-1878, National Academy of Sciences, United States (Mar. 1990).
Halabi, A., et al., "DNA mismatch repair complex MutSβ promotes GAA•TTC repeat expansion in human cells," The Journal of Biological Chemistry 287(35):29958-29967, Elsevier Inc., United States (Aug. 2012).
Hirao, I., et al., "Natural versus artificial creation of base pairs in DNA: origin of nucleobases from the perspectives of unnatural base pair studies," Accounts of Chemical Research 45(12):2055-2065, American Chemical Society, United States (Dec. 2012).
Hu, Z., et al., "Topical delivery of Ciclosporin-A from nonionic liposomal systems: an in vivo/in vitro correlation study using hairless mouse skin," STP Pharma Sci 4(6):466-469, Société Française des Sciences et Techniques Pharmaceutiques, France (1994).
International Search Report and Written Opinion for International Application No. PCT/US2019/064054 dated Feb. 21, 2020, 11 pages.
International Search Report and Written Opinion for International Application No. PCT/US2021/031428 dated Sep. 10, 2021, 13 pages.
Itani, T., et al., "A simple and efficient liposome method for transfection of DNA into mammalian cells grown in suspension," Gene 56(2-3):267-276, Elsevier, Netherlands (1987).
Jenson, T. B., et al., "Unlocked nucleic acid (UNA) and UNA derivatives: thermal denaturation studies," Nucleic Acids Symposium Series No. 52:133-134, 2008 Oxford University Press, United Kingdom (Sep. 2008).
Kabanov, A. V., et al., "A new class of antivirals: antisense oligonucleotides combined with a hydrophobic substituent effectively inhibit influenza virus reproduction and synthesis of virus-specific proteins in MDCK cells," FEBS letters 259(2):327-330, John Wiley & Sons Ltd, United Kingdom (1990).
Kalota, A., et al., "2'-deoxy-2'-fluoro-beta-D-arabinonucleic acid (2'F-ANA) modified oligonucleotides (ON) effect highly efficient, and persistent, gene silencing," Nucleic Acids Research 34(2):451-461, Oxford University Press, United Kingdom (Jan. 2006).
Kim, S., et al., "Preparation of multivesicular liposomes," Biochimica Et Biophysica Acta 728(3):339-348, Elsevier, Netherlands (Mar. 1983).
Kovtum, I. V., et al., "OGG1 initiates age-dependent CAG trinucleotide expansion in somatic cells," Nature 447(7143):447-452, Nature Publishing Group, United Kingdom (May 2007).
Kubo, T., et al., "Chemically modified symmetric and asymmetric duplex RNAs: an enhanced stability to nuclease degradation and gene silencing effect," Biochemical and Biophysical Research Communications 365(1):54-61, Elsevier, United States (Jan. 2008).
Kwoh, D. Y., et al., "Transcription-based amplification system and detection of amplified human immunodeficiency virus type 1 with a bead-based sandwich hybridization format," Proc Natl Acad Sci USA 86(4):1173-1177, National Academy of Sciences, United States (1989).
Lam, K. S., et al., "A new type of synthetic peptide library for identifying ligand-binding activity," Nature 354:82-84, Nature Publishing Group, United States (1991).
Larson, E., et al., "Age-, tissue- and length-dependent bidirectional somatic CAG•CTG repeat instability in an allelic series of R6/2 Huntington disease mice," Neurobiology of Disease 76:98-111, Academic Press, United States (Apr. 2015).
Lee, J. M., et al., "A novel approach to investigate tissue-specific trinucleotide repeat instability," BMC Systems Biology 4:29, BioMed Central, United Kingdom (Mar. 2010).
Letsinger, R. L., et al., "Cholesteryl-conjugated oligonucleotides: synthesis, properties, and activity as inhibitors of replication of human immunodeficiency virus in cell culture," Proc Natl Acad Sci USA 86(17):6553-6556, National Academy of Science, United States (Sep. 1989).
Li, Y., et al., "Establishment and maintenance of primary fibroblast repositories for rare diseases-friedreich's ataxia example," Biopreservation and Biobanking 14(4):324-329, Mary Ann Liebert Inc., United States (Aug. 2016).
Liu, S., "Radiolabeled multimeric cyclic RGD peptides as integrin alpha$_v$beta$_3$ targeted radiotracers for tumor imaging," Molecular Pharmaceutics 3(5):472-487, American Chemical Society, United States (Sep.-Oct. 2006).

(56) References Cited

OTHER PUBLICATIONS

Lizardi, P. M., et al., "Exponential amplification of recombinant-RNA hybridization probes," Nature Biotechnology 6:1197-1202, Nature Publishing Group, United Kingdom (Oct. 1988).
Long, J. D., et al., "Genetic modification of Huntington disease acts early in the prediagnosis phase," American Journal of Human Genetics 103(3):349-357, 9 pages, Elsevier, Netherlands (Sep. 2018).
Mangiarini, L., et al., "Exon 1 of the HD gene with an expanded CAG repeat is sufficient to cause a progressive neurological phenotype in transgenic mice," Cell 87(3):493-506, Cell Press, United States (Nov. 1996).
Mangiarini, L., et al., "Instability of highly expanded CAG repeats in mice transgenic for the Huntington's disease mutation," Nature Genetics 15(2):197-200, Nature Publishing Group, United Kingdom (Feb. 1997).
Mannino R. J., and Gould-Fogerite, S., "Liposome mediated gene transfer," BioTechniques, 6(7):682-690, Future Science, United Kingdom (Jul.-Aug. 1988).
Manoharan, M., et al., "Chemical modifications to improve uptake and bioavailability of antisense oligonucleotides," Annals of the New York Academy of Sciences 660:306-309, Blackwell, United States (Oct. 1992).
Manoharan, M., et al., "Cholic Acid Oligonucliotide Conjugates for Antisense Applications," Bioorganic & Medicinal Chemistry Letters 4(8):1053-1060, Elsevier, United States (1994).
Manoharan, M., et al., "Introduction of a lipophilic thioether tether in the minor groove of nucleic acids for antisense applications," Bioorganic & Medicinal Chemistry Letters 3(12):2765-2770, Elsevier, United States (Dec. 1993).
Manoharan, M., et al., "Oligonucleotide Conjugates: Alteration of the Pharmacokinetic Properties of Antisense Agents," Nucleosides and Nucleotides 14:969-973, M. Dekker, United States (1995).
Manoharan, M., et al., "Lipidic Nucleic Acids," Tetrahedron Letters 36:3651-3654, Elsevier, United Kingdom (1995).
Martin, P., "A New Access to 2'-O-alkylated ribonucleosides and properties of 2'-O-alkylated oligoribonucleotides," Helvetica Chimica Acta 78(2):486-504, John Wiley & Sons, Switzerland (Jan. 1995).
Mayer, L. D., et al., "Vesicles of variable sizes produced by a rapid extrusion procedure," Biochim Biophys Acta 858(1):161-168, Elsevier, Netherlands (Jun. 1986).
Mayhew, E., et al., "Characterization of liposomes prepared using a microemulsifier," Biochim Biophys Acta 775(2):169-174, Elsevier, Netherlands (Aug. 1984).
Min, K-L., et al., "Oligonucleotides comprised of alternating 2'-deoxy-2'-fluoro-beta-D-arabinonucleosides and D-2'-deoxyribonucleosides (2'F-ANA/DNA 'altimers') induce efficient RNA cleavage mediated by RNase H," Bioorganic & Medicinal Chemistry Letters 12(18):2651-2654, Elsevier Science Ltd., United Kingdom (Sep. 2002).
Mishra, R. K., et al., "Improved leishmanicidal effect of phosphorotioate antisense oligonucleotides by LDL-mediated delivery," Biochimica et Biophysica Acta 1264(2):229-237, Elsevier, Netherlands (1995).
Morales, F., et al., "A polymorphism in the MSH3 mismatch repair gene is associated with the levels of somatic instability of the expanded CTG repeat in the blood DNA of myotonic dystrophy type 1 patients," DNA Repair 40:57-66, Elsevier, Netherlands (Apr. 2016).
Mullis, K. B., and Faloona, F. A., "Specific synthesis of DNA in vitro via a polymerase-catalyzed chain reaction," Methods in Enzymology, 155:335-350, Academic Press, United States (1987).
Nabel, E. G., et al., "Gene transfer in vivo with DNA-liposome complexes: lack of autoimmunity and gonadal localization," Human Gene Therapy 3(6):649-656, Mary Ann Liebert Inc., United States (Dec. 1992).
Nabel, G. J., et al., "Direct gene transfer with DNA-liposome complexes in melanoma: expression, biologic activity, and lack of toxicity in humans," Proc Natl Acad Sci USA 90(23):11307-11311, National Academy of Sciences, United States (Dec. 1993).
Nicolau, C., et al., "Liposomes as carriers for in vivo gene transfer and expression," Methods in Enzymology 149:157-176, Academic Press, United States (1987).
Nielsen, P. E., et al., "Sequence-selective recognition of DNA by strand displacement with a thymine-substituted polyamide," Science 254(5037):1497-1500, American Association for the Advancement of Science, United States (Dec. 1991).
Oberhauser, B., and Wagner, E., "Effective incorporation of 2'-O-methyl-oligoribonucleotides into liposomes and enhanced cell association through modification with thiocholesterol," Nucleic Acids Research 20(3):533-538, Oxford University Press, United Kingdom (1992).
Olson, F., et al., "Preparation of liposomes of defined size distribution by extrusion through polycarbonate membranes," Biochimica Et Biophysica Acta 557(1):9-23, Elsevier, Netherlands (Oct. 1979).
Pal, A., et al., "Systemic delivery of RafsiRNA using cationic cardiolipin liposomes silences Raf-1 expression and inhibits tumor growth in xenograft model of human prostate cancer," International Journal of Oncology 26(4):1087-1091, Spandidos, Greece (Apr. 2005).
Pandey, S.K., et al., "Identification and characterization of modified antisense oligonucleotides targeting DMPK in mice and nonhuman primates for the treatment of myotonic dystrophy type 1," J Pharmacology and Experimental Therapeutics 355(2):329-340, American Society for Pharmacology and Experimental Therapeutics, United States (Nov. 2015).
Papahadjopoulos, D and Gabizon, A., "Targeting of liposomes to tumor cells in vivo," Annals of the New York Academy of Sciences 507:64-74, Blackwell, United States (1987).
Pinto, R. M., et al., "Mismatch repair genes Mlh1 and Mlh3 modify CAG instability in Huntington's disease mice: genome-wide and candidate approaches," PLoS Genetics 9(10):e1003930, Public Library of Science, United States (Oct. 2013).
Pouladi, M.A., et al., "Choosing an animal model for the study of Huntington's disease," Nature Reviews. Neuroscience 14(10):708-721, Nature Publishing Group, United Kingdom (Oct. 2013).
Saison-Behmoaras, T., et al., "Short modified antisense oligonucleotides directed against Ha-ras point mutation induce selective cleavage of the mRNA and inhibit T24 cells proliferation," The EMBO Journal 10(5):1111-1118, Wiley Blackwell, United Kingdom (1991).
Shea, R. G., et al., "Synthesis, hybridization properties and antiviral activity of lipid-oligodeoxynucleotide conjugates," Nucleic Acids Research 18(13):3777-3783, Oxford University Press, United Kingdom (1990).
Simeoni, F., et al., "Insight into the mechanism of the peptide-based gene delivery system MPG: implications for delivery of siRNA into mammalian cells," Nucleic Acids Research 31(11):2717-2724, Oxford University Press, United Kingdom (Jun. 2003).
Skotte, N. H., et al., "Allele-specific suppression of mutant huntingtin using antisense oligonucleotides: providing a therapeutic option for all Huntington disease patients," PLoS One 9(9):e107434, Public Library of Science, United States (Sep. 2014).
Sorensen, D. R., et al., "Gene silencing by systemic delivery of synthetic siRNAs in adult mice," Journal of Molecular Biology 327(4):761-766, Elsevier, United Kingdom (Apr. 2003).
Straubinger, R. M., and Papahadjopoulos, D., "Liposomes as carriers for intracellular delivery of nucleic acids," Methods in Enzymology 101:512-527, Academic Press, United States (1983).
Strauss, W. M., and Jaenisch, R., "Molecular complementation of a collagen mutation in mammalian cells using yeast artificial chromosomes," The EMBO Journal 11(2):417-422, Wiley Blackwell, United Kingdom (Feb. 1992).
Summerton, J., et al., "Morpholino and phosphorothioate antisense oligomers compared in cell-free and in-cell systems," Antisense and Nucleic Acid Drug Development 7(2):63-70, Mary Ann Liebert Inc., United States (Apr. 1997).
Svinarchuk, F. P., et al., "Inhibition of HIV proliferation in MT-4 cells by antisense oligonucleotide conjugated to lipophilic groups," Biochimie 75(1-2):49-54, Elsevier, France (1993).
Szoka Jr., F. S., and Papahadjopoulos, D., "Procedure for preparation of liposomes with large internal aqueous space and high capture

(56) References Cited

OTHER PUBLICATIONS by reverse-phase evaporation," Proc Natl Acad Sci USA 75(9):4194-4198, National Academy of Sciences, United States (Sep. 1978).
Tomalia, D. A., et al., "Dendrimers as multi-purpose nanodevices for oncology drug delivery and diagnostic imaging," Biochemical Society Transactions 35(Pt 1):61-67, Portland Press, United Kingdom (Feb. 2007).
Tome, S., et al., "MSH2 ATPase domain mutation affects CTG*CAG repeat instability in transgenic mice," PLoS Genetics 5(5):e1000482, Public Library of Science, United States (May 2009).
Verma, U. N., et al., "Small interfering RNAs directed against beta-catenin inhibit the in vitro and in vivo growth of colon cancer cells," Clinical Cancer Research 9(4):1291-1300, American Association for Cancer Research, United States (Apr. 2003).
Wang, C. Y., and Huang, L., "Plasmid DNA adsorbed to pH-sensitive liposomes efficiently transforms the target cells," Biochemical and Biophysical Research Communications 147(3):980-985, Elsevier, United States (Sep. 1987).
Wang, C. Y., and Huang, L., "pH-sensitive immunoliposomes mediate target-cell-specific delivery and controlled expression of a foreign gene in mouse," Proc Natl Acad Sci USA 84(22):7851-7855, National Academy of Sciences, United States (Nov. 1987).
Warby, S. C., et al., "CAG expansion in the Huntington disease gene is associated with a specific and targetable predisposing haplogroup," American Journal of Human Genetics 84(3):351-366, Cell Press, United States (Mar. 2009).
Weiner, N., et al., "Liposomes: a novel topical delivery system for pharmaceutical and cosmetic applications," Journal of Drug Targeting 2(5):405-410, Harwood Academic Publishers GmbH, United States (1994).
Wheeler, V. C., et al., "Length-dependent gametic CAG repeat instability in the Huntington's disease knock-in mouse," Human Molecular Genetics 8(1):115-122, Oxford University Press, United Kingdom (Jan. 1999).
Wheeler, V. C., et al., "Long glutamine tracts cause nuclear localization of a novel form of huntingtin in medium spiny striatal neurons in $Hdh^{Q92}$ and $Hdh^{Q111}$ knock-in mice," Human Molecular Genetics 9(4):503-513, Oxford University Press, United Kingdom (Mar. 2000).
Wu, N. Z., et al., "Increased microvascular permeability contributes to preferential accumulation of Stealth liposomes in tumor tissue," Cancer Research 53(16):3765-3670, American Association for Cancer Research, United States (Aug. 1993).
Xu, Z. Z., and Mathews, D. H., "Secondary Structure Prediction of Single Sequences Using RNAstructure," Methods in Molecular Biology 1490:15-34, Humana Press, United States (2016).
Yoo, H., et al., "PAMAM dendrimers as delivery agents for antisense oligonucleotides," Pharmaceutical Research 16(12):1799-1804, Kluwer Academic/Plenum Publishers, United States (Dec. 1999).
Zhang, W., et al., "Treatment of type 1 myotonic dystrophy by engineering site-specific RNA endonucleases that target (CUG)(n) repeats," Molecular Therapy 22(2):312-320, Cell Press, United States (Feb. 2014).
Zhou, X., et al., "Lipophilic polylysines mediate efficient DNA transfection in mammalian cells," Biochim Biophys Acta 1065(1):8-14, Elsevier, Netherlands (May 1991).
Zhou, X., and Huang, L., "Targeted delivery of DNA by liposomes and polymers," Journal of Controlled Release 19:269-274, Elsevier Science Publishers, United States (1992).
Zhou, C., et al., "Fine tuning of electrostatics around the internucleotidic phosphate through incorporation of modified 2',4'-carbocyclic-LNAs and -ENAs leads to significant modulation of antisense properties," The Journal of Organic Chemistry 74(1):118-134, American Chemical Society, United States (Jan. 2009).
Zimmermann, T. S., et al., "RNAi-mediated gene silencing in non-human primates," Nature 441(7089):111-114, Nature Publishing Group, United Kingdom (Mar. 2006).
Co-pending U.S. Appl. No. 17/299,186, inventors Bermingham, N. A., et al., int'l filed Dec. 2, 2019 (Not yet Published).
International Search Report and Written Opinion for International Application No. PCT/US2015/029724, ISA/US, Commissioner for Patents, Virginia, dated Nov. 12, 2015, 13 pages
International Search Report and Written Opinion for International Application No. PCT/U82019/064055, ISA/US, Commissioner for Patents, Virginia, dated Feb. 20, 2020, 10 pages.
International Search Report and Written Opinion for International Application No. PCT/US2019/065685, ISA/US, Commissioner for Patents, Virginia, dated Mar. 3, 2020, 12 pages.
Kolodner, R. D., et al., "Structure of the human MSH2 locus and analysis of two Muir-Torre kindreds for msh2 mutations," Genomics 24(3):516-526, Elsevier, Netherlands (Dec. 1994).

* cited by examiner

OLIGONUCLEOTIDES FOR THE TREATMENT OF NUCLEOTIDE REPEAT EXPANSION DISORDERS ASSOCIATED WITH MSH3 ACTIVITY

CROSS-REFERENCE TO RELATED APPLICATIONS

This patent application claims the priority benefit of U.S. Provisional Application No. 63/034,319 filed on Jun. 3, 2020, which is hereby incorporated by reference in its entirety.

INCORPORATION BY REFERENCE OF SEQUENCE LISTING

The content of the electronically submitted sequence listing (Name: 4398_0210001_Seqlisting_ST25.txt; Size: 154,926 Bytes; and Date of Creation: Jun. 2, 2021) is incorporated herein by reference in its entirety.

BACKGROUND

Nucleotide repeat expansion disorders (e.g., trinucleotide repeat expansion disorders) are genetic disorders caused by nucleotide repeat expansions (e.g., trinucleotide repeats). Nucleotide repeat expansions (e.g., trinucleotide repeat expansions) are a type of genetic mutation where nucleotide repeats in certain genes or introns exceed the normal, stable threshold for that gene. The nucleotide repeats (e.g., trinucleotide repeats) can result in defective or toxic gene products, impair RNA transcription, and/or cause toxic effects by forming toxic mRNA transcripts.

Nucleotide repeat expansion disorders (e.g., trinucleotide repeat expansion disorders) are generally categorized by the type of repeat expansion. For example, Type 1 disorders such as Huntington's disease are caused by CAG repeats which result in a series of glutamine residues known as a polyglutamine tract, Type 2 disorders are caused by heterogeneous expansions that are generally small in magnitude, and Type 3 disorders such as fragile X syndrome are characterized by large repeat expansions that are generally located outside of the protein coding region of the genes. Nucleotide repeat expansion disorders (e.g., trinucleotide repeat expansion disorders) are characterized by a wide variety of symptoms such as progressive degeneration of nerve cells that is common in the Type 1 disorders.

Subjects with a nucleotide repeat expansion disorder (e.g., a trinucleotide repeat expansion disorder) or those who are considered at risk for developing a nucleotide repeat expansion disorder (e.g., a trinucleotide repeat expansion disorder) have a constitutive nucleotide expansion in a gene associated with disease (i.e., the nucleotide repeat expansion is present in the gene during embryogenesis). Constitutive nucleotide repeat expansions (e.g., trinucleotide repeat expansions) can undergo expansion after embryogenesis (i.e., somatic nucleotide repeat expansion). Both constitutive nucleotide repeat expansion and somatic nucleotide repeat expansion can be associated with presence of disease, age at onset of disease, and/or rate of progression of disease.

SUMMARY OF THE DISCLOSURE

The present disclosure features useful compositions and methods to treat nucleotide repeat expansion disorders (e.g., trinucleotide repeat expansion disorders), e.g., in a subject in need thereof. In some aspects, the compositions and methods described herein are useful in the treatment of disorders associated with MSH3 activity.

Oligonucleotides

Some aspects of the disclosure are related to a single-stranded oligonucleotide of 15-30 linked nucleotides in length, wherein the oligonucleotide, or a portion thereof, is at least 95% complementary to at least 15 contiguous nucleobases at positions 2543-2573 of SEQ ID NO: 614, or a pharmaceutically acceptable salt thereof. In some aspects, the oligonucleotide, or a portion thereof, is at least 98% complementary to at least 15 contiguous nucleobases at positions 2543-2573 of SEQ ID NO: 614, or a pharmaceutically acceptable salt thereof. In some aspects, the oligonucleotide, or a portion thereof, is at least 99% complementary to at least 15 contiguous nucleobases at positions 2543-2573 of SEQ ID NO: 614, or a pharmaceutically acceptable salt thereof. In some aspects, the oligonucleotide, or a portion thereof, is 100% complementary to at least 15 contiguous nucleobases at positions 2543-2573 of SEQ ID NO: 614, or a pharmaceutically acceptable salt thereof. In some aspects, the oligonucleotide, or a portion thereof, is complementary to 17-23 contiguous nucleobases at positions 2543-2573 of SEQ ID NO: 614, or a pharmaceutically acceptable salt thereof. In some aspects, the oligonucleotide is complementary to 17-20 contiguous nucleobases at positions 2543-2573 of SEQ ID NO: 614, or a pharmaceutically acceptable salt thereof. In some aspects, the 17-20 contiguous nucleobases begin at position 2543, 2544, 2545, 2546, 2547, 2548, 2549, 2550, 2551, 2552, 2553, 2554, 2555, 2556, or 2557 of SEQ ID NO: 614, or a pharmaceutically acceptable salt thereof. In some aspects, the oligonucleotide is 17-20 linked nucleotides in length, or a pharmaceutically acceptable salt thereof.

In some aspects, the oligonucleotide, or a portion thereof, is complementary to 20-23 contiguous nucleobases at positions 2543-2573 of SEQ ID NO: 614, or a pharmaceutically acceptable salt thereof. In some aspects, the 20-23 contiguous nucleobases begin at position 2543, 2544, 2545, 2546, 2547, 2548, 2549, 2550, 2551, 2552, 2553, or 2554 of SEQ ID NO: 614, or a pharmaceutically acceptable salt thereof. In some aspects, the oligonucleotide is 20-23 linked nucleotides in length, or a pharmaceutically acceptable salt thereof.

In some aspects, the oligonucleotide, or a portion thereof, is complementary to positions 2543-2570 of SEQ ID NO: 614, or a pharmaceutically acceptable salt thereof.

The disclosure also relates to single-stranded oligonucleotides of 15-30 linked nucleotides in length, wherein the oligonucleotide, or a portion thereof, is at least 95% complementary to at least 15 contiguous nucleobases at positions 2685-2714 of SEQ ID NO: 614, or a pharmaceutically acceptable salt thereof. In some aspects, the oligonucleotide, or a portion thereof, is at least 98% complementary to at least 15 contiguous nucleobases at positions 2685-2714 of SEQ ID NO: 614, or a pharmaceutically acceptable salt thereof. In some aspects, the oligonucleotide, or a portion thereof, is at least 99% complementary to at least 15 contiguous nucleobases at positions 2685-2714 of SEQ ID NO: 614, or a pharmaceutically acceptable salt thereof. In some aspects, the oligonucleotide or a portion thereof, is 100% complementary to at least 15 contiguous nucleobases at positions 2685-2714 of SEQ ID NO: 614, or a pharmaceutically acceptable salt thereof. In some aspects, the oligonucleotide, or a portion thereof is complementary to 17-23 contiguous nucleobases at positions 2685-2714 of SEQ ID NO: 614, or a pharmaceutically acceptable salt thereof. In some aspects, the oligonucleotide, or a portion thereof, is complementary to 17-20 contiguous nucleobases at positions 2685-2714 of SEQ ID NO: 614, or a pharmaceutically acceptable salt thereof. In some aspects, the oligonucleotide, or a portion thereof, is complementary to 17-20 contiguous nucleobases beginning at position 2685, 2686, 2687, 2688, 2689, 2690, 2691, 2692, 2693, 2694, 2695, 2696, 2697, or 2698 of SEQ ID NO: 614, or a pharmaceutically acceptable salt thereof. In some aspects, the oligonucleotide is 17-20 linked nucleotides in length, or a pharmaceutically acceptable salt thereof.

In some aspects, the oligonucleotide, or a portion thereof, is complementary to 20-23 contiguous nucleobases at positions 2685-2714 of SEQ ID NO: 614, or a pharmaceutically acceptable salt thereof. In some aspects, the oligonucleotide is complementary to 20-23 contiguous nucleobases beginning at position 2685, 2686, 2687, 2688, 2689, 2690, 2691, 2692, 2693, 2694, or 2695 of SEQ ID NO: 614, or a pharmaceutically acceptable salt thereof. In some aspects, the oligonucleotide is 20-23 linked nucleotides in length, or a pharmaceutically acceptable salt thereof. In some aspects, the oligonucleotide, or a portion thereof, is complementary to positions 2685-2714 of SEQ ID NO: 614, or a pharmaceutically acceptable salt thereof.

In some aspects of the above, the oligonucleotide is not any one of Antisense Oligo Nos. 1, 97, 193, or 289 of Table 3. In some aspects of the above, the oligonucleotide does not have a nucleobase sequence consisting of any one of SEQ ID NOs: 1, 97, 193, or 289.

In some aspects of the above disclosure, the oligonucleotide comprises:

(a) a DNA core sequence comprising linked deoxyribonucleosides;

(b) a 5' flanking sequence comprising linked nucleosides; and (c) a 3' flanking sequence comprising linked nucleosides;

wherein the DNA core comprises a region of at least 10 contiguous nucleobases positioned between the 5' flanking sequence and the 3' flanking sequence; wherein the 5' flanking sequence and the 3' flanking sequence each comprises at least two linked nucleosides; and wherein at least one nucleoside of each flanking sequence comprises an alternative nucleoside, or a pharmaceutically acceptable salt thereof. In some aspects of the above disclosures, the oligonucleotide comprises at least one alternative internucleoside linkage, or a pharmaceutically acceptable salt thereof. In some aspects of the above disclosures, the at least one alternative internucleoside linkage is a phosphorothioate internucleoside linkage. In some aspects of the above disclosures, the at least one alternative internucleoside linkage is a 2'-alkoxy internucleoside linkage. In some aspects of the above disclosures, the at least one alternative internucleoside linkage is an alkyl phosphate internucleoside linkage.

In some aspects of the above disclosures, the oligonucleotide comprises at least one alternative nucleobase, or a pharmaceutically acceptable salt thereof. In some aspects of the above disclosures, the alternative nucleobase is 5'-methylcytosine, pseudouridine, or 5-methoxyuridine. In some aspects of the above disclosures, the oligonucleotide comprises at least one alternative sugar moiety, or a pharmaceutically acceptable salt thereof. In some aspects, the alternative sugar moiety is 2'-OMe or a bicyclic nucleic acid.

In some aspects of the above disclosures, the oligonucleotide further comprises a ligand conjugated to the 5' end or the 3' end of the oligonucleotide through a monovalent or branched bivalent or trivalent linker, or a pharmaceutically acceptable salt thereof.

In some aspects of the above disclosures, the oligonucleotide consists of a nucleobase sequence selected from the group consisting of any of SEQ ID NOs: 1-384 and 390-613, or a pharmaceutically acceptable salt thereof. In some aspects, the oligonucleotide consists of a nucleobase sequence selected from the group consisting of any of SEQ ID NOs: 2-96, 98-192, 194-288, 290-384, and 390-613, or a pharmaceutically acceptable salt thereof. In some aspects, the oligonucleotide consists of a nucleobase sequence selected from the group consisting of any of SEQ ID NOs: 1-384, or a pharmaceutically acceptable salt thereof. In some aspects, the oligonucleotide consists of a nucleobase sequence selected from the group consisting of any of SEQ ID NOs: 2-96, 98-192, 194-288, and 290-384, or a pharmaceutically acceptable salt thereof. In some aspects, the oligonucleotide consists of a nucleobase sequence selected from the group consisting of any of SEQ ID NOs: 1-96, or a pharmaceutically acceptable salt thereof. In some aspects, the oligonucleotide consists of a nucleobase sequence selected from the group consisting of any of SEQ ID NOs: 2-96, or a pharmaceutically acceptable salt thereof. In some aspects, the oligonucleotide consists of a nucleobase sequence selected from the group consisting of any of SEQ ID NOs: 97-192, or a pharmaceutically acceptable salt thereof. In some aspects, the oligonucleotide consists of a nucleobase sequence selected from the group consisting of any of SEQ ID NOs: 98-192, or a pharmaceutically acceptable salt thereof. In some aspects, the oligonucleotide consists of a nucleobase sequence selected from the group consisting of any of SEQ ID NOs: 193-288, or a pharmaceutically acceptable salt thereof. In some aspects, the oligonucleotide consists of a nucleobase sequence selected from the group consisting of any of SEQ ID NOs: 194-288, or a pharmaceutically acceptable salt thereof. In some aspects, the oligonucleotide consists of a nucleobase sequence selected from the group consisting of any of SEQ ID NOs: 289-384, or a pharmaceutically acceptable salt thereof. In some aspects, the oligonucleotide consists of a nucleobase sequence selected from the group consisting of any of SEQ ID NOs: 288-384, or a pharmaceutically acceptable salt thereof. In some aspects, the oligonucleotide consists of a nucleobase sequence selected from the group consisting of any of SEQ ID NOs: 390-613, or a pharmaceutically acceptable salt thereof. In some aspects, the oligonucleotide consists of a nucleobase sequence selected from the group consisting of any of SEQ ID NOs: 390-480, or a pharmaceutically acceptable salt thereof. In some aspects, the oligonucleotide consists of a nucleobase sequence selected from the group consisting of any of SEQ ID NOs: 481-571, or a pharmaceutically acceptable salt thereof. In some aspects, the oligonucleotide consists of a nucleobase sequence selected from the group consisting of any of SEQ ID NOs: 572-662, or a pharmaceutically acceptable salt thereof. In some aspects, the oligonucleotide consists of a nucleobase sequence selected from the group consisting of any of SEQ ID NOs: 663-613, or a pharmaceutically acceptable salt thereof. In some aspects, the oligonucleotide consists of a nucleobase sequence selected from the group consisting of any of SEQ ID NOs: 1, 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of a nucleobase sequence selected from the group consisting of any of SEQ ID NOs: 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of a nucleobase sequence that is SEQ ID NO: 1, or a pharmaceutically acceptable salt thereof. In some aspects, the oligonucleotide consists of a nucleobase sequence that is SEQ ID NO: 6, or a pharmaceutically acceptable salt thereof. In some aspects, the oligonucleotide consists of a nucleobase sequence selected from the group consisting of any of SEQ ID NOs: 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of a nucleobase sequence selected from the group consisting of any of SEQ ID NOs: 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of a nucleobase sequence that is SEQ ID NO: 97, or a pharmaceutically acceptable salt thereof. In some aspects, the oligonucleotide consists of a nucleobase sequence selected from the group consisting of any of SEQ ID NOs: 193-200, 202-230, 232-246, 248-253, 255, 258-261, 265, 270, 274-276, or 285-286, or a pharmaceutically acceptable salt thereof. In some aspects, the oligonucleotide consists of a nucleobase sequence selected from the group consisting of any of SEQ ID NOs: 194-200, 202-230, 232-246, 248-253, 255, 258-261, 265, 270, 274-276, or 285-286, or a pharmaceutically acceptable salt thereof. In some aspects, the oligonucleotide consists of a nucleobase sequence that is SEQ ID NO: 193, or a pharmaceutically acceptable salt thereof. In some aspects, the oligonucleotide consists of a nucleobase sequence selected from the group consisting of any of SEQ ID NOs: 226-227, 234, 240, or 243-244, or a pharmaceutically acceptable salt thereof. In some aspects, the oligonucleotide consists of a nucleobase sequence selected from the group consisting of any of SEQ ID NOs: 227, 234, 240, or 243-244, or a pharmaceutically acceptable salt thereof. In some aspects, the oligonucleotide consists of the nucleobase sequence that is SEQ ID NO: 226, or a pharmaceutically acceptable salt thereof. In some aspects, the oligonucleotide consists of a nucleobase sequence selected from the group consisting of any of SEQ ID NOs: 289-290, 292, 305, 307, 313, 318, 323-324, 326, 329-330, 332, 338-339, 341, 344, or 346, or a pharmaceutically acceptable salt thereof. In some aspects, the oligonucleotide consists of a nucleobase sequence selected from the group consisting of any of SEQ ID NOs: 290, 292, 305, 307, 313, 318, 323-324, 326, 329-330, 332, 338-339, 341, 344, or 346, or a pharmaceutically acceptable salt thereof. In some aspects, the oligonucleotide consists of a nucleobase sequence that is SEQ ID NO: 289, or a pharmaceutically acceptable salt thereof.

Some aspects of the disclosure are directed to single-stranded oligonucleotides, wherein the nucleobase sequence of the oligonucleotide consists of any one of SEQ ID NOs: 1-384 and 390-613, or a pharmaceutically acceptable salt thereof. In some aspects, the nucleobase sequence of the oligonucleotide consists of any one of SEQ ID NOs: 2-96, 98-192, 194-288, 290-384, and 390-613, or a pharmaceutically acceptable salt thereof. In some aspects, the nucleobase sequence of the oligonucleotide consists of any one of SEQ ID NOs: 1-384, or a pharmaceutically acceptable salt thereof. In some aspects, the nucleobase sequence of the oligonucleotide consists of any one of SEQ ID NOs: 2-96, 98-192, 194-288, or 290-384, or a pharmaceutically acceptable salt thereof. In some aspects, the oligonucleotide consists of the nucleobase sequence of any one of SEQ ID NOs: 1-96, or a pharmaceutically acceptable salt thereof. In some aspects, the oligonucleotide consists of the nucleobase sequence of any one of SEQ ID NOs: 2-96, or a pharmaceutically acceptable salt thereof. In some aspects, the oligonucleotide consists of the nucleobase sequence of any one of SEQ ID NOs: 97-192, or a pharmaceutically acceptable salt thereof. In some aspects, the oligonucleotide consists of the nucleobase sequence of any one of SEQ ID NOs: 96-192, or a pharmaceutically acceptable salt thereof. In some aspects, the oligonucleotide consists of the nucleobase sequence of any one of SEQ ID NOs: 193-288, or a pharmaceutically acceptable salt thereof. In some aspects, the oligonucleotide consists of the nucleobase sequence of any one of SEQ ID NOs: 194-288, or a pharmaceutically acceptable salt thereof. In some aspects, the oligonucleotide consists of the nucleobase sequence of any one of SEQ ID NOs: 289-384, or a pharmaceutically acceptable salt thereof. In some aspects, the oligonucleotide consists of the nucleobase sequence of any one of SEQ ID NOs: 290-384, or a pharmaceutically acceptable salt thereof. In some aspects, the oligonucleotide consists of the nucleobase sequence of any one of SEQ ID NOs: 390-613, or a pharmaceutically acceptable salt thereof. In some aspects, the oligonucleotide consists of the nucleobase sequence of any one of SEQ ID NOs: 390-480, or a pharmaceutically acceptable salt thereof. In some aspects, the oligonucleotide consists of the nucleobase sequence of any one of SEQ ID NOs: 481-571, or a pharmaceutically acceptable salt thereof. In some aspects, the oligonucleotide consists of the nucleobase sequence of any one of SEQ ID NOs: 572-662, or a pharmaceutically acceptable salt thereof. In some aspects, the oligonucleotide consists of the nucleobase sequence of any one of SEQ ID NOs: 663-613, or a pharmaceutically acceptable salt thereof. In some aspects, the oligonucleotide consists of the nucleobase sequence of any one of SEQ ID NOs: 1, 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of the nucleobase sequence of any one of SEQ ID NOs: 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of the nucleobase sequence of SEQ ID NO: 1, or a pharmaceutically acceptable salt thereof. In some aspects, the oligonucleotide consists of the nucleobase sequence of SEQ ID NO: 6, or a pharmaceutically acceptable salt thereof. In some aspects, the oligonucleotide consists of the nucleobase sequence of any one of SEQ ID NOs: 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of the nucleobase sequence of any one of SEQ ID NOs: 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of the nucleobase sequence of SEQ ID NO: 97, or a pharmaceutically acceptable salt thereof. In some aspects, the oligonucleotide consists of the nucleobase sequence of any one of SEQ ID NOs: 193-200, 202-230, 232-246, 248-253, 255, 258-261, 265, 270, 274-276, or 285-286, or a pharmaceutically acceptable salt thereof. In some aspects, the oligonucleotide consists of the nucleobase sequence of any one of SEQ ID NOs: 194-200, 202-230, 232-246, 248-253, 255, 258-261, 265, 270, 274-276, or 285-286, or a pharmaceutically acceptable salt thereof. In some aspects, the oligonucleotide consists of the nucleobase sequence of any one of SEQ ID NO: 193, or a pharmaceutically acceptable salt thereof. In some aspects, the oligonucleotide consists of the nucleobase sequence of any one of SEQ ID NOs: 226-227, 234, 240, or 243-244, or a pharmaceutically acceptable salt thereof. In some aspects, the oligonucleotide consists of the nucleobase sequence of any one of SEQ ID NOs: 227, 234, 240, or 243-244, or a pharmaceutically acceptable salt thereof. In some aspects, the oligonucleotide consists of the nucleobase sequence of SEQ ID NO: 226, or a pharmaceutically acceptable salt thereof. In some aspects, the oligonucleotide consists of the nucleobase sequence of any one of SEQ ID NOs: 289-290, 292, 305, 307, 313, 318, 323-324, 326, 329-330, 332, 338-339, 341, 344, or 346, or a pharmaceutically acceptable salt thereof. In some aspects, the oligonucleotide consists of the nucleobase sequence of any one of SEQ ID NOs: 290, 292, 305, 307, 313, 318, 323-324, 326, 329-330, 332, 338-339, 341, 344, or 346, or a pharmaceutically acceptable salt thereof. In some aspects, the oligonucleotide consists of the nucleobase sequence of SEQ ID NO: 289, or a pharmaceutically acceptable salt thereof.

Some aspects of the disclosure are directed to nn oligonucleotide selected from the group consisting of Antisense Oligo Nos. 1-384 of Table 3 or 390-613 of Table 4, or a pharmaceutically acceptable salt thereof. In some aspects, the oligonucleotide is selected from the group consisting of Antisense Oligo Nos. 2-96, 98-192, 194-288, 290-384 of Table 3 and 390-613 of Table 4, or a pharmaceutically acceptable salt thereof. In some aspects, the oligonucleotide is selected from the group consisting of Antisense Oligo Nos. 1-384 of Table 3, or a pharmaceutically acceptable salt thereof. In some aspects, the oligonucleotide is selected from the group consisting of Antisense Oligo Nos. 2-96, 98-192, 194-288, and 290-384 of Table 3, or a pharmaceutically acceptable salt thereof. In some aspects, the oligonucleotide is selected from the group consisting of Antisense Oligo Nos. 1-96 of Table 3, or a pharmaceutically acceptable salt thereof. In some aspects, the oligonucleotide is selected from the group consisting of Antisense Oligo Nos. 2-96 of Table 3, or a pharmaceutically acceptable salt thereof. In some aspects, the oligonucleotide is selected from the group consisting of Antisense Oligo Nos. 97-192 of Table 3, or a pharmaceutically acceptable salt thereof. In some aspects, the oligonucleotide is selected from the group consisting of Antisense Oligo Nos. 98-192 of Table 3, or a pharmaceutically acceptable salt thereof. In some aspects, the oligonucleotide is selected from the group consisting of Antisense Oligo Nos. 193-288 of Table 3, or a pharmaceutically acceptable salt thereof. In some aspects, the oligonucleotide is selected from the group consisting of Antisense Oligo Nos. 194-288 of Table 3, or a pharmaceutically acceptable salt thereof. In some aspects, the oligonucleotide is selected from the group consisting of Antisense Oligo Nos. 289-384 of Table 3, or a pharmaceutically acceptable salt thereof. In some aspects, the oligonucleotide is selected from the group consisting of Antisense Oligo Nos. 290-384 of Table 3, or a pharmaceutically acceptable salt thereof. In some aspects, the oligonucleotide is selected from the group consisting of Antisense Oligo Nos. 390-613 of Table 4, or a pharmaceutically acceptable salt thereof. In some aspects, the oligonucleotide is selected from the group consisting of Antisense Oligo Nos. 390-480 of Table 4, or a pharmaceutically acceptable salt thereof. In some aspects, the oligonucleotide is selected from the group consisting of Antisense Oligo Nos. 481-571 of Table 4, or a pharmaceutically acceptable salt thereof. In some aspects, the oligonucleotide is selected from the group consisting of Antisense Oligo Nos. 1, 6, 13, 17, 21, 24, 26, 29, 33-34, 37, 44, 49-55, 57, 60-73, 75-76, 79-82, 84-86, 88-92, or 94-96 of Table 3, or a pharmaceutically acceptable salt thereof. In some aspects, the oligonucleotide is selected from the group consisting of Antisense Oligo Nos. 6, 13, 17, 21, 24, 26, 29, 33-34, 37, 44, 49-55, 57, 60-73, 75-76, 79-82, 84-86, 88-92, or 94-96 of Table 3, or a pharmaceutically acceptable salt thereof. In some aspects, the oligonucleotide is Antisense Oligo No. 1 of Table 3, or a pharmaceutically acceptable salt thereof. In some aspects, the oligonucleotide is Antisense Oligo No. 6 of Table 3, or a pharmaceutically acceptable salt thereof. In some aspects, the oligonucleotide is selected from the group consisting of Antisense Oligo Nos. 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191 of Table 3, or a pharmaceutically acceptable salt thereof. In some aspects, the oligonucleotide is selected from the group consisting of Antisense Oligo Nos. 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191 of Table 3, or a pharmaceutically acceptable salt thereof. In some aspects, the oligonucleotide is Antisense Oligo No. 97 of Table 3, or a pharmaceutically acceptable salt thereof. In some aspects, the oligonucleotide is selected from the group consisting of Antisense Oligo Nos. 193-200, 202-230, 232-246, 248-253, 255, 258-261, 265, 270, 274-276, or 285-286 of Table 3, or a pharmaceutically acceptable salt thereof. In some aspects, the oligonucleotide is selected from the group consisting of Antisense Oligo Nos. 194-200, 202-230, 232-246, 248-253, 255, 258-261, 265, 270, 274-276, or 285-286 of Table 3, or a pharmaceutically acceptable salt thereof. In some aspects, the oligonucleotide is Antisense Oligo No. 193 of Table 3. In some aspects, the oligonucleotide is selected from the group consisting of Antisense Oligo Nos. 226-227, 234, 240, or 243-244 of Table 3, or a pharmaceutically acceptable salt thereof. In some aspects, the oligonucleotide is selected from the group consisting of Antisense Oligo Nos. 227, 234, 240, or 243-244 of Table 3, or a pharmaceutically acceptable salt thereof. In some aspects, the oligonucleotide is Antisense Oligo No. 226 of Table 3, or a pharmaceutically acceptable salt thereof. In some aspects, the oligonucleotide is selected from the group consisting of Antisense Oligo Nos. 289-290, 292, 305, 307, 313, 318, 323-324, 326, 329-330, 332, 338-339, 341, 344, or 346 of Table 3, or a pharmaceutically acceptable salt thereof. In some aspects, the oligonucleotide is selected from the group consisting of Antisense Oligo Nos. 290, 292, 305, 307, 313, 318, 323-324, 326, 329-330, 332, 338-339, 341, 344, or 346 of Table 3, or a pharmaceutically acceptable salt thereof. In some aspects, the oligonucleotide is Antisense Oligo No. 289 of Table 3, or a pharmaceutically acceptable salt thereof.

In some aspects, the oligonucleotide, or a pharmaceutically acceptable salt thereof, described herein causes at least a 50% reduction in MSH3 mRNA expression at an oligonucleotide concentration of 10 nM. In some aspects, the oligonucleotide, or a pharmaceutically acceptable salt thereof, described herein causes at least a 60% reduction in MSH3 mRNA expression at an oligonucleotide concentration of 10 nM. In some aspects, the oligonucleotide, or a pharmaceutically acceptable salt thereof, described herein causes at least a 70% reduction in MSH3 mRNA expression at an oligonucleotide concentration of 10 nM. In some aspects, the oligonucleotide, or a pharmaceutically acceptable salt thereof, described herein causes at least an 80% reduction in MSH3 mRNA expression at an oligonucleotide concentration of 10 nM.

In some aspects, the oligonucleotide, or a pharmaceutically acceptable salt thereof, described herein causes at least a 50% reduction in MSH3 mRNA expression at an oligonucleotide concentration of 1 nM. In some aspects, the oligonucleotide, or a pharmaceutically acceptable salt thereof, described herein causes at least a 60% reduction in MSH3 mRNA expression at an oligonucleotide concentration of 1 nM. In some aspects, the oligonucleotide, or a pharmaceutically acceptable salt thereof, described herein causes at least a 70% reduction in MSH3 mRNA expression at an oligonucleotide concentration of 1 nM.

In some aspects, the MSH3 mRNA expression is evaluated in vitro. In some aspects, the MSH3 mRNA expression is evaluated in a cell based assay. In some aspects, the MSH3 mRNA expression is evaluated in HeLa cells. In some aspects, the MSH3 mRNA expression is determined by the quantitative reverse transcription polymerase chain reaction (RT-qPCR). In some aspects, the MSH3 mRNA is expression is normalized to the mRNA expression of a reference gene. In some aspects, the MSH3 mRNA expression is normalized to the mRNA expression of beta-glucuronidase (GUSB). In some aspects, the reduction in MSH3 mRNA expression is relative to a control. In some aspects, the control is the MSH3 mRNA expression in the absence of the oligonucleotide, or pharmaceutically acceptable salt thereof. In some aspects, the control is the MSH3 mRNA expression in the absence of the oligonucleotide, or pharmaceutically acceptable salt thereof, but in the presence of a control oligonucleotide, or salt thereof. In some aspects, the control oligonucleotide, or salt thereof, is a scrambled luciferase targeting oligonucleotide. In some aspects, the reduction in MSH3 mRNA expression is calculated by a delta-delta Ct (ΔΔCT) method. In some aspects, the delta-delta Ct (ΔΔCT) method comprises the normalization of the MSH3 mRNA expression to the mRNA expression of a reference gene and to the MSH3 mRNA expression in the absence of the oligonucleotide, or pharmaceutically acceptable salt thereof but in the presence of a control oligonucleotide, or salt thereof. In some aspects, the reference gene is beta-glucuronidase (GUSB) and/or the control oligonucleotide, or salt thereof, is a scrambled luciferase targeting oligonucleotide. In some aspects, the reduction in MSH3 mRNA expression is determined by the method of Example 1. In some aspects, in the same assay, Antisense Oligo No. 1 causes approximately a 58% reduction in MSH3 mRNA expression at an oligonucleotide concentration of 10 nM. In some aspects, in the same assay, Antisense Oligo No. 1 causes approximately a 14% reduction in MSH3 mRNA expression at an oligonucleotide concentration of 1 nM.

In some aspects disclosed herein, the oligonucleotide is in the free base form.

In some aspects disclosed herein, the oligonucleotide is a pharmaceutically acceptable salt thereof. In some aspects, the oligonucleotide is a sodium salt.

Pharmaceutical Compositions and Methods of Treatment Using the Same

In some aspects, the application is directed to a pharmaceutical composition comprising one or more of the oligonucleotides, or pharmaceutically acceptable salts thereof, described herein and a pharmaceutically acceptable carrier or excipient.

In some aspects, the application is directed to a composition comprising one or more of the oligonucleotides or pharmaceutically acceptable salts thereof, described herein and a lipid nanoparticle, a polyplex nanoparticle, a lipoplex nanoparticle, or a liposome.

In some aspects, the application is directed to a method of inhibiting transcription of MSH3 in a cell, the method comprising contacting the cell with one or more of the oligonucleotides or pharmaceutically acceptable salts thereof, described herein, a pharmaceutical composition of one or more of the oligonucleotides or pharmaceutically acceptable salts thereof, described herein, or the composition of one or more oligonucleotides or pharmaceutically acceptable salts thereof, described herein and a lipid nanoparticle, a polyplex nanoparticle, a lipoplex nanoparticle, or a liposome; for a time sufficient to obtain degradation of an mRNA transcript of a MSH3 gene, inhibiting expression of the MSH3 gene in the cell.

In some aspects, the application is directed to a method of treating, preventing, or delaying the progression a nucleotide repeat expansion disorder (e.g., a trinucleotide repeat expansion disorder) in a subject in need thereof, the method comprising contacting the cell with one or more of the oligonucleotides or pharmaceutically acceptable salts thereof, described herein, a pharmaceutical composition of one or more of the oligonucleotides or pharmaceutically acceptable salts thereof, described herein, or the composition of one or more oligonucleotides or pharmaceutically acceptable salts thereof, described herein and a lipid nanoparticle, a polyplex nanoparticle, a lipoplex nanoparticle, or a liposome; for a time sufficient to obtain degradation of an mRNA transcript of a MSH3 gene, inhibiting expression of the MSH3 gene in the cell.

In some aspects, the application is directed to a method of reducing the level and/or activity of MSH3 in a cell of a subject identified as having a nucleotide repeat expansion disorder (e.g., a trinucleotide repeat expansion disorder), the method comprising contacting the cell with one or more of the oligonucleotides or pharmaceutically acceptable salts thereof, described herein, a pharmaceutical composition of one or more of the oligonucleotides or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome, for a time sufficient to obtain degradation of an mRNA transcript of a MSH3 gene, inhibiting expression of the MSH3 gene in the cell.

In some aspects, the application is directed to a method for inhibiting expression of an MSH3 gene in a cell comprising contacting the cell with one or more of the oligonucleotides, or pharmaceutically acceptable salts thereof, described herein, a pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome; for a time sufficient to obtain degradation of an mRNA transcript of a MSH3 gene, inhibiting expression of the MSH3 gene in the cell, and maintaining the cell for a time sufficient to obtain degradation of a mRNA transcript of an MSH3 gene, thereby inhibiting expression of the MSH3 gene in the cell.

In some aspects, the application is directed to a method of decreasing nucleotide repeat expansion (e.g., trinucleotide repeat expansion) in a cell, the method comprising contacting the cell with one or more of the oligonucleotides, or pharmaceutically acceptable salts thereof, described herein, a pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome; for a time sufficient to obtain degradation of an mRNA transcript of a MSH3 gene, inhibiting expression of the MSH3 gene in the cell.

In some aspects, the cell is in a subject. In some aspects, the subject is a human. In some aspects, the cell is a cell of the central nervous system or a muscle cell.

In some aspects, the subject is identified as having a nucleotide repeat expansion disorder (e.g., a trinucleotide repeat expansion disorder). In some aspects, the nucleotide repeat expansion disorder is spinocerebellar ataxia type 36 or frontotemporal dementia. In some aspects, the nucleotide repeat expansion disorder is a trinucleotide repeat expansion disorder. In some aspects, the trinucleotide repeat expansion disorder is a polyglutamine disease. In some aspects, the polyglutamine disease is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, and Huntington's disease-like 2. In some aspects, the nucleotide repeat expansion disorder (e.g., a trinucleotide repeat expansion disorder) is Huntington's disease.

In some aspects, the nucleotide repeat expansion disorder (e.g., a trinucleotide repeat expansion disorder) is a non-polyglutamine disease. In some aspects, the non-polyglutamine disease is selected from the group consisting of fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy. In some aspects, the nucleotide repeat expansion disorder (e.g., trinucleotide repeat expansion disorder) is Friedreich's ataxia. In some aspects, the nucleotide repeat expansion disorder (e.g., trinucleotide repeat expansion disorder) is myotonic dystrophy type 1.

In some aspects, the application is directed one or more of the oligonucleotides, or pharmaceutically acceptable salts thereof, described herein, a pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome, for use in the prevention or treatment of a nucleotide repeat expansion disorder (e.g., a trinucleotide repeat expansion disorder). In some aspects, the one or more of the oligonucleotides, or pharmaceutically acceptable salts thereof, described herein, the pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome is administered intrathecally.

In some aspects, the one or more of the oligonucleotides, or pharmaceutically acceptable salts thereof, described herein, the pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome is administered intraventricularly.

In some aspects, the one or more of the oligonucleotides, or pharmaceutically acceptable salts thereof, described herein, the pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome is administered intramuscularly.

In some aspects, the application is directed to a method of treating, preventing, or delaying progression a disorder in a subject in need thereof wherein the subject is suffering from a nucleotide repeat expansion disorder (e.g., a trinucleotide repeat expansion disorder), comprising administering to said subject one or more of the oligonucleotides, or pharmaceutically acceptable salts thereof, described herein, the pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome.

In some aspects, the method of treating, preventing, or delaying progression of a disorder in a subject further comprises administering an additional therapeutic agent. In some aspects, the additional therapeutic agent is another oligonucleotide, or pharmaceutically acceptable salt thereof, that hybridizes to an mRNA encoding the Huntingtin gene.

In some aspects, the method of treating, preventing, or delaying progression of a disorder in a subject progression delays progression of the nucleotide repeat expansion disorder (e.g., a trinucleotide repeat expansion disorder) by at least 120 days, for example, at least 6 months, at least 12 months, at least 2 years, at least 3 years, at least 4 years, at least 5 years, at least 10 years or more, when compared with a predicted progression.

In some aspects, the application is directed to one or more of the oligonucleotides, or pharmaceutically acceptable salts thereof, described herein, the pharmaceutical composition of one or more of the oligonucleotides, or pharmaceutically acceptable salts thereof, described herein, or the composition of one or more oligonucleotides, or pharmaceutically acceptable salts thereof, described herein and a lipid nanoparticle, a polyplex nanoparticle, a lipoplex nanoparticle, or a liposome for use in preventing or delaying progression of a nucleotide repeat expansion disorder (e.g., a trinucleotide repeat expansion disorder) in a subject Definitions For convenience, the meaning of some terms and phrases used in the specification, examples, and appended claims are provided below. Unless stated otherwise, or implicit from context, the following terms and phrases include the meanings provided below. The definitions are provided to aid in describing particular aspects, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

In this application, unless otherwise clear from context, (i) the term "a" can be understood to mean "at least one"; (ii) the term "or" can be understood to mean "and/or"; and (iii)

the terms "including" and "comprising" can be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5% includes 5.0%, 5.1%, and 5.18% without consideration of the number of significant figures.

As used herein, "no more than" or "less than" is understood as the value adjacent to the phrase and logical lower values or integers, as logical from context, to zero. For example, an oligonucleotide with "no more than 3 mismatches to a target sequence" has 3, 2, 1, or 0 mismatches to a target sequence. When "no more than" is present before a series of numbers or a range, it is understood that "no more than" can modify each of the numbers in the series or range.

As used herein, the term "administration" refers to the administration of a composition (e.g., a compound or a preparation that includes a compound as described herein) to a subject or system. Administration to an animal subject (e.g., to a human) can be by any appropriate route, such as one described herein.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some aspects, the delivery of the two or more agents is simultaneous or concurrent and the agents can be co-formulated. In some aspects, the two or more agents are not co-formulated and are administered in a sequential manner as part of a prescribed regimen. In some aspects, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intraocular routes, subcutaneous routes, intra cisterna *magna* routes, intravenous routes, intramuscular routes, and direct absorption through mucous membrane tissues. The therapeutic agents can be administered by the same route or by different routes. For example, one therapeutic agent of the combination can be administered by intravenous injection while an additional therapeutic agent of the combination can be administered orally.

As used herein, the term "MSH3" refers to MutS Homolog 3, a DNA mismatch repair protein, having an amino acid sequence from any vertebrate or mammalian source, including, but not limited to, human, bovine, chicken, rodent, mouse, rat, porcine, ovine, primate, monkey, and guinea pig, unless specified otherwise. The term also refers to fragments and variants of native MSH3 that maintain at least one in vivo or in vitro activity of a native MSH3. The term encompasses full-length unprocessed precursor forms of MSH3 as well as mature forms resulting from post-translational cleavage of the signal peptide. MSH3 is encoded by the MSH3 gene. The nucleic acid sequence of an exemplary *Homo sapiens* (human) MSH3 gene is set forth in NCBI Reference NM_002439.4 or in SEQ ID NO: 385. The term "MSH3" also refers to natural variants of the wild-type MSH3 protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type human MSH3, which is set forth in NCBI Reference No. NP_002430.3 or in SEQ ID NO: 386. The nucleic acid sequence of an exemplary *Mus musculus* (mouse) MSH3 gene is set forth in NCBI Reference No. NM_010829.2 or in SEQ ID NO: 387. The nucleic acid sequence of an exemplary *Rattus norvegicus* (rat) MSH3 gene is set forth in NCBI Reference No. NM_001191957.1 or in SEQ ID NO: 388. The nucleic acid sequence of an exemplary *Macaca fascicularis* (cyno) MSH3 gene is set forth in NCBI Reference No. XM_005557283.2 or in SEQ ID NO: 389.

The term "MSH3" as used herein also refers to a particular polypeptide expressed in a cell by naturally occurring DNA sequence variations of the MSH3 gene, such as a single nucleotide polymorphism in the MSH3 gene. Numerous SNPs within the MSH3 gene have been identified and can be found at, for example, NCBI dbSNP (see, e.g., www.ncbi.nlm.nih.gov/snp). Non-limiting examples of SNPs within the MSH3 gene can be found at, NCBI dbSNP Accession Nos.: rs1650697, rs70991108, rs10168, rs26279, rs26282, rs26779, rs26784, rs32989, rs33003, rs33008, rs33013, rs40139, rs181747, rs184967, rs245346, rs245397, rs249633, rs380691, rs408626, rs442767, rs836802, rs836808, rs863221, rs1105525, rs1428030, rs1478834, rs1650694, rs1650737, rs1677626, rs1677658, rs1805355, rs2897298, rs3045983, rs3797897, rs4703819, rs6151627, rs6151640, rs6151662, rs6151670, rs6151735, rs6151838, rs7709909, rs7712332, rs10079641, rs12513549, and rs12522132.

As used herein, "target sequence" refers to a contiguous portion of the nucleotide sequence of an mRNA molecule formed during the transcription of an MSH3 gene, including mRNA that is a product of RNA processing of a primary transcription product. In one aspect, the target portion of the sequence will be at least long enough to serve as a substrate for oligonucleotide-directed (e.g., antisense oligonucleotide (ASO)-directed) cleavage at or near that portion of the nucleotide sequence of an mRNA molecule formed during the transcription of a MSH3 gene. The target sequence can be, for example, from about 9-36 nucleotides in length, e.g., about 15-30 nucleotides in length. For example, the target sequence can be 15, 16, 17, 18, 19, 20, 21, 22, 23, 24, 25, 26, 27, 28, 29, or 30 or from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length.

Ranges and lengths intermediate to the above recited ranges and lengths are also contemplated.

"G," "C," "A," "T," and "U" each generally stand for a naturally-occurring nucleotide that contains guanine, cytosine, adenine, thymidine, and uracil as a base, respectively. However, it will be understood that the term "nucleotide" can refer to an alternative nucleotide, as further detailed below, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of oligonucleotides by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured herein.

The terms "nucleobase" and "base" include the purine (e.g. adenine and guanine) and pyrimidine (e.g. uracil, thymine, and cytosine) moiety present in nucleosides and nucleotides which form hydrogen bonds in nucleic acid hybridization. The term nucleobase also encompasses alternative nucleobases which can differ from naturally-occurring nucleobases, but are functional during nucleic acid hybridization. In this context, "nucleobase" refers to both naturally occurring nucleobases such as adenine, guanine, cytosine, thymidine, uracil, xanthine, and hypoxanthine, as well as alternative nucleobases. Such variants are for example described in Hirao et al (2012) Accounts of Chemical Research vol 45 page 2055 and Bergstrom (2009) Current Protocols in Nucleic Acid Chemistry Suppl. 37 1.4.1.

The term "nucleoside" refers to a monomeric unit of an oligonucleotide or a polynucleotide having a nucleobase and a sugar moiety. A nucleoside can include those that are naturally-occurring as well as alternative nucleosides, such as those described herein. The nucleobase of a nucleoside can be a naturally-occurring nucleobase or an alternative nucleobase. Similarly, the sugar moiety of a nucleoside can be a naturally-occurring sugar or an alternative sugar.

The term "alternative nucleoside" refers to a nucleoside having an alternative sugar or an alternative nucleobase, such as those described herein.

In some aspects the nucleobase moiety is modified by changing the purine or pyrimidine into a modified purine or pyrimidine, such as substituted purine or substituted pyrimidine, such as an "alternative nucleobase" selected from isocytosine, pseudoisocytosine, 5-methyl cytosine, 5-thiozolo-cytosine, 5-propynyl-cytosine, 5-propynyl-uridine, 5-bromouridine 5-thiazolo-uridine, 2-thio-uridine, pseudouridine, 1-methylpseudouridine, 5-methoxyuridine, 2'-thiothymine, inosine, diaminopurine, 6-aminopurine, 2-aminopurine, 2,6-diaminopurine, and 2-chloro-6-aminopurine.

The nucleobase moieties can be indicated by the letter code for each corresponding nucleobase, e.g. A, T, G, C, or U, wherein each letter can include alternative nucleobases of equivalent function. In some aspects, e.g., for gapmers, 5-methyl cytosine LNA nucleosides can be used.

A "sugar" or "sugar moiety," includes naturally occurring sugars having a furanose ring. A sugar also includes an "alternative sugar," defined as a structure that is capable of replacing the furanose ring of a nucleoside. In some aspects, alternative sugars are non-furanose (or 4'-substituted furanose) rings or ring systems or open systems. Such structures include simple changes relative to the natural furanose ring, such as a six-membered ring, or can be more complicated as is the case with the non-ring system used in peptide nucleic acid. Alternative sugars can include sugar surrogates wherein the furanose ring has been replaced with another ring system such as, for example, a morpholino or hexitol ring system. Sugar moieties useful in the preparation of oligonucleotides having motifs include, without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic alternative sugars (such as the 2'-O—$CH_2$-4' or 2'-O—$(CH_2)_2$-4' bridged ribose derived bicyclic sugars) and sugar surrogates (such as when the ribose ring has been replaced with a morpholino or a hexitol ring system). The type of heterocyclic base and internucleoside linkage used at each position is variable and is not a factor in determining the motif. In most nucleosides having an alternative sugar moiety, the heterocyclic nucleobase is generally maintained to permit hybridization.

A "nucleotide," as used herein, refers to a monomeric unit of an oligonucleotide or polynucleotide that comprises a nucleoside and an internucleosidic linkage. The internucleosidic linkage can include a phosphate linkage. Similarly, "linked nucleosides" can be linked by phosphate linkages. Many "alternative internucleosidic linkages" are known in the art, including, but not limited to, phosphate, phosphorothioate, and boronophosphate linkages. Alternative nucleosides include bicyclic nucleosides (BNAs) (e.g., locked nucleosides (LNAs (e.g., A-LNA, 5mC L-NA, G-LNA, T-LNA)) and constrained ethyl (cEt) nucleosides), peptide nucleosides (PNAs), phosphotriesters, phosphorothionates, phosphoramidates, and other variants of the phosphate backbone of native nucleoside, including those described herein.

An "alternative nucleotide," as used herein, refers to a nucleotide having an alternative nucleoside or an alternative sugar, and an internucleoside linkage, which can include alternative nucleoside linkages.

The terms "oligonucleotide" and "polynucleotide," as used herein, are defined as it is generally understood by the skilled person as a molecule comprising two or more covalently linked nucleosides. Such covalently bound nucleosides can be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide can be man-made. For example, the oligonucleotide can be chemically synthesized, and be purified or isolated. Oligonucleotide is also intended to include (i) compounds that have one or more furanose moieties that are replaced by furanose derivatives or by any structure, cyclic or acyclic, that can be used as a point of covalent attachment for the base moiety, (ii) compounds that have one or more phosphodiester linkages that are either modified, as in the case of phosphoramidate or phosphorothioate linkages, or completely replaced by a suitable linking moiety as in the case of formacetal or riboacetal linkages, and/or (iii) compounds that have one or more linked furanose-phosphodiester linkage moieties replaced by any structure, cyclic or acyclic, that can be used as a point of covalent attachment for the base moiety. The oligonucleotide can comprise one or more alternative nucleosides or nucleotides (e.g., including those described herein). It is also understood that oligonucleotide includes compositions lacking a sugar moiety or nucleobase but are still capable of forming a pairing with or hybridizing to a target sequence. "Oligonucleotide" refers to a short polynucleotide (e.g., of 100 or fewer linked nucleosides).

As used herein, the term "oligonucleotide comprising a nucleobase sequence" refers to an oligonucleotide comprising a chain of nucleotides or nucleosides that is described by the sequence referred to using the standard nucleotide nomenclature.

The term "contiguous nucleobase region" refers to the region of the oligonucleotide which is complementary to the target nucleic acid. The term can be used interchangeably herein with the term "contiguous nucleotide sequence" or "contiguous nucleobase sequence." In some aspects, all the nucleotides of the oligonucleotide are present in the contiguous nucleotide or nucleoside region. In some aspects, the oligonucleotide comprises the contiguous nucleotide region and can comprise further nucleotide(s) or nucleoside(s), for example a nucleotide linker region which can be used to attach a functional group to the contiguous nucleotide sequence. The nucleotide linker region can be complementary to the target nucleic acid. In some aspects, the internucleoside linkages present between the nucleotides of the contiguous nucleotide region are all phosphorothioate internucleoside linkages. In some aspects, the contiguous nucleotide region comprises one or more sugar-modified nucleosides.

The term "gapmer," as used herein, refers to an oligonucleotide which comprises a region of RNase H recruiting oligonucleotides (gap or DNA core) which is flanked 5' and 3' by regions which comprise one or more affinity enhancing alternative nucleosides (wings or flanking sequence). Various gapmer designs are described herein. Headmers and tailmers are oligonucleotides capable of recruiting RNase H where one of the flanks is missing, i.e. only one of the ends of the oligonucleotide comprises affinity enhancing alternative nucleosides. For headmers the 3' flanking sequence is missing (i.e. the 5' flanking sequence comprises affinity enhancing alternative nucleosides) and for tailmers the 5' flanking sequence is missing (i.e. the 3' flanking sequence comprises affinity enhancing alternative nucleosides). A "mixed flanking sequence gapmer" refers to a gapmer wherein the flanking sequences comprise at least one alternative nucleoside, such as at least one DNA nucleoside or at least one 2' substituted alternative nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, 2'-F-ANA nucleoside(s), or bicyclic nucleosides (e.g., locked nucleosides or constrained ethyl (cEt) nucleosides). In some aspects the mixed flanking sequence gapmer has one flanking sequence which comprises alternative nucleosides (e.g. 5' or 3') and the other flanking sequence (3' or 5' respectfully) comprises 2' substituted alternative nucleoside(s).

A "linker" or "linking group" is a connection between two atoms that links one chemical group or segment of interest to another chemical group or segment of interest via one or more covalent bonds. The oligonucleotides disclosed herein can comprise one or more linkers capable of linking one or more oligonucleotides disclosed herein to one or more other oligonucleotides disclosed herein, and/or to any other oligonucleotide, and/or to any conjugate moiety. For example, a linker could be used to link an oligonucleotide disclosed herein to an oligonucleotide that targets the Huntingtin gene.

Linkers may be susceptible to cleavage ("cleavable linker") thereby facilitating release of the different oligonucleotides and/or different conjugate moieties disclosed herein. Such cleavable linkers may be susceptible, for example, to nuclease-induced cleavage, acid-induced cleavage, photo-induced cleavage, peptidase-induced cleavage, esterase-induced cleavage, and disulfide bond cleavage, at suitable conditions. Suitable cleavable linking groups for use in cleavable linkers include those which are sufficiently stable outside the cell, but which upon entry into a target cell is cleaved to release the two parts the linker is holding together.

Alternatively, linkers may be substantially resistant to cleavage ("non-cleavable linker"). Such non-cleavable linkers can be any chemical moiety capable of linking one or more different oligonucleotides disclosed herein to one or more other oligonucleotides disclosed herein, and/or to any conjugate moiety in a stable, covalent manner and does not fall off under the categories listed above for cleavable linkers. Thus, non-cleavable linkers are substantially resistant to acid-induced cleavage, nuclease-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, a nuclease, photolabile-cleaving agent, a peptidase, an esterase, or a chemical or physiological compound that cleaves a disulfide bond, at conditions under which the oligonucleotides disclosed herein do not lose their activity or intended purpose.

Conjugate moieties can be attached to the oligonucleotide directly or through a linking moiety (e.g. linker or tether). Linkers serve to covalently connect a third region, e.g. a conjugate moiety to an oligonucleotide (e.g. the termini of region A or C). In some aspects, the conjugate or oligonucleotide conjugate can, comprise a linker region which is positioned between the oligonucleotide and the conjugate moiety. In some aspects, the linker between the conjugate and oligonucleotide is biocleavable. Phosphodiester containing biocleavable linkers are described in more detail in WO 2014/076195 (herein incorporated by reference).

In some aspects, two or more linkers can be linked in tandem. When multiple linkers connect one or more oligonucleotides disclosed herein to one or more other oligonucleotides disclosed herein, and/or to any conjugate moiety, each of the linkers can be the same or different.

As used herein, and unless otherwise indicated, the term "complementary," when used to describe a first nucleotide or nucleoside sequence in relation to a second nucleotide or nucleoside sequence, refers to the ability of an oligonucleotide or polynucleotide comprising the first nucleotide or nucleoside sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C., or 70° C., for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can be used. The skilled person will be able to determine the set of conditions most appropriate for a test of complementarity of two sequences in accordance with the ultimate application of the hybridized nucleotides or nucleosides.

"Complementary" sequences, as used herein, can include, or be formed entirely from, non-Watson-Crick base pairs and/or base pairs formed from non-natural and alternative nucleotides or nucleosides, in so far as the above requirements with respect to their ability to hybridize are fulfilled. Such non-Watson-Crick base pairs include, but are not limited to, G:U Wobble or Hoogstein base pairing. Complementary sequences between an oligonucleotide and a target sequence as described herein, include base-pairing of the oligonucleotide or polynucleotide comprising a first nucleotide or nucleoside sequence to an oligonucleotide or polynucleotide comprising a second nucleotide or nucleoside sequence over the entire length of one or both nucleotide or nucleoside sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via an RNase H-mediated pathway. "Substantially complementary" can refer to a polynucleotide that is substantially complementary to a contiguous portion of the mRNA of interest (e.g., an mRNA encoding MSH3). For example, a polynucleotide is complementary to at least a part of a MSH3 mRNA if the sequence is substantially complementary to a non-interrupted portion of an mRNA encoding MSH3.

As used herein, the term "region of complementarity" refers to the region on the oligonucleotide that is substantially complementary to all or a portion of a gene, primary transcript, a sequence (e.g., a target sequence, e.g., an MSH3 nucleotide sequence), or processed mRNA, so as to interfere with expression of the endogenous gene (e.g., MSH3). Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the oligonucleotide.

As used herein, an "agent that reduces the level and/or activity of MSH3" refers to any polynucleotide agent (e.g., an oligonucleotide, e.g., an ASO) that reduces the level of or inhibits expression of MSH3 in a cell or subject. The phrase "inhibiting expression of MSH3," as used herein, includes inhibition of expression of any MSH3 gene (such as, e.g., a mouse MSH3 gene, a rat MSH3 gene, a monkey MSH3 gene, or a human MSH3 gene) as well as variants or mutants of a MSH3 gene that encode a MSH3 protein. Thus, the MSH3 gene can be a wild-type MSH3 gene, a mutant MSH3 gene, or a transgenic MSH3 gene in the context of a genetically manipulated cell, group of cells, or organism.

By "reducing the activity of MSH3" is meant decreasing the level of an activity related to MSH3 (e.g., by reducing the amount of nucleotide repeats in a gene associated with a nucleotide repeat expansion disorder, e.g., a trinucleotide repeat expansion disorder, that is related to MSH3 activity). The activity level of MSH3 can be measured using any method known in the art (e.g., by directly sequencing a gene associated with a nucleotide repeat expansion disorder to measure the levels of nucleotide repeats).

By "reducing the level of MSH3" is meant decreasing the level of MSH3 in a cell or subject, e.g., by administering an oligonucleotide, or pharmaceutically acceptable salt thereof, to the cell or subject. The level of MSH3 can be measured using any method known in the art (e.g., by measuring the levels of MSH3 mRNA or levels of MSH3 protein in a cell or a subject).

By "modulating the activity of a MutSβ heterodimer comprising MSH3" is meant altering the level of an activity related to a MutSβ heterodimer, or a related downstream effect. The activity level of a MutSβ heterodimer can be measured using any method known in the art.

As used herein, the term "inhibitor" refers to any agent which reduces the level and/or activity of a protein (e.g., MSH3). Non-limiting examples of inhibitors include polynucleotides (e.g., oligonucleotide, e.g., ASOs). The term "inhibiting," as used herein, is used interchangeably with "reducing," "silencing," "downregulating," "suppressing," and other similar terms, and includes any level of inhibition.

The phrase "contacting a cell with an oligonucleotide," such as an oligonucleotide, as used herein, includes contacting a cell by any possible means. Contacting a cell with an oligonucleotide includes contacting a cell in vitro with the oligonucleotide or contacting a cell in vivo with the oligonucleotide. The contacting can be done directly or indirectly. Thus, for example, the oligonucleotide can be put into physical contact with the cell by the individual performing the method, or alternatively, the oligonucleotide agent can be put into a situation that will permit or cause it to subsequently come into contact with the cell.

Contacting a cell in vitro can be done, for example, by incubating the cell with the oligonucleotide. Contacting a cell in vivo can be done, for example, by injecting the oligonucleotide into or near the tissue where the cell is located, or by injecting the oligonucleotide agent into another area, e.g., the bloodstream or the subcutaneous space, such that the agent will subsequently reach the tissue where the cell to be contacted is located. For example, the oligonucleotide can contain and/or be coupled to a ligand, e.g., GalNAc3, that directs the oligonucleotide to a site of interest, e.g., the liver. Combinations of in vitro and in vivo methods of contacting are also possible. For example, a cell can be contacted in vitro with an oligonucleotide and subsequently transplanted into a subject.

In one aspect, contacting a cell with an oligonucleotide includes "introducing" or "delivering the oligonucleotide into the cell" by facilitating or effecting uptake or absorption into the cell. Absorption or uptake of an ASO can occur through unaided diffusive or active cellular processes, or by auxiliary agents or devices. Introducing an oligonucleotide into a cell can be in vitro and/or in vivo. For example, for in vivo introduction, oligonucleotides can be injected into a tissue site or administered systemically. In vitro introduction into a cell includes methods known in the art such as electroporation and lipofection. Further approaches are described herein below and/or are known in the art.

As used herein, "lipid nanoparticle" or "LNP" is a vesicle comprising a lipid layer encapsulating a pharmaceutically active molecule, such as a nucleic acid molecule, e.g., an oligonucleotide. LNP refers to a stable nucleic acid-lipid particle. LNPs typically contain a cationic lipid, a non-cationic lipid, and a lipid that prevents aggregation of the particle (e.g., a PEG-lipid conjugate). LNPs are described in, for example, U.S. Pat. Nos. 6,858,225; 6,815,432; 8,158,601; and 8,058,069, the entire contents of which are hereby incorporated herein by reference.

As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the oligonucleotide composition. The lipophilic material isolates the aqueous interior from an aqueous exterior, which typically does not include the oligonucleotide composition, although in some examples, it can. Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

The term "antisense," as used herein, refers to a nucleic acid comprising an oligonucleotide or polynucleotide that is sufficiently complementary to all or a portion of a gene, primary transcript, or processed mRNA, so as to interfere with expression of the endogenous gene (e.g., MSH3). "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides can hybridize to each other even if they are not completely complementary to each other, provided that each has at least one region that is substantially complementary to the other.

As used herein, the terms "effective amount," "therapeutically effective amount," and "a "sufficient amount" of an agent that reduces the level and/or activity of MSH3 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating a nucleotide repeat expansion disorder (e.g., a trinucleotide repeat expansion disorder), it is an amount of the agent that reduces the level and/or activity of MSH3 sufficient to achieve a treatment response as compared to the response obtained without administration of the agent that reduces the level and/or activity of MSH3. The amount of a given agent that reduces the level and/or activity of MSH3 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of MSH3 of the present disclosure is an amount which results in a beneficial or desired result in a subject as compared to a control. As defined herein, a therapeutically effective amount of an agent that reduces the level and/or activity of MSH3 of the present disclosure can be readily determined by one of ordinary skill by routine methods known in the art. Dosage regimen can be adjusted to provide the optimum therapeutic response.

"Prophylactically effective amount," as used herein, is intended to include the amount of an oligonucleotide that, when administered to a subject having or predisposed to have a nucleotide repeat expansion disorder (e.g., a trinucleotide repeat expansion disorder), is sufficient to prevent or ameliorate the disease or one or more symptoms of the disease. Ameliorating the disease includes slowing the course of the disease or reducing the severity of later-developing disease. The "prophylactically effective amount" can vary depending on the oligonucleotide, how the agent is administered, the degree of risk of disease, and the history, age, weight, family history, genetic makeup, the types of preceding or concomitant treatments, if any, and other individual characteristics of the patient to be treated. A prophylactically effective amount can refer to, for example, an amount of the agent that reduces the level and/or activity of MSH3 (e.g., in a cell or a subject) described herein or can refer to a quantity sufficient to, when administered to the subject, including a human, delay the onset of one or more of the nucleotide repeat disorders (e.g., trinucleotide repeat expansion disorders) described herein by at least 120 days, for example, at least 6 months, at least 12 months, at least 2 years, at least 3 years, at least 4 years, at least 5 years, at least 10 years or more, when compared with the predicted onset.

A "therapeutically-effective amount" or "prophylactically effective amount" also includes an amount (either administered in a single or in multiple doses) of an oligonucleotide that produces some desired local or systemic effect at a reasonable benefit/risk ratio applicable to any treatment. Oligonucleotides employed in the methods herein can be administered in a sufficient amount to produce a reasonable benefit/risk ratio applicable to such treatment.

As used herein, the term "region of complementarity" refers to the region on the oligonucleotide that is substantially complementary to all or a portion of a gene, primary transcript, a sequence (e.g., a target sequence, e.g., an MSH3 nucleotide sequence), or processed mRNA, so as to interfere with expression of the endogenous gene (e.g., MSH3). Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the oligonucleotide.

An "amount effective to reduce nucleotide repeat expansion" of a particular gene refers to an amount of the agent that reduces the level and/or activity of MSH3 (e.g., in a cell or a subject) described herein, or to a quantity sufficient to, when administered to the subject, including a human, to reduce the nucleotide repeat expansion of a particular gene (e.g., a gene associated with a nucleotide repeat expansion disorder, e.g., a trinucleotide repeat expansion disorder, described herein).

As used herein, the term "a subject identified as having a nucleotide repeat expansion disorder" refers to a subject identified as having a molecular or pathological state, disease or condition of or associated with a nucleotide repeat expansion disorder, such as the identification of a nucleotide repeat expansion disorder or symptoms thereof, or to identification of a subject having or suspected of having a nucleotide repeat expansion disorder who can benefit from a particular treatment regimen.

As used herein, "trinucleotide repeat expansion disorder" refers to a class of genetic diseases or disorders characterized by excessive trinucleotide repeats (e.g., trinucleotide repeats such as CAG) in a gene or intron in the subject which exceed the normal, stable threshold, for the gene or intron. Nucleotide repeats are common in the human genome and are not normally associated with disease. In some cases, however, the number of repeats expands beyond a stable threshold and can lead to disease, with the severity of symptoms generally correlated with the number of repeats. Nucleotide repeat expansion disorders include "polyglutamine" and "non-polyglutamine" disorders.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (MA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps (DNA core sequences), if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values can be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction $X/Y$)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

By "level" is meant a level or activity of a protein, or mRNA encoding the protein (e.g., MSH3), optionally as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than 10%, 15%, 20%, 50%, 75%, 100%, or 200%, as compared to a reference; a decrease or an increase by less than 0.01-fold, 0.02-fold, 0.1-fold, 0.3-fold, 0.5-fold, 0.8-fold, or less; or an increase by more than 1.2-fold, 1.4-fold, 1.5-fold, 1.8-fold, 2.0-fold, 3.0-fold, 3.5-fold, 4.5-fold, 5.0-fold, 10-fold, 15-fold, 20-fold, 30-fold, 40-fold, 50-fold, 100-fold, 1000-fold, or more). A level of a protein can be expressed in mass/vol (e.g., g/dL, mg/mL, μg/mL, or ng/mL) or percentage relative to total protein or mRNA in a sample.

The term "pharmaceutical composition," as used herein, represents a composition containing a compound described herein formulated with a pharmaceutically acceptable excipient, and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal injection; for intracerebroventricular injections; for intraparenchymal injection; for intraocular administration (e.g., for intravitreal or subretinal administration); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds described herein can have ionizable groups so as to be capable of preparation as pharmaceutically acceptable salts. These salts can be acid addition salts involving inorganic or organic acids or the salts can, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts can be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or mRNA levels or activity. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., a nucleotide or trinucleotide repeat expansion disorder); a subject that has been treated with a compound described herein. In some aspects, the reference sample, standard, or level is matched to the sample subject sample by at least one of the following criteria: age, weight, sex, disease stage, and overall health. A standard curve of levels of a purified protein, e.g., any described herein, within the normal reference range can be used as a reference.

As used herein, the term "subject" refers to any organism to which a composition can be administered, e.g., for experimental, diagnostic, prophylactic, and/or therapeutic purposes. Typical subjects include any animal (e.g., mammals such as mice, rats, rabbits, non-human primates, and humans). A subject can seek or be in need of treatment, require treatment, be receiving treatment, be receiving treatment in the future, or be a human or animal who is under care by a trained professional for a particular disease or condition.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein can retain or improve upon the biological activity of the original material.

The details of one or more aspects are set forth in the description below. Other features, objects, and advantages will be apparent from the description and from the claims.

DETAILED DESCRIPTION

The present inventors have found that inhibition or depletion of MSH3 level and/or activity in a cell is effective in the treatment of a nucleotide repeat expansion disorder (e.g., a trinucleotide repeat expansion disorder). Accordingly, useful compositions and methods to treat nucleotide repeat expansion disorders (e.g., a trinucleotide repeat expansion disorder), e.g., in a subject in need thereof are provided herein.

I. Nucleotide Repeat Expansion Disorders

Nucleotide repeat expansion disorders (e.g., trinucleotide repeat expansion disorders) are a family of genetic disorders characterized by the pathogenic expansion of a repeat region within a genomic region. In such disorders, the number of repeats exceeds that of a gene's normal, stable threshold, expanding into a diseased range.

Nucleotide repeat expansion disorders (e.g., trinucleotide repeat expansion disorders) generally can be categorized as "polyglutamine" or "non-polyglutamine." Polyglutamine disorders, including Huntington's disease (HD) and several spinocerebellar ataxias, are caused by a CAG (glutamine) repeats in the protein-coding regions of specific genes. Non-polyglutamine disorders are more heterogeneous and can be caused by CAG nucleotide repeat expansions in non-coding regions, as in Myotonic dystrophy, or by the expansion of nucleotide repeats other than CAG that can be in coding or non-coding regions such as the CGG repeat expansion responsible for Fragile X Syndrome.

Nucleotide repeat expansion disorders (e.g., trinucleotide repeat expansion disorders) are dynamic in the sense that the number of repeats can vary from generation-to-generation, or even from cell-to-cell in the same individual. Repeat expansion is believed to be caused by polymerase "slipping" during DNA replication. Tandem repeats in the DNA sequence can "loop out" while maintaining complementary base pairing between the parent strand and daughter strands. If the loop structure is formed from the daughter strand, the number of repeats will increase.

Conversely, if the loop structure is formed from the parent strand, the number of repeats will decrease. It appears that expansion is more common than reduction. In general, the length of repeat expansion is negatively correlated with prognosis; longer repeats are correlated with an earlier age of onset and worsened disease severity. Thus, nucleotide repeat expansion disorders (e.g., trinucleotide repeat expansion disorders) are subject to "anticipation," meaning the severity of symptoms and/or age of onset worsen through successive generations of affected families due to the expansion of these repeats from one generation to the next.

Nucleotide repeat expansion disorders (e.g., trinucleotide repeat expansion disorders) are well known in the art. For example, frontotemporal dementia (FTD) is a hexanucleotide repeat string of nucleotides GGGGCC that is repeated many more times in an individual than an individual without FTD. Additionally, an individual having spinocerebellar ataxia type 36 (SCA36) has many more GGCCTG repeats than an individual without SCA36.

Exemplary trinucleotide repeat expansion disorders and the trinucleotide repeats of the genes commonly associated with them are included in Table 1.

TABLE 1

Exemplary Trinucleotide Repeat Expansion Disorders

| Disease | Gene | Nucleotide Repeat |
|---|---|---|
| ARX-nonsyndromic X-linked mental retardation (XLMR) | ARX | GCG |
| Baratela-Scott Syndrome | XYLT1 | GGC |
| Blepharophimosis/Ptosis/Epicanthus inversus syndrome type II | FOXL2 | GCG |
| Cleidocranial dysplasia (CCD) | RUNX2 | GCG |
| Congenital central hypoventilation | PHOX-2B | GCG |
| Congenital central hypoventilation syndrome (CCHS) | PHOX2B | GCG |
| Creutzfeldt-Jakob disease | PRNP | |
| Dentatorubral-pallidoluysian atrophy (DRPLA)/Haw River syndrome | ATN1 | CAG |
| Early infantile epileptic encephalopathy (Ohtahara syndrome) | ARX | GCG |
| FRA2A syndrome | AFF3 | CGC |
| FRA7A syndrome | ZNF713 | CGG |
| Fragile X mental retardation (FRAX-E) | AFF2/FMR2 | GCC |
| Fragile X Syndrome (FXS) | FMR1 | CGG |
| Fragile X-associated Primary Ovarian Insufficiency (FXPOI) | FMR1 | CGG |
| Fragile X-associated Tremor Ataxia Syndrome (FXTAS) | FMR1 | CGG |
| Friedreich ataxia (FRDA) | FXN | GAA |
| TCF4 | | |
| Fuchs' Corneal Endothelial Dystrophy (FECD) | CTG | |
| Hand-foot genital syndrome (HFGS) | HOXA13 | GCG |
| Holoprosencephaly disorder (HPE) | ZIC2 | GCG |
| Huntington disease-like 2 (HDL2) | JPH3 | CTG |
| Huntington's Disease (HD) | HTT | CAG |
| Infantile spasm syndrome/West syndrome (ISS) | ARX | GCG |
| Jacobsen syndrome | | |
| KCNN3-associated (e.g., schizophrenia) | KCNN3 | CAG |
| Multiple Skeletal dysplasias | COMP | GAC |
| Myotonic Dystrophy type 1 (DM1) | DMPK | CTG |
| Myotonic Dystrophy type 2 (DM2) | CNBP | CCTG |
| NCOA3-associated (e.g., increased risk of prostate cancer) | NCOA3 | CAG |
| Neuronal intranuclear inclusion disease (NIID) | NOTCH2NLC | GGC |
| Oculopharyngeal Muscular Dystrophy (OPMD) | PABPN1 | GCG |
| Spastic ataxia—Charlevoix-Saguenay | | |
| Spinal Muscular Bulbar Atrophy (SMBA) | AR | CAG |
| Spinocerebellar ataxia type 1 (SCA1) | ATXN1 | CAG |
| Spinocerebellar ataxia type 10 (SCA10) | ATXN10 | ATTCT |
| Spinocerebellar ataxia type 12 (SCA12) | PPP2R2B | CAG |
| Spinocerebellar ataxia type 17 (SCA17) | TBP/ATXN17 | CAG |
| Spinocerebellar ataxia type 2 (SCA2) | ATXN2 | CAG |
| Spinocerebellar ataxia type 3 (SCA3)/ Machado-Joseph Disease | ATXN3 | CAG |
| Spinocerebellar ataxia type 45 (SCA45) | FAT2 | CAG |
| Spinocerebellar ataxia type 6 (SCA6) | CACNA1A | CAG |
| Spinocerebellar ataxia type 7 (SCA7) | ATXN7 | CAG |
| Spinocerebellar ataxia type 8 (SCA8) | ATXN8 | CTG |
| Syndromic neurodevelopmental disorder with cerebellar, ocular, craniofacial, and genital features (COFG syndrome) | MAB21L1 | CAG |
| Synpolydactyly (SPD I) | HOXD13 | GCG |
| Synpolydactyly (SPD II) | HOXD12 | GCG |

The proteins associated with nucleotide repeat expansion disorders (e.g., trinucleotide repeat expansion disorders) are typically selected based on an experimental association of the protein associated with a nucleotide repeat expansion disorder (e.g., a trinucleotide repeat expansion disorder) to a nucleotide repeat expansion disorder. For example, the production rate or circulating concentration of a protein associated with a nucleotide repeat expansion disorder (e.g., trinucleotide repeat expansion disorder) can be elevated or depressed in a population having a nucleotide repeat expansion disorder (e.g., a trinucleotide repeat expansion disorder) relative to a population lacking the nucleotide repeat expansion disorder (e.g., trinucleotide repeat expansion disorder). Differences in protein levels can be assessed using proteomic techniques including but not limited to Western blot, immunohistochemical staining, enzyme linked immunosorbent assay (ELISA), and mass spectrometry. Alternatively, the proteins associated with nucleotide repeat expansion disorders (e.g., trinucleotide repeat expansion disorders) can be identified by obtaining gene expression profiles of the genes encoding the proteins using genomic techniques including, but not limited to, DNA microarray analysis, serial analysis of gene expression (SAGE), and quantitative real-time polymerase chain reaction (qPCR).

II Evidence for the Involvement of Mismatch Repair Pathway in Nucleotide Repeat Expansion There is growing evidence that DNA repair pathways, particularly mismatch repair (MMR), are involved in the expansion of nucleotide repeats (e.g., trinucleotide repeats). A recent genome-wide association (GWA) analysis led to the identification of loci harboring genetic variations that alter the age at neurological onset of Huntington's disease (HD) (GEM-HD Consortium, Cell. 2015 Jul. 30; 162(3):516-26). The study identified MLH1, the human homolog of the *E. coli* DNA mismatch repair gene mutL. A subsequent GWA study in polyglutamine disease patients found significant association of age at onset when grouping all polyglutamine diseases (HD and SCAs) with DNA repair genes as a group, as well as significant associations for specific SNPs in FAN1 and PMS2 with the diseases (Bettencourt et al., (2016) *Ann. Neurol.,* 79: 983-990). These results were consistent with those from an earlier study comparing differences in repeat expansion in two different mouse models of Huntington's Disease, which identified Mlh1 and Mlh3 as novel critical modifiers of CAG instability (Pinto et al., (2013) Mismatch Repair Genes Mlh1 and Mlh3 Modify CAG Instability in Huntington's Disease Mice: Genome-Wide and Candidate Approaches. PLoS Genet 9(10): e1003930). Another member of the mismatch repair pathway, 8-oxo-guanine glycosylase (OGG1) has also been implicated in expansion, as somatic expansion was found to be reduced in transgenic mice lacking OGG1 (Kovtun I. V. et al. (2007) Nature 447, 447-452). However, another study found that human subjects containing a Ser326Cys polymorphism in hOGG1, which results in reduced OGG1 activity, results in increased mutant huntingtin (Coppede et al., (2009) *Toxicol.,* 278: 199-203). Likewise, complete inactivation of Fan1, another component of the DNA repair pathway, in a mouse HD model produces somatic CAG expansions (Long et al. (2018) *J. Hum Genet.,* 103: 1-9). MSH3, another component of the mismatch repair pathway, has been reported to be linked to somatic expansion: polymorphisms in Msh3 was associated with somatic instability of the expanded CTG trinucleotide repeat in myotonic dystrophy type 1 (DM1) patients (Morales et al., (2016) *DNA Repair* 40: 57-66). Furthermore, natural polymorphisms in Msh3 and Mlh1 have been revealed as mediators of mouse strain specific differences in CTG•CAG repeat instability (Pinto et al. (2013) ibid; Tome et al., (2013) *PLoS Genet.* 9 e1003280). Further evidence of Msh2 and Msh3's involvement in expansion repeats was reported in a study in which short hairpin RNA (shRNA) knockdown of either MSH2 or MSH3 slowed, and ectopic expression of either MSH2 or MSH3 induced GAA trinucleotide repeat expansion of the Friedreich Ataxia (FRDA) gene in fibroblasts derived from FRDA patients (Halabi et al., (2012) *J. Biol. Chem.* 287, 29958-29967). In spite of some inconsistent results provided above, there is strong evidence that the MMR pathway plays some role in the expansion of trinucleotide repeats in various disorders. Moreover, they are the first to recognize that the inhibition of the MMR pathway provides for the treatment or prevention of these repeat expansion disorders; however, no therapy is currently available or in development which modulates MMR for purposes of treating or preventing these repeat expansion disorders.

III. Oligonucleotide Agents

Agents described herein that reduce the level and/or activity of MSH3 in a cell can be, for example, a polynucleotide, e.g., an oligonucleotide, or pharmaceutically acceptable salt thereof. These agents reduce the level of an activity related to MSH3, or a related downstream effect, or reduce the level of MSH3 in a cell or subject.

In some aspects, the agent that reduces the level and/or activity of MSH3 is a polynucleotide. In some aspects, the polynucleotide is a single-stranded oligonucleotide, e.g., that acts by way of an RNase H-mediated pathway. Oligonucleotides include DNA and DNA/RNA chimeric molecules, typically about 10 to 30 nucleotides in length, which recognize polynucleotide target sequences or sequence portions through hydrogen bonding interactions with the nucleotide bases of the target sequence (e.g., MSH3). An oligonucleotide molecule can decrease the expression level (e.g., protein level or mRNA level) of MSH3. For example, an oligonucleotide includes oligonucleotides that targets full-length MSH3. In some aspects, the oligonucleotide molecule recruits an RNase H enzyme, leading to target mRNA degradation.

In some aspects, the oligonucleotide, or pharmaceutically acceptable salt thereof, decreases the level and/or activity of a positive regulator of function. In other aspects, the oligonucleotide, or pharmaceutically acceptable salt thereof, increases the level and/or activity of an inhibitor of a positive regulator of function. In some aspects, the oligonucleotide, or pharmaceutically acceptable salt thereof, increases the level and/or activity of a negative regulator of function.

In some aspects, the oligonucleotide, or pharmaceutically acceptable salt thereof, decreases the level and/or activity or function of MSH3. In some aspects, the oligonucleotide, or pharmaceutically acceptable salt thereof, inhibits expression of MSH3. In other aspects, the oligonucleotide, or pharmaceutically acceptable salt thereof, increases degradation of MSH3 and/or decreases the stability (i.e., half-life) of MSH3. The oligonucleotide, or pharmaceutically acceptable salt thereof, can be chemically synthesized.

An oligonucleotide, or pharmaceutically acceptable salt thereof, can be synthesized by standard methods known in the art as further discussed below, e.g., by use of an automated DNA synthesizer, such as are commercially available from, for example, Biosearch, Applied Biosystems, Inc.

The oligonucleotide, or pharmaceutically acceptable salt thereof, compound can be prepared using solution-phase or solid-phase organic synthesis or both. Organic synthesis offers the advantage that the oligonucleotide, or pharmaceutically acceptable salt thereof, comprising unnatural or alternative nucleotides can be easily prepared. A single-stranded oligonucleotide, or pharmaceutically acceptable salt thereof, can be prepared using solution-phase or solid-phase organic synthesis or both.

Some aspects of the disclosure are related to a single-stranded oligonucleotide of 15-30 linked nucleotides in length, wherein the oligonucleotide, or a portion thereof, is at least 95% complementary to at least 15 contiguous nucleobases at positions 2543-2573 of SEQ ID NO: 614, or a pharmaceutically acceptable salt thereof. In some aspects, the oligonucleotide, or a portion thereof, is at least 98% complementary to at least 15 contiguous nucleobases at positions 2543-2573 of SEQ ID NO: 614, or a pharmaceutically acceptable salt thereof. In some aspects, the oligonucleotide, or a portion thereof, is at least 99% complementary to at least 15 contiguous nucleobases at positions 2543-2573 of SEQ ID NO: 614, or a pharmaceutically acceptable salt thereof. In some aspects, the oligonucleotide, or a portion thereof, is 100% complementary to at least 15 contiguous nucleobases at positions 2543-2573 of SEQ ID NO: 614, or a pharmaceutically acceptable salt thereof. In some aspects, the oligonucleotide, or a portion thereof, is complementary to 17-23 contiguous nucleobases at positions 2543-2573 of SEQ ID NO: 614, or a pharmaceutically acceptable salt thereof. In some aspects, the oligonucleotide is complementary to 17-20 contiguous nucleobases at positions 2543-2573 of SEQ ID NO: 614, or a pharmaceutically acceptable salt thereof. In some aspects, the 17-20 contiguous nucleobases begin at position 2543, 2544, 2545, 2546, 2547, 2548, 2549, 2550, 2551, 2552, 2553, 2554, 2555, 2556, or 2557 of SEQ ID NO: 614, or a pharmaceutically acceptable salt thereof. In some aspects, the oligonucleotide is 17-20 linked nucleotides in length, or a pharmaceutically acceptable salt thereof.

In some aspects, the oligonucleotide, or a portion thereof, is complementary to 20-23 contiguous nucleobases at positions 2543-2573 of SEQ ID NO: 614, or a pharmaceutically acceptable salt thereof. In some aspects, the 20-23 contiguous nucleobases begin at position 2543, 2544, 2545, 2546, 2547, 2548, 2549, 2550, 2551, 2552, 2553, or 2554 of SEQ ID NO: 614, or a pharmaceutically acceptable salt thereof. In some aspects, the oligonucleotide is 20-23 linked nucleotides in length, or a pharmaceutically acceptable salt thereof.

In some aspects, the oligonucleotide, or a portion thereof, is complementary to positions 2543-2570 of SEQ ID NO: 614, or a pharmaceutically acceptable salt thereof.

The disclosure also relates to single-stranded oligonucleotides of 15-30 linked nucleotides in length, wherein the oligonucleotide, or a portion thereof, is at least 95% complementary to at least 15 contiguous nucleobases at positions 2685-2714 of SEQ ID NO: 614, or a pharmaceutically acceptable salt thereof. In some aspects, the oligonucleotide, or a portion thereof, is at least 98% complementary to at least 15 contiguous nucleobases at positions 2685-2714 of SEQ ID NO: 614, or a pharmaceutically acceptable salt thereof. In some aspects, the oligonucleotide, or a portion thereof, is at least 99% complementary to at least 15 contiguous nucleobases at positions 2685-2714 of SEQ ID NO: 614, or a pharmaceutically acceptable salt thereof. In some aspects, the oligonucleotide or a portion thereof, is 100% complementary to at least 15 contiguous nucleobases at positions 2685-2714 of SEQ ID NO: 614, or a pharmaceutically acceptable salt thereof. In some aspects, the oligonucleotide, or a portion thereof is complementary to 17-23 contiguous nucleobases at positions 2685-2714 of SEQ ID NO: 614, or a pharmaceutically acceptable salt thereof. In some aspects, the oligonucleotide, or a portion thereof, is complementary to 17-20 contiguous nucleobases at positions 2685-2714 of SEQ ID NO: 614, or a pharmaceutically acceptable salt thereof. In some aspects, the oligonucleotide, or a portion thereof, is complementary to 17-20 contiguous nucleobases beginning at position 2685, 2686, 2687, 2688, 2689, 2690, 2691, 2692, 2693, 2694, 2695, 2696, 2697, or 2698 of SEQ ID NO: 614, or a pharmaceutically acceptable salt thereof. In some aspects, the oligonucleotide is 17-20 linked nucleotides in length, or a pharmaceutically acceptable salt thereof.

In some aspects, the oligonucleotide, or a portion thereof, is complementary to 20-23 contiguous nucleobases at positions 2685-2714 of SEQ ID NO: 614, or a pharmaceutically acceptable salt thereof. In some aspects, the oligonucleotide is complementary to 20-23 contiguous nucleobases beginning at position 2685, 2686, 2687, 2688, 2689, 2690, 2691, 2692, 2693, 2694, or 2695 of SEQ ID NO: 614, or a pharmaceutically acceptable salt thereof. In some aspects, the oligonucleotide is 20-23 linked nucleotides in length, or a pharmaceutically acceptable salt thereof. In some aspects, the oligonucleotide, or a portion thereof, is complementary to positions 2685-2714 of SEQ ID NO: 614, or a pharmaceutically acceptable salt thereof.

In some aspects of the above, the oligonucleotide is not any one of Antisense Oligo Nos. 1, 97, 193, or 289 of Table 3. In some aspects of the above, the oligonucleotide does not have a nucleobase sequence consisting of any one of SEQ ID NOs: 1, 97, 193, or 289.

In some aspects of the above disclosures, the oligonucleotide consists of a nucleobase sequence selected from the group consisting of any of SEQ ID NOs: 1-384 and 390-613, or a pharmaceutically acceptable salt thereof. In some aspects, the oligonucleotide consists of a nucleobase sequence selected from the group consisting of any of SEQ ID NOs: 2-96, 98-192, 194-288, 290-384, and 390-613, or a pharmaceutically acceptable salt thereof. In some aspects, the oligonucleotide consists of a nucleobase sequence selected from the group consisting of any of SEQ ID NOs: 1-384, or a pharmaceutically acceptable salt thereof. In some aspects, the oligonucleotide consists of a nucleobase sequence selected from the group consisting of any of SEQ ID NOs: 2-96, 98-192, 194-288, and 290-384, or a pharmaceutically acceptable salt thereof. In some aspects, the oligonucleotide consists of a nucleobase sequence selected from the group consisting of any of SEQ ID NOs: 1-96, or a pharmaceutically acceptable salt thereof. In some aspects, the oligonucleotide consists of a nucleobase sequence selected from the group consisting of any of SEQ ID NOs: 2-96, or a pharmaceutically acceptable salt thereof. In some aspects, the oligonucleotide consists of a nucleobase sequence selected from the group consisting of any of SEQ ID NOs: 97-192, or a pharmaceutically acceptable salt thereof. In some aspects, the oligonucleotide consists of a nucleobase sequence selected from the group consisting of any of SEQ ID NOs: 98-192, or a pharmaceutically acceptable salt thereof. In some aspects, the oligonucleotide consists of a nucleobase sequence selected from the group consisting of any of SEQ ID NOs: 193-288, or a pharmaceutically acceptable salt thereof. In some aspects, the oligonucleotide consists of a nucleobase sequence selected from the group consisting of any of SEQ ID NOs: 194-288, or a pharmaceutically acceptable salt thereof. In some aspects, the oligonucleotide consists of a nucleobase sequence selected from the group consisting of any of SEQ ID NOs: 289-384, or a pharmaceutically acceptable salt thereof. In some aspects, the oligonucleotide consists of a nucleobase sequence selected from the group consisting of any of SEQ ID NOs: 288-384, or a pharmaceutically acceptable salt thereof. In some aspects, the oligonucleotide consists of a nucleobase sequence selected from the group consisting of any of SEQ ID NOs: 390-613, or a pharmaceutically acceptable salt thereof. In some aspects, the oligonucleotide consists of a nucleobase sequence selected from the group consisting of any of SEQ ID NOs: 390-480, or a pharmaceutically acceptable salt thereof. In some aspects, the oligonucleotide consists of a nucleobase sequence selected from the group consisting of any of SEQ ID NOs: 481-571, or a pharmaceutically acceptable salt thereof. In some aspects, the oligonucleotide consists of a nucleobase sequence selected from the group consisting of any of SEQ ID NOs: 572-662, or a pharmaceutically acceptable salt thereof. In some aspects, the oligonucleotide consists of a nucleobase sequence selected from the group consisting of any of SEQ ID NOs: 663-613, or a pharmaceutically acceptable salt thereof. In some aspects, the oligonucleotide consists of a nucleobase sequence selected from the group consisting of any of SEQ ID NOs: 1, 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of a nucleobase sequence selected from the group consisting of any of SEQ ID NOs: 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of a nucleobase sequence that is SEQ ID NO: 1, or a pharmaceutically acceptable salt thereof. In some aspects, the oligonucleotide consists of a nucleobase sequence that is SEQ ID NO: 6, or a pharmaceutically acceptable salt thereof. In some aspects, the oligonucleotide consists of a nucleobase sequence selected from the group consisting of any of SEQ ID NOs: 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of a nucleobase sequence selected from the group consisting of any of SEQ ID NOs: 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of a nucleobase sequence that is SEQ ID NO: 97, or a pharmaceutically acceptable salt thereof. In some aspects, the oligonucleotide consists of a nucleobase sequence selected from the group consisting of any of SEQ ID NOs: 193-200, 202-230, 232-246, 248-253, 255, 258-261, 265, 270, 274-276, or 285-286, or a pharmaceutically acceptable salt thereof. In some aspects, the oligonucleotide consists of a nucleobase sequence selected from the group consisting of any of SEQ ID NOs: 194-200, 202-230, 232-246, 248-253, 255, 258-261, 265, 270, 274-276, or 285-286, or a pharmaceutically acceptable salt thereof. In some aspects, the oligonucleotide consists of a nucleobase sequence that is SEQ ID NO: 193, or a pharmaceutically acceptable salt thereof. In some aspects, the oligonucleotide consists of a nucleobase sequence selected from the group consisting of any of SEQ ID NOs: 226-227, 234, 240, or 243-244, or a pharmaceutically acceptable salt thereof. In some aspects, the oligonucleotide consists of a nucleobase sequence selected from the group consisting of any of SEQ ID NOs: 227, 234, 240, or 243-244, or a pharmaceutically acceptable salt thereof. In some aspects, the oligonucleotide consists of the nucleobase sequence that is SEQ ID NO: 226, or a pharmaceutically acceptable salt thereof. In some aspects, the oligonucleotide consists of a nucleobase sequence selected from the group consisting of any of SEQ ID NOs: 289-290, 292, 305, 307, 313, 318, 323-324, 326, 329-330, 332, 338-339, 341, 344, or 346, or a pharmaceutically acceptable salt thereof. In some aspects, the oligonucleotide consists of a nucleobase sequence selected from the group consisting of any of SEQ ID NOs: 290, 292, 305, 307, 313, 318, 323-324, 326, 329-330, 332, 338-339, 341, 344, or 346, or a pharmaceutically acceptable salt thereof. In some aspects, the oligonucleotide consists of a nucleobase sequence that is SEQ ID NO: 289, or a pharmaceutically acceptable salt thereof.

Some aspects of the disclosure are directed to single-stranded oligonucleotides, wherein the nucleobase sequence of the oligonucleotide consists of any one of SEQ ID NOs: 1-384 and 390-613, or a pharmaceutically acceptable salt thereof. In some aspects, the nucleobase sequence of the oligonucleotide consists of any one of SEQ ID NOs: 2-96, 98-192, 194-288, 290-384, and 390-613, or a pharmaceutically acceptable salt thereof. In some aspects, the nucleobase sequence of the oligonucleotide consists of any one of SEQ ID NOs: 1-384, or a pharmaceutically acceptable salt thereof. In some aspects, the nucleobase sequence of the oligonucleotide consists of any one of SEQ ID NOs: 2-96, 98-192, 194-288, or 290-384, or a pharmaceutically acceptable salt thereof. In some aspects, the oligonucleotide consists of the nucleobase sequence of any one of SEQ ID NOs: 1-96, or a pharmaceutically acceptable salt thereof. In some aspects, the oligonucleotide consists of the nucleobase sequence of any one of SEQ ID NOs: 2-96, or a pharmaceutically acceptable salt thereof. In some aspects, the oligonucleotide consists of the nucleobase sequence of any one of SEQ ID NOs: 97-192, or a pharmaceutically acceptable salt thereof. In some aspects, the oligonucleotide consists of the nucleobase sequence of any one of SEQ ID NOs: 96-192, or a pharmaceutically acceptable salt thereof. In some aspects, the oligonucleotide consists of the nucleobase sequence of any one of SEQ ID NOs: 193-288, or a pharmaceutically acceptable salt thereof. In some aspects, the oligonucleotide consists of the nucleobase sequence of any one of SEQ ID NOs: 194-288, or a pharmaceutically acceptable salt thereof. In some aspects, the oligonucleotide consists of the nucleobase sequence of any one of SEQ ID NOs: 289-384, or a pharmaceutically acceptable salt thereof. In some aspects, the oligonucleotide consists of the nucleobase sequence of any one of SEQ ID NOs: 290-384, or a pharmaceutically acceptable salt thereof. In some aspects, the oligonucleotide consists of the nucleobase sequence of any one of SEQ ID NOs: 390-613, or a pharmaceutically acceptable salt thereof. In some aspects, the oligonucleotide consists of the nucleobase sequence of any one of SEQ ID NOs: 390-480, or a pharmaceutically acceptable salt thereof. In some aspects, the oligonucleotide consists of the nucleobase sequence of any one of SEQ ID NOs: 481-571, or a pharmaceutically acceptable salt thereof. In some aspects, the oligonucleotide consists of the nucleobase sequence of any one of SEQ ID NOs: 572-662, or a pharmaceutically acceptable salt thereof. In some aspects, the oligonucleotide consists of the nucleobase sequence of any one of SEQ ID NOs: 663-613, or a pharmaceutically acceptable salt thereof. In some aspects, the oligonucleotide consists of the nucleobase sequence of any one of SEQ ID NOs: 1, 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of the nucleobase sequence of any one of SEQ ID NOs: 6, 13, 17, 21, 24, 26, 29, 33-34, 37, 44, 49-55, 57, 60-73, 75-76, 79-82, 84-86, 88-92, or 94-96, or a pharmaceutically acceptable salt thereof. In some aspects, the oligonucleotide consists of the nucleobase sequence of SEQ ID NO: 1, or a pharmaceutically acceptable salt thereof. In some aspects, the oligonucleotide consists of the nucleobase sequence of SEQ ID NO: 6, or a pharmaceutically acceptable salt thereof. In some aspects, the oligonucleotide consists of the nucleobase sequence of any one of SEQ ID NOs: 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of the nucleobase sequence of any one of SEQ ID NOs: 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof. In some aspects, the oligonucleotide consists of the nucleobase sequence of SEQ ID NO: 97, or a pharmaceutically acceptable salt thereof. In some aspects, the oligonucleotide consists of the nucleobase sequence of any one of SEQ ID NOs: 193-200, 202-230, 232-246, 248-253, 255, 258-261, 265, 270, 274-276, or 285-286, or a pharmaceutically acceptable salt thereof. In some aspects, the oligonucleotide consists of the nucleobase sequence of any one of SEQ ID NOs: 194-200, 202-230, 232-246, 248-253, 255, 258-261, 265, 270, 274-276, or 285-286, or a pharmaceutically acceptable salt thereof. In some aspects, the oligonucleotide consists of the nucleobase sequence of any one of SEQ ID NO: 193, or a pharmaceutically acceptable salt thereof. In some aspects, the oligonucleotide consists of the nucleobase sequence of any one of SEQ ID NOs: 226-227, 234, 240, or 243-244, or a pharmaceutically acceptable salt thereof. In some aspects, the oligonucleotide consists of the nucleobase sequence of any one of SEQ ID NOs: 227, 234, 240, or 243-244, or a pharmaceutically acceptable salt thereof. In some aspects, the oligonucleotide consists of the nucleobase sequence of SEQ ID NO: 226, or a pharmaceutically acceptable salt thereof. In some aspects, the oligonucleotide consists of the nucleobase sequence of any one of SEQ ID NOs: 289-290, 292, 305, 307, 313, 318, 323-324, 326, 329-330, 332, 338-339, 341, 344, or 346, or a pharmaceutically acceptable salt thereof. In some aspects, the oligonucleotide consists of the nucleobase sequence of any one of SEQ ID NOs: 290, 292, 305, 307, 313, 318, 323-324, 326, 329-330, 332, 338-339, 341, 344, or 346, or a pharmaceutically acceptable salt thereof. In some aspects, the oligonucleotide consists of the nucleobase sequence of SEQ ID NO: 289, or a pharmaceutically acceptable salt thereof.

Some aspects of the disclosure are directed to nn oligonucleotide selected from the group consisting of Antisense Oligo Nos. 1-384 of Table 3 or 390-613 of Table 4, or a pharmaceutically acceptable salt thereof. In some aspects, the oligonucleotide is selected from the group consisting of Antisense Oligo Nos. 2-96, 98-192, 194-288, 290-384 of Table 3 and 390-613 of Table 4, or a pharmaceutically acceptable salt thereof. In some aspects, the oligonucleotide is selected from the group consisting of Antisense Oligo Nos. 1-384 of Table 3, or a pharmaceutically acceptable salt thereof. In some aspects, the oligonucleotide is selected from the group consisting of Antisense Oligo Nos. 2-96, 98-192, 194-288, and 290-384 of Table 3, or a pharmaceutically acceptable salt thereof. In some aspects, the oligonucleotide is selected from the group consisting of Antisense Oligo Nos. 1-96 of Table 3, or a pharmaceutically acceptable salt thereof. In some aspects, the oligonucleotide is selected from the group consisting of Antisense Oligo Nos. 2-96 of Table 3, or a pharmaceutically acceptable salt thereof. In some aspects, the oligonucleotide is selected from the group consisting of Antisense Oligo Nos. 97-192 of Table 3, or a pharmaceutically acceptable salt thereof. In some aspects, the oligonucleotide is selected from the group consisting of Antisense Oligo Nos. 98-192 of Table 3, or a pharmaceutically acceptable salt thereof. In some aspects, the oligonucleotide is selected from the group consisting of Antisense Oligo Nos. 193-288 of Table 3, or a pharmaceutically acceptable salt thereof. In some aspects, the oligonucleotide is selected from the group consisting of Antisense Oligo Nos. 194-288 of Table 3, or a pharmaceutically acceptable salt thereof. In some aspects, the oligonucleotide is selected from the group consisting of Antisense Oligo Nos. 289-384 of Table 3, or a pharmaceutically acceptable salt thereof. In some aspects, the oligonucleotide is selected from the group consisting of Antisense Oligo Nos. 290-384 of Table 3, or a pharmaceutically acceptable salt thereof. In some aspects, the oligonucleotide is selected from the group consisting of Antisense Oligo Nos. 390-613 of Table 4, or a pharmaceutically acceptable salt thereof. In some aspects, the oligonucleotide is selected from the group consisting of Antisense Oligo Nos. 390-480 of Table 4, or a pharmaceutically acceptable salt thereof. In some aspects, the oligonucleotide is selected from the group consisting of Antisense Oligo Nos. 481-571 of Table 4, or a pharmaceutically acceptable salt thereof. In some aspects, the oligonucleotide is selected from the group consisting of Antisense Oligo Nos. 1, 6, 13, 17, 21, 24, 26, 29, 33-34, 37, 44, 49-55, 57, 60-73, 75-76, 79-82, 84-86, 88-92, or 94-96 of Table 3, or a pharmaceutically acceptable salt thereof. In some aspects, the oligonucleotide is selected from the group consisting of Antisense Oligo Nos. 6, 13, 17, 21, 24, 26, 29, 33-34, 37, 44, 49-55, 57, 60-73, 75-76, 79-82, 84-86, 88-92, or 94-96 of Table 3, or a pharmaceutically acceptable salt thereof. In some aspects, the oligonucleotide is Antisense Oligo No. 1 of Table 3, or a pharmaceutically acceptable salt thereof. In some aspects, the oligonucleotide is Antisense Oligo No. 6 of Table 3, or a pharmaceutically acceptable salt thereof. In some aspects, the oligonucleotide is selected from the group consisting of Antisense Oligo Nos. 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191 of Table 3, or a pharmaceutically acceptable salt thereof. In some aspects, the oligonucleotide is selected from the group consisting of Antisense Oligo Nos. 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191 of Table 3, or a pharmaceutically acceptable salt thereof. In some aspects, the oligonucleotide is Antisense Oligo No. 97 of Table 3, or a pharmaceutically acceptable salt thereof. In some aspects, the oligonucleotide is selected from the group consisting of Antisense Oligo Nos. 193-200, 202-230, 232-246, 248-253, 255, 258-261, 265, 270, 274-276, or 285-286 of Table 3, or a pharmaceutically acceptable salt thereof. In some aspects, the oligonucleotide is selected from the group consisting of Antisense Oligo Nos. 194-200, 202-230, 232-246, 248-253, 255, 258-261, 265, 270, 274-276, or 285-286 of Table 3, or a pharmaceutically acceptable salt thereof. In some aspects, the oligonucleotide is Antisense Oligo No. 193 of Table 3. In some aspects, the oligonucleotide is selected from the group consisting of Antisense Oligo Nos. 226-227, 234, 240, or 243-244 of Table 3, or a pharmaceutically acceptable salt thereof. In some aspects, the oligonucleotide is selected from the group consisting of Antisense Oligo Nos. 227, 234, 240, or 243-244 of Table 3, or a pharmaceutically acceptable salt thereof. In some aspects, the oligonucleotide is Antisense Oligo No. 226 of Table 3, or a pharmaceutically acceptable salt thereof. In some aspects, the oligonucleotide is selected from the group consisting of Antisense Oligo Nos. 289-290, 292, 305, 307, 313, 318, 323-324, 326, 329-330, 332, 338-339, 341, 344, or 346 of Table 3, or a pharmaceutically acceptable salt thereof. In some aspects, the oligonucleotide is selected from the group consisting of Antisense Oligo Nos. 290, 292, 305, 307, 313, 318, 323-324, 326, 329-330, 332, 338-339, 341, 344, or 346 of Table 3, or a pharmaceutically acceptable salt thereof. In some aspects, the oligonucleotide is Antisense Oligo No. 289 of Table 3, or a pharmaceutically acceptable salt thereof.

In some aspects, the oligonucleotide, or a pharmaceutically acceptable salt thereof, described herein causes at least a 50% reduction in MSH3 mRNA expression at an oligonucleotide concentration of 10 nM. In some aspects, the oligonucleotide, or a pharmaceutically acceptable salt thereof, described herein causes at least a 60% reduction in MSH3 mRNA expression at an oligonucleotide concentration of 10 nM. In some aspects, the oligonucleotide, or a pharmaceutically acceptable salt thereof, described herein causes at least a 70% reduction in MSH3 mRNA expression at an oligonucleotide concentration of 10 nM. In some aspects, the oligonucleotide, or a pharmaceutically acceptable salt thereof, described herein causes at least an 80% reduction in MSH3 mRNA expression at an oligonucleotide concentration of 10 nM.

In some aspects, the oligonucleotide, or a pharmaceutically acceptable salt thereof, described herein causes at least a 50% reduction in MSH3 mRNA expression at an oligonucleotide concentration of 1 nM. In some aspects, the oligonucleotide, or a pharmaceutically acceptable salt thereof, described herein causes at least a 60% reduction in MSH3 mRNA expression at an oligonucleotide concentration of 1 nM. In some aspects, the oligonucleotide, or a pharmaceutically acceptable salt thereof, described herein causes at least a 70% reduction in MSH3 mRNA expression at an oligonucleotide concentration of 1 nM.

The cell assay can comprise transfecting mammalian cells, such as HEK293, NIH3T3, or HeLa cells, with the desired a concentration of oligonucleotide (e.g., 1 nM or 10 nM) using Lipofectamine 2000 (Invitrogen) and comparing MSH3 mRNA levels of transfected cells to MSH3 levels of control cells. Control cells can be transfected with oligonucleotides not specific to MSH3 or mock transfected. mRNA levels can be determined using RT-qPCR and MSH3 mRNA levels can be normalized to GAPDH mRNA levels. The percent inhibition can be calculated as the percent of MSH3 mRNA concentration relative to the MSH3 concentration of the control cells.

In some aspects, the MSH3 mRNA expression is evaluated in vitro. In some aspects, the MSH3 mRNA expression is evaluated in a cell based assay. In some aspects, the MSH3 mRNA expression is evaluated in HeLa cells. In some aspects, the MSH3 mRNA expression is determined by the quantitative reverse transcription polymerase chain reaction (RT-qPCR). In some aspects, the MSH3 mRNA is expression is normalized to the mRNA expression of a reference gene. In some aspects, the MSH3 mRNA expression is normalized to the mRNA expression of beta-glucuronidase (GUSB). In some aspects, the reduction in MSH3 mRNA expression is relative to a control. In some aspects, the control is the MSH3 mRNA expression in the absence of the oligonucleotide, or pharmaceutically acceptable salt thereof. In some aspects, the control is the MSH3 mRNA expression in the absence of the oligonucleotide, or pharmaceutically acceptable salt thereof, but in the presence of a control oligonucleotide, or salt thereof. In some aspects, the control oligonucleotide, or salt thereof, is a scrambled luciferase targeting oligonucleotide. In some aspects, the reduction in MSH3 mRNA expression is calculated by a delta-delta Ct (ΔΔCT) method. In some aspects, the delta-delta Ct (ΔΔCT) method comprises the normalization of the MSH3 mRNA expression to the mRNA expression of a reference gene and to the MSH3 mRNA expression in the absence of the oligonucleotide, or pharmaceutically acceptable salt thereof but in the presence of a control oligonucleotide, or salt thereof. In some aspects, the reference gene is beta-glucuronidase (GUSB) and/or the control oligonucleotide, or salt thereof, is a scrambled luciferase targeting oligonucleotide. In some aspects, the reduction in MSH3 mRNA expression is determined by the method of Example 1. In some aspects, in the same assay, Antisense Oligo No. 1 causes approximately a 58% reduction in MSH3 mRNA expression at an oligonucleotide concentration of 10 nM. In some aspects, in the same assay, Antisense Oligo No. 1 causes approximately a 14% reduction in MSH3 mRNA expression at an oligonucleotide concentration of 1 nM.

In some aspects, the oligonucleotide, or contiguous nucleotide region thereof, has a gapmer design or structure also referred herein merely as "gapmer." In a gapmer structure the oligonucleotide comprises at least three distinct structural regions a 5'-flanking sequence (also known as a 5'-wing), a DNA core sequence (also known as a gap) and a 3'-flanking sequence (also known as a 3'-wing), in '5→3' orientation. In this design, the 5' and 3' flanking sequences comprise at least one alternative nucleoside which is adjacent to a DNA core sequence, and can, in some aspects, comprise a contiguous stretch of 2-7 alternative nucleosides, or a contiguous stretch of alternative and DNA nucleosides (mixed flanking sequences comprising both alternative and DNA nucleosides).

The length of the 5'-flanking sequence region can be at least two nucleosides in length (e.g., at least at least 2, at least 3, at least 4, at least 5, at least 6, or more nucleosides in length). The length of the 3'-flanking sequence region can be at least two nucleosides in length (e.g., at least 2, at least 3, at least at least 4, at least 5, at least 6, or more nucleosides in length). The 5' and 3' flanking sequences can be symmetrical or asymmetrical with respect to the number of nucleosides they comprise. In some aspects, the DNA core sequence comprises about 10 nucleosides flanked by a 5' and a 3' flanking sequence each comprising about 5 nucleosides. In some aspects, the DNA core sequence comprises about 11 nucleosides flanked by a 5' and a 3' flanking sequence each comprising about 5 or about 6 nucleosides. In some aspects, the DNA core sequence comprises about 12 nucleosides flanked by a 5' sequence comprising about 5 nucleosides, and a 3' flanking sequence comprising about 6 nucleosides. In some aspects, the DNA core sequence comprises about 12 nucleosides flanked by a 5' sequence comprising about 6 nucleosides, and a 3' flanking sequence comprising about 5 nucleosides. In some aspects, the DNA core sequence comprises about 12 nucleosides flanked by a 5' and a 3' flanking sequence each comprising about 6 nucleosides.

Consequently, the nucleosides of the 5' flanking sequence and the 3' flanking sequence which are adjacent to the DNA core sequence are alternative nucleosides, such as 2' alternative nucleosides. The DNA core sequence comprises a contiguous stretch of nucleotides which are capable of recruiting RNase H, when the oligonucleotide is in duplex with the MSH3 target nucleic acid. In some aspects, the DNA core sequence comprises a contiguous stretch of 5-16 DNA nucleosides. In other aspects, the DNA core sequence comprises a region of at least 10 contiguous nucleobases having at least 80% (e.g., at least 85%, at least 90%, at least 95%, or at least 99%) complementarity to an MSH3 gene. In some aspects, the gapmer comprises a region complementary to at least 17 contiguous nucleotides, 19-23 contiguous nucleotides, or 19 contiguous nucleotides of a MSH3 gene. The gapmer is complementary to the MSH3 target nucleic acid, and can therefore be the contiguous nucleoside region of the oligonucleotide. In some aspects, the gapmer comprises a region complementary to at least 21 contiguous nucleotides, 20-25 contiguous nucleotides, or 23 contiguous nucleotides of a MSH3 gene. The gapmer is complementary to the MSH3 target nucleic acid, and can therefore be the contiguous nucleoside region of the oligonucleotide.

The 5' and 3' flanking sequences, flanking the 5' and 3' ends of the DNA core sequence, can comprise one or more affinity enhancing alternative nucleosides. In some aspects, the 5' and/or 3' flanking sequence comprises at least one 2'-O-methoxyethyl (MOE) nucleoside. In some aspects, the 5' and/or 3' flanking sequences, contain at least two MOE nucleosides. In some aspects, the 5' flanking sequence comprises at least one, at least two, at least three, at least four, at least five, or at least six or more MOE nucleosides. In some aspects, the 5' flanking sequence comprises at least one, at least two, at least three, at least four, at least five, or at least six or more MOE nucleosides. In some aspects, both the 5' and 3' flanking sequence comprise a MOE nucleoside. In some aspects, all the nucleosides in the flanking sequences are MOE nucleosides. In other aspects, the flanking sequence can comprise both MOE nucleosides and other nucleosides (mixed flanking sequence), such as DNA nucleosides and/or non-MOE alternative nucleosides, such as bicyclic nucleosides (BNAs) (e.g., LNA nucleosides (e.g., A-LNA, 5mC L-NA, G-LNA, T-LNA) or cET nucleosides), or other 2' substituted nucleosides. In this case the DNA core sequence is defined as a contiguous sequence of at least 5 RNase H recruiting nucleosides (such as 5-16 DNA nucleosides) flanked at the 5' and 3' end by an affinity enhancing alternative nucleoside, such as an MOE nucleoside.

In other aspects, the 5' and/or 3' flanking sequence comprises at least one BNA (e.g., at least one LNA nucleoside (e.g., A-LNA, 5mC L-NA, G-LNA, T-LNA) or cET nucleoside). In some aspects, 5' and/or 3' flanking sequence comprises at least 2 bicyclic nucleosides. In some aspects, the 5' flanking sequence comprises at least one BNA. In some aspects, both the 5' and 3' flanking sequence comprise a BNA. In some aspects, all the nucleosides in the flanking sequences are BNAs. In other aspects, the flanking sequence can comprise both BNAs and other nucleosides (mixed flanking sequences), such as DNA nucleosides and/or non-BNA alternative nucleosides, such as 2' substituted nucleosides. In this case the DNA core sequence is defined as a contiguous sequence of at least five RNase H recruiting nucleosides (such as 5-16 DNA nucleosides) flanked at the 5' and 3' end by an affinity enhancing alternative nucleoside, such as a BNA, such as an LNA, such as beta-D-oxy-LNA.

The 5' flank attached to the 5' end of the DNA core sequence comprises, contains, or consists of at least one alternative sugar moiety (e.g., at least three, at least four, at least five, at least six, at least seven, or more alternative sugar moieties). In some aspects, the flanking sequence comprises or consists of from 1 to 7 alternative nucleobases, such as from 2 to 6 alternative nucleobases, such as from 2 to 5 alternative nucleobases, such as from 2 to 4 alternative nucleobases, such as from 1 to 3 alternative nucleobases, such as one, two, three or four alternative nucleobases. In some aspects, the flanking sequence comprises or consists of at least one alternative internucleoside linkage (e.g., at least three, at least four, at least five, at least six, at least seven, or more alternative internucleoside linkages).

The 3' flank attached to the 3' end of the DNA core sequence comprises, contains, or consists of at least one alternative sugar moiety (e.g., at least three, at least four, at least five, at least six, at least seven, or more alternative sugar moieties). In some aspects, the flanking sequence comprises or consists of from 1 to 7 alternative nucleobases, such as from 2 to 6 alternative nucleobases, such as from 2 to 5 alternative nucleobases, such as from 2 to 4 alternative nucleobases, such as from 1 to 3 alternative nucleobases, such as one, two, three, or four alternative nucleobases. In some aspects, the flanking sequence comprises or consists of at least one alternative internucleoside linkage (e.g., at least three, at least four, at least five, at least six, at least seven, or more alternative internucleoside linkages).

In an aspect, one or more or all of the alternative sugar moieties in the flanking sequence are 2' alternative sugar moieties.

In a further aspect, one or more of the 2' alternative sugar moieties in the wing regions are selected from 2'-O-alkyl-sugar moieties, 2'-O-methyl-sugar moieties, 2'-amino-sugar moieties, 2'-fluoro-sugar moieties, 2'-alkoxy-sugar moieties, MOE sugar moieties, LNA sugar moieties, arabino nucleic acid (ANA) sugar moieties, and 2'-fluoro-ANA sugar moieties.

In one aspect, all the alternative nucleosides in the flanking sequences are bicyclic nucleosides. In a further aspect, the bicyclic nucleosides in the flanking sequences are independently selected from the group consisting of oxy-LNA, thio-LNA, amino-LNA, cET, and/or ENA, in either the beta-D or alpha-L configurations or combinations thereof.

In some aspects, the one or more alternative internucleoside linkages in the flanking sequences are phosphorothioate internucleoside linkages. In some aspects, the phosphorothioate linkages are stereochemically pure phosphorothioate linkages. In some aspects, the phosphorothioate linkages are Sp phosphorothioate linkages. In other aspects, the phosphorothioate linkages are Rp phosphorothioate linkages. In some aspects, the alternative internucleoside linkages are 2'-alkoxy internucleoside linkages. In other aspects, the alternative internucleoside linkages are alkyl phosphate internucleoside linkages.

The DNA core sequence can comprise, contain, or consist of at least 5-16 consecutive DNA nucleosides capable of recruiting RNase H. In some aspects, all of the nucleosides of the DNA core sequence are DNA units. In further aspects, the DNA core region can consist of a mixture of DNA and other nucleosides capable of mediating RNase H cleavage. In some aspects, at least 50% of the nucleosides of the DNA core sequence are DNA, such as at least 60%, at least 70% or at least 80%, or at least 90% DNA. In some aspects, all of the nucleosides of the DNA core sequence are RNA units.

The oligonucleotide comprises a contiguous region which is complementary to the target nucleic acid. In some aspects, the oligonucleotide can further comprise additional linked nucleosides positioned 5' and/or 3' to either the 5' and 3' flanking sequences. These additional linked nucleosides can be attached to the 5' end of the 5' flanking sequence or the 3' end of the 3' flanking sequence, respectively. The additional nucleosides can, in some aspects, form part of the contiguous sequence which is complementary to the target nucleic acid, or in other aspects, can be non-complementary to the target nucleic acid.

The inclusion of the additional nucleosides at either, or both of the 5' and 3' flanking sequences can independently comprise one, two, three, four, or five additional nucleotides, which can be complementary or non-complementary to the target nucleic acid. In this respect the oligonucleotide, can in some aspects comprise a contiguous sequence capable of modulating the target which is flanked at the 5' and/or 3' end by additional nucleotides. Such additional nucleosides can serve as a nuclease susceptible biocleavable linker, and can therefore be used to attach a functional group such as a conjugate moiety to the oligonucleotide. In some aspects, the additional 5' and/or 3' end nucleosides are linked with phosphodiester linkages, and can be DNA or RNA. In another aspect, the additional 5' and/or 3' end nucleosides are alternative nucleosides which can for example be included to enhance nuclease stability or for ease of synthesis.

In other aspects, the oligonucleotides utilize "altimer" design and comprise alternating 2'-fluoro-ANA and DNA regions that are alternated every three nucleosides. Altimer oligonucleotides are discussed in more detail in Min, et al., Bioorganic & Medicinal Chemistry Letters, 2002, 12(18): 2651-2654 and Kalota, et al., Nuc. Acid Res. 2006, 34(2): 451-61 (herein incorporated by reference).

In other aspects, the oligonucleotides utilize "hemimer" design and comprise a single 2'-modified flanking sequence adjacent to (on either side of the 5' or the 3' side of) a DNA core sequence. Hemimer oligonucleotides are discussed in more detail in Geary et al., 2001, J. Pharm. Exp. Therap., 296: 898-904 (herein incorporated by reference).

In some aspects, an oligonucleotide has a nucleic acid sequence with at least 50% (e.g., at least 50%, at least 60%, at least 70%, at least 80%, at least 85%, at least 90%, at least 95%, at least 96%, at least 97%, at least 98%, at least 99%, or 100%) sequence identity to the nucleic acid sequence of any one of SEQ ID NOs: 1-384 and 390-613. In some aspects, an oligonucleotide has a nucleic acid sequence with at least 85% sequence identity to the nucleic acid sequence of any one of SEQ ID NOs: 1-384 and 390-613.

It will be understood that the nucleosides of the oligonucleotide e.g., an oligonucleotide, can comprise any one of the sequences set forth in any one of SEQ ID NOs: 1-384 that is an alternative nucleoside and/or conjugated or linked as described in detail below.

In some aspects, the oligonucleotide is an oligonucleotide having at least 15 contiguous bases of the nucleobase sequence selected from the group consisting of Antisense Oligo Nos. 1-384 of Table 3 or 390-613 of Table 4. In some aspects, the oligonucleotide is an oligonucleotide having at least 15 contiguous bases of the nucleobase sequence selected from the group consisting of Antisense Oligo Nos. 1-384 of Table 3. In some aspects, the oligonucleotide is an oligonucleotide having at least 15 contiguous bases of the nucleobase sequence selected from the group consisting one of Antisense Oligo Nos. 1-96 of Table 3. In some aspects, the oligonucleotide is an oligonucleotide having at least 15 contiguous bases of the nucleobase sequence selected from the group consisting of Antisense Oligo Nos. 97-192 of Table 3. In some aspects, the oligonucleotide is an oligonucleotide having at least 15 contiguous bases of the nucleobase sequence selected from the group consisting of Antisense Oligo Nos. 193-288 of Table 3. In some aspects, the oligonucleotide is an oligonucleotide having at least 15 contiguous bases of the nucleobase sequence selected from the group consisting of Antisense Oligo Nos. 289-384 of Table 3. In some aspects, the oligonucleotide is an oligonucleotide having at least 15 contiguous bases of the nucleobase sequence selected from the group consisting of Antisense Oligo Nos. 390-613 of Table 4. In some aspects, the oligonucleotide is an oligonucleotide having at least 15 contiguous bases of the nucleobase sequence selected from the group consisting of Antisense Oligo Nos. 390-480 of Table 4. In some aspects, the oligonucleotide is an oligonucleotide having at least 15 contiguous bases of the nucleobase sequence selected from the group consisting of Antisense Oligo Nos. 481-501 of Table 4. In some aspects, the oligonucleotide is an oligonucleotide having at least 15 contiguous bases of the nucleobase sequence selected from the group consisting of Antisense Oligo Nos. 502-592 of Table 4. In some aspects, the oligonucleotide is an oligonucleotide having at least 15 contiguous bases of the nucleobase sequence selected from the group consisting of Antisense Oligo Nos. 593-613 of Table 4.

In some aspects, the oligonucleotide is an oligonucleotide having at least 15 contiguous bases of the nucleobase sequence selected from the group consisting of Antisense Oligo Nos. 1, 6, 13, 17, 21, 24, 26, 29, 33-34, 37, 44, 49-55, 57, 60-73, 75-76, 79-82, 84-86, 88-92, or 94-96 of Table 3. In some aspects, the oligonucleotide an oligonucleotide having at least 15 contiguous bases of the nucleobase sequence of Antisense Oligo No. 6 of Table 3.

In some aspects, the oligonucleotide is an oligonucleotide having at least 15 contiguous bases of the nucleobase sequence selected from the group consisting of Antisense Oligo Nos. 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191 of Table 3.

In some aspects, the oligonucleotide is an oligonucleotide having at least 15 contiguous bases of the nucleobase sequence selected from the group consisting of Antisense Oligo Nos. 193-200, 202-230, 232-246, 248-253, 255, 258-261, 265, 270, 274-276, or 285-286 of Table 3. In some aspects, the oligonucleotide is an oligonucleotide having at least 15 contiguous bases of the nucleobase sequence selected from the group consisting of Antisense Oligo Nos. 226-227, 234, 240, or 243-244 of Table 3.

In some aspects, the oligonucleotide is an oligonucleotide having at least 15 contiguous bases of the nucleobase sequence selected from the group consisting of Antisense Oligo Nos. 289-290, 292, 305, 307, 313, 318, 323-324, 326, 329-330, 332, 338-339, 341, 344, or 346 of Table 3.

An oligonucleotide agent as described herein can contain one or more mismatches to the target sequence. In one aspect, an oligonucleotide as described herein contains no more than 3 mismatches. If the oligonucleotide contains mismatches to a target sequence, in some aspects, the area of mismatch is not located in the center of the region of complementarity. If the oligonucleotide contains mismatches to the target sequence, in some aspects, the mismatch should be restricted to be within the last 5 nucleotides from either the 5'- or 3'-end of the region of complementarity. For example, for a 30-linked nucleoside oligonucleotide agent, the contiguous nucleobase region which is complementary to a region of a MSH3 gene, generally does not contain any mismatch within the central 5-10 linked nucleosides. The methods described herein or methods known in the art can be used to determine whether an oligonucleotide containing a mismatch to a target sequence is effective in inhibiting the expression of a MSH3 gene. Consideration of the efficacy of oligonucleotides with mismatches in inhibiting expression of a MSH3 gene is important, especially if the particular region of complementarity in a MSH3 gene is known to have polymorphic sequence variation within the population.

Construction of vectors for expression of polynucleotides can be accomplished using conventional techniques which do not require detailed explanation to one of ordinary skill in the art. For generation of efficient expression vectors, it is necessary to have regulatory sequences that control the expression of the polynucleotide. These regulatory sequences include promoter and enhancer sequences and are influenced by specific cellular factors that interact with these sequences, and are well known in the art.

A. Alternative Oligonucleosides

In one aspect, one or more of the linked nucleosides or internucleosidic linkages of the oligonucleotide, is naturally occurring, and does not comprise, e.g., chemical modifications and/or conjugations known in the art and described herein. In another aspect, one or more of the linked nucleosides or internucleosidic linkages of an oligonucleotide, is chemically modified to enhance stability or other beneficial characteristics. Without being bound by theory, it is believed that certain modifications can increase nuclease resistance and/or serum stability, or decrease immunogenicity. For example, oligonucleotides can contain nucleotides found to occur naturally in DNA or RNA (e.g., adenine, thymidine, guanosine, cytidine, uridine, or inosine) or can contain alternative nucleosides or internucleosidic linkages which have one or more chemical modifications to one or more components of the nucleotide (e.g., the nucleobase, sugar, or phospho-linker moiety). Oligonucleotides can be linked to one another through naturally occurring phosphodiester bonds, or can contain alternative linkages (e.g., covalently linked through phosphorothioate (e.g., Sp phosphorothioate or Rp phosphorothioate), 3'-methylenephosphonate, 5'-methylenephosphonate, 3'-phosphoamidate, 2'-5' phosphodiester, guanidinium, S-methylthiourea, 2'-alkoxy, alkyl phosphate, or peptide bonds).

In some aspects, substantially all of the nucleosides or internucleosidic linkages of an oligonucleotide are alternative nucleosides. In other aspects, all of the nucleosides or internucleosidic linkages of an oligonucleotide are alternative nucleosides. Oligonucleotides in which "substantially all of the nucleosides are alternative nucleosides" are largely but not wholly modified and can include not more than five, four, three, two, or one naturally-occurring nucleosides. In still other aspects, oligonucleotides can include not more than five, four, three, two, or one alternative nucleosides.

The nucleic acids can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Alternative nucleotides and nucleosides include those with modifications including, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. The nucleobase can be an iso-nucleoside in which the nucleobase is moved from the C1 position of the sugar moiety to a different position (e.g. C2, C3, C4, or C5). Specific examples of oligonucleotide compounds useful in the aspects described herein include, but are not limited to alternative nucleosides containing modified backbones or no natural internucleoside linkages. Nucleotides and nucleosides having modified backbones include, among others, those that do not have a phosphorus atom in the backbone. For the purposes of this specification, and as sometimes referenced in the art, alternative RNAs that do not have a phosphorus atom in their internucleoside backbone can be considered to be oligonucleosides. In some aspects, an oligonucleotide will have a phosphorus atom in its internucleoside backbone.

Alternative internucleoside linkages include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boronophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts, and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Alternative internucleoside linkages that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other aspects, suitable oligonucleotides include those in which both the sugar and the internucleoside linkage, i.e., the backbone, of the nucleotide units are replaced. The base units are maintained for hybridization with an appropriate nucleic acid target compound. One such oligomeric compound, a mimetic that has been shown to have excellent hybridization properties, is referred to as a peptide nucleic acid (PNA). In PNA compounds, the sugar of a nucleoside is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the oligonucleotides are described in, for example, in Nielsen et al., Science, 1991, 254, 1497-1500.

Some aspects include oligonucleotides with phosphorothioate backbones and oligonucleotides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$-[wherein the native phosphodiester backbone is represented as —O—P—O—$CH_2$-] of the above-referenced U.S. Pat. No. 5,489,677, and the amide backbones of the above-referenced U.S. Pat. No. 5,602,240. In some aspects, the oligonucleotides featured herein have morpholino backbone structures of the above-referenced U.S. Pat. No. 5,034,506. In other aspects, the oligonucleotides described herein include phosphorodiamidate morpholino oligomers (PMO), in which the deoxyribose moiety is replaced by a morpholine ring, and the charged phosphodiester inter-subunit linkage is replaced by an uncharged phophorodiamidate linkage, as described in Summerton, et al., Antisense Nucleic Acid Drug Dev. 1997, 7:63-70.

Alternative nucleosides and nucleotides can contain one or more substituted sugar moieties. The oligonucleotides, e.g., oligonucleotides, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $—O[(CH_2)_nO]_mCH_3$, $—O(CH_2)_nOCH_3$, $—O(CH_2)_n—NH_2$, $—O(CH_2)_nCH_3$, $—O(CH_2)_n—ONH_2$, and $—O(CH_2)_n—ON[(CH_2)_nCH_3]_2$, where n and m are from 1 to about 10. In other aspects, oligonucleotides include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In some aspects, the modification includes a 2'-methoxyethoxy (2'-O—$CH_2CH_2OCH_3$, also known as 2'-O-(2-methoxyethyl) or 2'-MOE) (Martin et al., Helv. Chin. Acta, 1995, 78:486-504) i.e., an alkoxy-alkoxy group. MOE nucleosides confer several beneficial properties to oligonucleotides including, but not limited to, increased nuclease resistance, improved pharmacokinetics properties, reduced non-specific protein binding, reduced toxicity, reduced immunostimulatory properties, and enhanced target affinity as compared to unmodified oligonucleotides.

Another exemplary alternative contains 2'-dimethylaminooxyethoxy, i.e., a $—O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$(CH_2)_2$—O—$(CH_2)_2$—$N(CH_3)_2$. Further exemplary alternatives include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other alternatives include 2'-methoxy (2'-$OCH_3$), 2'-aminopropoxy (2'-$OCH_2CH_2CH_2NH_2$) and 2'-fluoro (2'-F). Similar modifications can be made at other positions on the nucleosides and nucleotides of an oligonucleotide, particularly the 3' position of the sugar on the 3' terminal nucleotide or in 2'-5' linked oligonucleotides and the 5' position of 5' terminal nucleotide. Oligonucleotides can have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An oligonucleotide can include nucleobase (often referred to in the art simply as "base") alternatives (e.g., modifications or substitutions). Unmodified or natural nucleobases include the purine bases adenine (A) and guanine (G), and the pyrimidine bases thymine (T), cytosine (C) and uracil (U). Alternative nucleobases include other synthetic and natural nucleobases such as 5-methylcytidine, 5-hydroxymethylcytidine, 5-formylcytidine, 5-carboxycytidine, pyrrolocytidine, dideoxycytidine, uridine, 5-methoxyuridine, 5-hydroxydeoxyuridine, dihydrouridine, 4-thiourdine, pseudouridine, 1-methyl-pseudouridine, deoxyuridine, 5-hydroxybutynl-2'-deoxyuridine, xanthine, hypoxanthine, 7-deaza-xanthine, thienoguanine, 8-aza-7-deazaguanosine, 7-methylguanosine, 7-deazaguanosine, 6-aminomethyl-7-deazaguanosine, 8-aminoguanine, 2,2,7-trimethylguanosine, 8-methyladenine, 8-azidoadenine, 7-methyladenine, 7-deazaadenine, 3-deazaadenine, 2,6-diaminopurine, 2-aminopurine, 7-deaza-8-azaadenine, 8-amino-adenine, thymine, dideoxythymine, 5-nitroindole, 2-aminoadenine, 6-methyl and other alkyl derivatives of adenine and guanine, 2-propyl and other alkyl derivatives of adenine and guanine, 2-thiouridine, 2-thiothymine and 2-thiocytosine, 5-halouracil and cytosine, 5-propynyl uridine and cytidine, 6-azo uridine, cytidine and thymine, 4-thiouridine, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uridines and cytidines, 8-azaguanine and 8-azaadenine, and 3-deazaguanine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) Angewandte Chemie, International Edition, 30:613, and those disclosed by Sanghvi, Y S., Chapter 15, Antisense Research and Applications, pages 289-302, Crooke, S. T. and Lebleu, B., Ed., CRC Press, 1993. Certain of these nucleobases are particularly useful for increasing the binding affinity of the oligonucleotide. These include 5-substituted pyrimidines, 6-azapyrimidines, and N-2, N-6 and 0-6 substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., Antisense Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted alternative nucleobases as well as other alternative nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In other aspects, the sugar moiety in the nucleotide can be a ribose molecule, optionally having a 2'-O-methyl, 2'-O-MOE, 2'-F, 2'-amino, 2'-O-propyl, 2'-aminopropyl, or 2'-OH modification.

An oligonucleotide can include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In some aspects, the bridge connects the 4'-carbon and the 2'-carbon of the sugar ring. Thus, in some aspects, an oligonucleotide can include one or more locked nucleosides. A locked nucleoside is a nucleoside having a modified ribose moiety in which the ribose moiety comprises an extra bridge connecting the 2' and 4' carbons. In other words, a locked nucleoside is a nucleoside comprising a bicyclic sugar moiety comprising a 4'-$CH_2$—O-2' bridge. This structure effectively "locks" the ribose in the 3'-endo structural conformation. The addition of locked nucleosides to oligonucleotides has been shown to increase oligonucleotide stability in serum, and to reduce off-target effects (Grunweller, A. et al., (2003) Nucleic Acids Research 31(12):3185-3193). Examples of bicyclic nucleosides for use in the polynucleotides include without limitation nucleosides comprising a bridge between the 4' and the 2' ribosyl ring atoms. In some aspects, the polynucleotide agents include one or more bicyclic nucleosides comprising a 4' to 2' bridge. Examples of such 4' to 2' bridged bicyclic nucleosides, include but are not limited to 4'-$(CH_2)$—O-2' (LNA); 4'-$(CH_2)$—S-2'; 4'-$(CH_2)_2$—O-2' (ENA); 4'-CH$(CH_3)$—O-2' (also referred to as "constrained ethyl" or "cEt") and 4'-CH$(CH_2OCH_3)$—O-2' (and analogs thereof; see, e.g., U.S. Pat. No. 7,399,845); 4'-C$(CH_3)(CH_3)$—O-2' (and analogs thereof; see e.g., U.S. Pat. No. 8,278,283); 4'-$CH_2$—N$(OCH_3)$-2' (and analogs thereof; see e.g., U.S. Pat. No. 8,278,425); 4'-$CH_2$—O—N$(CH_3)_{2-2}$' (see, e.g., U.S. Patent Publication No. 2004/0171570); 4'-$CH_2$—N(R)—O-2', wherein R is H, $C_1$-$C_{12}$ alkyl, or a protecting group (see, e.g., U.S. Pat. No. 7,427,672); 4'-$CH_2$—C(H)$(CH_3)$-2' (see, e.g., Chattopadhyaya et al., J. Org. Chem., 2009, 74, 118-134); and 4'-$CH_2$—C(═$CH_2$)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

An oligonucleotide can be modified to include one or more constrained ethyl nucleosides. As used herein, a "constrained ethyl nucleoside" or "cEt" is a locked nucleoside comprising a bicyclic sugar moiety comprising a 4'-CH$(CH_3)$—O-2' bridge. In one aspect, a constrained ethyl nucleoside is in the S conformation referred to herein as "S-cEt."

An oligonucleotide can include one or more "conformationally restricted nucleosides" ("CRN"). CRN are nucleoside analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

In some aspects, an oligonucleotide comprises one or more monomers that are UNA (unlocked nucleoside) nucleosides. UNA is unlocked acyclic nucleoside, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see Nuc. Acids Symp. Series, 52, 133-134 (2008) and Fluiter et al., Mol. Biosyst., 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

The ribose molecule can be modified with a cyclopropane ring to produce a tricyclodeoxynucleic acid (tricyclo DNA). The ribose moiety can be substituted for another sugar such as 1,5,-anhydrohexitol, threose to produce a threose nucleoside (TNA), or arabinose to produce an arabino nucleoside. The ribose molecule can be replaced with non-sugars such as cyclohexene to produce cyclohexene nucleoside or glycol to produce glycol nucleosides.

Potentially stabilizing modifications to the ends of nucleoside molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other alternatives chemistries of an oligonucleotide include a 5' phosphate or 5' phosphate mimic, e.g., a 5'-terminal phosphate or phosphate mimic of an oligonucleotide. Suitable phosphate mimics are disclosed in, for example US Patent Publication No. 2012/0157511, the entire contents of which are incorporated herein by reference.

Exemplary oligonucleotides comprise nucleosides with alternative sugar moieties and can comprise DNA or RNA nucleosides. In some aspects, the oligonucleotide comprises nucleosides comprising alternative sugar moieties and DNA nucleosides. Incorporation of alternative nucleosides into the oligonucleotide can enhance the affinity of the oligonucleotide for the target nucleic acid. In that case, the alternative nucleosides can be referred to as affinity enhancing alternative nucleotides.

In some aspects, the oligonucleotide comprises at least 1 alternative nucleoside, such as at least 2, at least 3, at least 4, at least 5, at least 6, at least 7, at least 8, at least 9, at least 10, at least 11, at least 12, at least 13, at least 14, at least 15 or at least 16 alternative nucleosides. In other aspects, the oligonucleotides comprise from 1 to 10 alternative nucleosides, such as from 2 to 9 alternative nucleosides, such as from 3 to 8 alternative nucleosides, such as from 4 to 7 alternative nucleosides, such as 6 or 7 alternative nucleosides. In an aspect, the oligonucleotide can comprise alternatives, which are independently selected from these three types of alternatives (alternative sugar moiety, alternative nucleobase, and alternative internucleoside linkage), or a combination thereof. In one aspect, the oligonucleotide comprises one or more nucleosides comprising alternative sugar moieties, e.g., 2' sugar alternative nucleosides. In some aspect, the oligonucleotide comprises the one or more 2' sugar alternative nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA, and BNA (e.g., LNA) nucleosides. Exemplary structures of the LNAs are as follows (wherein the protecting groups are removed):

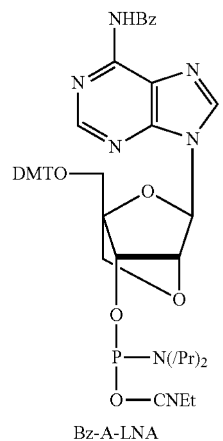

Bz-A-LNA

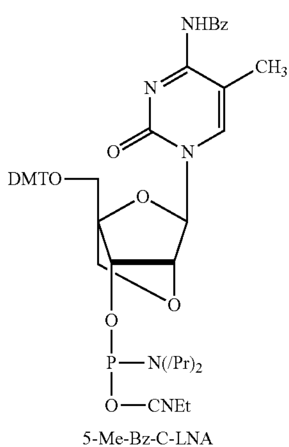

5-Me-Bz-C-LNA

-continued

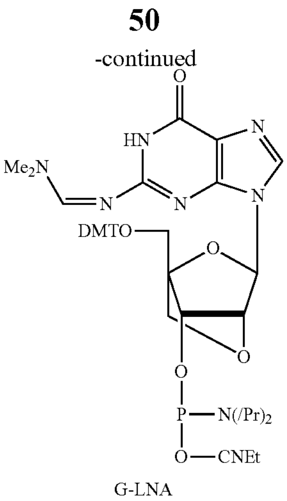

G-LNA

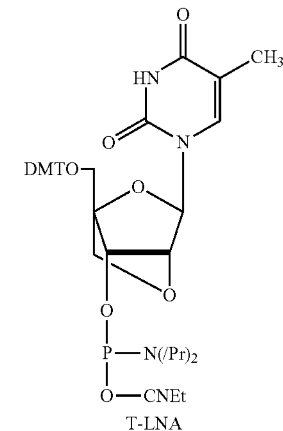

T-LNA

In some aspects, the one or more alternative nucleoside is a BNA.

In some aspects, at least 1 of the alternative nucleosides is a BNA (e.g., an LNA (e.g., A-LNA, 5mC L-NA, G-LNA, T-LNA)), such as at least 2, such as at least 3, at least 4, at least 5, at least 6, at least 7, or at least 8 of the alternative nucleosides are BNAs. In a still further aspect, all the alternative nucleosides are BNAs.

In a further aspect, the oligonucleotide comprises at least one alternative internucleoside linkage. In some aspects, the internucleoside linkages within the contiguous nucleotide sequence are phosphorothioate or boronophosphate internucleoside linkages. In some aspects, all the internucleotide linkages in the contiguous sequence of the oligonucleotide are phosphorothioate linkages. In some aspects, the phosphorothioate linkages are stereochemically pure phosphorothioate linkages. In some aspects, the phosphorothioate linkages are Sp phosphorothioate linkages. In other aspects, the phosphorothioate linkages are Rp phosphorothioate linkages.

In some aspects, the oligonucleotide comprises at least one alternative nucleoside which is a 2'-MOE-RNA, such as 2, 3, 4, 5, 6, 7, 8, 9, or 10 2'-MOE-RNA nucleoside units. In some aspects, the 2'-MOE-RNA nucleoside units are connected by phosphorothioate linkages. In some aspects, at least one of said alternative nucleoside is 2'-fluoro DNA, such as 2, 3, 4, 5, 6, 7, 8, 9, or 10 2'-fluoro-DNA nucleoside units. In some aspects, the oligonucleotide comprises at least one BNA unit and at least one 2' substituted modified nucleoside. In some aspects, the oligonucleotide comprises both 2' sugar modified nucleosides and DNA units. In some aspects, the oligonucleotide or contiguous nucleotide region thereof is a gapmer oligonucleotide.

B. Oligonucleotides Conjugated to Ligands

Oligonucleotides can be chemically linked to one or more ligands, moieties, or conjugates that enhance the activity, cellular distribution, or cellular uptake of the oligonucleotide. Such moieties include but are not limited to lipid moieties such as a cholesterol moiety (Letsinger et al., (1989) Proc. Natl. Acid. Sci. USA, 86: 6553-6556), cholic acid (Manoharan et al., (1994) Biorg. Med. Chem. Let., 4:1053-1060), a thioether, e.g., beryl-S-tritylthiol (Manoharan et al., (1992) Ann. N.Y. Acad. Sci., 660:306-309; Manoharan et al., (1993) Biorg. Med. Chem. Let., 3:2765-2770), a thiocholesterol (Oberhauser et al., (1992) Nucl. Acids Res., 20:533-538), an aliphatic chain, e.g., dodecandiol or undecyl residues (Saison-Behmoaras et al., (1991) EMBO J, 10:1111-1118; Kabanov et al., (1990) FEBS Lett., 259:327-330; Svinarchuk et al., (1993) Biochimie, 75:49-54), a phospholipid, e.g., di-hexadecyl-rac-glycerol or triethylammonium 1,2-di-O-hexadecyl-rac-glycero-3-phosphonate (Manoharan et al., (1995) Tetrahedron Lett., 36:3651-3654; Shea et al., (1990) Nucl. Acids Res., 18:3777-3783), a polyamine or a polyethylene glycol chain (Manoharan et al., (1995) Nucleosides & Nucleotides, 14:969-973), or adamantane acetic acid (Manoharan et al., (1995) Tetrahedron Lett., 36:3651-3654), a palmityl moiety (Mishra et al., (1995) Biochim. Biophys. Acta, 1264:229-237), or an octadecylamine or hexylamino-carbonyloxycholesterol moiety (Crooke et al., (1996) J. Pharmacol. Exp. Ther., 277:923-937).

In one aspect, a ligand alters the distribution, targeting, or lifetime of an oligonucleotide agent into which it is incorporated. In some aspects, a ligand provides an enhanced affinity for a selected target, e.g., molecule, cell or cell type, compartment, e.g., a cellular or organ compartment, tissue, organ, or region of the body, as, e.g., compared to a species absent such a ligand.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can include targeting groups, e.g., a cell or tissue targeting agent, e.g., a lectin, glycoprotein, lipid or protein, e.g., an antibody, that bind to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can include hormones and hormone receptors. They can include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose.

The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some aspects, a ligand attached to an oligonucleotide as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable as ligands (e.g. as PK modulating ligands). In addition, aptamers that bind serum components (e.g. serum proteins) are also suitable for use as PK modulating ligands in the aspects described herein.

Ligand-conjugated oligonucleotides can be synthesized by the use of an oligonucleotide that bears a pendant reactive functionality, such as that derived from the attachment of a linking molecule onto the oligonucleotide (described below). This reactive oligonucleotide can be reacted directly with commercially-available ligands, ligands that are synthesized bearing any of a variety of protecting groups, or ligands that have a linking moiety attached thereto.

The oligonucleotides used in the conjugates can be conveniently and routinely made through the well-known technique of solid-phase synthesis. Equipment for such synthesis is sold by several vendors including, for example, Applied Biosystems (Foster City, Calif.). Any other means for such synthesis known in the art can additionally or alternatively be employed. It is also known to use similar techniques to prepare other oligonucleotides, such as the phosphorothioates and alkylated derivatives.

In the ligand-conjugated oligonucleotides, such as the ligand-molecule bearing sequence-specific linked nucleosides, the oligonucleotides and oligonucleosides can be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using conjugate precursors that already bear a linking moiety, the synthesis of the sequence-specific linked nucleosides is typically completed, and the ligand molecule is then reacted with the linking moiety to form the ligand-conjugated oligonucleotide. In some aspects, the oligonucleotides or linked nucleosides are synthesized by an automated synthesizer using phosphoramidites derived from ligand-nucleoside conjugates in addition to the standard phosphoramidites and non-standard phosphoramidites that are commercially available and routinely used in oligonucleotide synthesis.

i. Lipid Conjugates

In one aspect, the ligand or conjugate is a lipid or lipid-based molecule. Such a lipid or lipid-based molecule can bind a serum protein, e.g., human serum albumin (HSA). An HSA binding ligand allows for distribution of the conjugate to a target tissue, e.g., a non-kidney target tissue of the body. A lipid or lipid-based ligand can (a) increase resistance to degradation of the conjugate, (b) increase targeting or transport into a target cell or cell membrane, and/or (c) be used to adjust binding to a serum protein, e.g., HSA.

In another aspect, the ligand is a moiety, e.g., a vitamin, which is taken up by a target cell, e.g., a proliferating cell. Exemplary vitamins include vitamin A, E, and K.

ii. Cell Permeation Agents

In another aspect, the ligand is a cell-permeation agent, such as a helical cell-permeation agent. In one aspect, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. In one aspect, the helical agent is an alpha-helical agent, which can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the oligonucleotide, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP. An RFGF analogue (e.g., amino acid sequence AALLPVLLAAP containing a hydrophobic MTS can be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ and the *Drosophila* Antennapedia protein (RQIKIWFQNRRMKWKK have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to an oligonucleotide agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods can be linear or cyclic, and can be modified, e.g., glycosylated or methylated, to facilitate targeting to a specific tissue(s). RGD-containing peptides and peptidiomimemtics can include D-amino acids, as well as synthetic RGD mimics. In addition to RGD, one can use other moieties that target the integrin ligand. Some conjugates of this ligand target PECAM-1 or VEGF.

A cell permeation peptide is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin, or bactenecin), or a peptide containing only one or two dominating amino acids (e.g., PR-39 or indolicidin). A cell permeation peptide can include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

iii. Carbohydrate Conjugates

In some aspects of the compositions and methods described herein, an oligonucleotide further comprises a carbohydrate. The carbohydrate conjugated oligonucleotides are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one aspect, a carbohydrate conjugate for use in the compositions and methods described herein is a monosaccharide.

In some aspects, the carbohydrate conjugate further comprises one or more additional ligands as described above, such as, but not limited to, a PK modulator and/or a cell permeation peptide.

Additional carbohydrate conjugates (and linkers) suitable for use include those described in PCT Publication Nos. WO 2014/179620 and WO 2014/179627, the entire contents of each of which are incorporated herein by reference.

iv. Linkers

In some aspects, the conjugate or ligand described herein can be attached to an oligonucleotide with various linkers that can be cleavable or non-cleavable.

Linkers typically comprise a direct bond or an atom such as oxygen or sulfur, a unit such as $NR^8$, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^8)$, C(O), substituted or unsubstituted aryl, substituted or unsubstituted heteroaryl, substituted or unsubstituted heterocyclic; where $R^8$ is hydrogen, acyl, aliphatic or substituted aliphatic. In one aspect, the linker is between about 1-24, 2-24, 3-24, 4-24, 5-24, 6-24, 6-18, 7-18, 8-18, 7-17, 8-17, 6-16, 7-17, 8-16 or 1, 2, 3, 4, 5, 6, 7, 8, 9, 10, 11, 12, 13, 14, 15, 16, 17, 18, 19, 20, 21, 21, 22, 23, or 24 atoms.

A cleavable linking group is one which is sufficiently stable outside the cell, but which upon entry into a target cell is cleaved to release the two parts the linker is holding together. In some aspects, the cleavable linking group is cleaved at least 10 times, 20 times, 30 times, 40 times, 50 times, 60 times, 70 times, 80 times, 90 times, or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selective for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to test the candidate cleavable linking group for the ability to resist cleavage in the blood or when in contact with other non-target tissue. Thus, one can determine the relative susceptibility to cleavage between at least two conditions, where at least one condition is selected to be indicative of cleavage in a target cell and another condition is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In some aspects, useful candidate compounds are cleaved at least 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

a. Redox Cleavable Linking Groups

In one aspect, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular oligonucleotide moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can be evaluated under conditions which are selected to mimic blood or serum conditions. In one aspect, candidate compounds are cleaved by at most about 10% in the blood. In other aspects, useful candidate compounds are degraded at least 2, 4, 10, 20, 30, 40, 50, 60, 70, 80, 90, or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

b. Phosphate-Based Cleavable Linking Groups

In another aspect, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—. These candidates can be evaluated using methods analogous to those described above.

c. Acid Cleavable Linking Groups

In another aspect, a cleavable linker comprises an acid cleavable linking group. An acid cleavable linking group is a linking group that is cleaved under acidic conditions. In some aspects, acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). In one aspect, the carbon is attached to the oxygen of the ester (the alkoxy group) is an aryl group, substituted alkyl group, or tertiary alkyl group such as dimethyl pentyl or t-butyl. These candidates can be evaluated using methods analogous to those described above.

d. Ester-Based Linking Groups

In another aspect, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

e. Peptide-Based Cleaving Groups

In yet another aspect, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene, or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCH$^B$C(O)—, where R$^A$ and R$^B$ are the R groups of the two adjacent amino acids. These candidates can be evaluated using methods analogous to those described above.

In one aspect, an oligonucleotide is conjugated to a carbohydrate through a linker. Linkers include bivalent and trivalent branched linker groups. Linkers for oligonucleotide carbohydrate conjugates include, but are not limited to, those described in formulas 24-35 of PCT Publication No. WO 2018/195165.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an oligonucleotide. Oligonucleotide compounds that are chimeric compounds are also contemplated. Chimeric oligonucleotides typically contain at least one region wherein the RNA is modified so as to confer upon the oligonucleotide increased resistance to nuclease degradation, increased cellular uptake, and/or increased binding affinity for the target nucleic acid. An additional region of the oligonucleotide can serve as a substrate for enzymes capable of cleaving RNA:DNA. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxy oligonucleotides hybridizing to the same target region. Cleavage of the RNA target can be routinely detected by gel electrophoresis and, if necessary, associated nucleic acid hybridization techniques known in the art.

In certain instances, the nucleotides of an oligonucleotide can be modified by a non-ligand group. A number of non-ligand molecules have been conjugated to oligonucleotides in order to enhance the activity, cellular distribution, or cellular uptake of the oligonucleotide, and procedures for performing such conjugations are available in the scientific literature. Such non-ligand moieties have included lipid moieties, such as cholesterol (Kubo, T. et al., Biochem. Biophys. Res. Comm, 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of an oligonucleotide bearing an aminolinker at one or more positions of the sequence. The amino group is then reacted with the molecule being conjugated using appropriate coupling or activating reagents. The conjugation reaction can be performed either with the oligonucleotide still bound to the solid support or following cleavage of the oligonucleotide, in solution phase. Purification of the oligonucleotide conjugate by HPLC typically affords the pure conjugate.

IV. Pharmaceutical Uses

The oligonucleotide, or pharmaceutically acceptable salt thereof, compositions described herein are useful in the methods described herein, and, while not bound by theory, are believed to exert their desirable effects through their ability to modulate the level, status, and/or activity of a MutSβ heterodimer comprising MSH3, e.g., by inhibiting the activity or level of the MSH3 protein in a cell in a mammal.

An aspect relates to methods of treating disorders related to DNA mismatch repair such as nucleotide repeat expansion disorders (e.g., trinucleotide repeat expansion disorders) in a subject in need thereof. Another aspect includes reducing the level of MSH3 in a cell of a subject identified as having a nucleotide repeat expansion disorder (e.g., a trinucleotide repeat expansion disorder). Still another aspect includes a method of inhibiting expression of MSH3 in a cell in a subject. Further aspects include methods of decreasing nucleotide repeat expansion in a cell. The methods include contacting a cell with an oligonucleotide, or pharmaceutically acceptable salt thereof, in an amount effective to inhibit expression of MSH3 in the cell, thereby inhibiting expression of MSH3 in the cell.

Based on the above methods, an oligonucleotide, or pharmaceutically acceptable salt thereof, or a composition comprising such an oligonucleotide, or pharmaceutically acceptable salt thereof, for use in therapy, or for use as a medicament, or for use in treating disorders related to DNA mismatch repair such as repeat expansion disorders in a subject in need thereof, or for use in reducing the level of MSH3 in a cell of a subject identified as having a nucleotide repeat expansion disorder (e.g., a trinucleotide repeat expansion disorder), or for use in inhibiting expression of MSH3 in a cell in a subject, or for use in decreasing nucleotide repeat expansion (e.g., trinucleotide repeat expansion) in a cell is contemplated. The uses include the contacting of a cell with the oligonucleotide, or pharmaceutically acceptable salt thereof, in an amount effective to inhibit expression of MSH3 in the cell, thereby inhibiting expression of MSH3 in the cell. Aspects described below in relation to the methods described herein are also applicable to these further aspects.

Contacting of a cell with an oligonucleotide, or pharmaceutically acceptable salt thereof, can be done in vitro or in vivo. Contacting a cell in vivo with the oligonucleotide, or pharmaceutically acceptable salt thereof, includes contacting a cell or group of cells within a subject, e.g., a human subject, with the oligonucleotide, or pharmaceutically acceptable salt thereof. Combinations of in vitro and in vivo methods of contacting a cell are also possible. Contacting a cell can be direct or indirect, as discussed above. Furthermore, contacting a cell can be accomplished via a targeting ligand, including any ligand described herein or known in the art. In some aspects, the targeting ligand is a carbohydrate moiety, e.g., a GalNAc3 ligand, or any other ligand that directs the oligonucleotide to a site of interest. Cells can include those of the central nervous system, or muscle cells.

Inhibiting expression of a MSH3 gene includes any level of inhibition of a MSH3 gene, e.g., at least partial suppression of the expression of a MSH3 gene, such as an inhibition by at least 20%. In some aspects, inhibition is by at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%.

The expression of a MSH3 gene can be assessed based on the level of any variable associated with MSH3 gene expression, e.g., MSH3 mRNA level or MSH3 protein level.

Inhibition can be assessed by a decrease in an absolute or relative level of one or more of these variables compared with a control level. The control level can be any type of control level that is utilized in the art, e.g., a pre-dose baseline level, or a level determined from a similar subject, cell, or sample that is untreated or treated with a control (such as, e.g., buffer only control or inactive agent control).

In some aspects, surrogate markers can be used to detect inhibition of MSH3. For example, effective treatment of a nucleotide repeat expansion disorder (e.g., a trinucleotide repeat expansion disorder), as demonstrated by acceptable diagnostic and monitoring criteria with an agent to reduce MSH3 expression can be understood to demonstrate a clinically relevant reduction in MSH3.

In some aspects of the methods, expression of a MSH3 gene is inhibited by at least 20%, 25%, 30%, 35%, 40%, 45%, 50%, 55%, 60%, 65%, 70%, 75%, 80%, 85%, 90%, or 95%, or to below the level of detection of the assay. In some aspects, the methods include a clinically relevant inhibition of expression of MSH3, e.g., as demonstrated by a clinically relevant outcome after treatment of a subject with an agent to reduce the expression of MSH3.

Inhibition of the expression of a MSH3 gene can be manifested by a reduction of the amount of mRNA expressed by a first cell or group of cells (such cells can be present, for example, in a sample derived from a subject) in which a MSH3 gene is transcribed and which has or have been treated (e.g., by contacting the cell or cells with an oligonucleotide, or pharmaceutically acceptable salt thereof, or by administering an oligonucleotide, or pharmaceutically acceptable salt thereof, to a subject in which the cells are or were present) such that the expression of a MSH3 gene is inhibited, as compared to a second cell or group of cells substantially identical to the first cell or group of cells but which has not or have not been so treated (control cell(s) not treated with an oligonucleotide, or pharmaceutically acceptable salt thereof, or not treated with an oligonucleotide, or pharmaceutically acceptable salt thereof, targeted to the gene of interest). The degree of inhibition can be expressed in terms of:

$$\frac{(mRNA \text{ in control cells}) - (mRNA \text{ in treated cells})}{(mRNA \text{ in control cells})} \times 100\%$$

In other aspects, inhibition of the expression of a MSH3 gene can be assessed in terms of a reduction of a parameter that is functionally linked to MSH3 gene expression, e.g., MSH3 protein expression or MSH3 signaling pathways. MSH3 gene silencing can be determined in any cell expressing MSH3, either endogenous or heterologous from an expression construct, and by any assay known in the art.

Inhibition of the expression of a MSH3 protein can be manifested by a reduction in the level of the MSH3 protein that is expressed by a cell or group of cells (e.g., the level of protein expressed in a sample derived from a subject). As explained above, for the assessment of mRNA suppression, the inhibition of protein expression levels in a treated cell or group of cells can similarly be expressed as a percentage of the level of protein in a control cell or group of cells.

A control cell or group of cells that can be used to assess the inhibition of the expression of a MSH3 gene includes a cell or group of cells that has not yet been contacted with an oligonucleotide. For example, the control cell or group of cells can be derived from an individual subject (e.g., a human or animal subject) prior to treatment of the subject with an oligonucleotide.

The level of MSH3 mRNA that is expressed by a cell or group of cells can be determined using any method known in the art for assessing mRNA expression. In one aspect, the level of expression of MSH3 in a sample is determined by detecting a transcribed polynucleotide, or portion thereof, e.g., mRNA of the MSH3 gene. RNA can be extracted from cells using RNA extraction techniques including, for example, using acid phenol/guanidine isothiocyanate extraction (RNAzol B; Biogenesis), RNEASY™ RNA preparation kits (Qiagen) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating MSH3 mRNA can be detected using methods the described in PCT Publication WO2012/177906, the entire contents of which are hereby incorporated herein by reference. In some aspects, the level of expression of MSH3 is determined using a nucleic acid probe. The term "probe," as used herein, refers to any molecule that is capable of selectively binding to a specific MSH3 sequence, e.g. to an mRNA or polypeptide. Probes can be synthesized by one of skill in the art, or derived from appropriate biological preparations. Probes can be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses, and probe arrays. One method for the determination of mRNA levels involves contacting the isolated mRNA with a nucleic acid molecule (probe) that can hybridize to MSH3 mRNA. In one aspect, the mRNA is immobilized on a solid surface and contacted with a probe, for example by running the isolated mRNA on an agarose gel and transferring the mRNA from the gel to a membrane, such as nitrocellulose. In an alternative aspect, the probe(s) are immobilized on a solid surface and the mRNA is contacted with the probe(s), for example, in an AFFYMETRIX gene chip array. A skilled artisan can readily adapt known mRNA detection methods for use in determining the level of MSH3 mRNA.

An alternative method for determining the level of expression of MSH3 in a sample involves the process of nucleic acid amplification and/or reverse transcriptase (to prepare cDNA) of for example mRNA in the sample, e.g., by RT-PCR (the experimental aspect set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In some aspects, the level of expression of MSH3 is determined by quantitative fluorogenic RT-PCR (i.e., the TAQMAN™ System) or the DUAL-GLO® Luciferase assay.

The expression levels of MSH3 mRNA can be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722; 5,874,219; 5,744,305; 5,677,195; and 5,445,934, which are incorporated herein by reference. The determination of MSH3 expression level can comprise using nucleic acid probes in solution.

In some aspects, the level of mRNA expression is assessed using branched DNA (bDNA) assays or real time PCR (qPCR). The use of this PCR method is described and exemplified in the Examples presented herein. Such methods can be used for the detection of MSH3 nucleic acids.

The level of MSH3 protein expression can be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (MA), enzyme-linked immunosorbent assays (ELISAs), immunofluorescent assays, electrochemiluminescence assays, and the like. Such assays can be used for the detection of proteins indicative of the presence or replication of MSH3 proteins.

In some aspects of the methods described herein, the oligonucleotide, or pharmaceutically acceptable salt thereof, is administered to a subject such that the oligonucleotide, or pharmaceutically acceptable salt thereof, is delivered to a specific site within the subject. The inhibition of expression of MSH3 can be assessed using measurements of the level or change in the level of MSH3 mRNA or MSH3 protein in a sample derived from a specific site within the subject. In some aspects, the methods include a clinically relevant inhibition of expression of MSH3, e.g., as demonstrated by a clinically relevant outcome after treatment of a subject with an agent to reduce the expression of MSH3.

In other aspects, the oligonucleotide, or pharmaceutically acceptable salt thereof, is administered in an amount and for a time effective to result in one of (or more, e.g., two or more, three or more, four or more of): (a) decrease the number of repeats, (b) decrease the level of polyglutamine, (c) decreased cell death (e.g., CNS cell death and/or muscle cell death), (d) delayed onset of the disorder, (e) increased survival of subject, and (f) increased progression free survival of a subject.

Treating nucleotide repeat expansion disorders (e.g., trinucleotide repeat expansion disorders) can result in an increase in average survival time of an individual or a population of subjects treated with an oligonucleotide, or pharmaceutically acceptable salt thereof, described herein in comparison to a population of untreated subjects. For example, the survival time of an individual or average survival time of a population is increased by more than 30 days (more than 60 days, 90 days, or 120 days). An increase in survival time of an individual or in average survival time of a population can be measured by any reproducible means. An increase in survival time of an individual can be measured, for example, by calculating for an individual the length of survival time following the initiation of treatment with the compound described herein. An increase in average survival time of a population can be measured, for example, by calculating for the average length of survival time following initiation of treatment with the compound described herein. An increase in survival time of an individual can be measured, for example, by calculating for an individual length of survival time following completion of a first round of treatment with a compound or pharmaceutically acceptable salt of a compound described herein. An increase in average survival time of a population can be measured, for example, by calculating for a population the average length of survival time following completion of a first round of treatment with a compound or pharmaceutically acceptable salt of a compound described herein.

Treating nucleotide repeat expansion disorders (e.g., trinucleotide repeat expansion disorders) can result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects can be measured by any reproducible means, for example, by calculating for a population the average number of disease-related deaths per unit time following initiation of treatment with a compound or pharmaceutically acceptable salt of a compound described herein. A decrease in the mortality rate of a population can be measured, for example, by calculating for a population the average number of disease-related deaths per unit time following completion of a first round of treatment with a compound or pharmaceutically acceptable salt of a compound described herein.

A. Delivery of Anti-MSH3 Agents

The delivery of an oligonucleotide to a cell e.g., a cell within a subject, such as a human subject e.g., a subject in need thereof, such as a subject having a nucleotide repeat expansion disorder (e.g., a trinucleotide repeat expansion disorder) can be achieved in a number of different ways. For example, delivery can be performed by contacting a cell with an oligonucleotide, or pharmaceutically acceptable salt thereof, either in vitro or in vivo. In vivo delivery can be performed directly by administering a composition comprising an oligonucleotide, or pharmaceutically acceptable salt thereof, to a subject. These alternatives are discussed further below.

In general, any method of delivering a nucleic acid molecule (in vitro or in vivo) can be adapted for use with an oligonucleotide (see e.g., Akhtar S. and Julian R L., (1992) Trends Cell. Biol. 2(5):139-144 and WO94/02595, which are incorporated herein by reference in their entireties). For in vivo delivery, factors to consider in order to deliver an oligonucleotide molecule include for example, biological stability of the delivered molecule, prevention of non-specific effects, and accumulation of the delivered molecule in the target tissue. The non-specific effects of an oligonucleotide can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the oligonucleotide, or pharmaceutically acceptable salt thereof, to be administered.

For administering an oligonucleotide, or pharmaceutically acceptable salt thereof, systemically for the treatment of a disease, the oligonucleotide can include alternative nucleobases, alternative sugar moieties, and/or alternative internucleoside linkages, or alternatively delivered using a drug delivery system; both methods act to prevent the rapid degradation of the oligonucleotide by endo- and exo-nucleases in vivo. Modification of the oligonucleotide, or the pharmaceutical carrier, can permit targeting of the oligonucleotide composition to the target tissue and avoid undesirable off-target effects. Oligonucleotide molecules can be modified by chemical conjugation to lipophilic groups such as cholesterol to enhance cellular uptake and prevent degradation. In an alternative aspect, the oligonucleotide can be delivered using drug delivery systems such as a nanoparticle, a lipid nanoparticle, a polyplex nanoparticle, a lipoplex nanoparticle, a dendrimer, a polymer, liposomes, or a cationic delivery system. Positively charged cationic delivery systems facilitate binding of an oligonucleotide molecule (negatively charged) and also enhance interactions at the negatively charged cell membrane to permit efficient uptake of an oligonucleotide by the cell. Cationic lipids, dendrimers, or polymers can either be bound to an oligonucleotide, or induced to form a vesicle or micelle that encases an oligonucleotide. The formation of vesicles or micelles further prevents degradation of the oligonucleotide when administered systemically. In general, any methods of delivery of nucleic acids known in the art may be adaptable to the delivery of the oligonucleotides described herein. Methods for making and administering cationic oligonucleotide complexes are well within the abilities of one skilled in the art (see e.g., Sorensen, D R., et al. (2003) J. Mol. Biol 327: 761-766; Verma, U N. et al., (2003) Clin. Cancer Res. 9:1291-1300; Arnold, A S et al., (2007) J. Hypertens. 25:197-205, which are incorporated herein by reference in their entirety). Some non-limiting examples of drug delivery systems useful for systemic delivery of oligonucleotides include DOTAP (Sorensen, D R., et al (2003), supra; Verma, U N. et al., (2003), supra), Oligofectamine, "solid nucleic acid lipid particles" (Zimmermann, T S. et al., (2006) Nature 441:111-114), cardiolipin (Chien, P Y. et al., (2005) Cancer Gene Ther. 12:321-328; Pal, A. et al., (2005) Int J. Oncol. 26:1087-1091), polyethyleneimine (Bonnet M E. et al., (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A. et al., (2007) Biochem. Soc. Trans. 35:61-67; Yoo, H. et al., (1999)

Pharm. Res. 16:1799-1804). In some aspects, an oligonucleotide forms a complex with cyclodextrin for systemic administration. Methods for administration and pharmaceutical compositions of oligonucleotides and cyclodextrins can be found in U.S. Pat. No. 7,427,605, which is herein incorporated by reference in its entirety. In some aspects, the oligonucleotides described herein are delivered by polyplex or lipoplex nanoparticles. Methods for administration and pharmaceutical compositions of oligonucleotides and polyplex nanoparticles and lipoplex nanoparticles can be found in U.S. Patent Application Nos. 2017/0121454; 2016/0369269; 2016/0279256; 2016/0251478; 2016/0230189; 2015/0335764; 2015/0307554; 2015/0174549; 2014/0342003; 2014/0135376; and 2013/0317086, which are herein incorporated by reference in their entirety.

i. Membranous Molecular Assembly Delivery Methods

The oligonucleotide, or pharmaceutically acceptable salt thereof, can be delivered using a variety of membranous molecular assembly delivery methods including polymeric, biodegradable microparticle, or microcapsule delivery devices known in the art. For example, a colloidal dispersion system can be used for targeted delivery of an oligonucleotide agent described herein. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 μm can encapsulate a substantial percentage of an aqueous buffer containing large macromolecules. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the oligonucleotide, or pharmaceutically acceptable salt thereof, are delivered into the cell where the oligonucleotide can specifically bind to a target RNA and can mediate RNase H-mediated gene silencing. In some cases, the liposomes are also specifically targeted, e.g., to direct the oligonucleotide to particular cell types. The composition of the liposome is usually a combination of phospholipids, usually in combination with steroids, especially cholesterol. Other phospholipids or other lipids can be used. The physical characteristics of liposomes depend on pH, ionic strength, and the presence of divalent cations.

A liposome containing an oligonucleotide, or pharmaceutically acceptable salt thereof, can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and can be nonionic. Exemplary detergents include cholate, CHAPS, octylglucoside, deoxycholate, and lauroyl sarcosine. The oligonucleotide, or pharmaceutically acceptable salt thereof, preparation is then added to the micelles that include the lipid component. The cationic groups on the lipid interact with the oligonucleotide, or pharmaceutically acceptable salt thereof, and condense around the oligonucleotide, or pharmaceutically acceptable salt thereof, to form a liposome. After condensation, the detergent is removed, e.g., by dialysis, to yield a liposomal preparation of oligonucleotide, or pharmaceutically acceptable salt thereof.

If necessary, a carrier compound that assists in condensation can be added during the condensation reaction, e.g., by controlled addition. For example, the carrier compound can be a polymer other than a nucleic acid (e.g., spermine or spermidine). The pH can be adjusted to favor condensation.

Methods for producing stable polynucleotide delivery vehicles, which incorporate a polynucleotide/cationic lipid complex as a structural component of the delivery vehicle, are further described in, e.g., WO 96/37194, the entire contents of which are incorporated herein by reference. Liposome formation can include one or more aspects of exemplary methods described in Feigner, P. L. et al., (1987) Proc. Natl. Acad. Sci. USA 8:7413-7417; U.S. Pat. Nos. 4,897,355; 5,171,678; Bangham et al., (1965) M. Mol. Biol. 23:238; Olson et al., (1979) Biochim. Biophys. Acta 557:9; Szoka et al., (1978) Proc. Natl. Acad. Sci. 75: 4194; Mayhew et al., (1984) Biochim. Biophys. Acta 775:169; Kim et al., (1983) Biochim. Biophys. Acta 728:339; and Fukunaga et al., (1984) Endocrinol. 115:757. Commonly used techniques for preparing lipid aggregates of appropriate size for use as delivery vehicles include sonication and freeze-thaw plus extrusion (see, e.g., Mayer et al., (1986) Biochim. Biophys. Acta 858:161. Microfluidization can be used when consistently small (50 to 200 nm) and relatively uniform aggregates are desired (Mayhew et al., (1984) Biochim. Biophys. Acta 775:169). These methods are readily adapted to packaging oligonucleotide, or pharmaceutically acceptable salt thereof, preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) Biochem. Biophys. Res. Commun., 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) Journal of Controlled Release, 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Feigner, (1994) J. Biol. Chem. 269:2550; Nabel, (1993) Proc. Natl. Acad. Sci. 90:11307; Nabel, (1992) Human Gene Ther. 3:649; Gershon, (1993) Biochem. 32:7143; and Strauss, (1992) EMBO J. 11:417.

Non-ionic liposomal systems have also been examined to determine their utility in the delivery of drugs to the skin, in particular systems comprising non-ionic surfactant and cholesterol. Non-ionic liposomal formulations comprising NOVASOME™ I (glyceryl dilaurate/cholesterol/polyoxyethylene-10-stearyl ether) and NOVASOME™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) S.T.P. Pharma. Sci., 4(6):466).

Liposomes can be sterically stabilized liposomes, comprising one or more specialized lipids that result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) FEBS Letters, 223:42; Wu et al., (1993) Cancer Research, 53:3765).

Various liposomes comprising one or more glycolipids are known in the art. Papahadjopoulos et al. (Ann. N.Y. Acad. Sci., (1987), 507:64) reported the ability of monosialoganglioside $G^{M1}$, galactocerebroside sulfate, and phosphatidylinositol to improve blood half-lives of liposomes. These findings were expounded upon by Gabizon et al. (Proc. Natl. Acad. Sci. U.S.A., (1988), 85:6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one aspect, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver oligonucleotides to macrophages.

Further advantages of liposomes include: liposomes obtained from natural phospholipids are biocompatible and biodegradable; liposomes can incorporate a wide range of water and lipid soluble drugs; liposomes can protect encapsulated oligonucleotides in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of oligonucleotide (see, e.g., Feigner, P. L. et al., (1987) Proc. Natl. Acad. Sci. USA 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. LIPOFECTIN™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (TRANSFECTAM™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) Biochim. Biophys. Res. Commun. 179:280). Lipopolylysine, made by conjugating polylysine to DOPE, has been reported to be effective for transfection in the presence of serum (Zhou, X. et al., (1991) Biochim. Biophys. Acta 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer oligonucleotide into the skin. In some implementations, liposomes are used for delivering oligonucleotide to epidermal cells and also to enhance the penetration of oligonucleotide into dermal tissues, e.g., into skin. For example, the liposomes can be applied topically. Topical delivery of drugs formulated as liposomes to the skin has been documented (see, e.g., Weiner et al., (1992) Journal of Drug Targeting, vol. 2, 405-410 and du Plessis et al., (1992) Antiviral Research, 18:259-265; Mannino, R. J. and Fould-Fogerite, S., (1998) Biotechniques 6:682-690; Itani, T. et al., (1987) Gene 56:267-276; Nicolau, C. et al. (1987) Meth. Enzymol. 149:157-176; Straubinger, R. M. and Papahadjopoulos, D. (1983) Meth. Enzymol. 101:512-527; Wang, C. Y. and Huang, L., (1987) Proc. Natl. Acad. Sci. USA 84:7851-7855).

Non-ionic liposomal systems have also been examined to determine their utility in the delivery of drugs to the skin, in particular systems comprising non-ionic surfactant and cholesterol. Non-ionic liposomal formulations comprising NOVASOME I (glyceryl dilaurate/cholesterol/polyoxyethylene-10-stearyl ether) and NOVASOME II (glyceryl distearate/cholesterol/polyoxyethylene-10-stearyl ether) were used to deliver a drug into the dermis of mouse skin. Such formulations with oligonucleotides are useful for treating a dermatological disorder.

The targeting of liposomes is also possible based on, for example, organ-specificity, cell-specificity, and organelle-specificity and is known in the art. In the case of a liposomal targeted delivery system, lipid groups can be incorporated into the lipid bilayer of the liposome to maintain the targeting ligand in stable association with the liposomal bilayer. Various linking groups can be used for joining the lipid chains to the targeting ligand. Additional methods are known in the art and are described, for example in U.S. Patent Application Publication No. 20060058255, the linking groups of which are herein incorporated by reference.

Liposomes that include oligonucleotides can be made highly deformable. Such deformability can enable the liposomes to penetrate through pore that are smaller than the average radius of the liposome. For example, transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes can be made by adding surface edge activators, usually surfactants, to a standard liposomal composition. Transfersomes that include oligonucleotides can be delivered, for example, subcutaneously by infection to deliver oligonucleotides to keratinocytes in the skin. To cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading. Transfersomes have been used to deliver serum albumin to the skin. The transfersome-mediated delivery of serum albumin has been shown to be as effective as subcutaneous injection of a solution containing serum albumin.

Other suitable formulations are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application No. PCT/US2007/080331, filed Oct. 3, 2007 also describes suitable. Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines, and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The oligonucleotides, or pharmaceutically acceptable salts thereof, for use in the methods can be provided as micellar formulations. Micelles are a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

ii. Lipid Nanoparticle-Based Delivery Methods

Oligonucleotides can be fully encapsulated in a lipid formulation, e.g., a lipid nanoparticle (LNP), or other nucleic acid-lipid particle. LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one aspect, the lipid to drug ratio (mass/mass ratio) (e.g., lipid to oligonucleotide ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated.

Non-limiting examples of cationic lipids include N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyetetrahydro-3aH-cyclopenta[d][1,3]dioxol-5-amine (ALN100), (6Z,9Z,28Z,31Z)-heptatriaconta-6,9,28,31-tetraen-19-yl4-(dimethylamino)butanoate (MC3), 1,1'-(2-(4-(2-((2-(bis(2-hydroxydodecyl)amino)ethyl)(2-hydroxydodecyl)amino) ethyl)piperazin-1-yeethylazanediyedidodecan-2-ol (Tech G1), or a mixture thereof. The cationic lipid can comprise, for example, from about 20 mol % to about 50 mol % or about 40 mol % of the total lipid present in the particle.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be, for example, from about 5 mol % to about 90 mol %, about 10 mol %, or about 60 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be, for example, from 0 mol % to about 20 mol % or about 2 mol % of the total lipid present in the particle.

In some aspects, the nucleic acid-lipid particle further includes cholesterol at, e.g., about 10 mol % to about 60 mol % or about 50 mol % of the total lipid present in the particle.

B. Combination Therapies

An oligonucleotide, or pharmaceutically acceptable salt thereof, can be used alone or in combination with at least one additional therapeutic agent, e.g., other agents that treat nucleotide repeat expansion disorders (e.g., trinucleotide repeat expansion disorders) or symptoms associated therewith, or in combination with other types of therapies to treat nucleotide repeat expansion disorders (e.g., trinucleotide repeat expansion disorders). In combination treatments, the dosages of one or more of the therapeutic compounds can be reduced from standard dosages when administered alone. For example, doses can be determined empirically from drug combinations and permutations or can be deduced by isobolographic analysis (e.g., Black et al., Neurology 65:S3-S6 (2005)). In this case, dosages of the compounds when combined should provide a therapeutic effect.

In some aspects, the oligonucleotide, or pharmaceutically acceptable salt thereof, agents described herein can be used in combination with at least one additional therapeutic agent to treat a nucleotide repeat expansion disorder (e.g., a trinucleotide repeat expansion disorder) associated with gene having a nucleotide repeat (e.g., any of the trinucleotide repeat expansion disorders and associated genes having a nucleotide repeat listed in Table 1). In some aspects, at least one of the additional therapeutic agents can be an oligonucleotide (e.g., an ASO) that hybridizes with the mRNA of gene associated with a nucleotide or trinucleotide repeat expansion disorder (e.g., any of the genes listed in Table 1). In some aspects, the nucleotide repeat expansion disorder (e.g., a trinucleotide repeat expansion disorder) is Huntington's disease (HD). In some aspects, the gene associated with a nucleotide repeat expansion disorder (e.g., a trinucleotide repeat expansion disorder) is Huntingtin (HTT). Several allelic variants of the Huntingtin gene have been implicated in the etiology of Huntington's disease. In some cases, these variants are identified on the basis of having unique HD-associated single nucleotide polymorphisms (SNPs). In some aspects, the oligonucleotide hybridizes to an mRNA of the Huntingtin gene containing any of the HD-associated SNPs known in the art (e.g., any of the HD-associated SNPs described in Skotte et al., PLoS One 2014, 9(9): e107434, Carroll et al., Mol. Ther. 2011, 19(12): 2178-85, Warby et al., Am. J. Hum. Gen. 2009, 84(3): 351-66 (herein incorporated by reference)). In some aspects, the oligonucleotide that is an additional therapeutic agent hybridizes to an mRNA of the Huntingtin gene lacking any of the HD-associated SNPs. In some of the aspects, the oligonucleotide, or pharmaceutically acceptable salt thereof, that is an additional therapeutic agent hybridizes to an mRNA of the Huntingtin gene having any of the SNPs selected from the group of rs362307 and rs365331. In some aspects, the oligonucleotide, or pharmaceutically acceptable salt thereof, that is an additional therapeutic agent can be a modified oligonucleotide (e.g., an oligonucleotide including any of the modifications described herein). In some aspects, the modified oligonucleotides that is an additional therapeutic agent comprise one or more phosphorothioate internucleoside linkages. In some aspects, the modified oligonucleotide comprises one or more 2'-MOE moieties. In some aspects, the oligonucleotide that is an additional therapeutic agent that hybridizes to the mRNA of the Huntingtin gene has a sequence selected from the SEQ ID NOs. 6-285 of U.S.

Pat. No. 9,006,198; SEQ ID NOs. 6-8 of US Patent Application Publication No. 2017/0044539; SEQ ID NOs. 1-1565 of US Patent Application Publication 2018/0216108; and SEQ ID NOs. 1-2432 of PCT Publication WO 2017/192679, the sequences of which are hereby incorporated by reference.

In some aspects, at least one of the additional therapeutic agents is a chemotherapeutic agent (e.g., a cytotoxic agent or other chemical compound useful in the treatment of a nucleotide repeat expansion disorder, e.g., a trinucleotide repeat expansion disorder).

In some aspects, at least one of the additional therapeutic agents can be a therapeutic agent which is a non-drug treatment. For example, at least one of the additional therapeutic agents is physical therapy.

In any of the combination aspects described herein, the two or more therapeutic agents are administered simultaneously or sequentially, in either order. For example, a first therapeutic agent can be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after one or more of the additional therapeutic agents.

V. Pharmaceutical Compositions

The oligonucleotides, or pharmaceutically acceptable salt thereof, described herein are formulated into pharmaceutical compositions for administration to human subjects in a biologically compatible form suitable for administration in vivo.

The compounds described herein can be used in the form of the free base, in the form of salts, solvates, and as prodrugs. All forms are within the methods described herein. In accordance with the methods described herein, the described oligonucleotides or salts, solvates, or prodrugs thereof can be administered to a patient in a variety of forms depending on the selected route of administration, as will be understood by those skilled in the art. The compounds described herein can be administered, for example, by oral, parenteral, intrathecal, intracerebroventricular, intraparenchymal, buccal, sublingual, intraocular (subretinal, intravitreal), intra cisterna magna (ICM), nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, intraocular, intracerebroventricular, intraparenchymal, rectal, and topical modes of administration. Parenteral administration can be by continuous infusion over a selected period of time.

A compound described herein can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, a compound described herein can be incorporated with an excipient and used in the form of ingestible tablets, buccal tablets, troches, capsules, elixirs, suspensions, syrups, and wafers. A compound described herein can be administered parenterally. Solutions of a compound described herein can be prepared in water suitably mixed with a surfactant, such as hydroxypropylcellulose. Dispersions can be prepared in glycerol, liquid polyethylene glycols, DMSO, and mixtures thereof with or without alcohol, and in oils. Under ordinary conditions of storage and use, these preparations can contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF 36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that can be easily administered via syringe. Compositions for nasal administration can conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container can be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter The compounds described herein can be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

VI. Dosages

The dosage of the compositions (e.g., a composition including an oligonucleotide, or pharmaceutically acceptable salt thereof, described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. The compositions described herein can be administered initially in a suitable dosage that can be adjusted as required, depending on the clinical response. In some aspects, the dosage of a composition (e.g., a composition including an oligonucleotide, or pharmaceutically acceptable salt thereof) is a prophylactically or a therapeutically effective amount.

VII. Kits

Kits including (a) a pharmaceutical composition including an oligonucleotide, or pharmaceutically acceptable salt thereof, agent that reduces the level and/or activity of MSH3 in a cell or subject described herein, and (b) a package insert with instructions to perform any of the methods described herein are contemplated. In some aspects, the kit includes (a) a pharmaceutical composition including an oligonucleotide, or pharmaceutically acceptable salt thereof, agent that reduces the level and/or activity of MSH3 in a cell or subject described herein, (b) an additional therapeutic agent, and (c) a package insert with instructions to perform any of the methods described herein.

EXAMPLE

Example 1. Design and Selection of Antisense Oligonucleotides

Identification and Selection of Target Transcripts: Target transcript selection and off-target scoring (below) utilized NCBI RefSeq sequences, downloaded from NCBI 21 Nov. 2018. Experimentally validated "NM" transcript models were used except for cynomolgus monkey, which only has "XM" predicted models for the large majority of genes. The longest human, mouse, rat, and cynomolgus monkey MSH3 transcript that contained all mapped internal exons was selected (SEQ IDs 385, 386, 387, and 388 for human, mouse, rat, and cynomolgus monkey, respectively, SEQ ID NO:389 is the protein sequence).

Knock Down by ASOs

ASO screen in Hela cells to identify the top ASO in Table 3 for the MSH3 gene was performed by Horizon.

In summary: ASO knockdown activity was evaluated in HeLa by transfection at 1 nM and 10 nM. mRNA knockdown was analyzed by quantitative reverse transcription polymerase chain reaction (RT-qPCR) using TaqMan Gene Expression probes. mRNA expression was calculated via delta-delta Ct (ΔΔCT) method where target expression was normalized to expression of the reference gene beta-glucuronidase (GUSB) and to cells treated with a scrambled luciferase targeting control ASO.

Transfection in HeLa Cells

ASOs were resuspended in dH2O to 1000-fold their final assay concentration (10 uM or 1 uM). ASOs were dispensed in quadruplicates and complexed with 5 ul of Lipofectamine 3000 (Invitrogen) for 20 minutes before HeLa cells were added at 2,500 cells/well. Cells were cultured under standard culturing conditions for 24 hours. Cells were processed for RT-qPCR readout using the Cells-to-CT 1-step TaqMan Kit (Invitrogen) according to manufacturer's instructions. TaqMan Gene Expression probe for MSH3 was Hs00989003_m1 (Life Technologies Ltd) on a QuantStudio 6 (Applied BioSystems).

TABLE 2

| Key to Chemical Modifiers in Tables 3 and 4 | |
|---|---|
| "s" after base | phosphorothioate linkage |
| "p" after base | phosphodiester linkage |
| "o" before base | moe (2'-O-methoxyethyl-RNA) |
| "d" before base | deoxy (a DNA nucleoside) |
| ACTG | core DNA bases: adenine; cytosine; thymine; and guanine |
| "5m" | methyl at position 5 on the nucleobase; all C (cytosine) are 5-methyl. |
| "moe U" | synonymous with "moe T" |
| "moe T" | synonymous with "moe U" |
| L | LNA (e.g., A-LNA, 5mC L-NA, G-LNA, T-LNA) |

moeT can be substituted for one or more of the moeU nucleotides listed in any of the sequences below. Similarly, moeU can be substituted for one or more of the moeT nucleotides listed in any of the sequences below.

In Table 3 below, the SEQ ID No. corresponds to the nucleobase sequence of the Antisense Oligo No. However, the specific Antisense Oligo No. (e.g., Antisense Oligo No. 1) includes the specified chemical modifications.

TABLE 3

| Antisense Oligo No./ SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 1 | [oCs\|oUs\|oAs\|oGs\|oGs\|dTs\|dGs\|dAs\|dTs\|dGs\|5mCs\|dAs\|5mCs\|dTs\|dGs\|oCs\|oUs\|oUs\|oUs\|oA] | 86.09785 | 41.79781 | 10.956696 | 1.978577 |
| 2 | [oCs\|oUs\|oAp\|oGs\|oGs\|dTs\|dGs\|dAs\|dTs\|dGs\|5mCs\|dAs\|5mCs\|dTs\|dGs\|oCs\|oUs\|oUs\|oUs\|oA] | 102.13406 | 40.30929 | 2.5403645 | 1.368438 |
| 3 | [oCs\|oUs\|oAs\|oGp\|oGs\|dTs\|dGs\|dAs\|dTs\|dGs\|5mCs\|dAs\|5mCs\|dTs\|dGs\|oCs\|oUs\|oUs\|oUs\|oA] | 86.89053 | 37.50409 | 4.95608 | 1.237848 |
| 4 | [oCs\|oUs\|oAp\|oGp\|oGs\|dTs\|dGs\|dAs\|dTs\|dGs\|5mCs\|dAs\|5mCs\|dTs\|dGs\|oCs\|oUs\|oUs\|oUs\|oA] | 88.21922 | 46.14382 | 8.324711 | 2.068448 |
| 5 | [oCs\|oUs\|oAs\|oGs\|oGs\|dTs\|dGs\|dAs\|dTs\|dGs\|5mCs\|dAs\|5mCs\|dTs\|dGs\|oCs\|oUp\|oUs\|oUs\|oA] | 88.06973 | 44.49033 | 7.0556625 | 1.637641 |
| 6 | [oCs\|oUs\|oAs\|oGs\|oGs\|dTs\|dGs\|dAs\|dTs\|dGs\|5mCs\|dAs\|5mCs\|dTs\|dGs\|oCp\|oUs\|oUs\|oUs\|oA] | 66.27929 | 38.82585 | 7.304814 | 2.701934 |
| 7 | [oCs\|oUs\|oAs\|oGs\|oGs\|dTs\|dGs\|dAs\|dTs\|dGs\|5mCs\|dAs\|5mCs\|dTs\|dGs\|oCp\|oUp\|oUs\|oUs\|oA] | 87.77148 | 39.91306 | 3.7650095 | 1.899814 |
| 8 | [oCs\|oUs\|oAp\|oGs\|oGs\|dTs\|dGs\|dAs\|dTs\|dGs\|5mCs\|dAs\|5mCs\|dTs\|dGs\|oCs\|oUp\|oUs\|oUs\|oA] | 93.78302 | 39.9579 | 5.800865 | 2.591389 |
| 9 | [oCs\|oUs\|oAp\|oGs\|oGs\|dTs\|dGs\|dAs\|dTs\|dGs\|5mCs\|dAs\|5mCs\|dTs\|dGs\|oCp\|oUs\|oUs\|oUs\|oA] | 91.70171 | 46.43532 | 6.7248825 | 1.898713 |

TABLE 3-continued

| Anti-sense Oligo No./ SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 10 | [oCs\|oUs\|oAs\|oGp\|oGs\|dTs\|dGs\|dAs\|dTs\|dGs\|5mCs\|dAs\|5mCs\|dTs\|dGs\|oCs\|oUp\|oUs\|oUs\|oA] | 90.12033 | 43.42065 | 11.205575 | 2.148471 |
| 11 | [oCs\|oUs\|oAs\|oGp\|oGs\|dTs\|dGs\|dAs\|dTs\|dGs\|5mCs\|dAs\|5mCs\|dTs\|dGs\|oCp\|oUs\|oUs\|oUs\|oA] | 99.38491 | 40.8259 | 7.1537125 | 4.453034 |
| 12 | [oCs\|oUs\|oAp\|oGs\|oGs\|dTs\|dGs\|dAs\|dTs\|dGs\|5mCs\|dAs\|5mCs\|dTs\|dGs\|oCp\|oUp\|oUs\|oUs\|oA] | 92.85072 | 47.68991 | 9.7849105 | 0.732238 |
| 13 | [oCs\|oUs\|oAs\|oGp\|oGs\|dTs\|dGs\|dAs\|dTs\|dGs\|5mCs\|dAs\|5mCs\|dTs\|dGs\|oCp\|oUp\|oUs\|oUs\|oA] | 82.76355 | 44.94987 | 2.3796215 | 1.213861 |
| 14 | [oCs\|oUs\|oAp\|oGp\|oGs\|dTs\|dGs\|dAs\|dTs\|dGs\|5mCs\|dAs\|5mCs\|dTs\|dGs\|oCs\|oUp\|oUs\|oUs\|oA] | 100.30431 | 42.47324 | 7.2137325 | 3.762178 |
| 15 | [oCs\|oUs\|oAp\|oGp\|oGs\|dTs\|dGs\|dAs\|dTs\|dGs\|5mCs\|dAs\|5mCs\|dTs\|dGs\|oCp\|oUs\|oUs\|oUs\|oA] | 90.00654 | 39.81399 | 10.431815 | 2.091189 |
| 16 | [oCs\|oUs\|oAp\|oGp\|oGs\|dTs\|dGs\|dAs\|dTs\|dGs\|5mCs\|dAs\|5mCs\|dTs\|dGs\|oCp\|oUp\|oUs\|oUs\|oA] | 93.50777 | 41.81402 | 6.027847 | 2.177984 |
| 17 | [oCs\|oUs\|oAs\|oGs\|oGs\|dTs\|dGs\|dAs\|dTs\|dGs\|5mCs\|dAs\|5mCs\|dTs\|dGs\|oCs\|oUs\|oUs\|oUs\|oAs\|oC] | 78.87919 | 39.04837 | 4.3289815 | 3.888626 |
| 18 | [oCs\|oUs\|oAp\|oGs\|oGs\|dTs\|dGs\|dAs\|dTs\|dGs\|5mCs\|dAs\|5mCs\|dTs\|dGs\|oCs\|oUs\|oUs\|oUs\|oAs\|oC] | 89.8343 | 37.95063 | 6.6130055 | 2.550701 |
| 19 | [oCs\|oUs\|oAs\|oGp\|oGs\|dTs\|dGs\|dAs\|dTs\|dGs\|5mCs\|dAs\|5mCs\|dTs\|dGs\|oCs\|oUs\|oUs\|oUs\|oAs\|oC] | 91.97128 | 45.99061 | 1.903787 | 2.837245 |
| 20 | [oCs\|oUs\|oAp\|oGp\|oGs\|dTs\|dGs\|dAs\|dTs\|dGs\|5mCs\|dAs\|5mCs\|dTs\|dGs\|oCs\|oUs\|oUs\|oUs\|oAs\|oC] | 90.0287 | 45.36505 | 7.652128 | 3.536383 |
| 21 | [oCs\|oUs\|oAs\|oGs\|oGs\|dTs\|dGs\|dAs\|dTs\|dGs\|5mCs\|dAs\|5mCs\|dTs\|dGs\|oCs\|oUp\|oUs\|oUs\|oAs\|oC] | 80.24857 | 37.65808 | 8.935247 | 5.090914 |
| 22 | [oCs\|oUs\|oAs\|oGs\|oGs\|dTs\|dGs\|dAs\|dTs\|dGs\|5mCs\|dAs\|5mCs\|dTs\|dGs\|oCp\|oUs\|oUs\|oUs\|oAs\|oC] | 101.45303 | 37.27497 | 23.097582 | 3.052247 |
| 23 | [oCs\|oUs\|oAs\|oGs\|oGs\|dTs\|dGs\|dAs\|dTs\|dGs\|5mCs\|dAs\|5mCs\|dTs\|dGs\|oCp\|oUp\|oUs\|oUs\|oAs\|oC] | 97.15427 | 41.07113 | 12.915649 | 3.502463 |
| 24 | [oCs\|oUs\|oAp\|oGs\|oGs\|dTs\|dGs\|dAs\|dTs\|dGs\|5mCs\|dAs\|5mCs\|dTs\|dGs\|oCs\|oUp\|oUs\|oUs\|oAs\|oC] | 80.67146 | 37.30983 | 3.1350315 | 4.460652 |
| 25 | [oCs\|oUs\|oAp\|oGs\|oGs\|dTs\|dGs\|dAs\|dTs\|dGs\|5mCs\|dAs\|5mCs\|dTs\|dGs\|oCp\|oUs\|oUs\|oUs\|oAs\|oC] | 90.35424 | 39.93492 | 10.3572485 | 3.866769 |
| 26 | [oCs\|oUs\|oAs\|oGp\|oGs\|dTs\|dGs\|dAs\|dTs\|dGs\|5mCs\|dAs\|5mCs\|dTs\|dGs\|oCs\|oUp\|oUs\|oUs\|oAs\|oC] | 82.80083 | 43.89603 | 2.679553 | 3.062266 |
| 27 | [oCs\|oUs\|oAs\|oGp\|oGs\|dTs\|dGs\|dAs\|dTs\|dGs\|5mCs\|dAs\|5mCs\|dTs\|dGs\|oCp\|oUs\|oUs\|oUs\|oAs\|oC] | 88.08068 | 46.08224 | 6.516991 | 2.883583 |
| 28 | [oCs\|oUs\|oAp\|oGs\|oGs\|dTs\|dGs\|dAs\|dTs\|dGs\|5mCs\|dAs\|5mCs\|dTs\|dGs\|oCp\|oUp\|oUs\|oUs\|oAs\|oC] | 100.38683 | 42.14532 | 7.9455835 | 2.066183 |
| 29 | [oCs\|oUs\|oAs\|oGp\|oGs\|dTs\|dGs\|dAs\|dTs\|dGs\|5mCs\|dAs\|5mCs\|dTs\|dGs\|oCp\|oUp\|oUs\|oUs\|oAs\|oC] | 82.39148 | 42.89111 | 4.9474165 | 1.687775 |
| 30 | [oCs\|oUs\|oAp\|oGp\|oGs\|dTs\|dGs\|dAs\|dTs\|dGs\|5mCs\|dAs\|5mCs\|dTs\|dGs\|oCs\|oUp\|oUs\|oUs\|oAs\|oC] | 92.49721 | 41.87519 | 4.286409 | 1.419928 |
| 31 | [oCs\|oUs\|oAp\|oGp\|oGs\|dTs\|dGs\|dAs\|dTs\|dGs\|5mCs\|dAs\|5mCs\|dTs\|dGs\|oCp\|oUs\|oUs\|oUs\|oAs\|oC] | 88.1524 | 43.50525 | 4.0152095 | 1.165505 |
| 32 | [oCs\|oUs\|oAp\|oGp\|oGs\|dTs\|dGs\|dAs\|dTs\|dGs\|5mCs\|dAs\|5mCs\|dTs\|dGs\|oCp\|oUp\|oUs\|oUs\|oAs\|oC] | 95.59035 | 44.36914 | 6.098232 | 1.947992 |
| 33 | [oCs\|oUs\|oAs\|oGs\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oA] | 81.5396 | 46.37686 | 5.051866 | 2.340369 |

TABLE 3-continued

| Antisense Oligo No./ SEQ ID NO: | Chem Mod Seq | Mean % mRNA Remaining | | SEM % mRNA Remaining | |
|---|---|---|---|---|---|
| | | 1 nM | 10 nM | 1 nM | 10 nM |
| 34 | [oCs\|oUs\|oAp\|oGs\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oA] | 75.50977 | 37.42608 | 6.55804 | 2.427113 |
| 35 | [oCs\|oUs\|oAs\|oGp\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oA] | 86.89931 | 38.66673 | 1.6915285 | 0.403006 |
| 36 | [oCs\|oUs\|oAp\|oGp\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oA] | 92.05609 | 44.46799 | 6.699515 | 0.811156 |
| 37 | [oCs\|oUs\|oAs\|oGs\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oA] | 82.63172 | 39.09093 | 8.238769 | 2.549669 |
| 38 | [oCs\|oUs\|oAs\|oGs\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oA] | 102.24694 | 36.96398 | 14.530799 | 2.884441 |
| 39 | [oCs\|oUs\|oAs\|oGs\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oA] | 87.2629 | 39.3864 | 12.0735685 | 1.500768 |
| 40 | [oCs\|oUs\|oAp\|oGs\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oA] | 96.78945 | 37.19026 | 9.535124 | 1.52692 |
| 41 | [oCs\|oUs\|oAp\|oGs\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oA] | 95.79925 | 45.78015 | 7.062957 | 5.396491 |
| 42 | [oCs\|oUs\|oAs\|oGp\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oA] | 87.43444 | 39.82331 | 10.1333325 | 1.186569 |
| 43 | [oCs\|oUs\|oAs\|oGp\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oA] | 93.03859 | 41.55274 | 8.5237595 | 1.542313 |
| 44 | [oCs\|oUs\|oAp\|oGs\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oA] | 79.29174 | 41.69657 | 9.4802245 | 3.7328 |
| 45 | [oCs\|oUs\|oAs\|oGp\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oA] | 97.84352 | 40.24762 | 4.024119 | 3.662828 |
| 46 | [oCs\|oUs\|oAp\|oGp\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oA] | 94.18266 | 36.69312 | 3.2339695 | 2.577563 |
| 47 | [oCs\|oUs\|oAp\|oGp\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oA] | 97.71451 | 49.27591 | 15.6053125 | 5.231299 |
| 48 | [oCs\|oUs\|oAp\|oGp\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oA] | 91.5412 | 44.77662 | 6.4424815 | 4.030398 |
| 49 | [oCs\|oUs\|oAs\|oGs\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oAs\|oC] | 85.14544 | 43.97438 | 5.329607 | 1.787627 |
| 50 | [oCs\|oUs\|oAp\|oGs\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oAs\|oC] | 81.85128 | 40.2583 | 5.194841 | 1.498131 |
| 51 | [oCs\|oUs\|oAs\|oGp\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oAs\|oC] | 79.48116 | 41.09427 | 2.3949705 | 1.899097 |
| 52 | [oCs\|oUs\|oAp\|oGp\|oGs\|dTs\|dGs\|dAs\|dTs\|dGs\|5mCs\|dAs\|5mCs\|dTs\|dGs\|oCs\|oUs\|oUs\|oUs\|oAs\|oCs\|oAs\|oC] | 82.36726 | 40.83192 | 5.178712 | 3.06104 |
| 53 | [oCs\|oUs\|oAs\|oGs\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oAs\|oC] | 73.45186 | 36.40204 | 4.508506 | 2.072795 |
| 54 | [oCs\|oUs\|oAs\|oGs\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oAs\|oC] | 83.26679 | 42.28042 | 9.2488475 | 3.422593 |
| 55 | [oCs\|oUs\|oAs\|oGs\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oAs\|oC] | 73.0733 | 44.80567 | 3.2515675 | 5.215558 |

TABLE 3-continued

| Anti-sense Oligo No./ SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 56 | [oCs\|oUs\|oAp\|oGs\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oAs\|oC] | 86.11374 | 41.79482 | 6.120118 | 3.145374 |
| 57 | [oCs\|oUs\|oAp\|oGs\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oAs\|oC] | 82.10891 | 41.5037 | 10.9839625 | 2.257748 |
| 58 | [oCs\|oUs\|oAs\|oGp\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oAs\|oC] | 89.70608 | 40.60014 | 3.8721065 | 0.87326 |
| 59 | [oCs\|oUs\|oAs\|oGp\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oAs\|oC] | 93.23447 | 43.85248 | 4.0394125 | 4.050107 |
| 60 | [oCs\|oUs\|oAp\|oGs\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oAs\|oC] | 80.85138 | 43.55119 | 6.949772 | 3.486459 |
| 61 | [oCs\|oUs\|oAs\|oGp\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oAs\|oC] | 77.98907 | 37.1955 | 9.4067375 | 1.362401 |
| 62 | [oCs\|oUs\|oAp\|oGp\|oGs\|dTs\|dGs\|dAs\|dTs\|dGs\|5mCs\|dAs\|5mCs\|dTs\|dGs\|oCs\|oUp\|oUs\|oUs\|oAs\|oCs\|oAs\|oC] | 71.11867 | 37.22296 | 7.9519255 | 2.922158 |
| 63 | [oCs\|oUs\|oAp\|oGp\|oGs\|dTs\|dGs\|dAs\|dTs\|dGs\|5mCs\|dAs\|5mCs\|dTs\|dGs\|oCp\|oUs\|oUs\|oUs\|oAs\|oCs\|oAs\|oC] | 81.67628 | 40.47476 | 2.889408 | 2.316071 |
| 64 | [oCs\|oUs\|oAp\|oGp\|oGs\|dTs\|dGs\|dAs\|dTs\|dGs\|5mCs\|dAs\|5mCs\|dTs\|dGs\|oCp\|oUp\|oUs\|oUs\|oAs\|oCs\|oAs\|oC] | 79.69746 | 38.81524 | 7.742031 | 0.204948 |
| 65 | [oCs\|oUs\|oAs\|oGs\|oGs\|dTs\|dGs\|dAs\|dTs\|dGs\|5mCs\|dAs\|5mCs\|dTs\|dGs\|5mCs\|oUs\|oUs\|oUs\|oAs\|oC] | 69.99261 | 32.0998 | 5.4826715 | 3.037028 |
| 66 | [oCs\|oUs\|oAp\|oGs\|oGs\|dTs\|dGs\|dAs\|dTs\|dGs\|5mCs\|dAs\|5mCs\|dTs\|dGs\|5mCs\|oUs\|oUs\|oUs\|oAs\|oC] | 75.98915 | 34.73835 | 3.798421 | 3.084744 |
| 67 | [oCs\|oUs\|oAs\|oGp\|oGs\|dTs\|dGs\|dAs\|dTs\|dGs\|5mCs\|dAs\|5mCs\|dTs\|dGs\|5mCs\|oUs\|oUs\|oUs\|oAs\|oC] | 83.04812 | 42.68424 | 4.758469 | 4.679494 |
| 68 | [oCs\|oUs\|oAp\|oGp\|oGs\|dTs\|dGs\|dAs\|dTs\|dGs\|5mCs\|dAs\|5mCs\|dTs\|dGs\|5mCs\|oUs\|oUs\|oUs\|oAs\|oC] | 74.06207 | 38.55632 | 9.9099225 | 7.981079 |
| 69 | [oCs\|oUs\|oAs\|oGs\|oGs\|dTs\|dGs\|dAs\|dTs\|dGs\|5mCs\|dAs\|5mCs\|dTs\|dGs\|5mCs\|oUp\|oUs\|oUs\|oAs\|oC] | 81.32662 | 38.51888 | 1.5401265 | 2.565575 |
| 70 | [oCs\|oUs\|oAs\|oGs\|oGs\|dTs\|dGs\|dAs\|dTs\|dGs\|5mCs\|dAs\|5mCs\|dTs\|dGs\|5mCp\|oUs\|oUs\|oUs\|oAs\|oC] | 79.67053 | 27.90351 | 2.039101 | 1.648429 |
| 71 | [oCs\|oUs\|oAs\|oGs\|oGs\|dTs\|dGs\|dAs\|dTs\|dGs\|5mCs\|dAs\|5mCs\|dTs\|dGs\|5mCp\|oUp\|oUs\|oUs\|oAs\|oC] | 72.32385 | 34.23619 | 4.994041 | 3.100586 |
| 72 | [oCs\|oUs\|oAp\|oGs\|oGs\|dTs\|dGs\|dAs\|dTs\|dGs\|5mCs\|dAs\|5mCs\|dTs\|dGs\|5mCs\|oUp\|oUs\|oUs\|oAs\|oC] | 73.88174 | 35.08737 | 3.987852 | 3.319998 |
| 73 | [oCs\|oUs\|oAp\|oGs\|oGs\|dTs\|dGs\|dAs\|dTs\|dGs\|5mCs\|dAs\|5mCs\|dTs\|dGs\|5mCp\|oUs\|oUs\|oUs\|oAs\|oC] | 73.84298 | 39.89966 | 6.744107 | 3.444095 |
| 74 | [oCs\|oUs\|oAs\|oGp\|oGs\|dTs\|dGs\|dAs\|dTs\|dGs\|5mCs\|dAs\|5mCs\|dTs\|dGs\|5mCs\|oUp\|oUs\|oUs\|oAs\|oC] | 87.48091 | 31.76795 | 4.7688275 | 2.561686 |
| 75 | [oCs\|oUs\|oAs\|oGp\|oGs\|dTs\|dGs\|dAs\|dTs\|dGs\|5mCs\|dAs\|5mCs\|dTs\|dGs\|5mCp\|oUs\|oUs\|oUs\|oAs\|oC] | 85.5695 | 37.95998 | 7.860177 | 4.320679 |
| 76 | [oCs\|oUs\|oAp\|oGs\|oGs\|dTs\|dGs\|dAs\|dTs\|dGs\|5mCs\|dAs\|5mCs\|dTs\|dGs\|5mCp\|oUp\|oUs\|oUs\|oAs\|oC] | 82.15887 | 38.7112 | 6.4298045 | 2.851738 |

TABLE 3-continued

| Anti-sense Oligo No./SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 77 | [oCs\|oUs\|oAs\|oGp\|oGs\|dTs\|dGs\|dAs\|dTs\|dGs\|5mCs\|dAs\|5mCs\|dTs\|dGs\|5mCp\|oUp\|oUs\|oUs\|oAs\|oC] | 92.45412 | 41.20665 | 7.931752 | 5.873654 |
| 78 | [oCs\|oUs\|oAp\|oGp\|oGs\|dTs\|dGs\|dAs\|dTs\|dGs\|5mCs\|dAs\|5mCs\|dTs\|dGs\|5mCs\|oUp\|oUs\|oUs\|oAs\|oC] | 87.20785 | 34.56143 | 6.5475275 | 3.904361 |
| 79 | [oCs\|oUs\|oAp\|oGp\|oGs\|dTs\|dGs\|dAs\|dTs\|dGs\|5mCs\|dAs\|5mCs\|dTs\|dGs\|5mCp\|oUs\|oUs\|oUs\|oAs\|oC] | 77.67484 | 47.25886 | 4.025454 | 9.140193 |
| 80 | [oCs\|oUs\|oAp\|oGp\|oGs\|dTs\|dGs\|dAs\|dTs\|dGs\|5mCs\|dAs\|5mCs\|dTs\|dGs\|5mCp\|oUp\|oUs\|oUs\|oAs\|oC] | 84.26525 | 44.90753 | 2.9419125 | 3.931427 |
| 81 | [oCs\|oUs\|oAs\|oGs\|oGs\|dTs\|dGs\|dAs\|dTs\|dGs\|5mCs\|dAs\|5mCs\|dTs\|dGs\|5mCs\|dTs\|oUs\|oUs\|oAs\|oCs\|oA] | 74.15488 | 28.91957 | 4.4416545 | 2.079845 |
| 82 | [oCs\|oUs\|oAp\|oGs\|oGs\|dTs\|dGs\|dAs\|dTs\|dGs\|5mCs\|dAs\|5mCs\|dTs\|dGs\|5mCs\|dTs\|oUs\|oUs\|oAs\|oCs\|oA] | 83.52985 | 34.76393 | 7.7233095 | 5.276733 |
| 83 | [oCs\|oUs\|oAs\|oGp\|oGs\|dTs\|dGs\|dAs\|dTs\|dGs\|5mCs\|dAs\|5mCs\|dTs\|dGs\|5mCs\|dTs\|oUs\|oUs\|oAs\|oCs\|oA] | 87.34228 | 34.26426 | 2.8872435 | 3.491405 |
| 84 | [oCs\|oUs\|oAp\|oGp\|oGs\|dTs\|dGs\|dAs\|dTs\|dGs\|5mCs\|dAs\|5mCs\|dTs\|dGs\|5mCs\|dTs\|oUs\|oUs\|oAs\|oCs\|oA] | 85.67873 | 35.6361 | 5.8302875 | 2.544952 |
| 85 | [oCs\|oUs\|oAs\|oGs\|oGs\|dTs\|dGs\|dAs\|dTs\|dGs\|5mCs\|dAs\|5mCs\|dTs\|dGs\|5mCs\|dTp\|oUs\|oUs\|oAs\|oCs\|oA] | 75.35312 | 32.86732 | 10.951265 | 3.621277 |
| 86 | [oCs\|oUs\|oAs\|oGs\|oGs\|dTs\|dGs\|dAs\|dTs\|dGs\|5mCs\|dAs\|5mCs\|dTs\|dGs\|5mCp\|dTs\|oUs\|oUs\|oAs\|oCs\|oA] | 79.96271 | 34.14079 | 9.351093 | 1.427892 |
| 87 | [oCs\|oUs\|oAs\|oGs\|oGs\|dTs\|dGs\|dAs\|dTs\|dGs\|5mCs\|dAs\|5mCs\|dTs\|dGs\|5mCp\|dTp\|oUs\|oUs\|oAs\|oCs\|oA] | 100.34146 | 32.93465 | 7.409104 | 1.965485 |
| 88 | [oCs\|oUs\|oAp\|oGs\|oGs\|dTs\|dGs\|dAs\|dTs\|dGs\|5mCs\|dAs\|5mCs\|dTs\|dGs\|5mCs\|dTp\|oUs\|oUs\|oAs\|oCs\|oA] | 76.43184 | 29.11159 | 1.9009085 | 1.712673 |
| 89 | [oCs\|oUs\|oAp\|oGs\|oGs\|dTs\|dGs\|dAs\|dTs\|dGs\|5mCs\|dAs\|5mCs\|dTs\|dGs\|5mCp\|dTs\|oUs\|oUs\|oAs\|oCs\|oA] | 84.95746 | 33.1336 | 6.0100595 | 0.819655 |
| 90 | [oCs\|oUs\|oAs\|oGp\|oGs\|dTs\|dGs\|dAs\|dTs\|dGs\|5mCs\|dAs\|5mCs\|dTs\|dGs\|5mCs\|dTp\|oUs\|oUs\|oAs\|oCs\|oA] | 77.40614 | 34.79199 | 2.737082 | 1.090979 |
| 91 | [oCs\|oUs\|oAs\|oGp\|oGs\|dTs\|dGs\|dAs\|dTs\|dGs\|5mCs\|dAs\|5mCs\|dTs\|dGs\|5mCp\|dTs\|oUs\|oUs\|oAs\|oCs\|oA] | 75.61531 | 41.57976 | 2.6137425 | 2.594538 |
| 92 | [oCs\|oUs\|oAp\|oGs\|oGs\|dTs\|dGs\|dAs\|dTs\|dGs\|5mCs\|dAs\|5mCs\|dTs\|dGs\|5mCp\|dTp\|oUs\|oUs\|oAs\|oCs\|oA] | 81.40445 | 36.37792 | 7.319196 | 0.14288 |
| 93 | [oCs\|oUs\|oAs\|oGp\|oGs\|dTs\|dGs\|dAs\|dTs\|dGs\|5mCs\|dAs\|5mCs\|dTs\|dGs\|5mCp\|dTp\|oUs\|oUs\|oAs\|oCs\|oA] | 87.14688 | 41.27511 | 2.983684 | 3.624091 |
| 94 | [oCs\|oUs\|oAp\|oGp\|oGs\|dTs\|dGs\|dAs\|dTs\|dGs\|5mCs\|dAs\|5mCs\|dTs\|dGs\|5mCs\|dTp\|oUs\|oUs\|oAs\|oCs\|oA] | 83.39023 | 40.63864 | 1.431887 | 1.205991 |
| 95 | [oCs\|oUs\|oAp\|oGp\|oGs\|dTs\|dGs\|dAs\|dTs\|dGs\|5mCs\|dAs\|5mCs\|dTs\|dGs\|5mCp\|dTs\|oUs\|oUs\|oAs\|oCs\|oA] | 78.10296 | 40.32743 | 4.682538 | 1.18152 |

TABLE 3-continued

| Antisense Oligo No./SEQ ID NO: | Chem Mod Seq | Mean % mRNA Remaining | | SEM % mRNA Remaining | |
|---|---|---|---|---|---|
| | | 1 nM | 10 nM | 1 nM | 10 nM |
| 96 | [oCs\|oUs\|oAp\|oGp\|oGs\|dTs\|dGs\|dAs\|dTs\|dGs\|5mCs\|dAs\|5mCs\|dTs\|dGs\|5mCp\|dTp\|oUs\|oUs\|oAs\|oCs\|oA] | 78.36184 | 41.53986 | 3.2471535 | 4.451705 |
| 97 | [oUs\|oGs\|oCs\|oUs\|oAs\|dGs\|dGs\|dTs\|dGs\|dAs\|dTs\|dGs\|5mCs\|dAs\|5mCs\|oUs\|oGs\|oCs\|oUs\|oU] | 73.53306 | 32.22054 | 5.7741956 | 1.828104 |
| 98 | [oUs\|oGs\|oCp\|oUs\|oAs\|dGs\|dGs\|dTs\|dGs\|dAs\|dTs\|dGs\|5mCs\|dAs\|5mCs\|oUs\|oGs\|oCs\|oUs\|oU] | 85.30286 | 28.26088 | 7.1938475 | 1.170224 |
| 99 | [oUs\|oGs\|oCs\|oUp\|oAs\|dGs\|dGs\|dTs\|dGs\|dAs\|dTs\|dGs\|5mCs\|dAs\|5mCs\|oUs\|oGs\|oCs\|oUs\|oU] | 80.72095 | 31.14705 | 6.94178635 | 0.847079 |
| 100 | [oUs\|oGs\|oCp\|oUp\|oAs\|dGs\|dGs\|dTs\|dGs\|dAs\|dTs\|dGs\|5mCs\|dAs\|5mCs\|oUs\|oGs\|oCs\|oUs\|oU] | 68.59723 | 30.44545 | 5.6598163 | 1.925702 |
| 101 | [oUs\|oGs\|oCs\|oUs\|oAs\|dGs\|dGs\|dTs\|dGs\|dAs\|dTs\|dGs\|5mCs\|dAs\|5mCs\|oUs\|oGp\|oCs\|oUs\|oU] | 78.30012 | 29.94689 | 6.2378524 | 4.046731 |
| 102 | [oUs\|oGs\|oCs\|oUs\|oAs\|dGs\|dGs\|dTs\|dGs\|dAs\|dTs\|dGs\|5mCs\|dAs\|5mCs\|oUp\|oGs\|oCs\|oUs\|oU] | 78.25236 | 30.06093 | 5.9663877 | 1.79938 |
| 103 | [oUs\|oGs\|oCs\|oUs\|oAs\|dGs\|dGs\|dTs\|dGs\|dAs\|dTs\|dGs\|5mCs\|dAs\|5mCs\|oUp\|oGp\|oCs\|oUs\|oU] | 69.03511 | 35.56989 | 2.59911095 | 2.403012 |
| 104 | [oUs\|oGs\|oCp\|oUs\|oAs\|dGs\|dGs\|dTs\|dGs\|dAs\|dTs\|dGs\|5mCs\|dAs\|5mCs\|oUs\|oGp\|oCs\|oUs\|oU] | 73.74024 | 30.77626 | 1.62019145 | 0.873961 |
| 105 | [oUs\|oGs\|oCp\|oUs\|oAs\|dGs\|dGs\|dTs\|dGs\|dAs\|dTs\|dGs\|5mCs\|dAs\|5mCs\|oUp\|oGs\|oCs\|oUs\|oU] | 72.2508 | 33.81869 | 4.46870435 | 3.070223 |
| 106 | [oUs\|oGs\|oCs\|oUp\|oAs\|dGs\|dGs\|dTs\|dGs\|dAs\|dTs\|dGs\|5mCs\|dAs\|5mCs\|oUs\|oGp\|oCs\|oUs\|oU] | 80.18669 | 27.94099 | 3.6700273 | 0.683295 |
| 107 | [oUs\|oGs\|oCs\|oUp\|oAs\|dGs\|dGs\|dTs\|dGs\|dAs\|dTs\|dGs\|5mCs\|dAs\|5mCs\|oUp\|oGs\|oCs\|oUs\|oU] | 74.09831 | 34.42556 | 6.01870395 | 1.988182 |
| 108 | [oUs\|oGs\|oCp\|oUs\|oAs\|dGs\|dGs\|dTs\|dGs\|dAs\|dTs\|dGs\|5mCs\|dAs\|5mCs\|oUp\|oGp\|oCs\|oUs\|oU] | 70.94729 | 35.1242 | 1.85488915 | 3.987895 |
| 109 | [oUs\|oGs\|oCs\|oUp\|oAs\|dGs\|dGs\|dTs\|dGs\|dAs\|dTs\|dGs\|5mCs\|dAs\|5mCs\|oUp\|oGp\|oCs\|oUs\|oU] | 78.33754 | 34.87067 | 4.7590703 | 1.027952 |
| 110 | [oUs\|oGs\|oCp\|oUp\|oAs\|dGs\|dGs\|dTs\|dGs\|dAs\|dTs\|dGs\|5mCs\|dAs\|5mCs\|oUs\|oGp\|oCs\|oUs\|oU] | 62.32599 | 33.30946 | 3.7307496 | 2.867815 |
| 111 | [oUs\|oGs\|oCp\|oUp\|oAs\|dGs\|dGs\|dTs\|dGs\|dAs\|dTs\|dGs\|5mCs\|dAs\|5mCs\|oUp\|oGs\|oCs\|oUs\|oU] | 70.12462 | 35.35927 | 3.28310255 | 2.413138 |
| 112 | [oUs\|oGs\|oCp\|oUp\|oAs\|dGs\|dGs\|dTs\|dGs\|dAs\|dTs\|dGs\|5mCs\|dAs\|5mCs\|oUp\|oGp\|oCs\|oUs\|oU] | 76.05292 | 32.20627 | 7.8049074 | 3.219622 |
| 113 | [oUs\|oGs\|oCs\|oUs\|oAs\|dGs\|dGs\|dTs\|dGs\|dAs\|dTs\|dGs\|5mCs\|dAs\|5mCs\|oUs\|oGs\|oCs\|oUs\|oUs\|oU] | 65.23498 | 32.17334 | 3.72245235 | 1.859401 |
| 114 | [oUs\|oGs\|oCp\|oUs\|oAs\|dGs\|dGs\|dTs\|dGs\|dAs\|dTs\|dGs\|5mCs\|dAs\|5mCs\|oUs\|oGs\|oCs\|oUs\|oUs\|oU] | 69.29675 | 32.68384 | 2.39326015 | 4.127576 |
| 115 | [oUs\|oGs\|oCs\|oUp\|oAs\|dGs\|dGs\|dTs\|dGs\|dAs\|dTs\|dGs\|5mCs\|dAs\|5mCs\|oUs\|oGs\|oCs\|oUs\|oUs\|oU] | 70.21315 | 28.19354 | 5.9917878 | 1.260233 |
| 116 | [oUs\|oGs\|oCp\|oUp\|oAs\|dGs\|dGs\|dTs\|dGs\|dAs\|dTs\|dGs\|5mCs\|dAs\|5mCs\|oUs\|oGs\|oCs\|oUs\|oUs\|oU] | 61.38246 | 27.89351 | 2.31272875 | 0.940955 |
| 117 | [oUs\|oGs\|oCs\|oUs\|oAs\|dGs\|dGs\|dTs\|dGs\|dAs\|dTs\|dGs\|5mCs\|dAs\|5mCs\|oUs\|oGp\|oCs\|oUs\|oUs\|oU] | 67.38278 | 29.83921 | 4.699614 | 3.62231 |
| 118 | [oUs\|oGs\|oCs\|oUs\|oAs\|dGs\|dGs\|dTs\|dGs\|dAs\|dTs\|dGs\|5mCs\|dAs\|5mCs\|oUp\|oGs\|oCs\|oUs\|oUs\|oU] | 74.8669 | 33.51358 | 4.66523895 | 3.23944 |
| 119 | [oUs\|oGs\|oCs\|oUs\|oAs\|dGs\|dGs\|dTs\|dGs\|dAs\|dTs\|dGs\|5mCs\|dAs\|5mCs\|oUp\|oGp\|oCs\|oUs\|oUs\|oU] | 75.87658 | 33.86225 | 3.36764485 | 2.561053 |

TABLE 3-continued

| Anti-sense Oligo No./ SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 120 | [oUs\|oGs\|oCp\|oUs\|oAs\|dGs\|dGs\|dTs\|dGs\|dAs\|dTs\|dGs\|5mCs\|dAs\|5mCs\|oUs\|oGp\|oCs\|oUs\|oUs\|oU] | 74.89974 | 30.42127 | 5.3692428 | 1.390075 |
| 121 | [oUs\|oGs\|oCp\|oUs\|oAs\|dGs\|dGs\|dTs\|dGs\|dAs\|dTs\|dGs\|5mCs\|dAs\|5mCs\|oUp\|oGs\|oCs\|oUs\|oUs\|oU] | 77.25051 | 35.01204 | 10.42313865 | 2.358081 |
| 122 | [oUs\|oGs\|oCs\|oUp\|oAs\|dGs\|dGs\|dTs\|dGs\|dAs\|dTs\|dGs\|5mCs\|dAs\|5mCs\|oUs\|oGp\|oCs\|oUs\|oUs\|oU] | 68.7315 | 29.79101 | 4.2400331 | 3.545545 |
| 123 | [oUs\|oGs\|oCs\|oUp\|oAs\|dGs\|dGs\|dTs\|dGs\|dAs\|dTs\|dGs\|5mCs\|dAs\|5mCs\|oUp\|oGs\|oCs\|oUs\|oUs\|oU] | 71.42427 | 34.17864 | 4.1743313 | 2.028014 |
| 124 | [oUs\|oGs\|oCp\|oUs\|oAs\|dGs\|dGs\|dTs\|dGs\|dAs\|dTs\|dGs\|5mCs\|dAs\|5mCs\|oUp\|oGp\|oCs\|oUs\|oUs\|oU] | 86.14101 | 31.27527 | 4.48923135 | 2.071295 |
| 125 | [oUs\|oGs\|oCs\|oUp\|oAs\|dGs\|dGs\|dTs\|dGs\|dAs\|dTs\|dGs\|5mCs\|dAs\|5mCs\|oUp\|oGp\|oCs\|oUs\|oUs\|oU] | 77.77647 | 31.7119 | 4.05551285 | 1.114638 |
| 126 | [oUs\|oGs\|oCp\|oUp\|oAs\|dGs\|dGs\|dTs\|dGs\|dAs\|dTs\|dGs\|5mCs\|dAs\|5mCs\|oUs\|oGp\|oCs\|oUs\|oUs\|oU] | 78.6535 | 37.61556 | 1.55106765 | 2.362156 |
| 127 | [oUs\|oGs\|oCp\|oUp\|oAs\|dGs\|dGs\|dTs\|dGs\|dAs\|dTs\|dGs\|5mCs\|dAs\|5mCs\|oUp\|oGs\|oCs\|oUs\|oUs\|oU] | 67.14048 | 33.39059 | 1.7917388 | 1.42932 |
| 128 | [oUs\|oGs\|oCp\|oUp\|oAs\|dGs\|dGs\|dTs\|dGs\|dAs\|dTs\|dGs\|5mCs\|dAs\|5mCs\|oUp\|oGp\|oCs\|oUs\|oUs\|oU] | 86.42336 | 39.03898 | 2.597663 | 2.239799 |
| 129 | [oUs\|oGs\|oCs\|oUs\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oA] | 68.63405 | 35.13624 | 1.53173715 | 2.451205 |
| 130 | [oUs\|oGs\|oCp\|oUs\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oA] | 69.38908 | 31.9245 | 4.0133836 | 3.413571 |
| 131 | [oUs\|oGs\|oCs\|oUp\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oA] | 82.64957 | 31.6315 | 10.9520439 | 1.487167 |
| 132 | [oUs\|oGs\|oCp\|oUp\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oA] | 76.22312 | 31.57458 | 5.88891735 | 2.253033 |
| 133 | [oUs\|oGs\|oCs\|oUs\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oA] | 73.47365 | 27.08401 | 3.77061195 | 0.92052 |
| 134 | [oUs\|oGs\|oCs\|oUs\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oA] | 70.30414 | 33.09977 | 4.27095005 | 3.045878 |
| 135 | [oUs\|oGs\|oCs\|oUs\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oA] | 72.20899 | 30.08256 | 6.4512196 | 1.841916 |
| 136 | [oUs\|oGs\|oCp\|oUs\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oA] | 67.44648 | 31.14491 | 2.3933433 | 2.847244 |
| 137 | [oUs\|oGs\|oCp\|oUs\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oA] | 73.72042 | 31.65609 | 3.1864744 | 1.736871 |
| 138 | [oUs\|oGs\|oCs\|oUp\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oA] | 67.00788 | 29.57105 | 4.13148395 | 0.996282 |
| 139 | [oUs\|oGs\|oCs\|oUp\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oA] | 67.67345 | 29.52463 | 2.84221865 | 1.821037 |

TABLE 3-continued

| Anti-sense Oligo No./ SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 140 | [oUs\|oGs\|oCp\|oUs\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oA] | 74.02419 | 34.75728 | 4.05854245 | 2.515477 |
| 141 | [oUs\|oGs\|oCs\|oUp\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oA] | 70.79225 | 32.87075 | 1.72015605 | 1.818799 |
| 142 | [oUs\|oGs\|oCp\|oUp\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oA] | 80.55014 | 28.38316 | 4.20708315 | 1.230702 |
| 143 | [oUs\|oGs\|oCp\|oUp\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oA] | 62.97423 | 33.06359 | 2.1320595 | 3.346436 |
| 144 | [oUs\|oGs\|oCp\|oUp\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oA] | 70.79163 | 33.67681 | 5.18027175 | 3.32755 |
| 145 | [oUs\|oGs\|oCs\|oUs\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oAs\|oC] | 61.07007 | 32.76229 | 1.578968 | 2.337807 |
| 146 | [oUs\|oGs\|oCp\|oUs\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oAs\|oC] | 77.42478 | 34.61478 | 7.0884636 | 3.366066 |
| 147 | [oUs\|oGs\|oCs\|oUp\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oAs\|oC] | 67.36325 | 38.44457 | 3.158251 | 2.192247 |
| 148 | [oUs\|oGs\|oCp\|oUp\|oAs\|dGs\|dGs\|dTs\|dGs\|dAs\|dTs\|dGs\|5mCs\|dAs\|5mCs\|oUs\|oGs\|oCs\|oUs\|oUs\|oUs\|oAs\|oC] | 69.55673 | 34.56908 | 2.1775117 | 2.805347 |
| 149 | [oUs\|oGs\|oCs\|oUs\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oAs\|oC] | 82.73055 | 33.15298 | 3.68306915 | 2.319368 |
| 150 | [oUs\|oGs\|oCs\|oUs\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oAs\|oC] | 74.0629 | 34.61137 | 4.9070243 | 1.082019 |
| 151 | [oUs\|oGs\|oCs\|oUs\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oAs\|oC] | 86.07845 | 39.51103 | 3.76062145 | 3.134823 |
| 152 | [oUs\|oGs\|oCp\|oUs\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oAs\|oC] | 82.2174 | 29.35929 | 3.78661745 | 1.69256 |
| 153 | [oUs\|oGs\|oCp\|oUs\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oAs\|oC] | 75.98421 | 35.81497 | 2.16191275 | 2.093193 |
| 154 | [oUs\|oGs\|oCs\|oUp\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oAs\|oC] | 68.75699 | 32.99567 | 4.0256092 | 1.228557 |
| 155 | [oUs\|oGs\|oCs\|oUp\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oAs\|oC] | 65.0077 | 33.91453 | 4.8970901 | 1.843589 |
| 156 | [oUs\|oGs\|oCp\|oUs\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oAs\|oC] | 81.28814 | 36.71857 | 4.66906275 | 3.495077 |
| 157 | [oUs\|oGs\|oCs\|oUp\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oAs\|oC] | 69.80645 | 66.34306 | 2.97949155 | 17.28836 |

TABLE 3-continued

| Anti-sense Oligo No./ SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 158 | [oUs\|oGs\|oCp\|oUp\|oAs\|dGs\|dGs\|dTs\|dGs\|dAs\|dTs\|dGs\|5mCs\|dAs\|5mCs\|oUs\|oGp\|oCs\|oUs\|oUs\|oUs\|oAs\|oC] | 68.37275 | 72.33517 | 4.17040095 | 18.58276 |
| 159 | [oUs\|oGs\|oCp\|oUp\|oAs\|dGs\|dGs\|dTs\|dGs\|dAs\|dTs\|dGs\|5mCs\|dAs\|5mCs\|oUp\|oGs\|oCs\|oUs\|oUs\|oUs\|oAs\|oC] | 72.61681 | 47.70773 | 2.2537468 | 6.897452 |
| 160 | [oUs\|oGs\|oCp\|oUp\|oAs\|dGs\|dGs\|dTs\|dGs\|dAs\|dTs\|dGs\|5mCs\|dAs\|5mCs\|oUp\|oGp\|oCs\|oUs\|oUs\|oUs\|oAs\|oC] | 68.78353 | 84.24789 | 3.0864697 | 31.8067 |
| 161 | [oUs\|oGs\|oCs\|oUs\|oAs\|dGs\|dGs\|dTs\|dGs\|dAs\|dTs\|dGs\|5mCs\|dAs\|5mCs\|dTs\|oGs\|oCs\|oUs\|oUs\|oU] | 69.3108 | 75.14277 | 5.38158025 | 25.56809 |
| 162 | [oUs\|oGs\|oCp\|oUs\|oAs\|dGs\|dGs\|dTs\|dGs\|dAs\|dTs\|dGs\|5mCs\|dAs\|5mCs\|dTs\|oGs\|oCs\|oUs\|oUs\|oU] | 72.9714 | 69.75189 | 5.9076121 | 32.69531 |
| 163 | [oUs\|oGs\|oCs\|oUp\|oAs\|dGs\|dGs\|dTs\|dGs\|dAs\|dTs\|dGs\|5mCs\|dAs\|5mCs\|dTs\|oGs\|oCs\|oUs\|oUs\|oU] | 59.9413 | 33.69336 | 2.7716944 | 2.300999 |
| 164 | [oUs\|oGs\|oCp\|oUp\|oAs\|dGs\|dGs\|dTs\|dGs\|dAs\|dTs\|dGs\|5mCs\|dAs\|5mCs\|dTs\|oGs\|oCs\|oUs\|oUs\|oU] | 65.88331 | 42.9639 | 6.38280315 | 2.950032 |
| 165 | [oUs\|oGs\|oCs\|oUs\|oAs\|dGs\|dGs\|dTs\|dGs\|dAs\|dTs\|dGs\|5mCs\|dAs\|5mCs\|dTs\|oGp\|oCs\|oUs\|oUs\|oU] | 60.39611 | 41.07525 | 4.74049725 | 1.401234 |
| 166 | [oUs\|oGs\|oCs\|oUs\|oAs\|dGs\|dGs\|dTs\|dGs\|dAs\|dTs\|dGs\|5mCs\|dAs\|5mCs\|dTp\|oGs\|oCs\|oUs\|oUs\|oU] | 75.65893 | 53.6832 | 6.7614234 | 2.709928 |
| 167 | [oUs\|oGs\|oCs\|oUs\|oAs\|dGs\|dGs\|dTs\|dGs\|dAs\|dTs\|dGs\|5mCs\|dAs\|5mCs\|dTp\|oGp\|oCs\|oUs\|oUs\|oU] | 78.27304 | 68.71663 | 3.6412356 | 20.69837 |
| 168 | [oUs\|oGs\|oCp\|oUs\|oAs\|dGs\|dGs\|dTs\|dGs\|dAs\|dTs\|\|dGs\|5mCs\|dAs\|5mCs\|dTs\|oGp\|oCs\|oUs\|oUs\|oU] | 69.66589 | 40.46645 | 4.8223807 | 1.966849 |
| 169 | [oUs\|oGs\|oCp\|oUs\|oAs\|dGs\|dGs\|dTs\|dGs\|dAs\|dTs\|dGs\|5mCs\|dAs\|5mCs\|dTp\|oGs\|oCs\|oUs\|oUs\|oU] | 65.01222 | 51.18193 | 2.0901017 | 5.432837 |
| 170 | [oUs\|oGs\|oCs\|oUp\|oAs\|dGs\|dGs\|dTs\|dGs\|dAs\|dTs\|dGs\|5mCs\|dAs\|5mCs\|dTs\|oGp\|oCs\|oUs\|oUs\|oU] | 64.20334 | 44.9343 | 3.03968285 | 2.38631 |
| 171 | [oUs\|oGs\|oCs\|oUp\|oAs\|dGs\|dGs\|dTs\|dGs\|dAs\|dTs\|dGs\|5mCs\|dAs\|5mCs\|dTp\|oGs\|oCs\|oUs\|oUs\|oU] | 74.50087 | 46.7009 | 7.1516196 | 3.17865 |
| 172 | oUs\|oGs\|oCp\|oUs\|oAs\|dGs\|dGs\|dTs\|dGs\|dAs\|dTs\|dGs\|5mCs\|dAs\|5mCs\|dTp\|oGp\|oCs\|oUs\|oUs\|oU] | 66.0219 | 51.29474 | 5.5452825 | 7.02709 |
| 173 | [oUs\|oGs\|oCs\|oUp\|oAs\|dGs\|dGs\|dTs\|dGs\|dAs\|dTs\|dGs\|5mCs\|dAs\|5mCs\|dTp\|oGp\|oCs\|oUs\|oUs\|oU] | 88.90626 | 43.66599 | 7.76517935 | 4.598041 |
| 174 | [oUs\|oGs\|oCp\|oUp\|oAs\|dGs\|dGs\|dTs\|dGs\|dAs\|dTs\|dGs\|5mCs\|dAs\|5mCs\|dTs\|oGp\|oCs\|oUs\|oUs\|oU] | 70.63885 | 81.73461 | 10.1429891 | 39.6005 |
| 175 | [oUs\|oGs\|oCp\|oUp\|oAs\|dGs\|dGs\|dTs\|dGs\|dAs\|dTs\|dGs\|5mCs\|dAs\|5mCs\|dTp\|oGs\|oCs\|oUs\|oUs\|oU] | 69.65344 | 57.02863 | 4.09660005 | 13.08032 |
| 176 | [oUs\|oGs\|oCp\|oUp\|oAs\|dGs\|dGs\|dTs\|dGs\|dAs\|dTs\|dGs\|5mCs\|dAs\|5mCs\|dTp\|oGp\|oCs\|oUs\|oUs\|oU] | 71.0292 | 88.44799 | 3.57082955 | 37.50085 |
| 177 | [oUs\|oGs\|oCs\|oUs\|oAs\|dGs\|dGs\|dTs\|dGs\|dAs\|dTs\|dGs\|5mCs\|dAs\|5mCs\|dTs\|dGs\|oCs\|oUs\|oUs\|oUs\|oA] | 66.62139 | 41.51005 | 2.37850925 | 4.804473 |
| 178 | [oUs\|oGs\|oCp\|oUs\|oAs\|dGs\|dGs\|dTs\|dGs\|dAs\|dTs\|dGs\|5mCs\|dAs\|5mCs\|dTs\|dGs\|oCs\|oUs\|oUs\|oUs\|oA] | 72.29763 | 44.50319 | 6.87317685 | 2.677576 |
| 179 | [oUs\|oGs\|oCs\|oUp\|oAs\|dGs\|dGs\|dTs\|dGs\|dAs\|dTs\|\|dGs\|5mCs\|dAs\|5mCs\|dTs\|dGs\|oCs\|oUs\|oUs\|oUs\|oA] | 68.20743 | 47.68644 | 5.01288235 | 7.92615 |

TABLE 3-continued

| Anti-sense Oligo No./ SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 180 | [oUs\|oGs\|oCp\|oUp\|oAs\|dGs\|dGs\|dTs\|dGs\|dAs\|dTs\|\|dGs\|5mCs\|dAs\|5mCs\|dTs\|dGs\|oCs\|oUs\|oUs\|oUs\|oA] | 68.99648 | 42.6724 | 0.11444645 | 1.915543 |
| 181 | [oUs\|oGs\|oCs\|oUs\|oAs\|dGs\|dGs\|dTs\|dGs\|dAs\|dTs\|dGs\|5mCs\|dAs\|5mCs\|dTs\|dGp\|oCs\|oUs\|oUs\|oUs\|oA] | 74.55986 | 75.31866 | 4.8690439 | 16.158 |
| 182 | [oUs\|oGs\|oCs\|oUs\|oAs\|dGs\|dGs\|dTs\|dGs\|dAs\|dTs\|dGs\|5mCs\|dAs\|5mCs\|dTp\|dGs\|oCs\|oUs\|oUs\|oUs\|oA] | 90.17217 | 57.85726 | 6.4500736 | 10.25964 |
| 183 | [oUs\|oGs\|oCs\|oUs\|oAs\|dGs\|dGs\|dTs\|dGs\|dAs\|dTs\|dGs\|5mCs\|dAs\|5mCs\|dTp\|dGp\|oCs\|oUs\|oUs\|oUs\|oA] | 79.6849 | 44.0499 | 4.4692627 | 2.659523 |
| 184 | [oUs\|oGs\|oCp\|oUs\|oAs\|dGs\|dGs\|dTs\|dGs\|dAs\|dTs\|dGs\|5mCs\|dAs\|5mCs\|dTs\|dGp\|oCs\|oUs\|oUs\|oUs\|oA] | 72.7416 | 46.00267 | 6.4985466 | 1.990908 |
| 185 | [oUs\|oGs\|oCp\|oUs\|oAs\|dGs\|dGs\|dTs\|dGs\|dAs\|dTs\|dGs\|5mCs\|dAs\|5mCs\|dTp\|dGs\|oCs\|oUs\|oUs\|oUs\|oA] | 78.36759 | 57.88874 | 8.4461547 | 7.916173 |
| 186 | [oUs\|oGs\|oCs\|oUp\|oAs\|dGs\|dGs\|dTs\|dGs\|dAs\|dTs\|dGs\|5mCs\|dAs\|5mCs\|dTs\|dGp\|oCs\|oUs\|oUs\|oUs\|oA] | 77.17065 | 41.09619 | 4.06900365 | 5.266146 |
| 187 | [oUs\|oGs\|oCs\|oUp\|oAs\|dGs\|dGs\|dTs\|dGs\|dAs\|dTs\|dGs\|5mCs\|dAs\|5mCs\|dTp\|dGs\|oCs\|oUs\|oUs\|oUs\|oA] | 71.80721 | 47.54313 | 4.0522398 | 4.300292 |
| 188 | [oUs\|oGs\|oCp\|oUs\|oAs\|dGs\|dGs\|dTs\|dGs\|dAs\|dTs\|dGs\|5mCs\|dAs\|5mCs\|dTp\|dGp\|oCs\|oUs\|oUs\|oUs\|oA] | 83.68087 | 47.27023 | 11.6233265 | 2.662367 |
| 189 | [oUs\|oGs\|oCs\|oUp\|oAs\|dGs\|dGs\|dTs\|dGs\|dAs\|dTs\|dGs\|5mCs\|dAs\|5mCs\|dTp\|dGp\|oCs\|oUs\|oUs\|oUs\|oA] | 90.45532 | 46.05918 | 4.6439005 | 3.872029 |
| 190 | [oUs\|oGs\|oCp\|oUp\|oAs\|dGs\|dGs\|dTs\|dGs\|dAs\|dTs\|dGs\|5mCs\|dAs\|5mCs\|dTs\|dGp\|oCs\|oUs\|oUs\|oUs\|oA] | 89.19433 | 34.62675 | 9.5661226 | 4.858138 |
| 191 | [oUs\|oGs\|oCp\|oUp\|oAs\|dGs\|dGs\|dTs\|dGs\|dAs\|dTs\|dGs\|5mCs\|dAs\|5mCs\|dTp\|dGs\|oCs\|oUs\|oUs\|oUs\|oA] | 64.72372 | 43.20547 | 3.7289791 | 2.557415 |
| 192 | [oUs\|oGs\|oCp\|oUp\|oAs\|dGs\|dGs\|dTs\|dGs\|dAs\|dTs\|dGs\|5mCs\|dAs\|5mCs\|dTp\|dGp\|oCs\|oUs\|oUs\|oUs\|oA] | 92.70258 | 41.35463 | 12.14039325 | 0.531077 |
| 193 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGs\|oCs\|oAs\|oA] | 41.82279 | 25.79387 | 2.85807925 | 1.785736 |
| 194 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGs\|oCs\|oAs\|oA] | 34.50835 | 24.88784 | 2.37599485 | 2.49983 |
| 195 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGs\|oCs\|oAs\|oA] | 34.48394 | 27.68268 | 3.0471537 | 1.050805 |
| 196 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGs\|oCs\|oAs\|oA] | 35.91642 | 27.09371 | 0.5861107 | 3.367908 |
| 197 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGp\|oCs\|oAs\|oA] | 40.41755 | 30.50893 | 3.2331104 | 1.618927 |

TABLE 3-continued

| Antisense Oligo No./SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 198 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGs\|oCs\|oAs\|oA] | 37.18947 | 26.7628 | 1.96874185 | 1.810888 |
| 199 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGp\|oCs\|oAs\|oA] | 41.58604 | 32.4533 | 2.0955341 | 3.083019 |
| 200 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGp\|oCs\|oAs\|oA] | 41.50165 | 29.4431 | 1.99516615 | 2.336989 |
| 201 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGs\|oCs\|oAs\|oA] | 42.01393 | 23.06252 | 1.3193855 | 4.944764 |
| 202 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGp\|oCs\|oAs\|oA] | 41.74463 | 27.31196 | 3.3971388 | 1.186669 |
| 203 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGs\|oCs\|oAs\|oA] | 40.8989 | 27.94533 | 2.5002774 | 2.019763 |
| 204 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGp\|oCs\|oAs\|oA] | 39.77508 | 30.17107 | 2.68253975 | 3.295311 |
| 205 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGp\|oCs\|oAs\|oA] | 40.56325 | 26.69679 | 1.7302717 | 0.745227 |
| 206 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGp\|oCs\|oAs\|oA] | 39.89604 | 19.42737 | 3.86707555 | 1.982879 |
| 207 | [oUs\|oGs\|oAp\|oUp\|oCs\|5mCs\|dTs\|dGs\|dTs\|dTs\|5mCs\|dTs\|5mCs\|5mCs\|5mCs\|oAp\|oGs\|oCs\|oAs\|oA] | 40.47438 | 25.35393 | 2.3847392 | 1.251586 |
| 208 | [oUs\|oGs\|oAp\|oUp\|oCs\|5mCs\|dTs\|dGs\|dTs\|dTs\|5mCs\|dTs\|5mCs\|5mCs\|5mCs\|oAp\|oGp\|oCs\|oAs\|oA] | 39.84144 | 26.46836 | 2.76645765 | 1.184643 |
| 209 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGs\|oCs\|oAs\|oAs\|oC] | 36.38624 | 24.02288 | 1.92817845 | 1.780277 |
| 210 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGs\|oCs\|oAs\|oAs\|oC] | 36.27817 | 23.59247 | 1.9107749 | 1.785808 |
| 211 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGs\|oCs\|oAs\|oAs\|oC] | 40.23379 | 26.02175 | 3.7752339 | 0.579919 |
| 212 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGs\|oCs\|oAs\|oAs\|oC] | 38.73671 | 25.57041 | 2.1198962 | 0.563413 |
| 213 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGp\|oCs\|oAs\|oAs\|oC] | 35.00403 | 27.29374 | 0.97998025 | 2.42817 |
| 214 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGs\|oCs\|oAs\|oAs\|oC] | 35.15246 | 27.73562 | 3.7541248 | 1.408177 |
| 215 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGp\|oCs\|oAs\|oAs\|oC] | 39.43029 | 24.36535 | 0.35631305 | 2.03814 |

TABLE 3-continued

| Antisense Oligo No./SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 216 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGp\|oCs\|oAs\|oAs\|oC] | 38.4821 | 24.80134 | 2.7737859 | 0.915852 |
| 217 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGs\|oCs\|oAs\|oAs\|oC] | 38.86511 | 22.24657 | 1.93345215 | 1.178782 |
| 218 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGp\|oCs\|oAs\|oAs\|oC] | 40.69835 | 26.7572 | 2.8425562 | 2.117941 |
| 219 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGs\|oCs\|oAs\|oAs\|oC] | 39.97252 | 26.31039 | 1.18627875 | 1.508108 |
| 220 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGp\|oCs\|oAs\|oAs\|oC] | 40.94544 | 24.39298 | 2.69640305 | 1.085099 |
| 221 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGp\|oCs\|oAs\|oAs\|oC] | 39.59504 | 26.25572 | 2.87140485 | 1.887767 |
| 222 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGp\|oCs\|oAs\|oAs\|oC] | 34.32736 | 25.9504 | 1.1160027 | 1.377325 |
| 223 | [oUs\|oGs\|oAp\|oUp\|oCs\|5mCs\|dTs\|dGs\|dTs\|dTs\|5mCs\|dTs\|5mCs\|5mCs\|5mCs\|oAp\|oGs\|oCs\|oAs\|oAs\|oC] | 40.65856 | 25.62251 | 1.38290445 | 2.322099 |
| 224 | [oUs\|oGs\|oAp\|oUp\|oCs\|5mCs\|dTs\|dGs\|dTs\|dTs\|5mCs\|dTs\|5mCs\|5mCs\|5mCs\|oAp\|oGp\|oCs\|oAs\|oAs\|oC] | 38.35045 | 24.81935 | 1.78788745 | 5.896552 |
| 225 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oA] | 38.20957 | 22.48775 | 0.8970076 | 2.000011 |
| 226 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oA] | 33.35769 | 27.38264 | 1.58936325 | 1.493528 |
| 227 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oA] | 30.72978 | 24.56478 | 1.12605755 | 0.803606 |
| 228 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oA] | 41.09495 | 22.65474 | 2.4141379 | 1.912592 |
| 229 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oA] | 36.5236 | 24.84599 | 1.6011969 | 1.293078 |
| 230 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oA] | 34.54957 | 26.61084 | 1.41653565 | 1.233035 |
| 231 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGp\|oCs\|oAs\|oAs\|oCs\|oA] | 46.03036 | 34.13517 | 3.10815325 | 2.788523 |
| 232 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oA] | 35.25195 | 23.45108 | 1.14545295 | 0.875176 |
| 233 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oA] | 39.59948 | 27.15972 | 1.1364332 | 1.671372 |

TABLE 3-continued

| Anti-sense Oligo No./SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 234 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oA] | 29.84471 | 24.57841 | 1.1966453 | 0.580119 |
| 235 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oA] | 35.45558 | 25.43503 | 3.1614937 | 2.281794 |
| 236 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGp\|oCs\|oAs\|oAs\|oCs\|oA] | 33.98368 | 25.36152 | 2.2232316 | 0.753668 |
| 237 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGp\|oCs\|oAs\|oAs\|oCs\|oA] | 35.20734 | 26.34259 | 2.31304315 | 1.232096 |
| 238 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oA] | 34.15353 | 22.53496 | 1.9007468 | 1.47269 |
| 239 | [oUs\|oGs\|oAp\|oUp\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oA] | 34.30311 | 25.10675 | 3.04473305 | 1.325174 |
| 240 | [oUs\|oGs\|oAp\|oUp\|oCs\|5mCs\|dTs\|dGs\|dTs\|dTs\|5mCs\|dTs\|5mCs\|5mCs\|5mCs\|oAp\|oGp\|oCs\|oAs\|oAs\|oCs\|oA] | 32.7831 | 26.79337 | 0.780257 | 1.496388 |
| 241 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oAs\|oC] | 36.83221 | 25.8787465 | 1.45951 | 1.20215 |
| 242 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oAs\|oC] | 35.39125 | 26.34255 | 2.0733604 | 1.939231 |
| 243 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oAs\|oC] | 31.25962 | 26.87411 | 1.1648233 | 1.9468 |
| 244 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGs\|oCs\|oAs\|oAs\|oCs\|oAs\|oC] | 33.7126 | 20.71987 | 2.985748 | 2.347571 |
| 245 | [oUs\|oGs\|oAs\|oUs\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oAs\|oC] | 37.45041 | 27.92649 | 2.2914196 | 1.775925 |
| 246 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oAs\|oC] | 37.40703 | 27.91025 | 0.37894275 | 2.801681 |
| 247 | [oUs\|oGs\|oAs\|oUs\|oCs\|5mCs\|dTs\|dGs\|dTs\|dTs\|5mCs\|dTs\|5mCs\|5mCs\|5mCs\|oAp\|oGp\|oCs\|oAs\|oAs\|oCs\|oAs\|oC] | 44.1762 | 24.73343 | 3.02169625 | 0.96668 |
| 248 | [oUs\|oGs\|oAp\|oUs\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oAs\|oC] | 38.30889 | 23.31712 | 1.4411529 | 1.489325 |
| 249 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oAs\|oC] | 38.31735 | 24.56753 | 2.5346059 | 1.77217 |
| 250 | [oUs\|oGs\|oAs\|oUp\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oAs\|oC] | 35.17502 | 26.1372 | 1.8152499 | 2.083902 |
| 251 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oAs\|oC] | 36.24617 | 24.66592 | 1.38376155 | 0.821536 |

TABLE 3-continued

| Antisense Oligo No./SEQ ID NO: | Chem Mod Seq | Mean % mRNA Remaining | | SEM % mRNA Remaining | |
|---|---|---|---|---|---|
| | | 1 nM | 10 nM | 1 nM | 10 nM |
| 252 | [oUs\|oGs\|oAp\|oUs\|oCs\|5mCs\|dTs\|dGs\|dTs\|dTs\|5mCs\|dTs\|5mCs\|5mCs\|5mCs\|oAp\|oGp\|oCs\|oAs\|oAs\|oCs\|oAs\|oC] | 38.74019 | 26.77353 | 1.6343742 | 1.579313 |
| 253 | [oUs\|oGs\|oAs\|oUp\|oCs\|5mCs\|dTs\|dGs\|dTs\|dTs\|5mCs\|dTs\|5mCs\|5mCs\|5mCs\|oAp\|oGp\|oCs\|oAs\|oAs\|oCs\|oAs\|oC] | 38.33121 | 30.17397 | 1.0889853 | 2.797118 |
| 254 | [oUs\|oGs\|oAp\|oUp\|oCs\|5mCs\|dTs\|dGs\|dTs\|dTs\|5mCs\|dTs\|5mCs\|5mCs\|5mCs\|oAs\|oGp\|oCs\|oAs\|oAs\|oCs\|oAs\|oC] | 44.32188 | 27.49314 | 2.67802585 | 1.31818 |
| 255 | [oUs\|oGs\|oAp\|oUp\|oCs\|5mCs\|dTs\|dGs\|dTs\|dTs\|5mCs\|dTs\|5mCs\|5mCs\|5mCs\|oAp\|oGs\|oCs\|oAs\|oAs\|oCs\|oAs\|oC] | 38.70488 | 30.24362 | 2.4257059 | 2.598832 |
| 256 | [oUs\|oGs\|oAp\|oUp\|oCs\|5mCs\|dTs\|dGs\|dTs\|dTs\|mCs\|dTs\|5mCs\|5mCs\|5mCs\|oAp\|oGp\|oCs\|oAs\|oAs\|oCs\|oAs\|oC] | 43.28825 | 28.25934 | 3.05476895 | 1.497906 |
| 257 | [oUs\|oGs\|oAs\|oUs\|oCs\|5mCs\|dTs\|dGs\|dTs\|dTs\|5mCs\|dTs\|5mCs\|5mCs\|5mCs\|dAs\|oGs\|oCs\|oAs\|oAs\|oC] | 45.77041 | 30.01057 | 2.41725105 | 2.688685 |
| 258 | [oUs\|oGs\|oAp\|oUs\|oCs\|5mCs\|dTs\|dGs\|dTs\|dTs\|5mCs\|dTs\|5mCs\|5mCs\|5mCs\|dAs\|oGs\|oCs\|oAs\|oAs\|oC] | 37.50516 | 29.19368 | 3.2609215 | 1.306107 |
| 259 | [oUs\|oGs\|oAs\|oUp\|oCs\|5mCs\|dTs\|dGs\|dTs\|dTs\|5mCs\|dTs\|5mCs\|5mCs\|5mCs\|dAs\|oGs\|oCs\|oAs\|oAs\|oC] | 37.61875 | 28.41851 | 4.79014865 | 1.914106 |
| 260 | [oUs\|oGs\|oAp\|oUp\|oCs\|5mCs\|dTs\|dGs\|dTs\|dTs\|5mCs\|dTs\|5mCs\|5mCs\|5mCs\|dAs\|oGs\|oCs\|oAs\|oAs\|oC] | 39.57219 | 25.95941 | 1.0745636 | 2.611124 |
| 261 | [oUs\|oGs\|oAs\|oUs\|oCs\|5mCs\|dTs\|dGs\|dTs\|dTs\|5mCs\|dTs\|5mCs\|5mCs\|5mCs\|dAs\|oGp\|oCs\|oAs\|oAs\|oC] | 40.85794 | 29.04845 | 2.10254735 | 0.910299 |
| 262 | [oUs\|oGs\|oAs\|oUs\|oCs\|5mCs\|dTs\|dGs\|dTs\|dTs\|5mCs\|dTs\|5mCs\|5mCs\|5mCs\|dAp\|oGs\|oCs\|oAs\|oAs\|oC] | 48.57987 | 31.96517 | 3.30537215 | 3.77167 |
| 263 | [oUs\|oGs\|oAs\|oUs\|oCs\|5mCs\|dTs\|dGs\|dTs\|dTs\|5mCs\|dTs\|5mCs\|5mCs\|5mCs\|dAp\|oGp\|oCs\|oAs\|oAs\|oC] | 42.44673 | 32.35736 | 1.9875946 | 2.639212 |
| 264 | [oUs\|oGs\|oAp\|oUs\|oCs\|5mCs\|dTs\|dGs\|dTs\|dTs\|5mCs\|dTs\|5mCs\|5mCs\|5mCs\|dAs\|oGp\|oCs\|oAs\|oAs\|oC] | 43.82073 | 27.45321 | 2.0919192 | 1.819505 |
| 265 | [oUs\|oGs\|oAp\|oUs\|oCs\|5mCs\|dTs\|dGs\|dTs\|dTs\|5mCs\|dTs\|5mCs\|5mCs\|5mCs\|dAp\|oGs\|oCs\|oAs\|oAs\|oC] | 40.81426 | 34.44821 | 3.2274531 | 3.246932 |
| 266 | [oUs\|oGs\|oAs\|oUp\|oCs\|5mCs\|dTs\|dGs\|dTs\|dTs\|5mCs\|dTs\|5mCs\|5mCs\|5mCs\|dAs\|oGp\|oCs\|oAs\|oAs\|oC] | 44.58453 | 32.33173 | 4.3552897 | 2.179554 |
| 267 | [oUs\|oGs\|oAs\|oUp\|oCs\|5mCs\|dTs\|dGs\|dTs\|dTs\|5mCs\|dTs\|5mCs\|5mCs\|5mCs\|dAp\|oGs\|oCs\|oAs\|oAs\|oC] | 45.58382 | 28.39511 | 0.9009167 | 1.911982 |
| 268 | [oUs\|oGs\|oAp\|oUs\|oCs\|5mCs\|dTs\|dGs\|dTs\|dTs\|5mCs\|dTs\|5mCs\|5mCs\|5mCs\|dAp\|oGp\|oCs\|oAs\|oAs\|oC] | 42.5512 | 29.79543 | 1.03173485 | 1.860662 |
| 269 | [oUs\|oGs\|oAs\|oUp\|oCs\|5mCs\|dTs\|dGs\|dTs\|dTs\|5mCs\|dTs\|5mCs\|5mCs\|5mCs\|dAp\|oGp\|oCs\|oAs\|oAs\|oC] | 44.6866 | 30.01983 | 2.5231542 | 4.434048 |

TABLE 3-continued

| Anti-sense Oligo No./SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 270 | [oUs\|oGs\|oAp\|oUp\|oCs\|5mCs\|dTs\|dGs\|dTs\|dTs\|5mCs\|dTs\|5mCs\|5mCs\|5mCs\|dAs\|oGp\|oCs\|oAs\|oAs\|oC] | 38.02311 | 32.80756 | 3.4793287 | 4.749247 |
| 271 | [oUs\|oGs\|oAp\|oUp\|oCs\|5mCs\|dTs\|dGs\|dTs\|dTs\|5mCs\|dTs\|5mCs\|5mCs\|5mCs\|dAp\|oGs\|oCs\|oAs\|oAs\|oC] | 48.88263 | 27.15217 | 3.5851377 | 1.816405 |
| 272 | [oUs\|oGs\|oAp\|oUp\|oCs\|5mCs\|dTs\|dGs\|dTs\|dTs\|5mCs\|dTs\|5mCs\|5mCs\|5mCs\|dAp\|oGp\|oCs\|oAs\|oAs\|oC] | 46.69598 | 30.73665 | 2.0490884 | 2.855452 |
| 273 | [oUs\|oGs\|oAs\|oUs\|oCs\|5mCs\|dTs\|dGs\|dTs\|dTs\|5mCs\|dTs\|5mCs\|5mCs\|5mCs\|dAs\|dGs\|oCs\|oAs\|oAs\|oCs\|oA] | 42.70873 | 30.68745 | 3.65148505 | 3.255575 |
| 274 | [oUs\|oGs\|oAp\|oUs\|oCs\|5mCs\|dTs\|dGs\|dTs\|dTs\|5mCs\|dTs\|5mCs\|5mCs\|5mCs\|dAs\|dGs\|oCs\|oAs\|oAs\|oCs\|oA] | 40.32396 | 26.35517 | 3.335113 | 2.701905 |
| 275 | [oUs\|oGs\|oAs\|oUp\|oCs\|5mCs\|dTs\|dGs\|dTs\|dTs\|5mCs\|dTs\|5mCs\|5mCs\|5mCs\|dAs\|dGs\|oCs\|oAs\|oAs\|oCs\|oA] | 40.74281 | 29.94494 | 0.6334559 | 2.557136 |
| 276 | [oUs\|oGs\|oAp\|oUp\|oCs\|5mCs\|dTs\|dGs\|dTs\|dTs\|5mCs\|dTs\|5mCs\|5mCs\|5mCs\|dAs\|dGs\|oCs\|oAs\|oAs\|oCs\|oA] | 40.29221 | 27.33965 | 0.8763938 | 2.574619 |
| 277 | [oUs\|oGs\|oAs\|oUs\|oCs\|5mCs\|dTs\|dGs\|dTs\|dTs\|5mCs\|dTs\|5mCs\|5mCs\|5mCs\|dAs\|dGp\|oCs\|oAs\|oAs\|oCs\|oA] | 47.44893 | 29.86629 | 2.4738361 | 2.55434 |
| 278 | [oUs\|oGs\|oAs\|oUs\|oCs\|5mCs\|dTs\|dGs\|dTs\|dTs\|5mCs\|dTs\|5mCs\|5mCs\|5mCs\|dAp\|dGs\|oCs\|oAs\|oAs\|oCs\|oA] | 46.17489 | 33.16617 | 3.1173163 | 1.327764 |
| 279 | [oUs\|oGs\|oAs\|oUs\|oCs\|5mCs\|dTs\|dGs\|dTs\|dTs\|5mCs\|dTs\|5mCs\|5mCs\|5mCs\|dAp\|dGp\|oCs\|oAs\|oAs\|oCs\|oA] | 46.58545 | 33.39568 | 3.2287529 | 1.864188 |
| 280 | [oUs\|oGs\|oAp\|oUs\|oCs\|5mCs\|dTs\|dGs\|dTs\|dTs\|5mCs\|dTs\|5mCs\|5mCs\|5mCs\|dAs\|dGp\|oCs\|oAs\|oAs\|oCs\|oA] | 43.27573 | 27.28916 | 2.31554215 | 1.262593 |
| 281 | [oUs\|oGs\|oAp\|oUs\|oCs\|5mCs\|dTs\|dGs\|dTs\|dTs\|5mCs\|dTs\|5mCs\|5mCs\|5mCs\|dAp\|dGs\|oCs\|oAs\|oAs\|oCs\|oA] | 47.10235 | 32.83978 | 1.53071395 | 4.229922 |
| 282 | [oUs\|oGs\|oAs\|oUp\|oCs\|5mCs\|dTs\|dGs\|dTs\|dTs\|5mCs\|dTs\|5mCs\|5mCs\|5mCs\|dAs\|dGp\|oCs\|oAs\|oAs\|oCs\|oA] | 47.70091 | 29.60736 | 3.7604108 | 2.052869 |
| 283 | [oUs\|oGs\|oAs\|oUp\|oCs\|5mCs\|dTs\|dGs\|dTs\|dTs\|5mCs\|dTs\|5mCs\|5mCs\|5mCs\|dAp\|dGs\|oCs\|oAs\|oAs\|oCs\|oA] | 49.28544 | 34.66856 | 1.59176345 | 3.017275 |
| 284 | [oUs\|oGs\|oAp\|oUs\|oCs\|5mCs\|dTs\|dGs\|dTs\|dTs\|5mCs\|dTs\|5mCs\|5mCs\|5mCs\|dAp\|dGp\|oCs\|oAs\|oAs\|oCs\|oA] | 49.84421 | 32.28262 | 4.79490775 | 5.858741 |
| 285 | [oUs\|oGs\|oAs\|oUp\|oCs\|5mCs\|dTs\|dGs\|dTs\|dTs\|5mCs\|dTs\|5mCs\|5mCs\|5mCs\|dAp\|dGp\|oCs\|oAs\|oAs\|oCs\|oA] | 34.59283 | 22.87145 | 3.0164757 | 2.082604 |
| 286 | [oUs\|oGs\|oAp\|oUp\|oCs\|5mCs\|dTs\|dGs\|dTs\|dTs\|5mCs\|dTs\|5mCs\|5mCs\|5mCs\|dAs\|dGp\|oCs\|oAs\|oAs\|oCs\|oA] | 39.38162 | 26.12473 | 1.8902058 | 1.570875 |
| 287 | [oUs\|oGs\|oAp\|oUp\|oCs\|5mCs\|dTs\|dGs\|dTs\|dTs\|5mCs\|dTs\|5mCs\|5mCs\|5mCs\|dAp\|dGs\|oCs\|oAs\|oAs\|oCs\|oA] | 50.21733 | 30.06642 | 3.10898985 | 1.234999 |

TABLE 3-continued

| Anti-sense Oligo No./SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 288 | [oUs\|oGs\|oAp\|oUp\|oCs\|5mCs\|dTs\|dGs\|dTs\|dTs\|5mCs\|dTs\|5mCs\|5mCs\|5mCs\|dAp\|dGp\|oCs\|oAs\|oAs\|oCs\|oA] | 50.69014 | 32.61033 | 2.79327395 | 1.497337 |
| 289 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAs\|oGs\|oCs\|oA] | 65.03387 | 39.71818 | 3.2453458 | 1.232538 |
| 290 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAs\|oGs\|oCs\|oA] | 61.89021 | 44.17769 | 3.0819054 | 2.818603 |
| 291 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAs\|oGs\|oCs\|oA] | 70.81215 | 39.23055 | 5.9432651 | 2.293842 |
| 292 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAs\|oGs\|oCs\|oA] | 64.28917 | 35.27306 | 4.4374966 | 2.084275 |
| 293 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAp\|oGs\|oCs\|oA] | 75.30924 | 41.75287 | 6.3677188 | 3.571926 |
| 294 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAs\|oGs\|oCs\|oA] | 72.21538 | 40.63977 | 9.45384065 | 2.395694 |
| 295 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAp\|oGs\|oCs\|oA] | 65.43466 | 40.60514 | 4.9966345 | 4.010523 |
| 296 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAp\|oGs\|oCs\|oA] | 70.68577 | 41.62804 | 4.61698135 | 0.639112 |
| 297 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAs\|oGs\|oCs\|oA] | 68.70839 | 43.19171 | 4.0611799 | 2.66127 |
| 298 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAp\|oGs\|oCs\|oA] | 68.74235 | 42.8638 | 6.63886525 | 2.69242 |
| 299 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAs\|oGs\|oCs\|oA] | 65.56432 | 41.13655 | 2.8508521 | 1.098556 |
| 300 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAp\|oGs\|oCs\|oA] | 73.25913 | 44.19704 | 0.3218877 | 3.006132 |
| 301 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAp\|oGs\|oCs\|oA] | 66.80031 | 44.33691 | 5.58574735 | 2.190286 |
| 302 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAp\|oGs\|oCs\|oA] | 67.79988 | 43.25911 | 3.47248465 | 2.245861 |
| 303 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAs\|oGs\|oCs\|oA] | 69.0764 | 39.9134 | 2.2580266 | 2.514186 |
| 304 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAp\|oGs\|oCs\|oA] | 68.85722 | 43.2033 | 2.66821415 | 1.577173 |
| 305 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAs\|oGs\|oCs\|oAs\|oA] | 64.32531 | 36.98857 | 6.6048679 | 1.862941 |
| 306 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAs\|oGs\|oCs\|oAs\|oA] | 79.43795 | 38.19117 | 10.61625475 | 3.700974 |
| 307 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAs\|oGs\|oCs\|oAs\|oA] | 65.05429 | 35.73871 | 5.07137215 | 2.026283 |
| 308 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAs\|oGs\|oCs\|oAs\|oA] | 67.69046 | 37.80261 | 3.3970135 | 1.359287 |
| 309 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAp\|oGs\|oCs\|oAs\|oA] | 72.9064 | 39.22807 | 2.6173443 | 1.983172 |

TABLE 3-continued

| Antisense Oligo No./SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 310 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAs\|oGs\|oCs\|oAs\|oA] | 65.42524 | 41.63383 | 1.64477605 | 2.287743 |
| 311 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAp\|oGs\|oCs\|oAs\|oA] | 79.57865 | 47.30341 | 3.2793354 | 4.879421 |
| 312 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAp\|oGs\|oCs\|oAs\|oA] | 74.90458 | 37.7908 | 7.9156018 | 2.492285 |
| 313 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAs\|oGs\|oCs\|oAs\|oA] | 64.17809 | 41.25918 | 3.60546685 | 2.451177 |
| 314 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAp\|oGs\|oCs\|oAs\|oA] | 77.79264 | 36.3895 | 5.16839925 | 1.47233 |
| 315 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAs\|oGs\|oCs\|oAs\|oA] | 69.27439 | 40.78583 | 0.70050225 | 3.765485 |
| 316 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAp\|oGs\|oCs\|oAs\|oA] | 66.79254 | 41.42264 | 4.07791885 | 2.517419 |
| 317 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAp\|oGs\|oCs\|oAs\|oA] | 69.95295 | 38.70855 | 5.1765897 | 1.322 |
| 318 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAp\|oGs\|oCs\|oAs\|oA] | 64.59882 | 36.2354 | 1.94088075 | 2.245535 |
| 319 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAs\|oGs\|oCs\|oAs\|oA] | 71.61855 | 40.11992 | 4.8955589 | 1.16262 |
| 320 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAp\|oGs\|oCs\|oAs\|oA] | 73.74875 | 40.87392 | 1.9294505 | 0.764434 |
| 321 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oC] | 69.14922 | 42.64199 | 6.9911749 | 2.990965 |
| 322 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oC] | 68.03041 | 40.82452 | 3.81307025 | 3.211419 |
| 323 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oC] | 64.06085 | 38.06864 | 3.2673432 | 2.579056 |
| 324 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oC] | 64.06883 | 40.38284 | 2.58838335 | 2.66873 |
| 325 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oC] | 73.59074 | 39.51843 | 5.5155268 | 1.608472 |
| 326 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oC] | 64.14324 | 38.43417 | 2.9521007 | 1.560155 |
| 327 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oC] | 67.68504 | 45.94997 | 5.2482586 | 2.096218 |

TABLE 3-continued

| Anti-sense Oligo No./SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 328 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oC] | 74.0999 | 38.3912 | 0.5712221 | 1.732884 |
| 329 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oC] | 59.85657 | 40.50332 | 4.4957246 | 1.479709 |
| 330 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oC] | 62.98679 | 36.72381 | 9.8570092 | 0.854923 |
| 331 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oC] | 66.22289 | 38.29377 | 7.80879995 | 2.702458 |
| 332 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oC] | 64.84554 | 38.62897 | 2.9279718 | 1.019158 |
| 333 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oC] | 72.02838 | 42.5541 | 4.6483644 | 3.24576 |
| 334 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oC] | 73.13125 | 37.42697 | 3.52337675 | 2.273121 |
| 335 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oC] | 65.10868 | 38.41509 | 2.69335365 | 3.463081 |
| 336 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oC] | 74.0986 | 41.06858 | 5.59980225 | 3.735298 |
| 337 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oCs\|oA] | 68.10988 | 33.22407 | 2.04506795 | 1.219344 |
| 338 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oCs\|oA] | 61.51268 | 39.42608 | 3.2210901 | 1.60843 |
| 339 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oCs\|oA] | 61.62901 | 38.10779 | 5.0486966 | 1.469955 |
| 340 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAs\|oGs\|oCs\|oAs\|oAs\|oCs\|oA] | 68.70971 | 37.9342 | 9.15707545 | 2.987791 |
| 341 | [oUs\|oUs\|oGs\|oAs\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oCs\|oA] | 64.63658 | 37.92174 | 8.0800218 | 2.867291 |
| 342 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oCs\|oA] | 71.59294 | 36.10313 | 4.23800025 | 2.212339 |
| 343 | [oUs\|oUs\|oGs\|oAs\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oCs\|oA] | 67.77124 | 42.50938 | 4.24974715 | 0.606911 |
| 344 | [oUs\|oUs\|oGp\|oAs\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oCs\|oA] | 62.77385 | 38.9199 | 1.20627285 | 2.566854 |
| 345 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oCs\|oA] | 65.30274 | 37.50644 | 3.3490132 | 1.120349 |

TABLE 3-continued

| Anti-sense Oligo No./ SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 346 | [oUs\|oUs\|oGs\|oAp\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oCs\|oA] | 59.99562 | 43.52686 | 2.17603655 | 3.501488 |
| 347 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oCs\|oA] | 76.91818 | 36.71682 | 5.11543135 | 1.003503 |
| 348 | [oUs\|oUs\|oGp\|oAs\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oCs\|oA] | 74.07843 | 40.52268 | 2.68814825 | 1.670121 |
| 349 | [oUs\|oUs\|oGs\|oAp\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oCs\|oA] | 66.80045 | 41.82373 | 5.23486615 | 1.955829 |
| 350 | [oUs\|oUs\|oGp\|oAp\|oUs\|5mCs\|5mCs\|dTs\|dGs\|dTs\|dTs\|5mCs\|dTs\|5mCs\|5mCs\|oCs\|oAp\|oGs\|oCs\|oAs\|oAs\|oCs\|oA] | 71.27418 | 43.95148 | 3.022233 | 1.912625 |
| 351 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAs\|oGs\|oCs\|oAs\|oAs\|oCs\|oA] | 68.26772 | 40.87145 | 1.67750485 | 1.489503 |
| 352 | [oUs\|oUs\|oGp\|oAp\|oUs\|5mCs\|5mCs\|dTs\|dGs\|dTs\|dTs\|5mCs\|dTs\|5mCs\|5mCs\|oCp\|oAp\|oGs\|oCs\|oAs\|oAs\|oCs\|oA] | 74.70355 | 46.98739 | 4.10748375 | 3.361829 |
| 353 | [oUs\|oUs\|oGs\|oAs\|oUs\|5mCs\|5mCs\|dTs\|dGs\|dTs\|dTs\|5mCs\|dTs\|5mCs\|5mCs\|5mCs\|oAs\|oGs\|oCs\|oAs\|oA] | 82.69998 | 45.53944 | 2.7748001 | 5.248864 |
| 354 | [oUs\|oUs\|oGp\|oAs\|oUs\|5mCs\|5mCs\|dTs\|dGs\|dTs\|dTs\|5mCs\|dTs\|5mCs\|5mCs\|5mCs\|oAs\|oGs\|oCs\|oAs\|oA] | 75.2964 | 41.58329 | 4.28755645 | 1.604165 |
| 355 | [oUs\|oUs\|oGs\|oAp\|oUs\|5mCs\|5mCs\|dTs\|dGs\|dTs\|dTs\|5mCs\|dTs\|5mCs\|5mCs\|5mCs\|oAs\|oGs\|oCs\|oAs\|oA] | 78.25078 | 38.04859 | 2.1756527 | 2.812668 |
| 356 | [oUs\|oUs\|oGp\|oAp\|oUs\|5mCs\|5mCs\|dTs\|dGs\|dTs\|dTs\|5mCs\|dTs\|5mCs\|5mCs\|5mCs\|oAs\|oGs\|oCs\|oAs\|oA] | 75.66047 | 46.42479 | 5.32824395 | 3.512293 |
| 357 | [oUs\|oUs\|oGs\|oAs\|oUs\|5mCs\|5mCs\|dTs\|dGs\|dTs\|dTs\|5mCs\|dTs\|5mCs\|5mCs\|5mCs\|oAp\|oGs\|oCs\|oAs\|oA] | 70.8279 | 39.60585 | 4.17139065 | 1.315399 |
| 358 | [oUs\|oUs\|oGs\|oAs\|oUs\|5mCs\|5mCs\|dTs\|dGs\|dTs\|dTs\|5mCs\|dTs\|5mCs\|5mCs\|5mCp\|oAs\|oGs\|oCs\|oAs\|oA] | 88.71474 | 41.43116 | 2.63982225 | 2.837026 |
| 359 | [oUs\|oUs\|oGs\|oAs\|oUs\|5mCs\|5mCs\|dTs\|dGs\|dTs\|dTs\|5mCs\|dTs\|5mCs\|5mCs\|5mCp\|oAp\|oGs\|oCs\|oAs\|oA] | 94.02871 | 55.61287 | 3.28254665 | 5.31701 |
| 360 | [oUs\|oUs\|oGp\|oAs\|oUs\|5mCs\|5mCs\|dTs\|dGs\|dTs\|dTs\|5mCs\|dTs\|5mCs\|5mCs\|5mCs\|oAp\|oGs\|oCs\|oAs\|oA] | 81.20155 | 48.93426 | 2.9797871 | 3.293206 |
| 361 | [oUs\|oUs\|oGp\|oAs\|oUs\|5mCs\|5mCs\|dTs\|dGs\|dTs\|dTs\|5mCs\|dTs\|5mCs\|5mCs\|5mCp\|oAs\|oGs\|oCs\|oAs\|oA] | 81.56161 | 43.33641 | 5.9890201 | 2.745271 |
| 362 | [oUs\|oUs\|oGs\|oAp\|oUs\|5mCs\|5mCs\|dTs\|dGs\|dTs\|dTs\|5mCs\|dTs\|5mCs\|5mCs\|5mCs\|oAp\|oGs\|oCs\|oAs\|oA] | 77.46717 | 40.6332 | 6.53245465 | 2.851351 |
| 363 | [oUs\|oUs\|oGs\|oAp\|oUs\|5mCs\|5mCs\|dTs\|dGs\|dTs\|dTs\|5mCs\|dTs\|5mCs\|5mCs\|5mCp\|oAs\|oGs\|oCs\|oAs\|oA] | 91.06332 | 37.09205 | 6.16485235 | 1.515162 |

TABLE 3-continued

| Anti-sense Oligo No./ SEQ ID | | Mean % mRNA Remaining | | SEM % mRNA Remaining | |
|---|---|---|---|---|---|
| NO: | Chem Mod Seq | 1 nM | 10 nM | 1 nM | 10 nM |
| 364 | [oUs\|oUs\|oGp\|oAs\|oUs\|5mCs\|5mCs\|dTs\|dGs\|dTs\|dTs\|5mCs\|dTs\|5mCs\|5mCs\|5mCp\|oAp\|oGs\|oCs\|oAs\|oA] | 87.55428 | 42.57427 | 3.1016107 | 2.002001 |
| 365 | [oUs\|oUs\|oGs\|oAp\|oUs\|5mCs\|5mCs\|dTs\|dGs\|dTs\|dTs\|5mCs\|dTs\|5mCs\|5mCs\|5mCp\|oAp\|oGs\|oCs\|oAs\|oA] | 90.76046 | 46.77878 | 4.93885515 | 3.608661 |
| 366 | [oUs\|oUs\|oGp\|oAp\|oUs\|5mCs\|5mCs\|dTs\|dGs\|dTs\|dTs\|5mCs\|dTs\|5mCs\|5mCs\|5mCs\|oAp\|oGs\|oCs\|oAs\|oA] | 76.47815 | 41.28109 | 4.02130685 | 3.175797 |
| 367 | [oUs\|oUs\|oGp\|oAp\|oUs\|5mCs\|5mCs\|dTs\|dGs\|dTs\|dTs\|5mCs\|dTs\|5mCs\|5mCs\|5mCp\|oAs\|oGs\|oCs\|oAs\|oA] | 81.30346 | 46.78571 | 5.4938338 | 2.280535 |
| 368 | [oUs\|oUs\|oGp\|oAp\|oUs\|5mCs\|5mCs\|dTs\|dGs\|dTs\|dTs\|5mCs\|dTs\|5mCs\|5mCs\|5mCp\|oAp\|oGs\|oCs\|oAs\|oA] | 84.12098 | 44.30416 | 5.38885525 | 2.935461 |
| 369 | [oUs\|oUs\|oGs\|oAs\|oUs\|5mCs\|5mCs\|dTs\|dGs\|dTs\|dTs\|5mCs\|dTs\|5mCs\|5mCs\|5mCs\|dAs\|oGs\|oCs\|oAs\|oAs\|oC] | 70.44063 | 38.60541 | 6.7004305 | 3.620983 |
| 370 | [oUs\|oUs\|oGp\|oAs\|oUs\|5mCs\|5mCs\|dTs\|dGs\|dTs\|dTs\|5mCs\|dTs\|5mCs\|5mCs\|5mCs\|dAs\|oGs\|oCs\|oAs\|oAs\|oC] | 74.17394 | 36.98506 | 2.4084315 | 1.467456 |
| 371 | [oUs\|oUs\|oGs\|oAp\|oUs\|5mCs\|5mCs\|dTs\|dGs\|dTs\|dTs\|5mCs\|dTs\|5mCs\|5mCs\|5mCs\|dAs\|oGs\|oCs\|oAs\|oAs\|oC] | 74.77409 | 37.54156 | 7.2673398 | 1.490426 |
| 372 | [oUs\|oUs\|oGp\|oAp\|oUs\|5mCs\|5mCs\|dTs\|dGs\|dTs\|dTs\|5mCs\|dTs\|5mCs\|5mCs\|5mCs\|dAs\|oGs\|oCs\|oAs\|oAs\|oC] | 78.93023 | 38.38505 | 5.56282815 | 3.943036 |
| 373 | [oUs\|oUs\|oGs\|oAs\|oUs\|5mCs\|5mCs\|dTs\|dGs\|dTs\|dTs\|5mCs\|dTs\|5mCs\|5mCs\|5mCs\|dAp\|oGs\|oCs\|oAs\|oAs\|oC] | 71.77732 | 36.26151 | 4.19725075 | 2.479808 |
| 374 | [oUs\|oUs\|oGs\|oAs\|oUs\|5mCs\|5mCs\|dTs\|dGs\|dTs\|dTs\|5mCs\|dTs\|5mCs\|5mCs\|5mCp\|dAs\|oGs\|oCs\|oAs\|oAs\|oC] | 75.98736 | 46.94162 | 3.67475295 | 2.387602 |
| 375 | [oUs\|oUs\|oGs\|oAs\|oUs\|5mCs\|5mCs\|dTs\|dGs\|dTs\|dTs\|5mCs\|dTs\|5mCs\|5mCs\|5mCp\|dAp\|oGs\|oCs\|oAs\|oAs\|oC] | 83.01221 | 48.4748 | 1.83557915 | 3.954731 |
| 376 | [oUs\|oUs\|oGp\|oAs\|oUs\|5mCs\|5mCs\|dTs\|dGs\|dTs\|dTs\|5mCs\|dTs\|5mCs\|5mCs\|5mCs\|dAp\|oGs\|oCs\|oAs\|oAs\|oC] | 73.40898 | 45.08328 | 1.55749415 | 2.879961 |
| 377 | [oUs\|oUs\|oGp\|oAs\|oUs\|5mCs\|5mCs\|dTs\|dGs\|dTs\|dTs\|5mCs\|dTs\|5mCs\|5mCs\|5mCp\|dAs\|oGs\|oCs\|oAs\|oAs\|oC] | 81.18265 | 43.25494 | 2.32470145 | 2.898854 |
| 378 | [oUs\|oUs\|oGs\|oAp\|oUs\|5mCs\|5mCs\|dTs\|dGs\|dTs\|dTs\|5mCs\|dTs\|5mCs\|5mCs\|5mCs\|dAp\|oGs\|oCs\|oAs\|oAs\|oC] | 85.8249 | 35.81711 | 7.0913574 | 1.999337 |
| 379 | [oUs\|oUs\|oGs\|oAp\|oUs\|5mCs\|5mCs\|dTs\|dGs\|dTs\|dTs\|5mCs\|dTs\|5mCs\|5mCs\|5mCp\|dAs\|oGs\|oCs\|oAs\|oAs\|oC] | 85.9207 | 39.07233 | 8.2451204 | 1.716324 |
| 380 | [oUs\|oUs\|oGp\|oAs\|oUs\|5mCs\|5mCs\|dTs\|dGs\|dTs\|dTs\|5mCs\|dTs\|5mCs\|5mCs\|5mCp\|dAp\|oGs\|oCs\|oAs\|oAs\|oC] | 89.28203 | 44.69979 | 3.57026875 | 2.48225 |
| 381 | [oUs\|oUs\|oGs\|oAp\|oUs\|5mCs\|5mCs\|dTs\|dGs\|dTs\|dTs\|5mCs\|dTs\|5mCs\|5mCs\|5mCp\|dAp\|oGs\|oCs\|oAs\|oAs\|oC] | 80.47781 | 43.39312 | 1.49203405 | 1.667053 |

TABLE 3-continued

| Antisense Oligo No./ SEQ ID NO: | Chem Mod Seq | Mean % mRNA Remaining 1 nM | Mean % mRNA Remaining 10 nM | SEM % mRNA Remaining 1 nM | SEM % mRNA Remaining 10 nM |
|---|---|---|---|---|---|
| 382 | [oUs\|oUs\|oGp\|oAp\|oUs\|5mCs\|5mCs\|dTs\|dGs\|dTs\|dTs\|5mCs\|dTs\|5mCs\|5mCs\|5mCs\|dAp\|oGs\|oCs\|oAs\|oAs\|oC] | 84.37027 | 35.88873 | 4.3911855 | 0.578314 |
| 383 | [oUs\|oUs\|oGp\|oAp\|oUs\|5mCs\|5mCs\|dTs\|dGs\|dTs\|dTs\|5mCs\|dTs\|5mCs\|5mCs\|5mCp\|dAs\|oGs\|oCs\|oAs\|oAs\|oC] | 78.04549 | 35.55957 | 3.76452225 | 3.138921 |
| 384 | [oUs\|oUs\|oGp\|oAp\|oUs\|5mCs\|5mCs\|dTs\|dGs\|dTs\|dTs\|5mCs\|dTs\|5mCs\|5mCs\|5mCp\|dAp\|oGs\|oCs\|oAs\|oAs\|oC] | 86.50257 | 42.97401 | 7.1309543 | 0.436476 |

TABLE 4

| Antisense Oligo No./ SEQ ID NO: | Variant Sequence |
|---|---|
| 390 | [oUs\|LGs\|o5mCs\|oUs\|oAs\|oGs\|oGs\|oUs\|dGs\|dAs\|dTs\|dGs\|5mCs\|dAs\|5mCs\|dTs\|dGs\|5mCs\|oUs\|oU] |
| 391 | [oUs\|oGs\|L5mCs\|oUs\|oAs\|oGs\|oGs\|oUs\|dGs\|dAs\|dTs\|dGs\|5mCs\|dAs\|5mCs\|dTs\|dGs\|5mCs\|oUs\|oU] |
| 392 | [oUs\|oGs\|o5mCs\|LTs\|oAs\|oGs\|oGs\|oUs\|dGs\|dAs\|dTs\|dGs\|5mCs\|dAs\|5mCs\|dTs\|dGs\|5mCs\|oUs\|oU] |
| 393 | [oUs\|oGs\|o5mCs\|oUs\|LAs\|oGs\|oGs\|oUs\|dGs\|dAs\|dTs\|dGs\|5mCs\|dAs\|5mCs\|dTs\|dGs\|5mCs\|oUs\|oU] |
| 394 | [oUs\|oGs\|o5mCs\|oUs\|oAs\|LGs\|oGs\|oUs\|dGs\|dAs\|dTs\|dGs\|5mCs\|dAs\|5mCs\|dTs\|dGs\|5mCs\|oUs\|oU] |
| 395 | [oUs\|oGs\|o5mCs\|oUs\|oAs\|oGs\|LGs\|oUs\|dGs\|dAs\|dTs\|dGs\|5mCs\|dAs\|5mCs\|dTs\|dGs\|5mCs\|oUs\|oU] |
| 396 | [oUs\|oGs\|5mCs\|dTs\|dAs\|dGs\|dGs\|dTs\|dGs\|dAs\|dTs\|dGs\|o5mCs\|oAs\|o5mCs\|oUs\|oGs\|o5mCs\|LTs\|oU] |
| 397 | [oUs\|oGs\|5mCs\|dTs\|dAs\|dGs\|dGs\|dTs\|dGs\|dAs\|dTs\|dGs\|o5mCs\|oAs\|o5mCs\|oUs\|oGs\|L5mCs\|oUs\|oU] |
| 398 | [oUs\|oGs\|5mCs\|dTs\|dAs\|dGs\|dGs\|dTs\|dGs\|dAs\|dTs\|dGs\|o5mCs\|oAs\|o5mCs\|oUs\|LGs\|o5mCs\|oUs\|oU] |
| 399 | [oUs\|oGs\|5mCs\|dTs\|dAs\|dGs\|dGs\|dTs\|dGs\|dAs\|dTs\|dGs\|o5mCs\|oAs\|o5mCs\|LTs\|oGs\|o5mCs\|oUs\|oU] |
| 400 | [oUs\|oGs\|5mCs\|dTs\|dAs\|dGs\|dGs\|dTs\|dGs\|dAs\|dTs\|dGs\|o5mCs\|oAs\|L5mCs\|oUs\|oGs\|o5mCs\|oUs\|oU] |
| 401 | [oUs\|oGs\|5mCs\|dTs\|dAs\|dGs\|dGs\|dTs\|dGs\|dAs\|dTs\|dGs\|o5mCs\|LAs\|o5mCs\|oUs\|oGs\|o5mCs\|oUs\|oU] |
| 402 | [oUs\|LGs\|o5mCs\|oUs\|oAs\|oGs\|oGs\|dTs\|dGs\|dAs\|dTs\|dGs\|5mCs\|dAs\|5mCs\|dTs\|dGs\|o5mCs\|oUs\|oU] |
| 403 | [oUs\|oGs\|L5mCs\|oUs\|oAs\|oGs\|oGs\|dTs\|dGs\|dAs\|dTs\|dGs\|5mCs\|dAs\|5mCs\|dTs\|dGs\|o5mCs\|oUs\|oU] |
| 404 | [oUs\|oGs\|o5mCs\|LTs\|oAs\|oGs\|oGs\|dTs\|dGs\|dAs\|dTs\|dGs\|5mCs\|dAs\|5mCs\|dTs\|dGs\|o5mCs\|oUs\|oU] |
| 405 | [oUs\|oGs\|o5mCs\|oUs\|LAs\|oGs\|oGs\|dTs\|dGs\|dAs\|dTs\|dGs\|5mCs\|dAs\|5mCs\|dTs\|dGs\|o5mCs\|oUs\|oU] |
| 406 | [oUs\|oGs\|o5mCs\|oUs\|oAs\|LGs\|oGs\|dTs\|dGs\|dAs\|dTs\|dGs\|5mCs\|dAs\|5mCs\|dTs\|dGs\|o5mCs\|oUs\|oU] |

TABLE 4-continued

| Antisense Oligo No./ SEQ ID NO: | Variant Sequence |
|---|---|
| 407 | [oUs\|oGs\|o5mCs\|dTs\|dAs\|dGs\|dGs\|dTs\|dGs\|dAs\|dTs\|dGs\|5mCs\|oAs\|o5mCs\|oUs\|oGs\|o5mCs\|LTs\|oU] |
| 408 | [oUs\|oGs\|o5mCs\|dTs\|dAs\|dGs\|dGs\|dTs\|dGs\|dAs\|dTs\|dGs\|5mCs\|oAs\|o5mCs\|oUs\|oGs\|L5mCs\|oUs\|oU] |
| 409 | [oUs\|oGs\|o5mCs\|dTs\|dAs\|dGs\|dGs\|dTs\|dGs\|dAs\|dTs\|dGs\|5mCs\|oAs\|o5mCs\|oUs\|LGs\|o5mCs\|oUs\|oU] |
| 410 | [oUs\|oGs\|o5mCs\|dTs\|dAs\|dGs\|dGs\|dTs\|dGs\|dAs\|dTs\|dGs\|5mCs\|oAs\|o5mCs\|LTs\|oGs\|o5mCs\|oUs\|oU] |
| 411 | [oUs\|oGs\|o5mCs\|dTs\|dAs\|dGs\|dGs\|dTs\|dGs\|dAs\|dTs\|dGs\|5mCs\|oAs\|L5mCs\|oUs\|oGs\|o5mCs\|oUs\|oU] |
| 412 | [oUs\|LGs\|o5mCs\|oUs\|oAs\|oGs\|oGs\|dTs\|dGs\|dAs\|dTs\|dGs\|5mCs\|dAs\|5mCs\|dTs\|dGs\|5mCs\|oUs\|oU] |
| 413 | [oUs\|oGs\|L5mCs\|oUs\|oAs\|oGs\|oGs\|dTs\|dGs\|dAs\|dTs\|dGs\|5mCs\|dAs\|5mCs\|dTs\|dGs\|5mCs\|oUs\|oU] |
| 414 | [oUs\|oGs\|o5mCs\|LTs\|oAs\|oGs\|oGs\|dTs\|dGs\|dAs\|dTs\|dGs\|5mCs\|dAs\|5mCs\|dTs\|dGs\|5mCs\|oUs\|oU] |
| 415 | [oUs\|oGs\|o5mCs\|oUs\|LAs\|oGs\|oGs\|dTs\|dGs\|dAs\|dTs\|dGs\|5mCs\|dAs\|5mCs\|dTs\|dGs\|5mCs\|oUs\|oU] |
| 416 | [oUs\|oGs\|o5mCs\|oUs\|oAs\|LGs\|oGs\|dTs\|dGs\|dAs\|dTs\|dGs\|5mCs\|dAs\|5mCs\|dTs\|dGs\|5mCs\|oUs\|oU] |
| 417 | [oGs\|o5mCs\|dTs\|dAs\|dGs\|dGs\|dTs\|dGs\|dAs\|dTs\|dGs\|5mCs\|oAs\|o5mCs\|oUs\|oGs\|o5mCs\|LTs\|oU] |
| 418 | [oGs\|o5mCs\|dTs\|dAs\|dGs\|dGs\|dTs\|dGs\|dAs\|dTs\|dGs\|5mCs\|oAs\|o5mCs\|oUs\|oGs\|L5mCs\|oUs\|oU] |
| 419 | [oGs\|o5mCs\|dTs\|dAs\|dGs\|dGs\|dTs\|dGs\|dAs\|dTs\|dGs\|5mCs\|oAs\|o5mCs\|oUs\|LGs\|o5mCs\|oUs\|oU] |
| 420 | [oGs\|o5mCs\|dTs\|dAs\|dGs\|dGs\|dTs\|dGs\|dAs\|dTs\|dGs\|5mCs\|oAs\|o5mCs\|LTs\|oGs\|o5mCs\|oUs\|oU] |
| 421 | [oGs\|o5mCs\|dTs\|dAs\|dGs\|dGs\|dTs\|dGs\|dAs\|dTs\|dGs\|5mCs\|oAs\|L5mCs\|oUs\|oGs\|o5mCs\|oUs\|oU] |
| 422 | [oUs\|LGs\|o5mCs\|oUs\|oAs\|oGs\|dGs\|dTs\|dGs\|dAs\|dTs\|dGs\|5mCs\|dAs\|5mCs\|dTs\|oGs\|o5mCs\|oUs\|oU] |
| 423 | [oUs\|oGs\|L5mCs\|oUs\|oAs\|oGs\|dGs\|dTs\|dGs\|dAs\|dTs\|dGs\|5mCs\|dAs\|5mCs\|dTs\|oGs\|o5mCs\|oUs\|oU] |
| 424 | [oUs\|oGs\|o5mCs\|LTs\|oAs\|oGs\|dGs\|dTs\|dGs\|dAs\|dTs\|dGs\|5mCs\|dAs\|5mCs\|dTs\|oGs\|o5mCs\|oUs\|oU] |
| 425 | [oUs\|oGs\|o5mCs\|oUs\|LAs\|oGs\|dGs\|dTs\|dGs\|dAs\|dTs\|dGs\|5mCs\|dAs\|5mCs\|dTs\|oGs\|o5mCs\|oUs\|oU] |
| 426 | [oUs\|oGs\|o5mCs\|oUs\|dAs\|dGs\|dGs\|dTs\|dGs\|dAs\|dTs\|dGs\|5mCs\|dAs\|o5mCs\|oUs\|oGs\|o5mCs\|LTs\|oU] |
| 427 | [oUs\|oGs\|o5mCs\|oUs\|dAs\|dGs\|dGs\|dTs\|dGs\|dAs\|dTs\|dGs\|5mCs\|dAs\|o5mCs\|oUs\|oGs\|L5mCs\|oUs\|oU] |
| 428 | [oUs\|oGs\|o5mCs\|oUs\|dAs\|dGs\|dGs\|dTs\|dGs\|dAs\|dTs\|dGs\|5mCs\|dAs\|o5mCs\|oUs\|LGs\|o5mCs\|oUs\|oU] |
| 429 | [oUs\|oGs\|o5mCs\|oUs\|dAs\|dGs\|dGs\|dTs\|dGs\|dAs\|dTs\|dGs\|5mCs\|dAs\|o5mCs\|LTs\|oGs\|o5mCs\|oUs\|oU] |
| 430 | [oUs\|LGs\|o5mCs\|oUs\|oAs\|oGs\|dGs\|dTs\|dGs\|dAs\|dTs\|dGs\|5mCs\|dAs\|5mCs\|dTs\|oGs\|o5mCs\|oU] |
| 431 | [oUs\|oGs\|L5mCs\|oUs\|oAs\|oGs\|dGs\|dTs\|dGs\|dAs\|dTs\|dGs\|5mCs\|dAs\|5mCs\|dTs\|oGs\|o5mCs\|oU] |

TABLE 4-continued

| Antisense Oligo No./ SEQ ID NO: | Variant Sequence |
|---|---|
| 432 | [oUs\|oGs\|o5mCs\|LTs\|oAs\|oGs\|dGs\|dTs\|dGs\|dAs\|dTs\|dGs\|5mCs\|dAs\|5mCs\|dTs\|oGs\|o5mCs\|oU] |
| 433 | [oUs\|oGs\|o5mCs\|oUs\|LAs\|oGs\|dGs\|dTs\|dGs\|dAs\|dTs\|dGs\|5mCs\|dAs\|5mCs\|dTs\|oGs\|o5mCs\|oU] |
| 434 | [oGs\|o5mCs\|oUs\|dAs\|dGs\|dGs\|dTs\|dGs\|dAs\|dTs\|dGs\|5mCs\|dAs\|o5mCs\|oUs\|oGs\|o5mCs\|LTs\|oU] |
| 435 | [oGs\|o5mCs\|oUs\|dAs\|dGs\|dGs\|dTs\|dGs\|dAs\|dTs\|dGs\|5mCs\|dAs\|o5mCs\|oUs\|oGs\|L5mCs\|oUs\|oU] |
| 436 | [oGs\|o5mCs\|oUs\|dAs\|dGs\|dGs\|dTs\|dGs\|dAs\|dTs\|dGs\|5mCs\|dAs\|o5mCs\|oUs\|LGs\|o5mCs\|oUs\|oU] |
| 437 | [oGs\|o5mCs\|oUs\|dAs\|dGs\|dGs\|dTs\|dGs\|dAs\|dTs\|dGs\|5mCs\|dAs\|o5mCs\|LTs\|oGs\|o5mCs\|oUs\|oU] |
| 438 | [oUs\|LGs\|o5mCs\|oUs\|oAs\|oGs\|dGs\|dTs\|dGs\|dAs\|dTs\|dGs\|5mCs\|dAs\|5mCs\|dTs\|oGs\|o5mC] |
| 439 | [oUs\|oGs\|L5mCs\|oUs\|oAs\|oGs\|dGs\|dTs\|dGs\|dAs\|dTs\|dGs\|5mCs\|dAs\|5mCs\|dTs\|oGs\|o5mC] |
| 440 | [oUs\|oGs\|o5mCs\|LTs\|oAs\|oGs\|dGs\|dTs\|dGs\|dAs\|dTs\|dGs\|5mCs\|dAs\|5mCs\|dTs\|oGs\|o5mC] |
| 441 | [oUs\|oGs\|o5mCs\|oUs\|LAs\|oGs\|dGs\|dTs\|dGs\|dAs\|dTs\|dGs\|5mCs\|dAs\|5mCs\|dTs\|oGs\|o5mC] |
| 442 | [o5mCs\|oUs\|c\|As\|dGs\|dGs\|dTs\|dGs\|dAs\|dTs\|dGs\|5mCs\|dAs\|o5mCs\|oUs\|oGs\|o5mCs\|LTs\|oU] |
| 443 | [o5mCs\|oUs\|c\|As\|dGs\|dGs\|dTs\|dGs\|dAs\|dTs\|dGs\|5mCs\|dAs\|o5mCs\|oUs\|oGs\|L5mCs\|oUs\|oU] |
| 444 | [o5mCs\|oUs\|c\|As\|dGs\|dGs\|dTs\|dGs\|dAs\|dTs\|dGs\|5mCs\|dAs\|o5mCs\|oUs\|LGs\|o5mCs\|oUs\|oU] |
| 445 | [o5mCs\|oUs\|c\|As\|dGs\|dGs\|dTs\|dGs\|dAs\|dTs\|dGs\|5mCs\|dAs\|o5mCs\|LTs\|oGs\|o5mCs\|oUs\|oU] |
| 446 | [oUs\|LGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|oUs\|oU] |
| 447 | [oUs\|oGs\|L5mCs\|oUs\|oAs\|dGs\|dGs\|dTs\|dGs\|dAs\|dTs\|dGs\|5mCs\|dAs\|5mCs\|oUs\|oGs\|o5mCs\|oUs\|oU] |
| 448 | [oUs\|oGs\|o5mCs\|LTs\|oAs\|dGs\|dGs\|dTs\|dGs\|dAs\|dTs\|dGs\|5mCs\|dAs\|5mCs\|oUs\|oGs\|o5mCs\|oUs\|oU] |
| 449 | [oUs\|oGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|LTs\|oU] |
| 450 | [oUs\|oGs\|o5mCs\|oUs\|oAs\|dGs\|dGs\|dTs\|dGs\|dAs\|dTs\|dGs\|5mCs\|dAs\|5mCs\|oUs\|oGs\|L5mCs\|oUs\|oU] |
| 451 | [oUs\|oGs\|o5mCs\|oUs\|oAs\|dGs\|dGs\|dTs\|dGs\|dAs\|dTs\|dGs\|5mCs\|dAs\|5mCs\|oUs\|LGs\|o5mCs\|oUs\|oU] |
| 452 | [oUs\|LGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|oU] |
| 453 | [oUs\|oGs\|L5mCs\|oUs\|oAs\|dGs\|dGs\|dTs\|dGs\|dAs\|dTs\|dGs\|5mCs\|dAs\|5mCs\|oUs\|oGs\|o5mCs\|oU] |
| 454 | [oUs\|oGs\|o5mCs\|LTs\|oAs\|dGs\|dGs\|dTs\|dGs\|dAs\|dTs\|dGs\|5mCs\|dAs\|5mCs\|oUs\|oGs\|o5mCs\|oU] |
| 455 | [oGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|LTs\|oU] |
| 456 | [oGs\|o5mCs\|oUs\|oAs\|dGs\|dGs\|dTs\|dGs\|dAs\|dTs\|dGs\|5mCs\|dAs\|5mCs\|oUs\|oGs\|L5mCs\|oUs\|oU] |
| 457 | [oGs\|o5mCs\|oUs\|oAs\|dGs\|dGs\|dTs\|dGs\|dAs\|dTs\|dGs\|5mCs\|dAs\|5mCs\|oUs\|LGs\|o5mCs\|oUs\|oU] |
| 458 | [oUs\|LGs\|o5mCs\|oUs\|oAs\|dGs\|dGs\|dTs\|dGs\|dAs\|dTs\|dGs\|5mCs\|dAs\|5mCs\|oUs\|oGs\|o5mC] |
| 459 | [oUs\|oGs\|L5mCs\|oUs\|oAs\|dGs\|dGs\|dTs\|dGs\|dAs\|dTs\|dGs\|5mCs\|dAs\|5mCs\|oUs\|oGs\|o5mC] |
| 460 | [oUs\|oGs\|o5mCs\|LTs\|oAs\|dGs\|dGs\|dTs\|dGs\|dAs\|dTs\|dGs\|5mCs\|dAs\|5mCs\|oUs\|oGs\|o5mC] |

TABLE 4-continued

| Antisense Oligo No./ SEQ ID NO: | Variant Sequence |
|---|---|
| 461 | [o5mCs\|oUs\|oAs\|dGs\|dGs dTs\|c1Gs\|dAs\|dTs\|dGs\|5mCs\|dAs\|5mCs\|oUs\|oGs\|o5mCs\|LTs\|oU] |
| 462 | [o5mCs\|oUs\|oAs\|dGs\|dGs\|dTs\|dGs\|dAs\|dTs\|dGs\|5mCs\|dAs\|5mCs\|oUs\|oGs\|L5mCs\|oUs\|oU] |
| 463 | [o5mCs\|oUs\|oAs\|dGs\|dGs\|dTs\|dGs\|dAs\|dTs\|dGs\|5mCs\|dAs\|5mCs\|oUs\|LGs\|o5mCs\|oUs\|oU] |
| 464 | [oUs\|LGs\|o5mCs\|oUs\|oAs\|dGs\|dGs\|dTs\|dGs\|dAs\|dTs\|dGs\|5mCs\|dAs\|5mCs\|oUs\|oG] |
| 465 | [oUs\|oGs\|L5mCs\|oUs\|oAs\|dGs\|dGs\|dTs\|dGs\|dAs\|dTs\|dGs\|5mCs\|dAs\|5mCs\|oUs\|oG] |
| 466 | [oUs\|oGs\|o5mCs\|LTs\|oAs\|dGs\|dGs\|dTs\|dGs\|dAs\|dTs\|dGs\|5mCs\|dAs\|5mCs\|oUs\|oG] |
| 467 | [oUs\|oAs\|dGs\|dGs\|dTs\|dGs\|dAs\|dTs\|dGs\|5mCs\|dAs\|5mCs\|oUs\|oGs\|o5mCs\|LTs\|oU] |
| 468 | [oUs\|oAs\|dGs\|dGs\|dTs\|dGs\|dAs\|dTs\|dGs\|5mCs\|dAs\|5mCs\|oUs\|oGs\|L5mCs\|oUs\|oU] |
| 469 | [oUs\|oAs\|dGs\|dGs\|dTs\|dGs\|dAs\|dTs\|dGs\|5mCs\|dAs\|5mCs\|oUs\|LGs\|o5mCs\|oUs\|oU] |
| 470 | [oGs\|L5mCs\|oUs\|oAs\|dGs\|dGs\|dTs\|dGs\|dAs\|dTs\|dGs\|5mCs\|dAs\|5mCs\|oUs\|oGs\|o5mCs\|oUs\|oU] |
| 471 | [oGs\|o5mCs\|LTs\|oAs\|dGs\|dGs\|dTs\|dGs\|dAs\|dTs\|dGs\|5mCs\|dAs\|5mCs\|oUs\|oGs\|o5mCs\|oUs\|oU] |
| 472 | [oUs\|oGs\|o5mCs\|oUs\|oAs\|dGs\|dGs\|dTs\|dGs\|dAs\|dTs\|dGs\|5mCs\|dAs\|5mCs\|oUs\|oGs\|L5mCs\|oU] |
| 473 | [oUs\|oGs\|o5mCs\|oUs\|oAs\|dGs\|dGs\|dTs\|dGs\|dAs\|dTs\|dGs\|5mCs\|dAs\|5mCs\|oUs\|LGs\|o5mCs\|oU] |
| 474 | [oGs\|L5mCs\|oUs\|oAs\|dGs\|dGs\|dTs\|dGs\|dAs\|dTs\|dGs\|5mCs\|dAs\|5mCs\|oUs\|oGs\|o5mCs\|oU] |
| 475 | [oGs\|o5mCs\|LTs\|oAs\|dGs\|dGs\|dTs\|dGs\|dAs\|dTs\|dGs\|5mCs\|dAs\|5mCs\|oUs\|oGs\|o5mCs\|oU] |
| 476 | [oGs\|o5mCs\|oUs\|oAs\|dGs\|dGs\|dTs\|dGs\|dAs\|dTs\|dGs\|5mCs\|dAs\|5mCs\|oUs\|oGs\|L5mCs\|oU] |
| 477 | [oGs\|o5mCs\|oUs\|oAs\|dGs\|dGs\|dTs\|dGs\|dAs\|dTs\|dGs\|5mCs\|dAs\|5mCs\|oUs\|LGs\|o5mCs\|oU] |
| 478 | [oGs\|L5mCs\|oUs\|oAs\|dGs\|dGs\|dTs\|dGs\|dAs\|dTs\|dGs\|5mCs\|dAs\|5mCs\|oUs\|oGs\|o5mC] |
| 479 | [oGs\|o5mCs\|LTs\|oAs\|dGs\|dGs\|dTs\|dGs\|dAs\|dTs\|dGs\|5mCs\|dAs\|5mCs\|oUs\|oGs\|o5mC] |
| 480 | [oGs\|o5mCs\|oUs\|oAs\|dGs\|dGs\|dTs\|dGs\|dAs\|dTs\|dGs\|5mCs\|dAs\|5mCs\|oUs\|LGs\|o5mC] |
| 481 | [oUs\|oGs\|o5mCs\|oUs\|oAs\|oGs\|oGs\|oUs\|dGs\|c\|As\|dTs\|dGs\|5mCs\|dAs\|5mCs\|dTs\|dGs\|5mCs\|oUs\|oU] |
| 482 | [oUs\|oGs\|5mCs\|dTs\|dAs\|dGs\|dGs\|dTs\|dGs\|dAs\|dTs\|dGs\|o5mCs\|oAs\|o5mCs\|oUs\|oGs\|o5mCs\|oUs\|oU] |
| 483 | [oUs\|oGs\|o5mCs\|oUs\|oAs\|oGs\|oGs\|dTs\|dGs\|dAs\|dTs\|dGs\|5mCs\|dAs\|5mCs\|dTs\|dGs\|o5mCs\|oUs\|oU] |
| 484 | [oUs\|oGs\|o5mCs\|dTs\|dAs\|dGs\|dGs\|dTs\|dGs\|dAs\|dTs\|dGs\|5mCs\|oAs\|o5mCs\|oUs\|oGs\|o5mCs\|oUs\|oU] |
| 485 | [oUs\|oGs\|o5mCs\|oUs\|oAs\|oGs\|oGs\|dTs\|dGs\|dAs\|dTs\|dGs\|5mCs\|dAs\|5mCs\|dTs\|dGs\|5mCs\|oUs\|oU] |
| 486 | [oGs\|o5mCs\|dTs\|dAs\|dGs\|dGs\|dTs\|dGs\|dAs\|dTs\|dGs\|5mCs\|oAs\|o5mCs\|oUs\|oGs\|o5mCs\|oUs\|oU] |
| 487 | [oUs\|oGs\|o5mCs\|oUs\|oAs\|oGs\|dGs\|dTs\|dGs\|dAs\|dTs\|dGs\|5mCs\|dAs\|5mCs\|dTs\|oGs\|o5mCs\|oUs\|oU] |
| 488 | [oUs\|oGs\|o5mCs\|oUs\|dAs\|dGs\|dGs\|dTs\|dGs\|dAs\|dTs\|dGs\|5mCs\|dAs\|o5mCs\|oUs\|oGs\|o5mCs\|oUs\|oU] |
| 489 | [oUs\|oGs\|o5mCs\|oUs\|oAs\|oGs\|dGs\|dTs\|dGs\|dAs\|dTs\|dGs\|5mCs\|dAs\|5mCs\|dTs\|oGs\|o5mCs\|oU] |
| 490 | [oGs\|o5mCs\|oUs\|dAs\|dGs\|dGs\|dTs\|dGs\|dAs\|dTs\|dGs\|5mCs\|dAs\|o5mCs\|oUs\|oGs\|o5mCs\|oUs\|oU] |
| 491 | [oUs\|oGs\|o5mCs\|oUs\|oAs\|oGs\|dGs\|dTs\|dGs\|dAs\|dTs\|dGs\|5mCs\|dAs\|5mCs\|dTs\|oGs\|o5mC] |
| 492 | [o5mCs\|oUs\|dAs\|dGs\|dGs\|dTs\|dGs\|dAs\|dTs\|dGs\|5mCs\|dAs\|o5mCs\|oUs\|oGs\|o5mCs\|oUs\|oU] |
| 493 | [oUs\|oGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|oUs\|oU] |

TABLE 4-continued

| Antisense Oligo No./ SEQ ID NO: | Variant Sequence |
|---|---|
| 494 | [oUs\|oGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|oU] |
| 495 | [oUs\|oGs\|o5mCs\|oUs\|oAs\|dGs\|dGs\|dTs\|dGs\|dAs\|dTs\|dGs\|5mCs\|dAs\|5mCs\|oUs\|oGs\|o5mC] |
| 496 | [o5mCs\|oUs\|oAs\|dGs\|dGs\|dTs\|dGs\|dAs\|dTs\|dGs\|5mCs\|dAs\|5mCs\|oUs\|oGs\|o5mCs\|oUs\|oU] |
| 497 | [oUs\|oGs\|o5mCs\|oUs\|oAs\|dGs\|dGs\|dTs\|dGs\|dAs\|dTs\|dGs\|5mCs\|dAs\|5mCs\|oUs\|oG] |
| 498 | [oUs\|oAs\|dGs\|dGs\|dTs\|dGs\|dAs\|dTs\|dGs\|5mCs\|dAs\|5mCs\|oUs\|oGs\|o5mCs\|oUs\|oU] |
| 499 | [oGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|oUs\|oU] |
| 500 | [oGs\|o5mCs\|oUs\|oAs\|dGs\|dGs\|dTs\|dGs\|dAs\|dTs\|dGs\|5mCs\|dAs\|5mCs\|oUs\|oGs\|o5mCs\|oU] |
| 501 | [oGs\|o5mCs\|oUs\|oAs\|dGs\|dGs\|dTs\|dGs\|dAs\|dTs\|dGs\|5mCs\|dAs\|5mCs\|oUs\|oGs\|o5mC] |
| 502 | [oUs\|LTs\|oGs\|oAs\|oUs\|o5mCs\|o5mCs\|oUs\|dGs\|dTs\|dTs\|5mCs\|dTs\|5mCs\|5mCs\|5mCs\|dAs\|dGs\|o5mCs\|oA] |
| 503 | [oUs\|oUs\|LGs\|oAs\|oUs\|o5mCs\|o5mCs\|oUs\|dGs\|dTs\|dTs\|5mCs\|dTs\|5mCs\|5mCs\|5mCs\|dAs\|dGs\|o5mCs\|oA] |
| 504 | [oUs\|oUs\|oGs\|LAs\|oUs\|o5mCs\|o5mCs\|oUs\|dGs\|dTs\|dTs\|5mCs\|dTs\|5mCs\|5mCs\|5mCs\|dAs\|dGs\|o5mCs\|oA] |
| 505 | [oUs\|oUs\|oGs\|oAs\|LTs\|o5mCs\|o5mCs\|oUs\|dGs\|dTs\|dTs\|5mCs\|dTs\|5mCs\|5mCs\|5mCs\|dAs\|dGs\|o5mCs\|oA] |
| 506 | [oUs\|oUs\|oGs\|oAs\|oUs\|L5mCs\|o5mCs\|oUs\|dGs\|dTs\|dTs\|5mCs\|dTs\|5mCs\|5mCs\|5mCs\|dAs\|dGs\|o5mCs\|oA] |
| 507 | [oUs\|oUs\|oGs\|oAs\|oUs\|o5mCs\|L5mCs\|oUs\|dGs\|dTs\|dTs\|5mCs\|dTs\|5mCs\|5mCs\|5mCs\|dAs\|dGs\|o5mCs\|oA] |
| 508 | [oUs\|oUs\|dGs\|dAs\|dTs\|5mCs\|5mCs\|dTs\|dGs\|dTs\|dTs\|5mCs\|oUs\|o5mCs\|o5mCs\|o5mCs\|oAs\|oGs\|L5mCs\|oA] |
| 509 | [oUs\|oUs\|dGs\|dAs\|dTs\|5mCs\|5mCs\|dTs\|dGs\|dTs\|dTs\|5mCs\|oUs\|o5mCs\|o5mCs\|o5mCs\|oAs\|LGs\|o5mCs\|oA] |
| 510 | [oUs\|oUs\|dGs\|dAs\|dTs\|5mCs\|5mCs\|dTs\|dGs\|dTs\|dTs\|5mCs\|oUs\|o5mCs\|o5mCs\|o5mCs\|LAs\|oGs\|o5mCs\|oA] |
| 511 | [oUs\|oUs\|dGs\|dAs\|dTs\|5mCs\|5mCs\|dTs\|dGs\|dTs\|dTs\|5mCs\|oUs\|o5mCs\|o5mCs\|L5mCs\|oAs\|oGs\|o5mCs\|oA] |
| 512 | [oUs\|oUs\|dGs\|dAs\|dTs\|5mCs\|5mCs\|dTs\|dGs\|dTs\|dTs\|5mCs\|oUs\|o5mCs\|L5mCs\|o5mCs\|oAs\|oGs\|o5mCs\|oA] |
| 513 | [oUs\|oUs\|dGs\|dAs\|dTs\|5mCs\|5mCs\|dTs\|dGs\|dTs\|dTs\|5mCs\|oUs\|L5mCs\|o5mCs\|o5mCs\|oAs\|oGs\|o5mCs\|oA] |
| 514 | [oUs\|LTs\|oGs\|oAs\|oUs\|o5mCs\|o5mCs\|dTs\|dGs\|dTs\|dTs\|5mCs\|dTs\|5mCs\|5mCs\|5mCs\|dAs\|oGs\|o5mCs\|oA] |
| 515 | [oUs\|oUs\|LGs\|oAs\|oUs\|o5mCs\|o5mCs\|dTs\|dGs\|dTs\|dTs\|5mCs\|dTs\|5mCs\|5mCs\|5mCs\|dAs\|oGs\|o5mCs\|oA] |
| 516 | [oUs\|oUs\|oGs\|LAs\|oUs\|o5mCs\|o5mCs\|dTs\|dGs\|dTs\|dTs\|5mCs\|dTs\|5mCs\|5mCs\|5mCs\|dAs\|oGs\|o5mCs\|oA] |
| 517 | [oUs\|oUs\|oGs\|oAs\|LTs\|o5mCs\|o5mCs\|dTs\|dGs\|dTs\|dTs\|5mCs\|dTs\|5mCs\|5mCs\|5mCs\|dAs\|oGs\|o5mCs\|oA] |
| 518 | [oUs\|oUs\|oGs\|oAs\|oUs\|L5mCs\|o5mCs\|dTs\|dGs\|dTs\|dTs\|5mCs\|dTs\|5mCs\|5mCs\|5mCs\|dAs\|oGs\|o5mCs\|oA] |
| 519 | [oUs\|oUs\|oGs\|dAs\|dTs\|5mCs\|5mCs\|c\|Ts\|dGs\|dTs\|dTs\|5mCs\|dTs\|o5mCs\|o5mCs\|o5mCs\|oAs\|oGs\|L5mCs\|oA] |
| 520 | [oUs\|oUs\|oGs\|dAs\|dTs\|5mCs\|5mCs\|c\|Ts\|dGs\|dTs\|dTs\|5mCs\|dTs\|o5mCs\|o5mCs\|o5mCs\|oAs\|LGs\|o5mCs\|oA] |
| 521 | [oUs\|oUs\|oGs\|dAs\|dTs\|5mCs\|5mCs\|c\|Ts\|dGs\|dTs\|dTs\|5mCs\|dTs\|o5mCs\|o5mCs\|o5mCs\|LAs\|oGs\|o5mCs\|oA] |

TABLE 4-continued

| Antisense Oligo No./ SEQ ID NO: | Variant Sequence |
|---|---|
| 522 | [oUs\|oUs\|oGs\|dAs\|dTs\|5mCs\|5mCs\|c\|Ts\|dGs\|dTs\|dTs\|5mCs\|dTs\|o5mCs\|o5mCs\|L5mCs\|oAs\|oGs\|o5mCs\|oA] |
| 523 | [oUs\|oUs\|oGs\|dAs\|dTs\|5mCs\|5mCs\|c\|Ts\|dGs\|dTs\|dTs\|5mCs\|dTs\|o5mCs\|L5mCs\|o5mCs\|oAs\|oGs\|o5mCs\|oA] |
| 524 | [oUs\|LTs\|oGs\|oAs\|oUs\|o5mCs\|o5mCs\|dTs\|dGs\|dTs\|dTs\|5mCs\|dTs\|5mCs\|5mCs\|5mCs\|dAs\|oGs\|o5mC] |
| 525 | [oUs\|oUs\|LGs\|oAs\|oUs\|o5mCs\|o5mCs\|dTs\|dGs\|dTs\|dTs\|5mCs\|dTs\|5mCs\|5mCs\|5mCs\|dAs\|oGs\|o5mC] |
| 526 | [oUs\|oUs\|oGs\|LAs\|oUs\|o5mCs\|o5mCs\|dTs\|dGs\|dTs\|dTs\|5mCs\|dTs\|5mCs\|5mCs\|5mCs\|dAs\|oGs\|o5mC] |
| 527 | [oUs\|oUs\|oGs\|oAs\|LTs\|o5mCs\|o5mCs\|dTs\|dGs\|dTs\|dTs\|5mCs\|dTs\|5mCs\|5mCs\|5mCs\|dAs\|oGs\|o5mC] |
| 528 | [oUs\|oUs\|oGs\|oAs\|oUs\|L5mCs\|o5mCs\|dTs\|dGs\|dTs\|dTs\|5mCs\|dTs\|5mCs\|5mCs\|5mCs\|dAs\|oGs\|o5mC] |
| 529 | [oUs\|oGs\|dAs\|dTs\|5mCs\|5mCs\|dTs\|dGs\|dTs\|dTs\|5mCs\|dTs\|o5mCs\|o5mCs\|o5mCs\|oAs\|oGs\|L5mCs\|oA] |
| 530 | [oUs\|oGs\|dAs\|dTs\|5mCs\|5mCs\|dTs\|dGs\|dTs\|dTs\|5mCs\|dTs\|o5mCs\|o5mCs\|o5mCs\|oAs\|LGs\|o5mCs\|oA] |
| 531 | [oUs\|oGs\|dAs\|dTs\|5mCs\|5mCs\|dTs\|dGs\|dTs\|dTs\|5mCs\|dTs\|o5mCs\|o5mCs\|o5mCs\|LAs\|oGs\|o5mCs\|oA] |
| 532 | [oUs\|oGs\|dAs\|dTs\|5mCs\|5mCs\|dTs\|dGs\|dTs\|dTs\|5mCs\|dTs\|o5mCs\|o5mCs\|L5mCs\|oAs\|oGs\|o5mCs\|oA] |
| 533 | [oUs\|oGs\|dAs\|dTs\|5mCs\|5mCs\|dTs\|dGs\|dTs\|dTs\|5mCs\|dTs\|o5mCs\|L5mCs\|o5mCs\|oAs\|oGs\|o5mCs\|oA] |
| 534 | [oUs\|LTs\|oGs\|oAs\|oUs\|o5mCs\|5mCs\|dTs\|dGs\|dTs\|dTs\|5mCs\|dTs\|5mCs\|5mCs\|5mCs\|oAs\|oGs\|o5mCs\|oA] |
| 535 | [oUs\|oUs\|LGs\|oAs\|oUs\|o5mCs\|5mCs\|dTs\|dGs\|dTs\|dTs\|5mCs\|dTs\|5mCs\|5mCs\|5mCs\|oAs\|oGs\|o5mCs\|oA] |
| 536 | [oUs\|oUs\|oGs\|LAs\|oUs\|o5mCs\|5mCs\|dTs\|dGs\|dTs\|dTs\|5mCs\|dTs\|5mCs\|5mCs\|5mCs\|oAs\|oGs\|o5mCs\|oA] |
| 537 | [oUs\|oUs\|oGs\|oAs\|LTs\|o5mCs\|5mCs\|dTs\|dGs\|dTs\|dTs\|5mCs\|dTs\|5mCs\|5mCs\|5mCs\|oAs\|oGs\|o5mCs\|oA] |
| 538 | [oUs\|oUs\|oGs\|oAs\|dTs\|5mCs\|5mCs\|dTs\|dGs\|dTs\|dTs\|5mCs\|dTs\|5mCs\|o5mCs\|o5mCs\|oAs\|oGs\|L5mCs\|oA] |
| 539 | [oUs\|oUs\|oGs\|oAs\|dTs\|5mCs\|5mCs\|dTs\|dGs\|dTs\|dTs\|5mCs\|dTs\|5mCs\|o5mCs\|o5mCs\|oAs\|LGs\|o5mCs\|oA] |
| 540 | [oUs\|oUs\|oGs\|oAs\|dTs\|5mCs\|5mCs\|dTs\|dGs\|dTs\|dTs\|5mCs\|dTs\|5mCs\|o5mCs\|o5mCs\|LAs\|oGs\|o5mCs\|oA] |
| 541 | [oUs\|oUs\|oGs\|oAs\|dTs\|5mCs\|5mCs\|dTs\|dGs\|dTs\|dTs\|5mCs\|dTs\|5mCs\|o5mCs\|L5mCs\|oAs\|oGs\|o5mCs\|oA] |
| 542 | [oUs\|LTs\|oGs\|oAs\|oUs\|o5mCs\|5mCs\|dTs\|dGs\|dTs\|dTs\|5mCs\|dTs\|5mCs\|5mCs\|5mCs\|oAs\|oGs\|o5mC] |
| 543 | [oUs\|oUs\|LGs\|oAs\|oUs\|o5mCs\|5mCs\|dTs\|dGs\|dTs\|dTs\|5mCs\|dTs\|5mCs\|5mCs\|5mCs\|oAs\|oGs\|o5mC] |
| 544 | [oUs\|oUs\|oGs\|LAs\|oUs\|o5mCs\|5mCs\|dTs\|dGs\|dTs\|dTs\|5mCs\|dTs\|5mCs\|5mCs\|5mCs\|oAs\|oGs\|o5mC] |
| 545 | [oUs\|oUs\|oGs\|oAs\|LTs\|o5mCs\|5mCs\|dTs\|dGs\|dTs\|dTs\|5mCs\|dTs\|5mCs\|5mCs\|5mCs\|oAs\|oGs\|o5mC] |
| 546 | [oUs\|oUs\|oGs\|dAs\|dTs\|5mCs\|5mCs\|dTs\|dGs\|dTs\|dTs\|5mCs\|dTs\|5mCs\|o5mCs\|o5mCs\|oAs\|oGs\|L5mCs\|oA] |

TABLE 4-continued

| Antisense Oligo No./ SEQ ID NO: | Variant Sequence |
|---|---|
| 547 | [oUs\|oUs\|oGs\|dAs\|dTs\|5mCs\|5mCs\|dTs\|dGs\|dTs\|dTs\|5mCs\|dTs\|5mCs\|o5mCs\|o5mCs\|oAs\|LGs\|o5mCs\|oA] |
| 548 | [oUs\|oUs\|oGs\|dAs\|dTs\|5mCs\|5mCs\|dTs\|dGs\|dTs\|dTs\|5mCs\|dTs\|5mCs\|o5mCs\|o5mCs\|LAs\|oGs\|o5mCs\|oA] |
| 549 | [oUs\|oUs\|oGs\|oAs\|dTs\|5mCs\|5mCs\|dTs\|dGs\|dTs\|dTs\|5mCs\|dTs\|5mCs\|o5mCs\|L5mCs\|oAs\|oGs\|o5mCs\|oA] |
| 550 | [oUs\|LTs\|oGs\|oAs\|oUs\|o5mCs\|5mCs\|dTs\|dGs\|dTs\|dTs\|5mCs\|dTs\|5mCs\|5mCs\|5mCs\|oAs\|oG] |
| 551 | [oUs\|oUs\|LGs\|oAs\|oUs\|o5mCs\|5mCs\|dTs\|dGs\|dTs\|dTs\|5mCs\|dTs\|5mCs\|5mCs\|5mCs\|oAs\|oG] |
| 552 | [oUs\|oUs\|oGs\|LAs\|oUs\|o5mCs\|5mCs\|dTs\|dGs\|dTs\|dTs\|5mCs\|dTs\|5mCs\|5mCs\|5mCs\|oAs\|oG] |
| 553 | [oUs\|oUs\|oGs\|oAs\|LTs\|o5mCs\|5mCs\|dTs\|dGs\|dTs\|dTs\|5mCs\|dTs\|5mCs\|5mCs\|5mCs\|oAs\|oG] |
| 554 | [oGs\|oAs\|dTs\|5mCs\|5mCs\|dTs\|dGs\|dTs\|dTs\|5mCs\|dTs\|5mCs\|o5mCs\|o5mCs\|oAs\|oGs\|L5mCs\|oA] |
| 555 | [oGs\|oAs\|dTs\|5mCs\|5mCs\|dTs\|dGs\|dTs\|dTs\|5mCs\|dTs\|5mCs\|o5mCs\|o5mCs\|oAs\|LGs\|o5mCs\|oA] |
| 556 | [oGs\|oAs\|dTs\|5mCs\|5mCs\|dTs\|dGs\|dTs\|dTs\|5mCs\|dTs\|5mCs\|o5mCs\|o5mCs\|LAs\|oGs\|o5mCs\|oA] |
| 557 | [oGs\|oAs\|dTs\|5mCs\|5mCs\|dTs\|dGs\|dTs\|dTs\|5mCs\|dTs\|5mCs\|o5mCs\|L5mCs\|oAs\|oGs\|o5mCs\|oA] |
| 558 | [oUs\|LTs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 559 | [oUs\|oUs\|LGs\|oAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 560 | [oUs\|oUs\|oGs\|LAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 561 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|L5mCs\|oA] |
| 562 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|oAs\|LGs\|o5mCs\|oA] |
| 563 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|LAs\|oGs\|o5mCs\|oA] |
| 564 | [oUs\|LTs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|o5mC] |
| 565 | [oUs\|oUs\|LGs\|oAs\|oUs\|5mCs\|5mCs\|dTs\|dGs\|dTs\|dTs\|5mCs\|dTs\|5mCs\|5mCs\|o5mCs\|oAs\|oGs\|o5mC] |
| 566 | [oUs\|oUs\|oGs\|LAs\|oUs\|5mCs\|5mCs\|dTs\|dGs\|dTs\|dTs\|5mCs\|dTs\|5mCs\|5mCs\|o5mCs\|oAs\|oGs\|o5mC] |
| 567 | [oUs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|L5mCs\|oA] |
| 568 | [oUs\|oGs\|oAs\|oUs\|5mCs\|5mCs\|dTs\|dGs\|dTs\|dTs\|5mCs\|dTs\|5mCs\|5mCs\|o5mCs\|oAs\|LGs\|o5mCs\|oA] |
| 569 | [oUs\|oGs\|oAs\|oUs\|5mCs\|5mCs\|dTs\|dGs\|dTs\|dTs\|5mCs\|dTs\|5mCs\|5mCs\|o5mCs\|LAs\|oGs\|o5mCs\|oA] |
| 570 | [oUs\|LTs\|oGs\|oAs\|oUs\|5mCs\|5mCs\|dTs\|dGs\|dTs\|dTs\|5mCs\|dTs\|5mCs\|5mCs\|o5mCs\|oAs\|oG] |
| 571 | [oUs\|oUs\|LGs\|oAs\|oUs\|5mCs\|5mCs\|dTs\|dGs\|dTs\|dTs\|5mCs\|dTs\|5mCs\|5mCs\|o5mCs\|oAs\|oG] |
| 572 | [oUs\|oUs\|oGs\|LAs\|oUs\|5mCs\|5mCs\|dTs\|dGs\|dTs\|dTs\|5mCs\|dTs\|5mCs\|5mCs\|o5mCs\|oAs\|oG] |
| 573 | [oGs\|oAs\|oUs\|5mCs\|5mCs\|dTs\|dGs\|dTs\|dTs\|5mCs\|dTs\|5mCs\|5mCs\|o5mCs\|oAs\|oGs\|L5mCs\|oA] |
| 574 | [oGs\|oAs\|oUs\|5mCs\|5mCs\|dTs\|dGs\|dTs\|dTs\|5mCs\|dTs\|5mCs\|5mCs\|o5mCs\|oAs\|LGs\|o5mCs\|oA] |
| 575 | [oGs\|oAs\|oUs\|5mCs\|5mCs\|dTs\|dGs\|dTs\|dTs\|5mCs\|dTs\|5mCs\|5mCs\|o5mCs\|LAs\|oGs\|o5mCs\|oA] |
| 576 | [oUs\|LTs\|oGs\|oAs\|oUs\|5mCs\|5mCs\|dTs\|dGs\|dTs\|dTs\|5mCs\|dTs\|5mCs\|5mCs\|o5mCs\|oA] |
| 577 | [oUs\|oUs\|LGs\|oAs\|oUs\|5mCs\|5mCs\|dTs\|dGs\|dTs\|dTs\|5mCs\|dTs\|5mCs\|5mCs\|o5mCs\|oA] |

TABLE 4-continued

| Antisense Oligo No./ SEQ ID NO: | Variant Sequence |
|---|---|
| 578 | [oUs\|oUs\|oGs\|LAs\|oUs\|5mCs\|5mCs\|dTs\|dGs\|dTs\|dTs\|5mCs\|dTs\|5mCs\|5mCs\|o5mCs\|oA] |
| 579 | [oAs\|oUs\|5mCs\|5mCs\|dTs\|dGs\|dTs\|dTs\|5mCs\|dTs\|5mCs\|5mCs\|o5mCs\|oAs\|oGs\|L5mCs\|oA] |
| 580 | [oAs\|oUs\|5mCs\|5mCs\|dTs\|dGs\|dTs\|dTs\|5mCs\|dTs\|5mCs\|5mCs\|o5mCs\|oAs\|LGs\|o5mCs\|oA] |
| 581 | [oAs\|oUs\|5mCs\|5mCs\|dTs\|dGs\|dTs\|dTs\|5mCs\|dTs\|5mCs\|5mCs\|o5mCs\|LAs\|oGs\|o5mCs\|oA] |
| 582 | [oUs\|LGs\|oAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 583 | [oUs\|oGs\|LAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 584 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|oAs\|LGs\|o5mC] |
| 585 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|LAs\|oGs\|o5mC] |
| 586 | [oUs\|LGs\|oAs\|oUs\|5mCs\|5mCs\|dTs\|dGs\|dTs\|dTs\|5mCs\|dTs\|5mCs\|5mCs\|o5mCs\|oAs\|oGs\|o5mC] |
| 587 | [oUs\|oGs\|LAs\|oUs\|5mCs\|5mCs\|dTs\|dGs\|dTs\|dTs\|5mCs\|dTs\|5mCs\|5mCs\|o5mCs\|oAs\|oGs\|o5mC] |
| 588 | [oUs\|oGs\|oAs\|oUs\|5mCs\|5mCs\|dTs\|dGs\|dTs\|dTs\|5mCs\|dTs\|5mCs\|5mCs\|o5mCs\|oAs\|LGs\|o5mC] |
| 589 | [oUs\|oGs\|oAs\|oUs\|5mCs\|5mCs\|dTs\|dGs\|dTs\|dTs\|5mCs\|dTs\|5mCs\|5mCs\|o5mCs\|LAs\|oGs\|o5mC] |
| 590 | [oUs\|LGs\|oAs\|oUs\|5mCs\|5mCs\|dTs\|dGs\|dTs\|dTs\|5mCs\|dTs\|5mCs\|5mCs\|o5mCs\|oAs\|oG] |
| 591 | [oUs\|oGs\|LAs\|oUs\|5mCs\|5mCs\|dTs\|dGs\|dTs\|dTs\|5mCs\|dTs\|5mCs\|5mCs\|o5mCs\|oAs\|oG] |
| 592 | [oUs\|oGs\|oAs\|oUs\|5mCs\|5mCs\|dTs\|dGs\|dTs\|dTs\|5mCs\|dTs\|5mCs\|5mCs\|o5mCs\|LAs\|oG] |
| 593 | [oUs\|oUs\|oGs\|oAs\|oUs\|o5mCs\|o5mCs\|oUs\|dGs\|dTs\|dTs\|5mCs\|dTs\|5mCs\|5mCs\|5mCs\|dAs\|dGs\|o5mCs\|oA] |
| 594 | [oUs\|oUs\|dGs\|dAs\|dTs\|5mCs\|5mCs\|dTs\|dGs\|dTs\|dTs\|5mCs\|oUs\|o5mCs\|o5mCs\|o5mCs\|oAs\|oGs\|o5mCs\|oA] |
| 595 | [oUs\|oUs\|oGs\|oAs\|oUs\|o5mCs\|o5mCs\|dTs\|dGs\|dTs\|dTs\|5mCs\|dTs\|5mCs\|5mCs\|5mCs\|dAs\|oGs\|o5mCs\|oA] |
| 596 | [oUs\|oUs\|oGs\|dAs\|dTs\|5mCs\|5mCs\|dTs\|dGs\|dTs\|dTs\|5mCs\|dTs\|o5mCs\|o5mCs\|o5mCs\|oAs\|oGs\|o5mCs\|oA] |
| 597 | [oUs\|oUs\|oGs\|oAs\|oUs\|o5mCs\|o5mCs\|dTs\|dGs\|dTs\|dTs\|5mCs\|dTs\|5mCs\|5mCs\|5mCs\|dAs\|oGs\|o5mC] |
| 598 | [oUs\|oGs\|dAs\|dTs\|5mCs\|5mCs\|dTs\|dGs\|dTs\|dTs\|5mCs\|dTs\|o5mCs\|o5mCs\|o5mCs\|oAs\|oGs\|o5mCs\|oA] |
| 599 | [oUs\|oUs\|oGs\|oAs\|oUs\|o5mCs\|5mCs\|dTs\|dGs\|dTs\|dTs\|5mCs\|dTs\|5mCs\|5mCs\|5mCs\|oAs\|oGs\|o5mCs\|oA] |
| 600 | [oUs\|oUs\|oGs\|oAs\|dTs\|5mCs\|5mCs\|dTs\|dGs\|dTs\|dTs\|5mCs\|dTs\|5mCs\|o5mCs\|o5mCs\|oAs\|oGs\|o5mCs\|oA] |
| 601 | [oUs\|oUs\|oGs\|oAs\|oUs\|o5mCs\|5mCs\|dTs\|dGs\|dTs\|dTs\|5mCs\|dTs\|5mCs\|5mCs\|5mCs\|oAs\|oGs\|o5mC] |
| 602 | [oUs\|oUs\|oGs\|dAs\|dTs\|5mCs\|5mCs\|dTs\|dGs\|dTs\|dTs\|5mCs\|dTs\|5mCs\|o5mCs\|o5mCs\|oAs\|oGs\|o5mCs\|oA] |
| 603 | [oUs\|oUs\|oGs\|oAs\|oUs\|o5mCs\|5mCs\|dTs\|dGs\|dTs\|dTs\|5mCs\|dTs\|5mCs\|5mCs\|5mCs\|oAs\|oG] |
| 604 | [oGs\|oAs\|dTs\|5mCs\|5mCs\|dTs\|dGs\|dTs\|dTs\|5mCs\|dTs\|5mCs\|o5mCs\|o5mCs\|oAs\|oGs\|o5mCs\|oA] |
| 605 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 606 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|o5mC] |
| 607 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|oAs\|oG] |

TABLE 4-continued

| Antisense Oligo No./ SEQ ID NO: | Variant Sequence |
|---|---|
| 608 | [oGs\|oAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 609 | [oUs\|oUs\|oGs\|oAs\|oUs\|5mCs\|5mCs\|dTs\|dGs\|dTs\|dTs\|5mCs\|dTs\|5mCs\|5mCs\|o5mCs\|oA] |
| 610 | [oAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 611 | [oUs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|o5mCs\|oA] |
| 612 | [oUs\|oGs\|oAs\|oUs\|5mCs\|5mCs\|dTs\|dGs\|dTs\|dTs\|5mCs\|dTs\|5mCs\|5mCs\|o5mCs\|oAs\|oGs\|o5mC] |
| 613 | [oUs\|oGs\|oAs\|oUs\|5mCs\|5mCs\|dTs\|dGs\|dTs\|dTs\|5mCs\|dTs\|5mCs\|5mCs\|o5mCs\|oAs\|oG] |

The mRNA sequence of reference MSH3 mRNA NM_002439.4 (SEQ ID NO: 614) (https://www.ncbi.nlm.nih.gov/nuccore/NM_002439.4, incorporated herein by reference), is provided below.

```
   1 ccgcagacgc ctgggaactg cggccgcggg ctcgcgctcc tcgccaggcc ctgccgccgg
  61 gctgccatcc ttgccctgcc atgtctcgcc ggaagcctgc gtcgggcggc ctcgctgcct
 121 ccagctcagc ccctgcgagg caagcggttt tgagccgatt cttccagtct acgggaagcc
 181 tgaaatccac ctcctcctcc acaggtgcag ccgaccaggt ggaccctggc gctgcagcgg
 241 ctgcagcggc cgcagcggcc gcagcgcccc cagcgccccc agctcccgcc ttcccgcccc
 301 agctgccgcc gcacatagct acagaaattg acagaagaaa gaagagacca ttggaaaatg
 361 atgggcctgt taaaaagaaa gtaaagaaag tccaacaaaa ggaaggagga agtgatctgg
 421 gaatgtctgg caactctgag ccaaagaaat gtctgaggac caggaatgtt tcaaagtctc
 481 tggaaaaatt gaaagaattc tgctgcgatt ctgcccttcc tcaaagtaga gtccagacag
 541 aatctctgca ggagagattt gcagttctgc caaaatgtac tgattttgat gatatcagtc
 601 ttctacacgc aaagaatgca gtttcttctg aagattcgaa acgtcaaatt aatcaaaagg
 661 acacaacact tttgatctc agtcagtttg gatcatcaaa tacaagtcat gaaaatttac
 721 agaaaactgc ttccaaatca gctaacaaac ggtccaaaag catctatacg ccgctagaat
 781 tacaatacat agaaatgaag cagcagcaca aagatgcagt tttgtgtgtg gaatgtggat
 841 ataagtatag attctttggg gaagatgcag agattgcagc ccgagagctc aatatttatt
 901 gccatttaga tcacaacttt atgacagcaa gtatacctac tcacagactg tttgttcatg
 961 tacgccgcct ggtggcaaaa ggatataagg tgggagttgt gaagcaaact gaaactgcag
1021 cattaaaggc cattggagac aacagaagtt cactcttttc ccggaaattg actgcccttt
1081 atacaaaatc tacacttatt ggagaagatg tgaatcccct aatcaagctg gatgatgctg
1141 taaatgttga tgagataatg actgatactt ctaccagcta tcttctgtgc atctctgaaa
1201 ataaggaaaa tgttagggac aaaaaaaagg gcaacatttt tattggcatt gtgggagtgc
1261 agcctgccac aggcgaggtt gtgtttgata gtttccagga ctctgcttct cgttcagagc
1321 tagaaacccg gatgtcaagc ctgcagccag tagagctgct gcttccttcg gccttgtccg
1381 agcaaacaga ggcgctcatc cacagagcca catctgttag tgtgcaggat gacagaattc
1441 gagtcgaaag gatggataac atttattttg aatacagcca tgctttccag gcagttacag
1501 agttttatgc aaaagataca gttgacatca aaggttctca aattatttct ggcattgtta
1561 acttagagaa gcctgtgatt tgctctttgg ctgccatcat aaaataccte aaagaattca
```

-continued

```
1621 acttggaaaa gatgctctcc aaacctgaga attttaaaca gctatcaagt aaaatggaat
1681 ttatgacaat taatggaaca acattaagga atctggaaat cctacagaat cagactgata
1741 tgaaaaccaa aggaagtttg ctgtgggttt tagaccacac taaaacttca tttgggagac
1801 ggaagttaaa gaagtgggtg acccagccac tccttaaatt aagggaaata aatgcccggc
1861 ttgatgctgt atcggaagtt ctccattcag aatctagtgt gtttggtcag atagaaaatc
1921 atctacgtaa attgcccgac atagagaggg gactctgtag catttatcac aaaaaatgtt
1981 ctacccaaga gttcttcttg attgtcaaaa ctttatatca cctaaagtca gaatttcaag
2041 caataatacc tgctgttaat tcccacattc agtcagactt gctccggacc gttattttag
2101 aaattcctga actcctcagt ccagtggagc attacttaaa gatactcaat gaacaagctg
2161 ccaaagttgg ggataaaact gaattattta aagacctttc tgacttccct ttaataaaaa
2221 agaggaagga tgaaattcaa ggtgttattg acgagatccg aatgcatttg caagaaatac
2281 gaaaaatact aaaaaatcct tctgcacaat atgtgacagt atcaggacag gagtttatga
2341 tagaaataaa gaactctgct gtatcttgta taccaactga ttgggtaaag gttggaagca
2401 caaaagctgt gagccgcttt cactctcctt ttattgtaga aaattacaga catctgaatc
2461 agctccggga gcagctagtc cttgactgca gtgctgaatg gcttgatttt ctagagaaat
2521 tcagtgaaca ttatcactcc ttgtgtaaag cagtgcatca cctagcaact gttgactgca
2581 ttttctccct ggccaaggtc gctaagcaag gagattactg cagaccaact gtacaagaag
2641 aaagaaaaat tgtaataaaa aatggaaggc accctgtgat tgatgtgttg ctgggagaac
2701 aggatcaata tgtcccaaat aatacagatt tatcagagga ctcagagaga gtaatgataa
2761 ttaccggacc aaacatgggt ggaaagagct cctacataaa acaagttgca ttgattacca
2821 tcatggctca gattggctcc tatgttcctg cagaagaagc gacaattggg attgtggatg
2881 gcattttcac aaggatgggt gctgcagaca atatatataa aggacagagt acatttatgg
2941 aagaactgac tgacacagca gaaataatca gaaaagcaac atcacagtcc ttggttatct
3001 tggatgaact aggaagaggg acgagcactc atgatggaat tgccattgcc tatgctacac
3061 ttgagtattt catcagagat gtgaaatcct taaccctgtt tgtcacccat tatccgccag
3121 tttgtgaact agaaaaaaat tactcacacc aggtggggaa ttaccacatg ggattcttgg
3181 tcagtgagga tgaaagcaaa ctggatccag gcgcagcaga acaagtccct gattttgtca
3241 ccttccttta ccaaataact agaggaattg cagcaaggag ttatggatta aatgtggcta
3301 aactagcaga tgttcctgga gaaattttga agaaagcagc tcacaagtca aaagagctgg
3361 aaggattaat aaatacgaaa agaaagagac tcaagtattt tgcaaagtta tggacgatgc
3421 ataatgcaca agacctgcag aagtggacag aggagttcaa catggaagaa acacagactt
3481 ctcttcttca ttaaaatgaa gactacattt gtgaacaaaa aatggagaat taaaaatacc
3541 aactgtacaa aataactctc cagtaacagc ctatctttgt gtgacatgtg agcataaaat
3601 tatgaccatg gtatattcct attggaaaca gagaggtttt tctgaagaca gtctttttca
3661 agtttctgtc ttcctaactt ttctacgtat aaacactctt gaatagactt ccactttgta
3721 attagaaaat tttatggaca gtaagtccag taaagcctta agtggcagaa tataattccc
3781 aagcttttgg agggtgatat aaaaatttac ttgatatttt tatttgtttc agttcagata
3841 attggcaact gggtgaatct ggcaggaatc tatccattga actaaaataa ttttattatg
3901 caaccagttt atccaccaag aacataagaa ttttttataa gtagaaagaa ttggccaggc
3961 atggtggctc atgcctgtaa tcccagcact ttgggaggcc aaggtaggca gatcacctga
```

-continued

```
4021 ggtcaggagt tcaagaccag cctggccaac atggcaaaac cccatcttta ctaaaaatat

4081 aaagtacatc tctactaaaa atacgaaaaa attagctggg catggtggcg cacacctgta

4141 gtcccagcta ctccggaggc tgaggcagga gaatctcttg aacctgggag gcggaggttg

4201 caatgagccg agatcacgtc actgcactcc agcttgggca acagagcaag actccatctc

4261 aaaaaaaaaa aaagaaaaaa gaaaagaaat agaattatca agcttttaaa aactagagca

4321 cagaaggaat aaggtcatga aatttaaaag gttaaatatt gtcataggat taagcagttt

4381 aaagattgtt ggatgaaatt atttgtcatt cattcaagta ataaatattt aatgaatact

4441 tgctataaaa aaaaaaaaaa aaaaaaaaaa aa
```

OTHER ASPECTS

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claimed.

In addition to the various aspects described herein, the present disclosure includes the following aspects numbered E1 through. This list of aspects is presented as an exemplary list and the application is not limited to these particular.

E1. A single-stranded oligonucleotide of 15-30 linked nucleotides in length, wherein the oligonucleotide, or a portion thereof, is at least 95% complementary to at least 15 contiguous nucleobases at positions 2543-2573 of SEQ ID NO: 614, or a pharmaceutically acceptable salt thereof.

E2. The oligonucleotide of E1, wherein the oligonucleotide, or a portion thereof, is at least 98% complementary to at least 15 contiguous nucleobases at positions 2543-2573 of SEQ ID NO: 614, or a pharmaceutically acceptable salt thereof.

E3. The oligonucleotide of E1, wherein the oligonucleotide, or a portion thereof, is at least 99% complementary to at least 15 contiguous nucleobases at positions 2543-2573 of SEQ ID NO: 614, or a pharmaceutically acceptable salt thereof.

E4. The oligonucleotide of E1, wherein the oligonucleotide, or a portion thereof, is 100% complementary to at least 15 contiguous nucleobases at positions 2543-2573 of SEQ ID NO: 614, or a pharmaceutically acceptable salt thereof.

E5. The oligonucleotide of any one of E1-E5, wherein the oligonucleotide, or a portion thereof, is complementary to 17-23 contiguous nucleobases at positions 2543-2573 of SEQ ID NO: 614, or a pharmaceutically acceptable salt thereof.

E6. The oligonucleotide of any one of E1-E5, wherein the oligonucleotide is complementary to 17-20 contiguous nucleobases at positions 2543-2573 of SEQ ID NO: 614, or a pharmaceutically acceptable salt thereof.

E7. The oligonucleotide of E6, wherein the 17-20 contiguous nucleobases begin at position 2543, 2544, 2545, 2546, 2547, 2548, 2549, 2550, 2551, 2552, 2553, 2554, 2555, 2556, or 2557 of SEQ ID NO: 614, or a pharmaceutically acceptable salt thereof.

E8. The oligonucleotide of any one of E1-E7, wherein the oligonucleotide is 17-20 linked nucleotides in length, or a pharmaceutically acceptable salt thereof.

E9. The oligonucleotide of any one of E1-E5, wherein the oligonucleotide, or a portion thereof, is complementary to 20-23 contiguous nucleobases at positions 2543-2573 of SEQ ID NO: 614, or a pharmaceutically acceptable salt thereof.

E10. The oligonucleotide of E9, wherein the 20-23 contiguous nucleobases begin at position 2543, 2544, 2545, 2546, 2547, 2548, 2549, 2550, 2551, 2552, 2553, or 2554 of SEQ ID NO: 614, or a pharmaceutically acceptable salt thereof.

E11. The oligonucleotide of any one of E1-E10, wherein the oligonucleotide is 20-23 linked nucleotides in length, or a pharmaceutically acceptable salt thereof.

E12. The oligonucleotide of any one of E1-E11, wherein the oligonucleotide, or a portion thereof, is complementary to positions 2543-2570 of SEQ ID NO: 614, or a pharmaceutically acceptable salt thereof.

E13. A single-stranded oligonucleotide of E15-E30 linked nucleotides in length, wherein the oligonucleotide, or a portion thereof, is at least 95% complementary to at least 15 contiguous nucleobases at positions 2685-2714 of SEQ ID NO: 614, or a pharmaceutically acceptable salt thereof.

E14. The oligonucleotide of E13, wherein the oligonucleotide, or a portion thereof, is at least 98% complementary to at least 15 contiguous nucleobases at positions 2685-2714 of SEQ ID NO: 614, or a pharmaceutically acceptable salt thereof.

E15. The oligonucleotide of E13, wherein the oligonucleotide, or a portion thereof, is at least 99% complementary to at least 15 contiguous nucleobases at positions 2685-2714 of SEQ ID NO: 614, or a pharmaceutically acceptable salt thereof.

E16. The oligonucleotide of E13, wherein the oligonucleotide or a portion thereof, is 100% complementary to at least 15 contiguous nucleobases at positions 2685-2714 of SEQ ID NO: 614, or a pharmaceutically acceptable salt thereof.

E17. The oligonucleotide of any one of claims E13-E16, wherein the oligonucleotide, or a portion thereof is complementary to 17-23 contiguous nucleobases at positions 2685-2714 of SEQ ID NO: 614, or a pharmaceutically acceptable salt thereof.

E18. The oligonucleotide of any one of claims E13-E17, wherein the oligonucleotide, or a portion thereof, is complementary to 17-20 contiguous nucleobases at positions 2685-2714 of SEQ ID NO: 614, or a pharmaceutically acceptable salt thereof.

E19. The oligonucleotide of E18, wherein the oligonucleotide, or a portion thereof, is complementary to 17-20 contiguous nucleobases beginning at position 2685, 2686, 2687, 2688, 2689, 2690, 2691, 2692, 2693, 2694, 2695, 2696, 2697, or 2698 of SEQ ID NO: 614, or a pharmaceutically acceptable salt thereof.

E20. The oligonucleotide of any one of E13-E19, wherein the oligonucleotide is 17-20 linked nucleotides in length, or a pharmaceutically acceptable salt thereof.

E21. The oligonucleotide of any one of E13-E16, wherein the oligonucleotide, or a portion thereof, is complementary to 20-23 contiguous nucleobases at positions 2685-2714 of SEQ ID NO: 614, or a pharmaceutically acceptable salt thereof.

E22. The oligonucleotide of E21, wherein the oligonucleotide is complementary to 20-23 contiguous nucleobases beginning at position 2685, 2686, 2687, 2688, 2689, 2690, 2691, 2692, 2693, 2694, or 2695 of SEQ ID NO: 614, or a pharmaceutically acceptable salt thereof.

E23. The oligonucleotide of any one of E13-E22, wherein the oligonucleotide is 20-23 linked nucleotides in length, or a pharmaceutically acceptable salt thereof.

E24. The oligonucleotide of E13-E23, wherein the oligonucleotide, or a portion thereof, is complementary to positions 2685-2714 of SEQ ID NO: 614, or a pharmaceutically acceptable salt thereof.

E25. The oligonucleotide of any one of E1-E24, wherein the oligonucleotide is not any one of Antisense Oligo Nos. 1, 97, 193, or 289 of Table 3.

E26. The oligonucleotide of any one of E1-E25, wherein the oligonucleotide does not have a nucleobase sequence consisting of any one of SEQ ID NOs: 1, 97, 193, or 289.

E27. The oligonucleotide of any one of E1-E26, wherein the oligonucleotide comprises:

(a) a DNA core sequence comprising linked deoxyribonucleosides;

(b) a 5' flanking sequence comprising linked nucleosides; and (c) a 3' flanking sequence comprising linked nucleosides;

wherein the DNA core comprises a region of at least 10 contiguous nucleobases positioned between the 5' flanking sequence and the 3' flanking sequence; wherein the 5' flanking sequence and the 3' flanking sequence each comprises at least two linked nucleosides; and wherein at least one nucleoside of each flanking sequence comprises an alternative nucleoside, or a pharmaceutically acceptable salt thereof.

E28. The oligonucleotide of any one of E1-E27, wherein the oligonucleotide comprises at least one alternative internucleoside linkage, or a pharmaceutically acceptable salt thereof.

E29. The oligonucleotide of E28, wherein the at least one alternative internucleoside linkage is a phosphorothioate internucleoside linkage.

E30. The oligonucleotide of E28, wherein the at least one alternative internucleoside linkage is a 2'-alkoxy internucleoside linkage.

E31. The oligonucleotide of E28, wherein the at least one alternative internucleoside linkage is an alkyl phosphate internucleoside linkage.

E32. The oligonucleotide of any one of claims E1-E31, wherein the oligonucleotide comprises at least one alternative nucleobase, or a pharmaceutically acceptable salt thereof.

E33. The oligonucleotide of claim E32, wherein the alternative nucleobase is 5'-methylcytosine, pseudouridine, or 5-methoxyuridine.

E34. The oligonucleotide of any one of E1-E33, wherein the oligonucleotide comprises at least one alternative sugar moiety, or a pharmaceutically acceptable salt thereof.

E35. The oligonucleotide of E34, wherein the alternative sugar moiety is 2'-OMe or a bicyclic nucleic acid.

E36. The oligonucleotide of any one of E1-E35, wherein the oligonucleotide further comprises a ligand conjugated to the 5' end or the 3' end of the oligonucleotide through a monovalent or branched bivalent or trivalent linker, or a pharmaceutically acceptable salt thereof.

E37. The oligonucleotide of any one of E1-E36, wherein the oligonucleotide consists of a nucleobase sequence selected from the group consisting of any of SEQ ID NOs: 1-384 and 390-613, or a pharmaceutically acceptable salt thereof.

E38. The oligonucleotide of E37, wherein the oligonucleotide consists of a nucleobase sequence selected from the group consisting of any of SEQ ID NOs: 2-96, 98-192, 194-288, 290-384, and 390-613, or a pharmaceutically acceptable salt thereof.

E39. The oligonucleotide of E37, wherein the oligonucleotide consists of a nucleobase sequence selected from the group consisting of any of SEQ ID NOs: 1-384, or a pharmaceutically acceptable salt thereof.

E40. The oligonucleotide of E37, wherein the oligonucleotide consists of a nucleobase sequence selected from the group consisting of any of SEQ ID NOs: 2-96, 98-192, 194-288, and 290-384, or a pharmaceutically acceptable salt thereof.

E41. The oligonucleotide of E37, wherein the oligonucleotide consists of a nucleobase sequence selected from the group consisting of any of SEQ ID NOs: 1-96, or a pharmaceutically acceptable salt thereof.

E42. The oligonucleotide of E37, wherein the oligonucleotide consists of a nucleobase sequence selected from the group consisting of any of SEQ ID NOs: 2-96, or a pharmaceutically acceptable salt thereof.

E43. The oligonucleotide of E37, wherein the oligonucleotide consists of a nucleobase sequence selected from the group consisting of any of SEQ ID NOs: 97-192, or a pharmaceutically acceptable salt thereof.

E44. The oligonucleotide of E37, wherein the oligonucleotide consists of a nucleobase sequence selected from the group consisting of any of SEQ ID NOs: 98-192, or a pharmaceutically acceptable salt thereof.

E45. The oligonucleotide of E37, wherein the oligonucleotide consists of a nucleobase sequence selected from the group consisting of any of SEQ ID NOs: 193-288, or a pharmaceutically acceptable salt thereof.

E46. The oligonucleotide of E37, wherein the oligonucleotide consists of a nucleobase sequence selected from the group consisting of any of SEQ ID NOs: 194-288, or a pharmaceutically acceptable salt thereof.

E47. The oligonucleotide of E37, wherein the oligonucleotide consists of a nucleobase sequence selected from the group consisting of any of SEQ ID NOs: 289-384, or a pharmaceutically acceptable salt thereof.

E48. The oligonucleotide of E37, wherein the oligonucleotide consists of a nucleobase sequence selected from the group consisting of any of SEQ ID NOs: 288-384, or a pharmaceutically acceptable salt thereof.

E49. The oligonucleotide of E37, wherein the oligonucleotide consists of a nucleobase sequence selected from the group consisting of any of SEQ ID NOs: 390-613, or a pharmaceutically acceptable salt thereof.

E50. The oligonucleotide of E37, wherein the oligonucleotide consists of a nucleobase sequence selected from the group consisting of any of SEQ ID NOs: 390-480, or a pharmaceutically acceptable salt thereof.

E51. The oligonucleotide of E37, wherein the oligonucleotide consists of a nucleobase sequence selected from the group consisting of any of SEQ ID NOs: 481-571, or a pharmaceutically acceptable salt thereof.

E52. The oligonucleotide of E37, wherein the oligonucleotide consists of a nucleobase sequence selected from the group consisting of any of SEQ ID NOs: 572-662, or a pharmaceutically acceptable salt thereof.

E53. The oligonucleotide of E37, wherein the oligonucleotide consists of a nucleobase sequence selected from the group consisting of any of SEQ ID NOs: 663-613, or a pharmaceutically acceptable salt thereof.

E54. The oligonucleotide of E37, wherein the oligonucleotide consists of a nucleobase sequence selected from the group consisting of any of SEQ ID NOs: 1, 6, 13, 17, 21, 24, 26, 29, 33-34, 37, 44, 49-55, 57, 60-73, 75-76, 79-82, 84-86, 88-92, or 94-96, or a pharmaceutically acceptable salt thereof.

E55. The oligonucleotide of E37, wherein the oligonucleotide consists of a nucleobase sequence selected from the group consisting of any of SEQ ID NOs: 6, 13, 17, 21, 24, 26, 29, 33-34, 37, 44, 49-55, 57, 60-73, 75-76, 79-82, 84-86, 88-92, or 94-96, or a pharmaceutically acceptable salt thereof.

E56. The oligonucleotide of E37, wherein the oligonucleotide consists of a nucleobase sequence that is SEQ ID NO: 1, or a pharmaceutically acceptable salt thereof.

E57. The oligonucleotide of claim E37, wherein the oligonucleotide consists of a nucleobase sequence that is SEQ ID NO: 6, or a pharmaceutically acceptable salt thereof.

E58. The oligonucleotide of E37, wherein the oligonucleotide consists of a nucleobase sequence selected from the group consisting of any of SEQ ID NOs: 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof.

E59. The oligonucleotide of E37, wherein the oligonucleotide consists of a nucleobase sequence selected from the group consisting of any of SEQ ID NOs: 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof.

E60. The oligonucleotide of E37, wherein the oligonucleotide consists of a nucleobase sequence that is SEQ ID NO: 97, or a pharmaceutically acceptable salt thereof.

E61. The oligonucleotide of E 37, wherein the oligonucleotide consists of a nucleobase sequence selected from the group consisting of any of SEQ ID NOs: 193-200, 202-230, 232-246, 248-253, 255, 258-261, 265, 270, 274-276, or 285-286, or a pharmaceutically acceptable salt thereof.

E62. The oligonucleotide of E37, wherein the oligonucleotide consists of a nucleobase sequence selected from the group consisting of any of SEQ ID NOs: 194-200, 202-230, 232-246, 248-253, 255, 258-261, 265, 270, 274-276, or 285-286, or a pharmaceutically acceptable salt thereof.

E63. The oligonucleotide of E37, wherein the oligonucleotide consists of a nucleobase sequence that is SEQ ID NO: 193, or a pharmaceutically acceptable salt thereof.

E64. The oligonucleotide of E37, wherein the oligonucleotide consists of a nucleobase sequence selected from the group consisting of any of SEQ ID NOs: 226-227, 234, 240, or 243-244, or a pharmaceutically acceptable salt thereof.

E65. The oligonucleotide of E37, wherein the oligonucleotide consists of a nucleobase sequence selected from the group consisting of any of SEQ ID NOs: 227, 234, 240, or 243-244, or a pharmaceutically acceptable salt thereof.

E66. The oligonucleotide of E37, wherein oligonucleotide consists of the nucleobase sequence that is SEQ ID NO: 226, or a pharmaceutically acceptable salt thereof.

E67. The oligonucleotide of E37, wherein the oligonucleotide consists of a nucleobase sequence selected from the group consisting of any of SEQ ID NOs: 289-290, 292, 305, 307, 313, 318, 323-324, 326, 329-330, 332, 338-339, 341, 344, or 346, or a pharmaceutically acceptable salt thereof.

E68. The oligonucleotide of E37, wherein the oligonucleotide consists of a nucleobase sequence selected from the group consisting of any of SEQ ID NOs: 290, 292, 305, 307, 313, 318, 323-324, 326, 329-330, 332, 338-339, 341, 344, or 346, or a pharmaceutically acceptable salt thereof.

E69. The oligonucleotide of E37, wherein the oligonucleotide consists of a nucleobase sequence that is SEQ ID NO: 289, or a pharmaceutically acceptable salt thereof.

E70. A single-stranded oligonucleotide, wherein the nucleobase sequence of the oligonucleotide consists of any one of SEQ ID NOs: 1-384 and 390-613, or a pharmaceutically acceptable salt thereof.

E71. The oligonucleotide of E70, wherein the nucleobase sequence of the oligonucleotide consists of any one of SEQ ID NOs: 2-96, 98-192, 194-288, 290-384, and 390-613, or a pharmaceutically acceptable salt thereof.

E72. The oligonucleotide of E70, wherein the nucleobase sequence of the oligonucleotide consists of any one of SEQ ID NOs: 1-384, or a pharmaceutically acceptable salt thereof.

E73. The oligonucleotide of E70, wherein the nucleobase sequence of the oligonucleotide consists of any one of SEQ ID NOs: 2-96, 98-192, 194-288, or 290-384, or a pharmaceutically acceptable salt thereof.

E74. The oligonucleotide of E70, wherein the oligonucleotide consists of the nucleobase sequence of any one of SEQ ID NOs: 1-96, or a pharmaceutically acceptable salt thereof.

E75. The oligonucleotide of E70, wherein the oligonucleotide consists of the nucleobase sequence of any one of SEQ ID NOs: 2-96, or a pharmaceutically acceptable salt thereof.

E76. The oligonucleotide of E70, wherein the oligonucleotide consists of the nucleobase sequence of any one of SEQ ID NOs: 97-192, or a pharmaceutically acceptable salt thereof.

E77. The oligonucleotide of E70, wherein the oligonucleotide consists of the nucleobase sequence of any one of SEQ ID NOs: 96-192, or a pharmaceutically acceptable salt thereof.

E78. The oligonucleotide of E70, wherein the oligonucleotide consists of the nucleobase sequence of any one of SEQ ID NOs: 193-288, or a pharmaceutically acceptable salt thereof.

E79. The oligonucleotide of E70, wherein the oligonucleotide consists of the nucleobase sequence of any one of SEQ ID NOs: 194-288, or a pharmaceutically acceptable salt thereof.

E80. The oligonucleotide of E70, wherein the oligonucleotide consists of the nucleobase sequence of any one of SEQ ID NOs: 289-384, or a pharmaceutically acceptable salt thereof.

E81. The oligonucleotide of claim E70, wherein the oligonucleotide consists of the nucleobase sequence of any one of SEQ ID NOs: 290-384, or a pharmaceutically acceptable salt thereof.

E82. The oligonucleotide of E70, wherein the oligonucleotide consists of the nucleobase sequence of any one of SEQ ID NOs: 390-613, or a pharmaceutically acceptable salt thereof.

E83. The oligonucleotide of E70, wherein the oligonucleotide consists of the nucleobase sequence of any one of SEQ ID NOs: 390-480, or a pharmaceutically acceptable salt thereof.

E84. The oligonucleotide of E70, wherein the oligonucleotide consists of the nucleobase sequence of any one of SEQ ID NOs: 481-571, or a pharmaceutically acceptable salt thereof.

E85. The oligonucleotide of E70, wherein the oligonucleotide consists of the nucleobase sequence of any one of SEQ ID NOs: 572-662, or a pharmaceutically acceptable salt thereof.

E86. The oligonucleotide of E70, wherein the oligonucleotide consists of the nucleobase sequence of any one of SEQ ID NOs: 663-613, or a pharmaceutically acceptable salt thereof.

E87. The oligonucleotide of E70, wherein the oligonucleotide consists of the nucleobase sequence of any one of SEQ ID NOs: 1, 6, 13, 17, 21, 24, 26, 29, 33-34, 37, 44, 49-55, 57, 60-73, 75-76, 79-82, 84-86, 88-92, or 94-96, or a pharmaceutically acceptable salt thereof.

E88. The oligonucleotide of E70, wherein the oligonucleotide consists of the nucleobase sequence of any one of SEQ ID NOs: 6, 13, 17, 21, 24, 26, 29, 33-34, 37, 44, 49-55, 57, 60-73, 75-76, 79-82, 84-86, 88-92, or 94-96, or a pharmaceutically acceptable salt thereof.

E89. The oligonucleotide of E70, wherein the oligonucleotide consists of the nucleobase sequence of SEQ ID NO: 1, or a pharmaceutically acceptable salt thereof.

E90. The oligonucleotide of E70, wherein the oligonucleotide consists of the nucleobase sequence of SEQ ID NO: 6, or a pharmaceutically acceptable salt thereof.

E91. The oligonucleotide of E70, wherein the oligonucleotide consists of the nucleobase sequence of any one of SEQ ID NOs: 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof.

E92. The oligonucleotide of E70, wherein the oligonucleotide consists of the nucleobase sequence of any one of SEQ ID NOs: 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191, or a pharmaceutically acceptable salt thereof.

E93. The oligonucleotide of E70, wherein the oligonucleotide consists of the nucleobase sequence of SEQ ID NO: 97, or a pharmaceutically acceptable salt thereof.

E94. The oligonucleotide of E70, wherein the oligonucleotide consists of the nucleobase sequence of any one of SEQ ID NOs: 193-200, 202-230, 232-246, 248-253, 255, 258-261, 265, 270, 274-276, or 285-286, or a pharmaceutically acceptable salt thereof.

E95. The oligonucleotide of E70, wherein the oligonucleotide consists of the nucleobase sequence of any one of SEQ ID NOs: 194-200, 202-230, 232-246, 248-253, 255, 258-261, 265, 270, 274-276, or 285-286, or a pharmaceutically acceptable salt thereof.

E96. The oligonucleotide of E70, wherein the oligonucleotide consists of the nucleobase sequence of any one of SEQ ID NO: 193, or a pharmaceutically acceptable salt thereof.

E97. The oligonucleotide of E70, wherein the oligonucleotide consists of the nucleobase sequence of any one of SEQ ID NOs: 226-227, 234, 240, or 243-244, or a pharmaceutically acceptable salt thereof.

E98. The oligonucleotide of E70, wherein the oligonucleotide consists of the nucleobase sequence of any one of SEQ ID NOs: 227, 234, 240, or 243-244, or a pharmaceutically acceptable salt thereof.

E99. The oligonucleotide of E70, wherein the oligonucleotide consists of the nucleobase sequence of SEQ ID NO: 226, or a pharmaceutically acceptable salt thereof.

E100. The oligonucleotide of E70, wherein the oligonucleotide consists of the nucleobase sequence of any one of SEQ ID NOs: 289-290, 292, 305, 307, 313, 318, 323-324, 326, 329-330, 332, 338-339, 341, 344, or 346, or a pharmaceutically acceptable salt thereof.

E101. The oligonucleotide of E70, wherein the oligonucleotide consists of the nucleobase sequence of any one of SEQ ID NOs: 290, 292, 305, 307, 313, 318, 323-324, 326, 329-330, 332, 338-339, 341, 344, or 346, or a pharmaceutically acceptable salt thereof.

E102. The oligonucleotide of E70, wherein the oligonucleotide consists of the nucleobase sequence of SEQ ID NO: 289, or a pharmaceutically acceptable salt thereof.

E103. An oligonucleotide selected from the group consisting of Antisense Oligo Nos. 1-384 of Table 3 or 390-613 of Table 4, or a pharmaceutically acceptable salt thereof.

E104. The oligonucleotide of E103, wherein the oligonucleotide is selected from the group consisting of Antisense Oligo Nos. 2-96, 98-192, 194-288, 290-384 of Table 3 and 390-613 of Table 4, or a pharmaceutically acceptable salt thereof.

E105. The oligonucleotide of E103, wherein the oligonucleotide is selected from the group consisting of Antisense Oligo Nos. 1-384 of Table 3, or a pharmaceutically acceptable salt thereof.

E106. The oligonucleotide of E103, wherein the oligonucleotide is selected from the group consisting of Antisense Oligo Nos. 2-96, 98-192, 194-288, and 290-384 of Table 3, or a pharmaceutically acceptable salt thereof.

E107. The oligonucleotide E103, wherein the oligonucleotide is selected from the group consisting of Antisense Oligo Nos. 1-96 of Table 3, or a pharmaceutically acceptable salt thereof.

E108. The oligonucleotide E103, wherein the oligonucleotide is selected from the group consisting of Antisense Oligo Nos. 2-96 of Table 3, or a pharmaceutically acceptable salt thereof.

E109. The oligonucleotide E103, wherein the oligonucleotide is selected from the group consisting of Antisense Oligo Nos. 97-192 of Table 3, or a pharmaceutically acceptable salt thereof.

E110. The oligonucleotide E103, wherein the oligonucleotide is selected from the group consisting of Antisense Oligo Nos. 98-192 of Table 3, or a pharmaceutically acceptable salt thereof.

E111. The oligonucleotide E103, wherein the oligonucleotide is selected from the group consisting of Antisense Oligo Nos. 193-288 of Table 3, or a pharmaceutically acceptable salt thereof.

E112. The oligonucleotide E103, wherein the oligonucleotide is selected from the group consisting of Antisense Oligo Nos. 194-288 of Table 3, or a pharmaceutically acceptable salt thereof.

E113. The oligonucleotide E103, wherein the oligonucleotide is selected from the group consisting of Antisense Oligo Nos. 289-384 of Table 3, or a pharmaceutically acceptable salt thereof.

E114. The oligonucleotide E103, wherein the oligonucleotide is selected from the group consisting of Antisense Oligo Nos. 290-384 of Table 3, or a pharmaceutically acceptable salt thereof.

E115. The oligonucleotide of E103, wherein the oligonucleotide is selected from the group consisting of Antisense Oligo Nos. 390-613 of Table 4, or a pharmaceutically acceptable salt thereof.

E116. The oligonucleotide of E103, wherein the oligonucleotide is selected from the group consisting of Antisense Oligo Nos. 390-480 of Table 4, or a pharmaceutically acceptable salt thereof.

E117. The oligonucleotide of E103, wherein the oligonucleotide is selected from the group consisting of Antisense Oligo Nos. 481-571 of Table 4, or a pharmaceutically acceptable salt thereof.

E118. The oligonucleotide of E103, wherein the oligonucleotide is selected from the group consisting of Antisense Oligo Nos. 1, 6, 13, 17, 21, 24, 26, 29, 33-34, 37, 44, 49-55, 57, 60-73, 75-76, 79-82, 84-86, 88-92, or 94-96 of Table 3, or a pharmaceutically acceptable salt thereof.

E119. The oligonucleotide of E103, wherein the oligonucleotide is selected from the group consisting of Antisense Oligo Nos. 6, 13, 17, 21, 24, 26, 29, 33-34, 37, 44, 49-55, 57, 60-73, 75-76, 79-82, 84-86, 88-92, or 94-96 of Table 3, or a pharmaceutically acceptable salt thereof.

E120. The oligonucleotide of E103, wherein the oligonucleotide is Antisense Oligo No. 1 of Table 3, or a pharmaceutically acceptable salt thereof.

E121. The oligonucleotide of E103, wherein the oligonucleotide is Antisense Oligo No. 6 of Table 3, or a pharmaceutically acceptable salt thereof.

E122. The oligonucleotide of E103, wherein the oligonucleotide is selected from the group consisting of Antisense Oligo Nos. 97, 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191 of Table 3, or a pharmaceutically acceptable salt thereof.

E123. The oligonucleotide of E103, wherein the oligonucleotide is selected from the group consisting of Antisense Oligo Nos. 100, 103, 105, 108, 110-111, 113-117, 122-123, 127, 129-130, 133-136, 138-139, 141, 143-145, 147-148, 154-155, 157-165, 168-170, 172, 174-180, 184, 187, or 191 of Table 3, or a pharmaceutically acceptable salt thereof.

E124. The oligonucleotide of E103, wherein the oligonucleotide is Antisense Oligo No. 97 of Table 3, or a pharmaceutically acceptable salt thereof.

E125. The oligonucleotide of E103, wherein the oligonucleotide is selected from the group consisting of Antisense Oligo Nos. 193-200, 202-230, 232-246, 248-253, 255, 258-261, 265, 270, 274-276, or 285-286 of Table 3, or a pharmaceutically acceptable salt thereof.

E126. The oligonucleotide of E103, wherein the oligonucleotide is selected from the group consisting of Antisense Oligo Nos. 194-200, 202-230, 232-246, 248-253, 255, 258-261, 265, 270, 274-276, or 285-286 of Table 3, or a pharmaceutically acceptable salt thereof.

E127. The oligonucleotide of E103, wherein the oligonucleotide is Antisense Oligo No. 193 of Table 3.

E128. The oligonucleotide of E103, wherein the oligonucleotide is selected from the group consisting of Antisense Oligo Nos. 226-227, 234, 240, or 243-244 of Table 3, or a pharmaceutically acceptable salt thereof.

E129. The oligonucleotide of E103, wherein the oligonucleotide is selected from the group consisting of Antisense Oligo Nos. 227, 234, 240, or 243-244 of Table 3, or a pharmaceutically acceptable salt thereof.

E130. The oligonucleotide of E103, wherein the oligonucleotide is Antisense Oligo No. 226 of Table 3, or a pharmaceutically acceptable salt thereof.

E131. The oligonucleotide of E103, wherein the oligonucleotide is selected from the group consisting of Antisense Oligo Nos. 289-290, 292, 305, 307, 313, 318, 323-324, 326, 329-330, 332, 338-339, 341, 344, or 346 of Table 3, or a pharmaceutically acceptable salt thereof.

E132. The oligonucleotide of E103, wherein the oligonucleotide is selected from the group consisting of Antisense Oligo Nos. 290, 292, 305, 307, 313, 318, 323-324, 326, 329-330, 332, 338-339, 341, 344, or 346 of Table 3, or a pharmaceutically acceptable salt thereof.

E133. The oligonucleotide of E103, wherein the oligonucleotide is Antisense Oligo No. 289 of Table 3, or a pharmaceutically acceptable salt thereof.

E134. The oligonucleotide of any one of E1-E133, wherein the oligonucleotide, or a pharmaceutically acceptable salt thereof, causes at least a 50% reduction in MSH3 mRNA expression at an oligonucleotide concentration of 10 nM.

E135. The oligonucleotide of any one of E1-E133, wherein the oligonucleotide, or a pharmaceutically acceptable salt thereof, causes at least a 60% reduction in MSH3 mRNA expression at an oligonucleotide concentration of 10 nM.

E136. The oligonucleotide of any one of E1-E133, wherein the oligonucleotide, or a pharmaceutically acceptable salt thereof, causes at least a 70% reduction in MSH3 mRNA expression at an oligonucleotide concentration of 10 nM.

E137. The oligonucleotide of any one of E1-E133, wherein the oligonucleotide, or a pharmaceutically acceptable salt thereof, causes at least an 80% reduction in MSH3 mRNA expression at an oligonucleotide concentration of 10 nM.

E138. The oligonucleotide of any one of E1-E133, wherein the oligonucleotide, or a pharmaceutically acceptable salt thereof, causes at least a 50% reduction in MSH3 mRNA expression at an oligonucleotide concentration of 1 nM.

E139. The oligonucleotide of any one of E1-E133, wherein the oligonucleotide, or a pharmaceutically acceptable salt thereof, causes at least a 60% reduction in MSH3 mRNA expression at an oligonucleotide concentration of 1 nM.

E140. The oligonucleotide of any one of E1-E133, wherein the oligonucleotide, or a pharmaceutically acceptable salt thereof, causes at least a 70% reduction in MSH3 mRNA expression at an oligonucleotide concentration of 1 nM.

E141. The oligonucleotide of any one of E135-E140, wherein the MSH3 mRNA expression is evaluated in vitro.

E142. The oligonucleotide of E141, wherein the MSH3 mRNA expression is evaluated in a cell based assay.

E143. The oligonucleotide of E142, wherein the MSH3 mRNA expression is evaluated in HeLa cells.

E144. The oligonucleotide of any one of E134-E143, wherein the MSH3 mRNA expression is determined by the quantitative reverse transcription polymerase chain reaction (RT-qPCR).

E145. The oligonucleotide of any one of E134-E144, wherein the MSH3 mRNA is expression is normalized to the mRNA expression of a reference gene.

E146. The oligonucleotide of E145, wherein the MSH3 mRNA expression is normalized to the mRNA expression of beta-glucuronidase (GUSB).

E147. The oligonucleotide of any one of E134-E147, wherein the reduction in MSH3 mRNA expression is relative to a control.

E148. The oligonucleotide of E 147, wherein the control is the MSH3 mRNA expression in the absence of the oligonucleotide, or pharmaceutically acceptable salt thereof.

E149. The oligonucleotide of E148, wherein the control is the MSH3 mRNA expression in the absence of the oligonucleotide, or pharmaceutically acceptable salt thereof, but in the presence of a control oligonucleotide, or salt thereof.

E150. The oligonucleotide of E149, wherein the control oligonucleotide, or salt thereof, is a scrambled luciferase targeting oligonucleotide.

E151. The oligonucleotide of any one of E134-E150, wherein the reduction in MSH3 mRNA expression is calculated by a delta-delta Ct (ΔΔCT) method.

E152. The oligonucleotide of any one of E151, wherein the delta-delta Ct (ΔΔCT) method comprises the normalization of the MSH3 mRNA expression to the mRNA expression of a reference gene and to the MSH3 mRNA expression in the absence of the oligonucleotide, or pharmaceutically acceptable salt thereof but in the presence of a control oligonucleotide, or salt thereof.

E153. The oligonucleotide of E152, wherein the reference gene is beta-glucuronidase (GUSB) and/or the control oligonucleotide, or salt thereof, is a scrambled luciferase targeting oligonucleotide.

E154. The oligonucleotide of any one of E134-E153, wherein the reduction in MSH3 mRNA expression is determined by the method of Example 1.

E155. The oligonucleotide of any one of E134-E137 and E141-E154, wherein in the same assay, Antisense Oligo No. 1 causes approximately a 58% reduction in MSH3 mRNA expression at an oligonucleotide concentration of 10 nM.

E156. The oligonucleotide of any one of E138-E154, wherein in the same assay, Antisense Oligo No. 1 causes approximately a 14% reduction in MSH3 mRNA expression at an oligonucleotide concentration of 1 nM.

E157. The oligonucleotide of any one of E1-E156, wherein the oligonucleotide is in the free base form.

E158. The oligonucleotide of any one of E1-E156, wherein the oligonucleotide is a pharmaceutically acceptable salt thereof.

E159. The oligonucleotide of E158, wherein the oligonucleotide is a sodium salt.

E160. A pharmaceutical composition comprising one or more of the oligonucleotides, or pharmaceutically acceptable salts thereof, of any one of E1-E159 and a pharmaceutically acceptable carrier or excipient.

E161. A composition comprising one or more of the oligonucleotides, or pharmaceutically acceptable salts thereof, of any one of E1-E159 and a lipid nanoparticle, a polyplex nanoparticle, a lipoplex nanoparticle, or a liposome.

E162. A method of inhibiting transcription of MSH3 in a cell, the method comprising contacting the cell with one or more of the oligonucleotides, or pharmaceutically acceptable salts thereof, of any one of E1-E159, the pharmaceutical composition of E160, or the composition of E161 for a time sufficient to obtain degradation of an mRNA transcript of a MSH3 gene, inhibits expression of the MSH3 gene in the cell.

E163. A method of treating, preventing, or delaying the progression a nucleotide repeat expansion disorder in a subject in need thereof, the method comprising administering to the subject one or more of the oligonucleotides, or pharmaceutically acceptable salts thereof, of any one of E1-E159, the pharmaceutical composition of E160, or the composition of E161.

E164. A method of reducing the level and/or activity of MSH3 in a cell of a subject identified as having a nucleotide repeat expansion disorder, the method comprising contacting the cell with one or more of the oligonucleotides, or pharmaceutically acceptable salts thereof, of any one of E1-E159, the pharmaceutical composition of E160, or the composition of E161.

E165. A method for inhibiting expression of an MSH3 gene in a cell comprising contacting the cell with one or more of the oligonucleotides, or pharmaceutically acceptable salts thereof, of any one of E1-E159, the pharmaceutical composition of E160, or the composition of E161 and maintaining the cell for a time sufficient to obtain degradation of a mRNA transcript of an MSH3 gene, thereby inhibiting expression of the MSH3 gene in the cell.

E166. A method of decreasing nucleotide repeat expansion in a cell, the method comprising contacting the cell with one or more of the oligonucleotides, or pharmaceutically acceptable salts thereof, of any one of E1-E159, the pharmaceutical composition of E160, or the composition of E161.

E167. The method of E162 and E164-E166, wherein the cell is in a subject.

E168. The method of E163 or E164, wherein the subject is a human.

E169. The method of E168, wherein the cell is a cell of the central nervous system or a muscle cell.

E170. The method of E163, wherein the subject is identified as having a nucleotide repeat expansion disorder.

E171. The method of E170, wherein the nucleotide repeat expansion disorder is spinocerebellar ataxia type 36 or frontotemporal dementia.

E172. The method of E170, wherein the nucleotide repeat expansion disorder is a trinucleotide repeat expansion disorder.

E173. The method of E172, wherein the trinucleotide repeat expansion disorder is a polyglutamine disease.

E174. The method of E173, wherein the polyglutamine disease is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, and Huntington's disease-like 2.

E175. The method of E172, wherein the trinucleotide repeat expansion disorder is a non-polyglutamine disease.

E176. The method of E175, wherein the non-polyglutamine disease is selected from the group consisting of fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

E177. One or more of the oligonucleotides, or pharmaceutically acceptable salts thereof, of any one of E1-E159, the pharmaceutical composition of E160, or the composition of E161 for use in the prevention or treatment of a nucleotide repeat expansion disorder.

E178. The oligonucleotide, or pharmaceutically acceptable salt thereof, pharmaceutical composition, or composition for the use of E177, wherein the nucleotide repeat expansion disorder is spinocerebellar ataxia type 36 or frontotemporal dementia.

E179. The oligonucleotide, or pharmaceutically acceptable salt thereof, pharmaceutical composition, or composition for the use of E177, wherein the nucleotide repeat expansion disorder is a trinucleotide repeat expansion disorder.

E180. The oligonucleotide, or pharmaceutically acceptable salt thereof, pharmaceutical composition, or composition for the use of E179, wherein the trinucleotide repeat expansion disorder is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, Huntington's disease-like 2, fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

E181. The oligonucleotide, or pharmaceutically acceptable salt thereof, pharmaceutical composition, or composition for the use of E179 or E180, wherein the trinucleotide repeat expansion disorder is Huntington's disease.

E182. The oligonucleotide, or pharmaceutically acceptable salt thereof, pharmaceutical composition, or composition of E179 or E180, wherein the trinucleotide repeat expansion disorder is Friedreich's ataxia.

E183. The oligonucleotide, or pharmaceutically acceptable salt thereof, pharmaceutical composition, or composition for the use of E179 or E180, wherein the trinucleotide repeat expansion disorder is myotonic dystrophy type 1.

E184. The oligonucleotide, or pharmaceutically acceptable salt thereof, pharmaceutical composition, or composition of any of E177-E183, wherein the oligonucleotide, pharmaceutical composition, or composition is administered intrathecally, intraventricularly, intracerebroventricularly, intraocularly, subcutaneously, intravenously, intra cisterna magnally, intramuscularly, or orally.

E185. A method of treating, preventing, or delaying the progression a disorder in a subject in need thereof wherein the subject is suffering from nucleotide repeat expansion disorder, comprising administering to said subject one or more of the oligonucleotides, or pharmaceutically acceptable salts thereof, of any one of E1-E159, the pharmaceutical composition of E160, or the composition of E161.

E186. The method of E185, further comprising administering an additional therapeutic agent.

E187. The method of E185, wherein the additional therapeutic agent is another oligonucleotide that hybridizes to an mRNA encoding the Huntingtin gene.

E188. A method of preventing or delaying the progression of a nucleotide repeat expansion disorder in a subject, the method comprising administering to the subject one or more of the oligonucleotides, or pharmaceutically acceptable salts thereof, of any one of E1-E159, the pharmaceutical composition of E160, or the composition of E161 or the composition of E159 in an amount effective to delay progression of a nucleotide repeat expansion disorder of the subject.

E189. The method of E188, wherein the nucleotide repeat expansion disorder is spinocerebellar ataxia type 36 or frontotemporal dementia.

E190. The method of E188, wherein the nucleotide repeat expansion disorder is a trinucleotide repeat expansion disorder.

E191. The method of E190, wherein the trinucleotide repeat expansion disorder is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, Huntington's disease-like 2, fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

E192. The method of E190 or E191, wherein the trinucleotide repeat expansion disorder is Huntington's disease.

E193. The method of E190 or E191, wherein the trinucleotide repeat expansion disorder is Friedrich's ataxia.

E194. The method of E190 or E191, wherein the trinucleotide repeat expansion disorder is myotonic Dystrophy type 1.

E195. The method of E190 or E191, further comprising administering an additional therapeutic agent.

E196. The method of E195, wherein the additional therapeutic agent is an oligonucleotide that hybridizes to an mRNA encoding the Huntingtin gene.

E197. The method of any of E188-E196, wherein progression of the nucleotide repeat expansion disorder is delayed by at least 120 days, for example, at least 6 months, at least 12 months, at least 2 years, at least 3 years, at least 4 years, at least 5 years, at least 10 years or more, when compared with a predicted progression.

E198. One or more of the oligonucleotides, or pharmaceutically acceptable salts thereof, of any one of E1-E159, the pharmaceutical composition of E160, or the composition of E161 for use in preventing or delaying progression of a nucleotide repeat expansion disorder in a subject.

E199. The oligonucleotide, or pharmaceutically acceptable salt thereof, pharmaceutical composition, or composition of E198, wherein the nucleotide repeat expansion disorder is spinocerebellar ataxia type 36 or frontotemporal dementia.

E200. The oligonucleotide, or pharmaceutically acceptable salt thereof, pharmaceutical composition, or composition of E198, wherein the nucleotide repeat expansion disorder is a trinucleotide repeat expansion disorder.

E201. The oligonucleotide, or pharmaceutically acceptable salt thereof, pharmaceutical composition, or composition of E200, wherein the trinucleotide repeat expansion disorder is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, Huntington's disease-like 2, fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

E202. The oligonucleotide, or pharmaceutically acceptable salt thereof, pharmaceutical composition, or composition of E200 or E201, wherein the trinucleotide repeat expansion disorder is Huntington's disease.

E203. The oligonucleotide, or pharmaceutically acceptable salt thereof, pharmaceutical composition, or composition of E200 or E201, wherein the trinucleotide repeat expansion disorder is Friedrich's ataxia.

E204. The oligonucleotide, or pharmaceutically acceptable salt thereof, pharmaceutical composition, or composition of E200 or E201, wherein the trinucleotide repeat expansion disorder is myotonic Dystrophy type 1.

E205. The oligonucleotide, or pharmaceutically acceptable salt thereof, pharmaceutical composition, or composition of any one of E198-E204, wherein progression of the nucleotide repeat expansion disorder is delayed by at least 120 days, for example, at least 6 months, at least 12 months, at least 2 years, at least 3 years, at least 4 years, at least 5 years, at least 10 years or more, when compared with a predicted progression.

We claim:

1. A single-stranded oligonucleotide of 15-30 linked nucleotides in length, wherein the oligonucleotide, or a portion thereof, is at least 95% complementary to at least 15 contiguous nucleobases at positions 2685-2714 of SEQ ID NO: 614, or a pharmaceutically acceptable salt thereof, wherein the oligonucleotide comprises:

(a) a DNA core sequence comprising linked deoxyribonucleosides;

(b) a 5' flanking sequence comprising linked nucleosides; and (c) a 3' flanking sequence comprising linked nucleosides;

wherein the DNA core comprises a region of at least 10 contiguous nucleobases positioned between the 5' flanking sequence and the 3' flanking sequence; wherein the 5' flanking sequence and the 3' flanking sequence each comprises at least two linked nucleosides; and wherein at least one nucleoside of each flanking sequence comprises an alternative nucleoside, or a pharmaceutically acceptable salt thereof.

2. The oligonucleotide of claim 1, wherein the oligonucleotide comprises at least one alternative internucleoside linkage, or a pharmaceutically acceptable salt thereof.

3. The oligonucleotide of claim 2, wherein the at least one alternative internucleoside linkage is a phosphorothioate internucleoside linkage.

4. The oligonucleotide of claim 1, wherein the oligonucleotide comprises at least one alternative nucleobase, or a pharmaceutically acceptable salt thereof.

5. The oligonucleotide of claim 1, wherein the alternative nucleobase is 5'-methylcytosine, pseudouridine, or 5-methoxyuridine.

6. The oligonucleotide of claim 1, wherein the oligonucleotide comprises at least one alternative sugar moiety, or a pharmaceutically acceptable salt thereof.

7. The oligonucleotide of claim 6, wherein the alternative sugar moiety is 2'-OMe or a bicyclic nucleic acid.

8. The oligonucleotide of claim 1, wherein the oligonucleotide consists of a nucleobase sequence that is SEQ ID NO: 289, or a pharmaceutically acceptable salt thereof.

9. A pharmaceutical composition comprising one or more of the oligonucleotides, or pharmaceutically acceptable salts thereof, of claim 1 and a pharmaceutically acceptable carrier or excipient.

10. A pharmaceutical composition comprising the oligonucleotide, or pharmaceutically acceptable salt thereof of claim 8, and a pharmaceutically acceptable carrier or excipient.

* * * * *

SEQUENCE LISTING

```
<160> NUMBER OF SEQ ID NOS: 616

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1

cuaggtgatg cactgcuuua                                                  20


<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2

cuaggtgatg cactgcuuua                                                  20


<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3

cuaggtgatg cactgcuuua                                                  20


<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4

cuaggtgatg cactgcuuua                                                  20


<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5

cuaggtgatg cactgcuuua                                                  20
```

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
cuaggtgatg cactgcuuua 20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
cuaggtgatg cactgcuuua 20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
cuaggtgatg cactgcuuua 20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
cuaggtgatg cactgcuuua 20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
cuaggtgatg cactgcuuua 20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
cuaggtgatg cactgcuuua 20

<210> SEQ ID NO 12
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 12
cuaggtgatg cactgcuuua 20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
cuaggtgatg cactgcuuua 20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
cuaggtgatg cactgcuuua 20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
cuaggtgatg cactgcuuua 20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
cuaggtgatg cactgcuuua 20

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
cuaggtgatg cactgcuuua c 21

<210> SEQ ID NO 18
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 18
cuaggtgatg cactgcuuua c 21

```
<210> SEQ ID NO 19
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 19

cuaggtgatg cactgcuuua c                                              21


<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 20

cuaggtgatg cactgcuuua c                                              21


<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 21

cuaggtgatg cactgcuuua c                                              21


<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 22

cuaggtgatg cactgcuuua c                                              21


<210> SEQ ID NO 23
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 23

cuaggtgatg cactgcuuua c                                              21


<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24

cuaggtgatg cactgcuuua c                                              21


<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide
```

<400> SEQUENCE: 25
cuaggtgatg cactgcuuua c 21

<210> SEQ ID NO 26
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 26
cuaggtgatg cactgcuuua c 21

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
cuaggtgatg cactgcuuua c 21

<210> SEQ ID NO 28
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 28
cuaggtgatg cactgcuuua c 21

<210> SEQ ID NO 29
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 29
cuaggtgatg cactgcuuua c 21

<210> SEQ ID NO 30
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 30
cuaggtgatg cactgcuuua c 21

<210> SEQ ID NO 31
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 31
cuaggtgatg cactgcuuua c 21

<210> SEQ ID NO 32
<211> LENGTH: 21

<212> TYPE: DNA
<213> ORGANISM: Artificial Sequence
<220> FEATURE:
<223> OTHER INFORMATION: synthetic oligonucleotide

<400> SEQUENCE: 32
cuaggtgatg cactgcuuua c 21

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
cuaggtgatg cactgcuuua ca 22

<210> SEQ ID NO 34
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 34
cuaggtgatg cactgcuuua ca 22

<210> SEQ ID NO 35
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 35
cuaggtgatg cactgcuuua ca 22

<210> SEQ ID NO 36
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 36
cuaggtgatg cactgcuuua ca 22

<210> SEQ ID NO 37
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 37
cuaggtgatg cactgcuuua ca 22

<210> SEQ ID NO 38
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 38
cuaggtgatg cactgcuuua ca 22

<210> SEQ ID NO 39
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 39
cuaggtgatg cactgcuuua ca 22

<210> SEQ ID NO 40
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 40
cuaggtgatg cactgcuuua ca 22

<210> SEQ ID NO 41
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 41
cuaggtgatg cactgcuuua ca 22

<210> SEQ ID NO 42
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 42
cuaggtgatg cactgcuuua ca 22

<210> SEQ ID NO 43
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 43
cuaggtgatg cactgcuuua ca 22

<210> SEQ ID NO 44
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 44
cuaggtgatg cactgcuuua ca 22

<210> SEQ ID NO 45
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 45
cuaggtgatg cactgcuuua ca 22

<210> SEQ ID NO 46
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 46
cuaggtgatg cactgcuuua ca 22

<210> SEQ ID NO 47
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 47
cuaggtgatg cactgcuuua ca 22

<210> SEQ ID NO 48
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 48
cuaggtgatg cactgcuuua ca 22

<210> SEQ ID NO 49
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 49
cuaggtgatg cactgcuuua cac 23

<210> SEQ ID NO 50
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 50
cuaggtgatg cactgcuuua cac 23

<210> SEQ ID NO 51
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 51
cuaggtgatg cactgcuuua cac 23

<210> SEQ ID NO 52
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 52
cuaggtgatg cactgcuuua cac 23

<210> SEQ ID NO 53
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 53
cuaggtgatg cactgcuuua cac 23

<210> SEQ ID NO 54
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 54
cuaggtgatg cactgcuuua cac 23

<210> SEQ ID NO 55
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 55
cuaggtgatg cactgcuuua cac 23

<210> SEQ ID NO 56
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 56
cuaggtgatg cactgcuuua cac 23

<210> SEQ ID NO 57
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 57
cuaggtgatg cactgcuuua cac 23

<210> SEQ ID NO 58
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 58
cuaggtgatg cactgcuuua cac 23

<210> SEQ ID NO 59
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 59
cuaggtgatg cactgcuuua cac 23

<210> SEQ ID NO 60
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 60
cuaggtgatg cactgcuuua cac 23

<210> SEQ ID NO 61
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 61
cuaggtgatg cactgcuuua cac 23

<210> SEQ ID NO 62
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 62
cuaggtgatg cactgcuuua cac 23

<210> SEQ ID NO 63
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 63
cuaggtgatg cactgcuuua cac 23

<210> SEQ ID NO 64
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 64
cuaggtgatg cactgcuuua cac 23

<210> SEQ ID NO 65

<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 65
cuaggtgatg cactgcuuua c 21

<210> SEQ ID NO 66
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 66
cuaggtgatg cactgcuuua c 21

<210> SEQ ID NO 67
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 67
cuaggtgatg cactgcuuua c 21

<210> SEQ ID NO 68
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 68
cuaggtgatg cactgcuuua c 21

<210> SEQ ID NO 69
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 69
cuaggtgatg cactgcuuua c 21

<210> SEQ ID NO 70
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 70
cuaggtgatg cactgcuuua c 21

<210> SEQ ID NO 71
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 71

```
cuaggtgatg cactgcuuua c                                              21


<210> SEQ ID NO 72
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 72

cuaggtgatg cactgcuuua c                                              21


<210> SEQ ID NO 73
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 73

cuaggtgatg cactgcuuua c                                              21


<210> SEQ ID NO 74
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 74

cuaggtgatg cactgcuuua c                                              21


<210> SEQ ID NO 75
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 75

cuaggtgatg cactgcuuua c                                              21


<210> SEQ ID NO 76
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 76

cuaggtgatg cactgcuuua c                                              21


<210> SEQ ID NO 77
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 77

cuaggtgatg cactgcuuua c                                              21


<210> SEQ ID NO 78
<211> LENGTH: 21
<212> TYPE: DNA
```

<213> ORGANISM: Artificial Sequence
<220> FEATURE:
<223> OTHER INFORMATION: synthetic oligonucleotide

<400> SEQUENCE: 78
cuaggtgatg cactgcuuua c 21

<210> SEQ ID NO 79
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 79
cuaggtgatg cactgcuuua c 21

<210> SEQ ID NO 80
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 80
cuaggtgatg cactgcuuua c 21

<210> SEQ ID NO 81
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 81
cuaggtgatg cactgctuua ca 22

<210> SEQ ID NO 82
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 82
cuaggtgatg cactgctuua ca 22

<210> SEQ ID NO 83
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 83
cuaggtgatg cactgctuua ca 22

<210> SEQ ID NO 84
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 84
cuaggtgatg cactgctuua ca 22

<210> SEQ ID NO 85
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 85
cuaggtgatg cactgctuua ca 22

<210> SEQ ID NO 86
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 86
cuaggtgatg cactgctuua ca 22

<210> SEQ ID NO 87
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 87
cuaggtgatg cactgctuua ca 22

<210> SEQ ID NO 88
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 88
cuaggtgatg cactgctuua ca 22

<210> SEQ ID NO 89
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 89
cuaggtgatg cactgctuua ca 22

<210> SEQ ID NO 90
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 90
cuaggtgatg cactgctuua ca 22

<210> SEQ ID NO 91
<211> LENGTH: 22
<212> TYPE: DNA
<213> ORGANISM: Artificial Sequence
<220> FEATURE:

<223> OTHER INFORMATION: synthetic oligonucleotide

<400> SEQUENCE: 91
cuaggtgatg cactgctuua ca 22

<210> SEQ ID NO 92
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 92
cuaggtgatg cactgctuua ca 22

<210> SEQ ID NO 93
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 93
cuaggtgatg cactgctuua ca 22

<210> SEQ ID NO 94
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 94
cuaggtgatg cactgctuua ca 22

<210> SEQ ID NO 95
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 95
cuaggtgatg cactgctuua ca 22

<210> SEQ ID NO 96
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 96
cuaggtgatg cactgctuua ca 22

<210> SEQ ID NO 97
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 97
ugcuaggtga tgcacugcuu 20

<210> SEQ ID NO 98
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 98
ugcuaggtga tgcacugcuu 20

<210> SEQ ID NO 99
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 99
ugcuaggtga tgcacugcuu 20

<210> SEQ ID NO 100
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 100
ugcuaggtga tgcacugcuu 20

<210> SEQ ID NO 101
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 101
ugcuaggtga tgcacugcuu 20

<210> SEQ ID NO 102
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 102
ugcuaggtga tgcacugcuu 20

<210> SEQ ID NO 103
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 103
ugcuaggtga tgcacugcuu 20

<210> SEQ ID NO 104
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 104
ugcuaggtga tgcacugcuu 20

<210> SEQ ID NO 105
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 105
ugcuaggtga tgcacugcuu 20

<210> SEQ ID NO 106
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 106
ugcuaggtga tgcacugcuu 20

<210> SEQ ID NO 107
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 107
ugcuaggtga tgcacugcuu 20

<210> SEQ ID NO 108
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 108
ugcuaggtga tgcacugcuu 20

<210> SEQ ID NO 109
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 109
ugcuaggtga tgcacugcuu 20

<210> SEQ ID NO 110
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 110
ugcuaggtga tgcacugcuu 20

<210> SEQ ID NO 111
<211> LENGTH: 20

<212> TYPE: DNA
<213> ORGANISM: Artificial Sequence
<220> FEATURE:
<223> OTHER INFORMATION: synthetic oligonucleotide

<400> SEQUENCE: 111
ugcuaggtga tgcacugcuu 20

<210> SEQ ID NO 112
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 112
ugcuaggtga tgcacugcuu 20

<210> SEQ ID NO 113
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 113
ugcuaggtga tgcacugcuu u 21

<210> SEQ ID NO 114
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 114
ugcuaggtga tgcacugcuu u 21

<210> SEQ ID NO 115
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 115
ugcuaggtga tgcacugcuu u 21

<210> SEQ ID NO 116
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 116
ugcuaggtga tgcacugcuu u 21

<210> SEQ ID NO 117
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 117
ugcuaggtga tgcacugcuu u 21

<210> SEQ ID NO 118
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 118
ugcuaggtga tgcacugcuu u 21

<210> SEQ ID NO 119
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 119
ugcuaggtga tgcacugcuu u 21

<210> SEQ ID NO 120
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 120
ugcuaggtga tgcacugcuu u 21

<210> SEQ ID NO 121
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 121
ugcuaggtga tgcacugcuu u 21

<210> SEQ ID NO 122
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 122
ugcuaggtga tgcacugcuu u 21

<210> SEQ ID NO 123
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 123
ugcuaggtga tgcacugcuu u 21

<210> SEQ ID NO 124
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 124
ugcuaggtga tgcacugcuu u 21

<210> SEQ ID NO 125
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 125
ugcuaggtga tgcacugcuu u 21

<210> SEQ ID NO 126
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 126
ugcuaggtga tgcacugcuu u 21

<210> SEQ ID NO 127
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 127
ugcuaggtga tgcacugcuu u 21

<210> SEQ ID NO 128
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 128
ugcuaggtga tgcacugcuu u 21

<210> SEQ ID NO 129
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 129
ugcuaggtga tgcacugcuu ua 22

<210> SEQ ID NO 130
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 130
ugcuaggtga tgcacugcuu ua 22

<210> SEQ ID NO 131
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 131
ugcuaggtga tgcacugcuu ua 22

<210> SEQ ID NO 132
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 132
ugcuaggtga tgcacugcuu ua 22

<210> SEQ ID NO 133
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 133
ugcuaggtga tgcacugcuu ua 22

<210> SEQ ID NO 134
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 134
ugcuaggtga tgcacugcuu ua 22

<210> SEQ ID NO 135
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 135
ugcuaggtga tgcacugcuu ua 22

<210> SEQ ID NO 136
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 136
ugcuaggtga tgcacugcuu ua 22

<210> SEQ ID NO 137
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 137
ugcuaggtga tgcacugcuu ua 22

<210> SEQ ID NO 138
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 138
ugcuaggtga tgcacugcuu ua 22

<210> SEQ ID NO 139
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 139
ugcuaggtga tgcacugcuu ua 22

<210> SEQ ID NO 140
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 140
ugcuaggtga tgcacugcuu ua 22

<210> SEQ ID NO 141
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 141
ugcuaggtga tgcacugcuu ua 22

<210> SEQ ID NO 142
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 142
ugcuaggtga tgcacugcuu ua 22

<210> SEQ ID NO 143
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 143
ugcuaggtga tgcacugcuu ua 22

<210> SEQ ID NO 144

<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 144
ugcuaggtga tgcacugcuu ua 22

<210> SEQ ID NO 145
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 145
ugcuaggtga tgcacugcuu uac 23

<210> SEQ ID NO 146
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 146
ugcuaggtga tgcacugcuu uac 23

<210> SEQ ID NO 147
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 147
ugcuaggtga tgcacugcuu uac 23

<210> SEQ ID NO 148
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 148
ugcuaggtga tgcacugcuu uac 23

<210> SEQ ID NO 149
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 149
ugcuaggtga tgcacugcuu uac 23

<210> SEQ ID NO 150
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 150
ugcuaggtga tgcacugcuu uac 23

<210> SEQ ID NO 151
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 151
ugcuaggtga tgcacugcuu uac 23

<210> SEQ ID NO 152
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 152
ugcuaggtga tgcacugcuu uac 23

<210> SEQ ID NO 153
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 153
ugcuaggtga tgcacugcuu uac 23

<210> SEQ ID NO 154
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 154
ugcuaggtga tgcacugcuu uac 23

<210> SEQ ID NO 155
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 155
ugcuaggtga tgcacugcuu uac 23

<210> SEQ ID NO 156
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 156
ugcuaggtga tgcacugcuu uac 23

<210> SEQ ID NO 157
<211> LENGTH: 23
<212> TYPE: DNA

<213> ORGANISM: Artificial Sequence
<220> FEATURE:
<223> OTHER INFORMATION: synthetic oligonucleotide

<400> SEQUENCE: 157
ugcuaggtga tgcacugcuu uac 23

<210> SEQ ID NO 158
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 158
ugcuaggtga tgcacugcuu uac 23

<210> SEQ ID NO 159
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 159
ugcuaggtga tgcacugcuu uac 23

<210> SEQ ID NO 160
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 160
ugcuaggtga tgcacugcuu uac 23

<210> SEQ ID NO 161
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 161
ugcuaggtga tgcactgcuu u 21

<210> SEQ ID NO 162
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 162
ugcuaggtga tgcactgcuu u 21

<210> SEQ ID NO 163
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 163
ugcuaggtga tgcactgcuu u 21

<210> SEQ ID NO 164
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 164
ugcuaggtga tgcactgcuu u 21

<210> SEQ ID NO 165
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 165
ugcuaggtga tgcactgcuu u 21

<210> SEQ ID NO 166
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 166
ugcuaggtga tgcactgcuu u 21

<210> SEQ ID NO 167
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 167
ugcuaggtga tgcactgcuu u 21

<210> SEQ ID NO 168
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 168
ugcuaggtga tgcactgcuu u 21

<210> SEQ ID NO 169
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 169
ugcuaggtga tgcactgcuu u 21

<210> SEQ ID NO 170
<211> LENGTH: 21
<212> TYPE: DNA
<213> ORGANISM: Artificial Sequence
<220> FEATURE:

<223> OTHER INFORMATION: synthetic oligonucleotide

<400> SEQUENCE: 170
ugcuaggtga tgcactgcuu u 21

<210> SEQ ID NO 171
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 171
ugcuaggtga tgcactgcuu u 21

<210> SEQ ID NO 172
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 172
ugcuaggtga tgcactgcuu u 21

<210> SEQ ID NO 173
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 173
ugcuaggtga tgcactgcuu u 21

<210> SEQ ID NO 174
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 174
ugcuaggtga tgcactgcuu u 21

<210> SEQ ID NO 175
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 175
ugcuaggtga tgcactgcuu u 21

<210> SEQ ID NO 176
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 176
ugcuaggtga tgcactgcuu u 21

<210> SEQ ID NO 177
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 177
ugcuaggtga tgcactgcuu ua 22

<210> SEQ ID NO 178
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 178
ugcuaggtga tgcactgcuu ua 22

<210> SEQ ID NO 179
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 179
ugcuaggtga tgcactgcuu ua 22

<210> SEQ ID NO 180
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 180
ugcuaggtga tgcactgcuu ua 22

<210> SEQ ID NO 181
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 181
ugcuaggtga tgcactgcuu ua 22

<210> SEQ ID NO 182
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 182
ugcuaggtga tgcactgcuu ua 22

<210> SEQ ID NO 183
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 183
ugcuaggtga tgcactgcuu ua 22

<210> SEQ ID NO 184
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 184
ugcuaggtga tgcactgcuu ua 22

<210> SEQ ID NO 185
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 185
ugcuaggtga tgcactgcuu ua 22

<210> SEQ ID NO 186
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 186
ugcuaggtga tgcactgcuu ua 22

<210> SEQ ID NO 187
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 187
ugcuaggtga tgcactgcuu ua 22

<210> SEQ ID NO 188
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 188
ugcuaggtga tgcactgcuu ua 22

<210> SEQ ID NO 189
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 189
ugcuaggtga tgcactgcuu ua 22

<210> SEQ ID NO 190
<211> LENGTH: 22

<212> TYPE: DNA
<213> ORGANISM: Artificial Sequence
<220> FEATURE:
<223> OTHER INFORMATION: synthetic oligonucleotide

<400> SEQUENCE: 190
ugcuaggtga tgcactgcuu ua 22

<210> SEQ ID NO 191
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 191
ugcuaggtga tgcactgcuu ua 22

<210> SEQ ID NO 192
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 192
ugcuaggtga tgcactgcuu ua 22

<210> SEQ ID NO 193
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 193
ugaucctgtt ctcccagcaa 20

<210> SEQ ID NO 194
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 194
ugaucctgtt ctcccagcaa 20

<210> SEQ ID NO 195
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 195
ugaucctgtt ctcccagcaa 20

<210> SEQ ID NO 196
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 196
ugaucctgtt ctcccagcaa 20

<210> SEQ ID NO 197
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 197
ugaucctgtt ctcccagcaa 20

<210> SEQ ID NO 198
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 198
ugaucctgtt ctcccagcaa 20

<210> SEQ ID NO 199
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 199
ugaucctgtt ctcccagcaa 20

<210> SEQ ID NO 200
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 200
ugaucctgtt ctcccagcaa 20

<210> SEQ ID NO 201
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 201
ugaucctgtt ctcccagcaa 20

<210> SEQ ID NO 202
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 202
ugaucctgtt ctcccagcaa 20

<210> SEQ ID NO 203
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 203
ugaucctgtt ctcccagcaa 20

<210> SEQ ID NO 204
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 204
ugaucctgtt ctcccagcaa 20

<210> SEQ ID NO 205
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 205
ugaucctgtt ctcccagcaa 20

<210> SEQ ID NO 206
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 206
ugaucctgtt ctcccagcaa 20

<210> SEQ ID NO 207
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 207
ugaucctgtt ctcccagcaa 20

<210> SEQ ID NO 208
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 208
ugaucctgtt ctcccagcaa 20

<210> SEQ ID NO 209
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 209
ugaucctgtt ctcccagcaa c 21

<210> SEQ ID NO 210
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 210
ugaucctgtt ctcccagcaa c 21

<210> SEQ ID NO 211
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 211
ugaucctgtt ctcccagcaa c 21

<210> SEQ ID NO 212
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 212
ugaucctgtt ctcccagcaa c 21

<210> SEQ ID NO 213
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 213
ugaucctgtt ctcccagcaa c 21

<210> SEQ ID NO 214
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 214
ugaucctgtt ctcccagcaa c 21

<210> SEQ ID NO 215
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 215
ugaucctgtt ctcccagcaa c 21

<210> SEQ ID NO 216
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 216
ugaucctgtt ctcccagcaa c 21

<210> SEQ ID NO 217
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 217
ugaucctgtt ctcccagcaa c 21

<210> SEQ ID NO 218
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 218
ugaucctgtt ctcccagcaa c 21

<210> SEQ ID NO 219
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 219
ugaucctgtt ctcccagcaa c 21

<210> SEQ ID NO 220
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 220
ugaucctgtt ctcccagcaa c 21

<210> SEQ ID NO 221
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 221
ugaucctgtt ctcccagcaa c 21

<210> SEQ ID NO 222
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 222
ugaucctgtt ctcccagcaa c 21

<210> SEQ ID NO 223

<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 223
ugaucctgtt ctcccagcaa c 21

<210> SEQ ID NO 224
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 224
ugaucctgtt ctcccagcaa c 21

<210> SEQ ID NO 225
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 225
ugaucctgtt ctcccagcaa ca 22

<210> SEQ ID NO 226
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 226
ugaucctgtt ctcccagcaa ca 22

<210> SEQ ID NO 227
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 227
ugaucctgtt ctcccagcaa ca 22

<210> SEQ ID NO 228
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 228
ugaucctgtt ctcccagcaa ca 22

<210> SEQ ID NO 229
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 229
ugaucctgtt ctcccagcaa ca 22

<210> SEQ ID NO 230
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 230
ugaucctgtt ctcccagcaa ca 22

<210> SEQ ID NO 231
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 231
ugaucctgtt ctcccagcaa ca 22

<210> SEQ ID NO 232
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 232
ugaucctgtt ctcccagcaa ca 22

<210> SEQ ID NO 233
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 233
ugaucctgtt ctcccagcaa ca 22

<210> SEQ ID NO 234
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 234
ugaucctgtt ctcccagcaa ca 22

<210> SEQ ID NO 235
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 235
ugaucctgtt ctcccagcaa ca 22

<210> SEQ ID NO 236
<211> LENGTH: 22
<212> TYPE: DNA

<213> ORGANISM: Artificial Sequence
<220> FEATURE:
<223> OTHER INFORMATION: synthetic oligonucleotide

<400> SEQUENCE: 236
ugaucctgtt ctcccagcaa ca 22

<210> SEQ ID NO 237
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 237
ugaucctgtt ctcccagcaa ca 22

<210> SEQ ID NO 238
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 238
ugaucctgtt ctcccagcaa ca 22

<210> SEQ ID NO 239
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 239
ugaucctgtt ctcccagcaa ca 22

<210> SEQ ID NO 240
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 240
ugaucctgtt ctcccagcaa ca 22

<210> SEQ ID NO 241
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 241
ugaucctgtt ctcccagcaa cac 23

<210> SEQ ID NO 242
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 242
ugaucctgtt ctcccagcaa cac 23

<210> SEQ ID NO 243
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 243
ugaucctgtt ctcccagcaa cac 23

<210> SEQ ID NO 244
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 244
ugaucctgtt ctcccagcaa cac 23

<210> SEQ ID NO 245
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 245
ugaucctgtt ctcccagcaa cac 23

<210> SEQ ID NO 246
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 246
ugaucctgtt ctcccagcaa cac 23

<210> SEQ ID NO 247
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 247
ugaucctgtt ctcccagcaa cac 23

<210> SEQ ID NO 248
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 248
ugaucctgtt ctcccagcaa cac 23

<210> SEQ ID NO 249
<211> LENGTH: 23
<212> TYPE: DNA
<213> ORGANISM: Artificial Sequence
<220> FEATURE:

<223> OTHER INFORMATION: synthetic oligonucleotide

<400> SEQUENCE: 249
ugaucctgtt ctcccagcaa cac 23

<210> SEQ ID NO 250
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 250
ugaucctgtt ctcccagcaa cac 23

<210> SEQ ID NO 251
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 251
ugaucctgtt ctcccagcaa cac 23

<210> SEQ ID NO 252
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 252
ugaucctgtt ctcccagcaa cac 23

<210> SEQ ID NO 253
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 253
ugaucctgtt ctcccagcaa cac 23

<210> SEQ ID NO 254
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 254
ugaucctgtt ctcccagcaa cac 23

<210> SEQ ID NO 255
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 255
ugaucctgtt ctcccagcaa cac 23

<210> SEQ ID NO 256
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 256
ugaucctgtt ctcccagcaa cac 23

<210> SEQ ID NO 257
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 257
ugaucctgtt ctcccagcaa c 21

<210> SEQ ID NO 258
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 258
ugaucctgtt ctcccagcaa c 21

<210> SEQ ID NO 259
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 259
ugaucctgtt ctcccagcaa c 21

<210> SEQ ID NO 260
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 260
ugaucctgtt ctcccagcaa c 21

<210> SEQ ID NO 261
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 261
ugaucctgtt ctcccagcaa c 21

<210> SEQ ID NO 262
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 262
ugaucctgtt ctcccagcaa c 21

<210> SEQ ID NO 263
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 263
ugaucctgtt ctcccagcaa c 21

<210> SEQ ID NO 264
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 264
ugaucctgtt ctcccagcaa c 21

<210> SEQ ID NO 265
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 265
ugaucctgtt ctcccagcaa c 21

<210> SEQ ID NO 266
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 266
ugaucctgtt ctcccagcaa c 21

<210> SEQ ID NO 267
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 267
ugaucctgtt ctcccagcaa c 21

<210> SEQ ID NO 268
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 268
ugaucctgtt ctcccagcaa c 21

<210> SEQ ID NO 269
<211> LENGTH: 21

<212> TYPE: DNA
<213> ORGANISM: Artificial Sequence
<220> FEATURE:
<223> OTHER INFORMATION: synthetic oligonucleotide

<400> SEQUENCE: 269
ugaucctgtt ctcccagcaa c 21

<210> SEQ ID NO 270
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 270
ugaucctgtt ctcccagcaa c 21

<210> SEQ ID NO 271
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 271
ugaucctgtt ctcccagcaa c 21

<210> SEQ ID NO 272
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 272
ugaucctgtt ctcccagcaa c 21

<210> SEQ ID NO 273
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 273
ugaucctgtt ctcccagcaa ca 22

<210> SEQ ID NO 274
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 274
ugaucctgtt ctcccagcaa ca 22

<210> SEQ ID NO 275
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 275
ugaucctgtt ctcccagcaa ca 22

<210> SEQ ID NO 276
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 276
ugaucctgtt ctcccagcaa ca 22

<210> SEQ ID NO 277
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 277
ugaucctgtt ctcccagcaa ca 22

<210> SEQ ID NO 278
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 278
ugaucctgtt ctcccagcaa ca 22

<210> SEQ ID NO 279
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 279
ugaucctgtt ctcccagcaa ca 22

<210> SEQ ID NO 280
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 280
ugaucctgtt ctcccagcaa ca 22

<210> SEQ ID NO 281
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 281
ugaucctgtt ctcccagcaa ca 22

<210> SEQ ID NO 282
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 282
ugaucctgtt ctcccagcaa ca 22

<210> SEQ ID NO 283
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 283
ugaucctgtt ctcccagcaa ca 22

<210> SEQ ID NO 284
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 284
ugaucctgtt ctcccagcaa ca 22

<210> SEQ ID NO 285
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 285
ugaucctgtt ctcccagcaa ca 22

<210> SEQ ID NO 286
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 286
ugaucctgtt ctcccagcaa ca 22

<210> SEQ ID NO 287
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 287
ugaucctgtt ctcccagcaa ca 22

<210> SEQ ID NO 288
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 288
ugaucctgtt ctcccagcaa ca 22

<210> SEQ ID NO 289
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 289
uugaucctgt tctcccagca 20

<210> SEQ ID NO 290
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 290
uugaucctgt tctcccagca 20

<210> SEQ ID NO 291
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 291
uugaucctgt tctcccagca 20

<210> SEQ ID NO 292
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 292
uugaucctgt tctcccagca 20

<210> SEQ ID NO 293
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 293
uugaucctgt tctcccagca 20

<210> SEQ ID NO 294
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 294
uugaucctgt tctcccagca 20

<210> SEQ ID NO 295
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 295
uugaucctgt tctcccagca 20

<210> SEQ ID NO 296
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 296
uugaucctgt tctcccagca 20

<210> SEQ ID NO 297
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 297
uugaucctgt tctcccagca 20

<210> SEQ ID NO 298
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 298
uugaucctgt tctcccagca 20

<210> SEQ ID NO 299
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 299
uugaucctgt tctcccagca 20

<210> SEQ ID NO 300
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 300
uugaucctgt tctcccagca 20

<210> SEQ ID NO 301
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 301
uugaucctgt tctcccagca 20

<210> SEQ ID NO 302

<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 302
uugaucctgt tctcccagca 20

<210> SEQ ID NO 303
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 303
uugaucctgt tctcccagca 20

<210> SEQ ID NO 304
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 304
uugaucctgt tctcccagca 20

<210> SEQ ID NO 305
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 305
uugaucctgt tctcccagca a 21

<210> SEQ ID NO 306
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 306
uugaucctgt tctcccagca a 21

<210> SEQ ID NO 307
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 307
uugaucctgt tctcccagca a 21

<210> SEQ ID NO 308
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 308
uugaucctgt tctcccagca a 21

<210> SEQ ID NO 309
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 309
uugaucctgt tctcccagca a 21

<210> SEQ ID NO 310
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 310
uugaucctgt tctcccagca a 21

<210> SEQ ID NO 311
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 311
uugaucctgt tctcccagca a 21

<210> SEQ ID NO 312
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 312
uugaucctgt tctcccagca a 21

<210> SEQ ID NO 313
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 313
uugaucctgt tctcccagca a 21

<210> SEQ ID NO 314
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 314
uugaucctgt tctcccagca a 21

<210> SEQ ID NO 315
<211> LENGTH: 21
<212> TYPE: DNA

<213> ORGANISM: Artificial Sequence
<220> FEATURE:
<223> OTHER INFORMATION: synthetic oligonucleotide

<400> SEQUENCE: 315
uugaucctgt tctcccagca a 21

<210> SEQ ID NO 316
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 316
uugaucctgt tctcccagca a 21

<210> SEQ ID NO 317
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 317
uugaucctgt tctcccagca a 21

<210> SEQ ID NO 318
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 318
uugaucctgt tctcccagca a 21

<210> SEQ ID NO 319
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 319
uugaucctgt tctcccagca a 21

<210> SEQ ID NO 320
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 320
uugaucctgt tctcccagca a 21

<210> SEQ ID NO 321
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 321
uugaucctgt tctcccagca ac 22

<210> SEQ ID NO 322
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 322
uugaucctgt tctcccagca ac 22

<210> SEQ ID NO 323
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 323
uugaucctgt tctcccagca ac 22

<210> SEQ ID NO 324
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 324
uugaucctgt tctcccagca ac 22

<210> SEQ ID NO 325
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 325
uugaucctgt tctcccagca ac 22

<210> SEQ ID NO 326
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 326
uugaucctgt tctcccagca ac 22

<210> SEQ ID NO 327
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 327
uugaucctgt tctcccagca ac 22

<210> SEQ ID NO 328
<211> LENGTH: 22
<212> TYPE: DNA
<213> ORGANISM: Artificial Sequence
<220> FEATURE:

<223> OTHER INFORMATION: synthetic oligonucleotide

<400> SEQUENCE: 328
uugaucctgt tctcccagca ac 22

<210> SEQ ID NO 329
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 329
uugaucctgt tctcccagca ac 22

<210> SEQ ID NO 330
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 330
uugaucctgt tctcccagca ac 22

<210> SEQ ID NO 331
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 331
uugaucctgt tctcccagca ac 22

<210> SEQ ID NO 332
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 332
uugaucctgt tctcccagca ac 22

<210> SEQ ID NO 333
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 333
uugaucctgt tctcccagca ac 22

<210> SEQ ID NO 334
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 334
uugaucctgt tctcccagca ac 22

<210> SEQ ID NO 335
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 335
uugaucctgt tctcccagca ac 22

<210> SEQ ID NO 336
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 336
uugaucctgt tctcccagca ac 22

<210> SEQ ID NO 337
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 337
uugaucctgt tctcccagca aca 23

<210> SEQ ID NO 338
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 338
uugaucctgt tctcccagca aca 23

<210> SEQ ID NO 339
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 339
uugaucctgt tctcccagca aca 23

<210> SEQ ID NO 340
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 340
uugaucctgt tctcccagca aca 23

<210> SEQ ID NO 341
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 341
uugaucctgt tctcccagca aca 23

<210> SEQ ID NO 342
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 342
uugaucctgt tctcccagca aca 23

<210> SEQ ID NO 343
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 343
uugaucctgt tctcccagca aca 23

<210> SEQ ID NO 344
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 344
uugaucctgt tctcccagca aca 23

<210> SEQ ID NO 345
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 345
uugaucctgt tctcccagca aca 23

<210> SEQ ID NO 346
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 346
uugaucctgt tctcccagca aca 23

<210> SEQ ID NO 347
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 347
uugaucctgt tctcccagca aca 23

<210> SEQ ID NO 348
<211> LENGTH: 23

<212> TYPE: DNA
<213> ORGANISM: Artificial Sequence
<220> FEATURE:
<223> OTHER INFORMATION: synthetic oligonucleotide

<400> SEQUENCE: 348
uugaucctgt tctcccagca aca 23

<210> SEQ ID NO 349
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 349
uugaucctgt tctcccagca aca 23

<210> SEQ ID NO 350
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 350
uugaucctgt tctcccagca aca 23

<210> SEQ ID NO 351
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 351
uugaucctgt tctcccagca aca 23

<210> SEQ ID NO 352
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 352
uugaucctgt tctcccagca aca 23

<210> SEQ ID NO 353
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 353
uugaucctgt tctcccagca a 21

<210> SEQ ID NO 354
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 354
uugaucctgt tctcccagca a 21

<210> SEQ ID NO 355
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 355
uugaucctgt tctcccagca a 21

<210> SEQ ID NO 356
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 356
uugaucctgt tctcccagca a 21

<210> SEQ ID NO 357
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 357
uugaucctgt tctcccagca a 21

<210> SEQ ID NO 358
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 358
uugaucctgt tctcccagca a 21

<210> SEQ ID NO 359
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 359
uugaucctgt tctcccagca a 21

<210> SEQ ID NO 360
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 360
uugaucctgt tctcccagca a 21

<210> SEQ ID NO 361
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 361
uugaucctgt tctcccagca a 21

<210> SEQ ID NO 362
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 362
uugaucctgt tctcccagca a 21

<210> SEQ ID NO 363
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 363
uugaucctgt tctcccagca a 21

<210> SEQ ID NO 364
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 364
uugaucctgt tctcccagca a 21

<210> SEQ ID NO 365
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 365
uugaucctgt tctcccagca a 21

<210> SEQ ID NO 366
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 366
uugaucctgt tctcccagca a 21

<210> SEQ ID NO 367
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 367
uugaucctgt tctcccagca a 21

<210> SEQ ID NO 368
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 368
uugaucctgt tctcccagca a 21

<210> SEQ ID NO 369
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 369
uugaucctgt tctcccagca ac 22

<210> SEQ ID NO 370
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 370
uugaucctgt tctcccagca ac 22

<210> SEQ ID NO 371
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 371
uugaucctgt tctcccagca ac 22

<210> SEQ ID NO 372
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 372
uugaucctgt tctcccagca ac 22

<210> SEQ ID NO 373
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 373
uugaucctgt tctcccagca ac 22

<210> SEQ ID NO 374
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 374
uugaucctgt tctcccagca ac 22

<210> SEQ ID NO 375
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 375
uugaucctgt tctcccagca ac 22

<210> SEQ ID NO 376
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 376
uugaucctgt tctcccagca ac 22

<210> SEQ ID NO 377
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 377
uugaucctgt tctcccagca ac 22

<210> SEQ ID NO 378
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 378
uugaucctgt tctcccagca ac 22

<210> SEQ ID NO 379
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 379
uugaucctgt tctcccagca ac 22

<210> SEQ ID NO 380
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 380
uugaucctgt tctcccagca ac 22

<210> SEQ ID NO 381

<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 381
uugaucctgt tctcccagca ac 22

<210> SEQ ID NO 382
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 382
uugaucctgt tctcccagca ac 22

<210> SEQ ID NO 383
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 383
uugaucctgt tctcccagca ac 22

<210> SEQ ID NO 384
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 384
uugaucctgt tctcccagca ac 22

<210> SEQ ID NO 385
<211> LENGTH: 4472
<212> TYPE: DNA
<213> ORGANISM: Artificial Sequence
<220> FEATURE:
<223> OTHER INFORMATION: nucleotide sequence

<400> SEQUENCE: 385
ccgcagacgc ctgggaactg cggccgcggg ctcgcgctcc tcgccaggcc ctgccgccgg 60
gctgccatcc ttgccctgcc atgtctcgcc ggaagcctgc gtcgggcggc ctcgctgcct 120
ccagctcagc ccctgcgagg caagcggttt tgagccgatt cttccagtct acgggaagcc 180
tgaaatccac ctcctcctcc acaggtgcag ccgaccaggt ggaccctggc gctgcagcgg 240
ctgcagcggc cgcagcggcc gcagcgcccc cagcgccccc agctcccgcc ttcccgcccc 300
agctgccgcc gcacatagct acagaaattg acagaagaaa gaagagacca ttggaaaatg 360
atgggcctgt taaaaagaaa gtaaagaaag tccaacaaaa ggaaggagga agtgatctgg 420
gaatgtctgg caactctgag ccaaagaaat gtctgaggac caggaatgtt tcaaagtctc 480
tggaaaaatt gaaagaattc tgctgcgatt ctgcccttcc tcaaagtaga gtccagacag 540
aatctctgca ggagagattt gcagttctgc caaaatgtac tgattttgat gatatcagtc 600
ttctacacgc aaagaatgca gtttcttctg aagattcgaa acgtcaaatt aatcaaaagg 660
acacaacact ttttgatctc agtcagtttg gatcatcaaa tacaagtcat gaaaatttac 720

```
agaaaactgc ttccaaatca gctaacaaac ggtccaaaag catctatacg ccgctagaat    780
tacaatacat agaaatgaag cagcagcaca aagatgcagt tttgtgtgtg gaatgtggat    840
ataagtatag attctttggg gaagatgcag agattgcagc ccgagagctc aatatttatt    900
gccatttaga tcacaacttt atgacagcaa gtatacctac tcacagactg tttgttcatg    960
tacgccgcct ggtggcaaaa ggatataagg tgggagttgt gaagcaaact gaaactgcag   1020
cattaaaggc cattggagac aacagaagtt cactcttttc ccggaaattg actgcccttt   1080
atacaaaatc tacacttatt ggagaagatg tgaatcccct aatcaagctg gatgatgctg   1140
taaatgttga tgagataatg actgatactt ctaccagcta tcttctgtgc atctctgaaa   1200
ataaggaaaa tgttagggac aaaaaaaagg gcaacatttt tattggcatt gtgggagtgc   1260
agcctgccac aggcgaggtt gtgtttgata gtttccagga ctctgcttct cgttcagagc   1320
tagaaacccg gatgtcaagc ctgcagccag tagagctgct gcttccttcg gccttgtccg   1380
agcaaacaga ggcgctcatc cacagagcca catctgttag tgtgcaggat gacagaattc   1440
gagtcgaaag gatggataac atttattttg aatacagcca tgctttccag gcagttacag   1500
agttttatgc aaaagataca gttgacatca aaggttctca aattatttct ggcattgtta   1560
acttagagaa gcctgtgatt tgctctttgg ctgccatcat aaaataccte aaagaattca   1620
acttggaaaa gatgctctcc aaacctgaga attttaaaca gctatcaagt aaaatggaat   1680
ttatgacaat taatggaaca acattaagga atctggaaat cctacagaat cagactgata   1740
tgaaaaccaa aggaagtttg ctgtgggttt tagaccacac taaaacttca tttgggagac   1800
ggaagttaaa gaagtgggtg acccagccac tccttaaatt aagggaaata aatgcccggc   1860
ttgatgctgt atcggaagtt ctccattcag aatctagtgt gtttggtcag atagaaaatc   1920
atctacgtaa attgcccgac atagagaggg gactctgtag catttatcac aaaaaatgtt   1980
ctacccaaga gttcttcttg attgtcaaaa ctttatatca cctaaagtca gaatttcaag   2040
caataatacc tgctgttaat tcccacattc agtcagactt gctccggacc gttattttag   2100
aaattcctga actcctcagt ccagtggagc attacttaaa gatactcaat gaacaagctg   2160
ccaaagttgg ggataaaact gaattattta aagacctttc tgacttccct ttaataaaaa   2220
agaggaagga tgaaattcaa ggtgttattg acgagatccg aatgcatttg caagaaatac   2280
gaaaaatact aaaaaatcct tctgcacaat atgtgacagt atcaggacag gagtttatga   2340
tagaaataaa gaactctgct gtatcttgta taccaactga ttgggtaaag gttggaagca   2400
caaaagctgt gagccgcttt cactctcctt ttattgtaga aaattacaga catctgaatc   2460
agctccggga gcagctagtc cttgactgca gtgctgaatg gcttgatttt ctagagaaat   2520
tcagtgaaca ttatcactcc ttgtgtaaag cagtgcatca cctagcaact gttgactgca   2580
ttttctccct ggccaaggtc gctaagcaag gagattactg cagaccaact gtacaagaag   2640
aaagaaaaat tgtaataaaa aatggaaggc accctgtgat tgatgtgttg ctgggagaac   2700
aggatcaata tgtcccaaat aatacagatt tatcagagga ctcagagaga gtaatgataa   2760
ttaccggacc aaacatgggt ggaaagagct cctacataaa acaagttgca ttgattacca   2820
tcatggctca gattggctcc tatgttcctg cagaagaagc gacaattggg attgtggatg   2880
gcattttcac aaggatgggt gctgcagaca atatatataa aggacagagt acatttatgg   2940
aagaactgac tgacacagca gaaataatca gaaaagcaac atcacagtcc ttggttatct   3000
tggatgaact aggaagaggg acgagcactc atgatggaat tgccattgcc tatgctacac   3060
```

```
ttgagtattt catcagagat gtgaaatcct taaccctgtt tgtcacccat tatccgccag   3120
tttgtgaact agaaaaaaat tactcacacc aggtggggaa ttaccacatg ggattcttgg   3180
tcagtgagga tgaaagcaaa ctggatccag gcgcagcaga acaagtccct gattttgtca   3240
ccttccttta ccaaataact agaggaattg cagcaaggag ttatggatta aatgtggcta   3300
aactagcaga tgttcctgga gaaattttga agaaagcagc tcacaagtca aaagagctgg   3360
aaggattaat aaatacgaaa agaaagagac tcaagtattt tgcaaagtta tggacgatgc   3420
ataatgcaca agacctgcag aagtggacag aggagttcaa catggaagaa acacagactt   3480
ctcttcttca ttaaaatgaa gactacattt gtgaacaaaa aatggagaat taaaaatacc   3540
aactgtacaa aataactctc cagtaacagc ctatctttgt gtgacatgtg agcataaaat   3600
tatgaccatg gtatattcct attggaaaca gagaggtttt tctgaagaca gtctttttca   3660
agtttctgtc ttcctaactt ttctacgtat aaacactctt gaatagactt ccactttgta   3720
attagaaaat tttatggaca gtaagtccag taaagcctta agtggcagaa tataattccc   3780
aagcttttgg agggtgatat aaaaatttac ttgatatttt tatttgtttc agttcagata   3840
attggcaact gggtgaatct ggcaggaatc tatccattga actaaaataa ttttattatg   3900
caaccagttt atccaccaag aacataagaa ttttttataa gtagaaagaa ttggccaggc   3960
atggtggctc atgcctgtaa tcccagcact ttgggaggcc aaggtaggca gatcacctga   4020
ggtcaggagt tcaagaccag cctggccaac atggcaaaac cccatcttta ctaaaaatat   4080
aaagtacatc tctactaaaa atacgaaaaa attagctggg catggtggcg cacacctgta   4140
gtcccagcta ctccggaggc tgaggcagga gaatctcttg aacctgggag gcggaggttg   4200
caatgagccg agatcacgtc actgcactcc agcttgggca acagagcaag actccatctc   4260
aaaaaaaaaa aaagaaaaaa gaaaagaaat agaattatca agcttttaaa aactagagca   4320
cagaaggaat aaggtcatga aatttaaaag gttaaatatt gtcataggat taagcagttt   4380
aaagattgtt ggatgaaatt atttgtcatt cattcaagta ataaatattt aatgaatact   4440
tgctataaaa aaaaaaaaaa aaaaaaaaaa aa                                 4472
```

<210> SEQ ID NO 386
<211> LENGTH: 4472
<212> TYPE: DNA
<213> ORGANISM: Artificial Sequence
<220> FEATURE:
<223> OTHER INFORMATION: nucleotide sequence

<400> SEQUENCE: 386

```
ccgcagacgc ctgggaactg cggccgcggg ctcgcgctcc tcgccaggcc ctgccgccgg     60
gctgccatcc ttgccctgcc atgtctcgcc ggaagcctgc gtcgggcggc ctcgctgcct    120
ccagctcagc ccctgcgagg caagcggttt tgagccgatt cttccagtct acgggaagcc    180
tgaaatccac ctcctcctcc acaggtgcag ccgaccaggt ggaccctggc gctgcagcgg    240
ctgcagcggc cgcagcggcc gcagcgcccc cagcgccccc agctcccgcc ttcccgcccc    300
agctgccgcc gcacatagct acagaaattg acagaagaaa gaagagacca ttggaaaatg    360
atgggcctgt taaaaagaaa gtaaagaaag tccaacaaaa ggaaggagga agtgatctgg    420
gaatgtctgg caactctgag ccaaagaaat gtctgaggac caggaatgtt tcaaagtctc    480
tggaaaaatt gaaagaattc tgctgcgatt ctgcccttcc tcaaagtaga gtccagacag    540
aatctctgca ggagagattt gcagttctgc caaaatgtac tgattttgat gatatcagtc    600
ttctacacgc aaagaatgca gtttcttctg aagattcgaa acgtcaaatt aatcaaaagg    660
```

```
acacaacact ttttgatctc agtcagtttg gatcatcaaa tacaagtcat gaaaatttac    720
agaaaactgc ttccaaatca gctaacaaac ggtccaaaag catctatacg ccgctagaat    780
tacaatacat agaaatgaag cagcagcaca aagatgcagt tttgtgtgtg gaatgtggat    840
ataagtatag attctttggg gaagatgcag agattgcagc ccgagagctc aatatttatt    900
gccatttaga tcacaacttt atgacagcaa gtatacctac tcacagactg tttgttcatg    960
tacgccgcct ggtggcaaaa ggatataagg tgggagttgt gaagcaaact gaaactgcag   1020
cattaaaggc cattggagac aacagaagtt cactcttttc ccggaaattg actgcccttt   1080
atacaaaatc tacacttatt ggagaagatg tgaatcccct aatcaagctg gatgatgctg   1140
taaatgttga tgagataatg actgatactt ctaccagcta tcttctgtgc atctctgaaa   1200
ataaggaaaa tgttagggac aaaaaaaagg gcaacatttt tattggcatt gtgggagtgc   1260
agcctgccac aggcgaggtt gtgtttgata gtttccagga ctctgcttct cgttcagagc   1320
tagaaacccg gatgtcaagc ctgcagccag tagagctgct gcttccttcg gccttgtccg   1380
agcaaacaga ggcgctcatc cacagagcca catctgttag tgtgcaggat gacagaattc   1440
gagtcgaaag gatggataac atttattttg aatacagcca tgctttccag gcagttacag   1500
agttttatgc aaaagataca gttgacatca aaggttctca aattatttct ggcattgtta   1560
acttagagaa gcctgtgatt tgctctttgg ctgccatcat aaaatacctc aaagaattca   1620
acttggaaaa gatgctctcc aaacctgaga attttaaaca gctatcaagt aaaatggaat   1680
ttatgacaat taatggaaca acattaagga atctggaaat cctacagaat cagactgata   1740
tgaaaaccaa aggaagtttg ctgtgggttt tagaccacac taaaacttca tttgggagac   1800
ggaagttaaa gaagtgggtg acccagccac tccttaaatt aagggaaata aatgcccggc   1860
ttgatgctgt atcggaagtt ctccattcag aatctagtgt gtttggtcag atagaaaatc   1920
atctacgtaa attgcccgac atagagaggg gactctgtag catttatcac aaaaaatgtt   1980
ctacccaaga gttcttcttg attgtcaaaa ctttatatca cctaaagtca gaatttcaag   2040
caataatacc tgctgttaat tcccacattc agtcagactt gctccggacc gttattttag   2100
aaattcctga actcctcagt ccagtggagc attacttaaa gatactcaat gaacaagctg   2160
ccaaagttgg ggataaaact gaattattta aagacctttc tgacttccct ttaataaaaa   2220
agaggaagga tgaaattcaa ggtgttattg acgagatccg aatgcatttg caagaaatac   2280
gaaaaatact aaaaaatcct tctgcacaat atgtgacagt atcaggacag gagtttatga   2340
tagaaataaa gaactctgct gtatcttgta taccaactga ttgggtaaag gttggaagca   2400
caaaagctgt gagccgcttt cactctcctt ttattgtaga aaattacaga catctgaatc   2460
agctccggga gcagctagtc cttgactgca gtgctgaatg gcttgatttt ctagagaaat   2520
tcagtgaaca ttatcactcc ttgtgtaaag cagtgcatca cctagcaact gttgactgca   2580
ttttctccct ggccaaggtc gctaagcaag gagattactg cagaccaact gtacaagaag   2640
aaagaaaaat tgtaataaaa aatggaaggc accctgtgat tgatgtgttg ctgggagaac   2700
aggatcaata tgtcccaaat aatacagatt tatcagagga ctcagagaga gtaatgataa   2760
ttaccggacc aaacatgggt ggaaagagct cctacataaa acaagttgca ttgattacca   2820
tcatggctca gattggctcc tatgttcctg cagaagaagc gacaattggg attgtggatg   2880
gcattttcac aaggatgggt gctgcagaca atatatataa aggacagagt acatttatgg   2940
aagaactgac tgacacagca gaaataatca gaaaagcaac atcacagtcc ttggttatct   3000
```

```
tggatgaact aggaagaggg acgagcactc atgatggaat tgccattgcc tatgctacac   3060

ttgagtattt catcagagat gtgaaatcct taaccctgtt tgtcacccat tatccgccag   3120

tttgtgaact agaaaaaaat tactcacacc aggtggggaa ttaccacatg ggattcttgg   3180

tcagtgagga tgaaagcaaa ctggatccag gcgcagcaga acaagtccct gattttgtca   3240

ccttccttta ccaaataact agaggaattg cagcaaggag ttatggatta aatgtggcta   3300

aactagcaga tgttcctgga gaaattttga agaaagcagc tcacaagtca aaagagctgg   3360

aaggattaat aaatacgaaa agaaagagac tcaagtattt tgcaaagtta tggacgatgc   3420

ataatgcaca agacctgcag aagtggacag aggagttcaa catggaagaa acacagactt   3480

ctcttcttca ttaaaatgaa gactacattt gtgaacaaaa aatggagaat taaaaatacc   3540

aactgtacaa aataactctc cagtaacagc ctatctttgt gtgacatgtg agcataaaat   3600

tatgaccatg gtatattcct attggaaaca gagaggtttt tctgaagaca gtctttttca   3660

agtttctgtc ttcctaactt ttctacgtat aaacactctt gaatagactt ccactttgta   3720

attagaaaat tttatggaca gtaagtccag taaagcctta agtggcagaa tataattccc   3780

aagcttttgg agggtgatat aaaaatttac ttgatatttt tatttgtttc agttcagata   3840

attggcaact gggtgaatct ggcaggaatc tatccattga actaaaataa ttttattatg   3900

caaccagttt atccaccaag aacataagaa ttttttataa gtagaaagaa ttggccaggc   3960

atggtggctc atgcctgtaa tcccagcact ttgggaggcc aaggtaggca gatcacctga   4020

ggtcaggagt tcaagaccag cctggccaac atggcaaaac cccatcttta ctaaaaatat   4080

aaagtacatc tctactaaaa atacgaaaaa attagctggg catggtggcg cacacctgta   4140

gtcccagcta ctccggaggc tgaggcagga gaatctcttg aacctgggag gcggaggttg   4200

caatgagccg agatcacgtc actgcactcc agcttgggca acagagcaag actccatctc   4260

aaaaaaaaaa aaagaaaaaa gaaaagaaat agaattatca agcttttaaa aactagagca   4320

cagaaggaat aaggtcatga aatttaaaag gttaaatatt gtcataggat taagcagttt   4380

aaagattgtt ggatgaaatt atttgtcatt cattcaagta ataaatattt aatgaatact   4440

tgctataaaa aaaaaaaaaa aaaaaaaaaa aa                                 4472
```

<210> SEQ ID NO 387
<211> LENGTH: 3945
<212> TYPE: DNA
<213> ORGANISM: Artificial Sequence
<220> FEATURE:
<223> OTHER INFORMATION: nucleotide sequence

<400> SEQUENCE: 387

```
ccaaggccgg tcccgcacag gttgaggcgt gcgcgcgcgc aggcgcgaga aagtgcggcc     60

gcgcgctcgc gctcctagca ggccggctct tctgcacact gcaatgcccc gcgggaaatc    120

cgcgtcggga ggctctactg ccgccggccc aggcccgggg aggcaaacgg ttctaagccg    180

gttcttcagg tctgcgggaa gcctaagatc cagcgcgtcc tccacggagc cagcagagaa    240

ggtgacagaa ggtgacagca ggaagaggtc actgggaaat ggtgggccca ctaagaaaaa    300

agcaaggaaa gttccagaga aggaggaaga aaacatctca gtagcagctc accaccctga    360

ggcaaagaaa tgtctgaggc ccaggattgt tttaaagtcc ctggaaaagt tgaaagaatt    420

ctgctgtgat tctgccctcc ctcaaaacag agtccagaca gaagctcttc gggagagact    480

tgaagttctg ccaaggtgta ctgattttga agatatcact ctgcaacgtg caaagaatgc    540

ggttttgtcc gaagattcca aatctcaggc taatcagaaa gacagtcaat ttggaccctg    600
```

```
ccctgaagtt ttccagaaga cttccgattg taaacctttt aacaagcgat ccaagagcgt    660
ctatacaccg ttagaactgc agtacttaga tatgaagcag cagcataaag acgcagtttt    720
gtgtgtggag tgtggttaca agtacagatt ctttggggaa gatgcagaaa ttgctgcccg    780
ggaactcaat atttattgcc acttagacca caactttatg actgcaagca tacctaccca    840
cagactgttc gtgcatgtcc gccgacttgt ggccaaaggg tacaaggtgg gagttgtgaa    900
gcaaactgaa actgccgcat taaaggccat cggagacaat aaaagttctg tcttctcccg    960
gaaattgacc gctctttata cgaaatccac acttattggt gaagatgtga atcctctcat   1020
caggctggat gattctgtaa atatcgatga ggtaatgaca gatacatcta ccaactatct   1080
tctgtgtatc tacgaagaaa aggagaacat taaagacaaa aagaagggga acctttccgt   1140
tggtatcgtg ggagtgcagc ccgcaactgg cgaggttgtg tttgactgct tccaggactc   1200
tgcttccaga ctggagctgg agactcgcat atcaagcctg cagcctgtgg aattactgct   1260
tccctccgac ctgtctgtgc caacagagat gctcatccaa agagccacca atgtcagtgt   1320
gcgggatgac aggattcgag tagaaaggat gaataatact tactttgaat acagccatgc   1380
tttccagaca gttacggagt tttatgctag agagatagtt gacagccagg gctctcagag   1440
tctctctggt gtcattaact tggagaagcc tgtgatctgc gccttggctg ccgtaataag   1500
gtacctcaag gaatttaacc tggaaaagat gctgtccaaa cccgagagtt ttaaacagct   1560
gtcaagtgga atggaattca tgagaattaa tgggaccacg ctaaggaatc tggagatcct   1620
tcagaatcag actgatatga agaccaaagg aagcttgctt tgggttttag accacactaa   1680
aacttcattt gggagaagga agttaaagaa ttgggttacc cagccactgc ttaaattaag   1740
ggaaataaat gcccgacttg atgcagtatc tgatgttctc cactcagaat ccagtgtgtt   1800
tgagcagata gaaaaccttc ttcgtaagtt accggatgtc gagagaggac tatgtagcat   1860
ttatcacaag aagtgctcta cccaagagtt cttcttgatc gtcaaaagcc tatgtcaact   1920
gaagtcagag cttcaagcat taatgcctgc tgttaattcc cacgttcagt ccgacttact   1980
ccgagcactc atcgtggagg ctcctgagct cctcagccca gtggaacatt acttaaaggt   2040
tctgaatggg ccagctgcca aagttggcga taaaactgaa ttattcaaag acctctctga   2100
cttcccttta ataaaaaaga ggaaaaatga aattcaggaa gtcattcaca gcatccaaat   2160
gcgtttacag gaatttcgga aaatattaaa acttccttct ttacagtatg tgactgtatc   2220
aggacaagag tttatgattg aaataaagaa ctcggctgta tcttgcatcc cagctgattg   2280
ggtgaaggtt ggaagcacaa aagctgtgag ccgctttcac cctcccttca tcgtggaaag   2340
ctacagacgt ctgaatcagc tccgggagca gctagtcctt gactgcaatg ctgaatggct   2400
tggcttccta gagaatttg gtgaacatta tcacactttg tgtaaggctg tggatcacct   2460
agcaactgtt gactgtattt tctccctggc caaggtcgct aaacaaggaa attactgcag   2520
gccaactcta caagaagaaa agaagatcat cataaaaaat ggaaggcacc ctatgattga   2580
tgtgttgctg ggtgaacaag atcagtttgt gcccaacagt acgagtttat cacaggactc   2640
ggagagagta atgataatca ccggaccaaa catgggtggg aaaagctcct acataaaaca   2700
ggttgcactg gttaccatca tggctcagat tggctcctac gtccctgcag aggaagccac   2760
aattgggatt gtggatggca ttttcacaag gatgggtgct gcagacaata tatacaaagg   2820
ccggagtact ttcatggaag aactgacgga cacagcggaa ataatcagga gagcgtcccc   2880
acagtccttg gttatcctgg atgagctggg gagagggaca agcacccatg acggaatcgc   2940
```

```
catcgcctat gcaactctag agtattttat cagagacgtg aaatccttaa cactgttcgt   3000

tacccactat ccaccagtct gtgaactaga aaaatgttac ccagaacaag tggggaatta   3060

ccacatggga ttcttggtca atgaagatga aagcaagcag gactcaggtg acatggagca   3120

gatgccggat tctgtcactt ttctctatca gataacccga ggaattgcag cgagaagtta   3180

tggacttaat gtggcgaagt tagcagatgt acctagagaa gtcttacaga aagccgcgca   3240

caagtctaag gagctggaag gcttagtcag cctgagaagg aaaaggcttg aatgttttac   3300

cgacttatgg acgacacaca gtgtgaagga cctgcacaca tgggcagata agctggaaat   3360

ggaggaaata cagacttctc tcccacatta aaatgaaaac tgcatttttg gagtaaaata   3420

cagagaactg aagattcaaa ctgtacaaaa caactctgtg gcaacagccg tctctgtggt   3480

cttccttttg agatggcttc tgctctgtga agggagcttt tcaggctctt gtcctcctgc   3540

tttcagaaga aaaagacaat ggagtgtaaa ggcctcaatt ttcctaggca gtacatttca   3600

taccaaagcg ggttcttcta agtaaaacct aaaacggagg ttcttggtgc ctacattatc   3660

agaggggcag tgcctattta ggttcagaca attgacaaca ggctaatctg acaggaacct   3720

acttttgtga gaactaaaga actttataat gccagggttt gctcaccaaa cacataaacg   3780

tttttatgag aaggagaatc gcgaagcttc tagaagccag agcacaggaa ggaaaggcca   3840

catgaagtgt gaagggctaa atgtcgtcat ctttttaaca gcttgaaggt tggtgtataa   3900

aattattttg tcatttactt aaataaaaat atggaatgaa tactt                   3945
```

<210> SEQ ID NO 388
<211> LENGTH: 3780
<212> TYPE: DNA
<213> ORGANISM: Artificial Sequence
<220> FEATURE:
<223> OTHER INFORMATION: nucleotide sequence

<400> SEQUENCE: 388

```
atgccccgca ggaaatccgc gtcgggaggc tctaatgccg ccggcccaga cccggggagg     60

caagtggttc tgagccggtt cttcaagtct gcgggaagcc taagatccag cgtgtccccc    120

acagaaccag cagagaaggt gacagaaggt gacagcagga agaggtcact ggggaatggt    180

gagcccacta acaagaaagc aaagaaagtt ccagaggagg aaggagaaaa tacctcagta    240

gcatctcaca atcctgagcc aaagaaatgt ctgaggccca ggattgtttc aaagtccctg    300

gaaaagttga aagaattctg ctgtgattct gccctccctc aaaacagagt ccagacagaa    360

gcccctttggg agagacttgc agttctgcca aagtgtactg atttcgaaga tatcactctg    420

caacgtgcaa agaatgcggt tttgtccgaa gattccaagt ctcaggctaa tcagaaagac    480

actcaatttg gaccttcccc tgaagctttc cagaagactt ccacttgtaa accttttaac    540

aggcggtcca agagcatcta tactccacta gaactgcagt accttgatgt gaagcagctg    600

cataaagacg cggttttgtg tgtggaatgt gggtacaagt acaggttctt tggggaagat    660

gcagaaattg ctgcccggga actcaatatt tattgccact tggaccacaa ctttatgacg    720

gcgagcatac ccacccacag actgttcgtg catgtccgcc gactggtggc caaaggatac    780

aaggtgggag ttgtgaagca aactgaaact gcggcattaa aggccattgg agacaataaa    840

agttctgtct tttcccggaa attgactgct ctttatacga aatccacact gattggagaa    900

gatgtgaatc ctctgatcag gctggatgat tctgtaaata ttgatgaggc agtgacggat    960

acttctacca actatcttct gtgtatctac gaagaaaagg aaaacattaa agacaaaaag   1020

aaggggaaca tttcttttgg catcgtggga gtgcagcctg cgacgggcga ggtcgtgttc   1080
```

```
gactgcttcc aggactcggc ttccagactg gagctggaga ctcgaacagc aagcctgcag   1140
cccgtggagc tgctgctccc ctcacagctg tccgagccaa cggagatgct catccgtaga   1200
gccaccgctg tcagtgttgg ggatgacaga attcgagtag aaaggatgaa taatactcac   1260
tttgaataca gccatgcttt ccagacagtt atggagttct atgccagaga gacagttgac   1320
acccagggct ctcagagcct gtctggtgtc attcacttgg agaagcctgt gatctgcgcc   1380
ctggctgcca taatacggta cctcaaggaa tttaacttgg acaaggtgct gtccaaaccc   1440
gagaatttta aacagctgtc aagtggaatg gaattcatga gaatcaatgg aacaacgcta   1500
aggaatctgg aaatcctaca gaatcagact gatatgaaga ccagaggaag tttgctttgg   1560
gttttagacc acactaaaac ctcatttggg agaaggaagt taaaaaaatg ggttacccaa   1620
ccattgctta aattaaggga cataaatgcc cgacttgatg caatatccga tgttctccac   1680
tcagaatcca gtgtgtttga acagatagaa aaccttctac ggaaactacc ggatgtcgag   1740
agaggactgt gtagcattta tcacaagaag tgctctactc aggagttctt cttgatcgtc   1800
aaaaacctgt gtcaactcaa atcagagctt caagcgttaa tgcctgctgt taattcccac   1860
gtacagtcag acttgctccg agcacgcgtc ttagaagtgc ctgagctcct cagtccagtg   1920
gagccttatt taaaggttct gaatgaacaa gctgccaaag ctggcgataa aactgaatta   1980
ttcaaagacc tctctgactt ccctttaata aaaaagagga aaaatgaaat tcaagaagtc   2040
attcacagca tccaaatgca tttacaagaa ttgcgaaaaa tattaaaact tccttcttta   2100
caatatgtga ctgtatcagg acaagagttt atggttgaaa taaagaactc agctgtgtct   2160
tgcgtcccga ctgactgggt gaaggttgga agcacaaaag ctgtgagccg ctttcactct   2220
ccttttgtcg tggaaaacta cagacgtctg aatcaactcc gggagcagct agtccttgac   2280
tgcaatgctg aatggcttga ctttctagag aattttggtg aacattacca cactttgtgt   2340
aaggccgtgg atcacctagc aactgtggac tgcattttct ccctggccaa ggtcgccaag   2400
caaggaagtt actgcaggcc aactctacaa gaagaaaaga aaatcatcat aaaaaatgga   2460
aggcacccta tgattgatgt gttgctgggt gaacaagatc agtttgtgcc caacagtaca   2520
aatttatcac aggactctga gagagtaatg ataatcaccg gaccgaacat gggtggcaag   2580
agctcctaca taaaacaggt tgctctggtt gtgatcatgg ctcagatcgg ctcctacgtt   2640
cctgcagagg aagccacaat tgggattgtg gacggcattt tcacaaggag gggtgctgca   2700
gacaatatat acaaaggccg gagtactttc atggaagagc tgacagacac ggcggagata   2760
atccagaaag caacacagcg gtccctggtt atcctggacg agctgggaag agggaccagc   2820
acccacgacg gaatcgccat tgcctatgcg actctagagt attttatcag agacgtgaaa   2880
tccttaaccc tgttcgtcac ccactatcca ccagtctgtg aactagagaa acgttaccca   2940
gagcaggtgg ggaattacca catgggcttc ttggtcaatg aggacggaag caagcaggac   3000
tcaggtgaca tggagcagat gccggactct gtcactttcc tctatcagat aaccagagga   3060
attgcagcga ggagttacgg actgaatgtg gcgaagctag cagatgtgcc cagagaaatc   3120
ttacagaaag ctgctcacaa gtctaaagag ctggaaggct tagtcaatct gagaaggaaa   3180
agacttgaat attttataga tctgtggacg acacatagtg taaaggacct gcacacgcgg   3240
gcagctgagc tggaaataca ggaaatacag acgtctcccc acaatgaaat gaaaactaca   3300
cttttggagc tgaagtagca ctgtatgatc atgcgagcca gtggccgact ggagatacaa   3360
actgaacaaa cagctttgag gtagcagctg tcagtggcgt gagcacggag gaagagcgac   3420
```

gtcttccctt tgagctggtt ccttctctgt gaagggggag cttttcaggc tctcgtcctc 3480
cgcactcggt gcctgcacag ccagagcggc agtgtcattt ccgctcagac agctgaccgc 3540
agggtaacct gacagggatc ttttgtgaga actgaagatt ttataatgct agcggtttgt 3600
tcaccaaagc catgagcatt tttatgagga gtagaatcat gaagcttcta gaatccagag 3660
cacagggagg aaacagccat atgaacttgg aggacctaag agtagctgtc actttaaaca 3720
gctgcggtcg ttaaataaaa ttattttgtc atcacttatt ggaataaata cttgctcaga 3780

<210> SEQ ID NO 389
<211> LENGTH: 3372
<212> TYPE: DNA
<213> ORGANISM: Artificial Sequence
<220> FEATURE:
<223> OTHER INFORMATION: nucleotide sequence

<400> SEQUENCE: 389
atgagccgcc gcaaaccggc gctgggcggc ctggcggcga gcagcccggt gccggcgcgc 60
caggcggtgc tgagccgctt ttttcagagc accggcagcc tgaaaagcac cagcagcccg 120
accggcgcga ccgatcaggt ggatcgcgat gcggcggcgc cgccggcgag cacctttccg 180
ccgcagctgc cgccgctggt ggcgccggaa attgatcgca gcaaaaaacg cccgctggaa 240
aacgatggcc cggtgaaaaa aaaagtgaaa aaagcgcagc agaaagaagg cggcagcgat 300
ctgggcatga gcggcaacag cgaaccgaaa aaatgcctgc gcacccgcaa cgtgctgaaa 360
agcctggaaa aactgaaaga attttgctgc gatagcgcgc tgccgcagag ccgcgtgcag 420
accgaaagcc tgcaggaacg ctttgcggtg ctgccgaaat gcaccgattt tgatgatatt 480
agcctgctgc gcgcgaaaaa cgcggtgagc agcgaagata gcaaatgcca gattaaacag 540
aaagatacca ccctgtttga tgtgagccag tttggcagca gcaacaccag ccatgaaaac 600
ctgcagaaaa ccgcgagcaa accggcgaac aaacgcagca aaagcattta taccccgctg 660
gaactgcagt atattgaaat gaaacagcag cataaagatg cggtgctgtg cgtggaatgc 720
ggctataaat atcgcttttt tggcgaagat gcggaaattg cggcgcgcga actgaacatt 780
tattgccatc tggatcataa ctttatgacc gcgagcattc cgacccatcg cctgtttgtg 840
catgtgcgcc gcctggtggc gaaaggctat aaagtgggcg tggtgaaaca gaccgaaacc 900
gcggcgctga aagcgattgg cgataaccgc agcagcctgt ttagccgcaa actgaccgcg 960
ctgtatacca aaagcaccct gattggcgaa gatgtgaacc cgctgattaa actggatgat 1020
gcggtgaacg tggatgaaat tatgaccgat accagcacca gctatctgct gtgcattagc 1080
gaaaacaaag aaaacgtgcg cgataaaaaa aaaggcattg tgtttattgg cattgtgggc 1140
gtgcagccgg cgaccggcga agtggtgttt gatagctttc aggatagcgc gagccgcagc 1200
gaactggaaa cccgcatgag caacctgcag ccggtggaac tgctgctgcc gagcgcgctg 1260
agcgaacaga ccgaaatgct gattcatcgc gcgaccagcg tgagcgtgca ggatgatcgc 1320
attcgcgtgg aacgcatgga taacatttat tttgaatata gccatgcgtt tcaggcggtg 1380
accgaatttt atgcgaaaga taccgtggat attaaaggca gccagattat tagcggcatt 1440
gtgaacctgg aaaaaccggt gatttgcagc ctggcggcga ttattaaata tctgaaagaa 1500
tttaacctgg aaaaaatgct gagcaaaccg gaaaacttta aacagctgag cagcaaaatg 1560
gaatttatga ccattaacgg caccaccctg cgcaacctgg aaattctgca gaaccagacc 1620
gatatgaaaa ccaaaggcag cctgctgtgg gtgctggatc ataccaaaac cagctttggc 1680
cgccgcaaac tgaaaaaatg ggtgacccag ccgctgctga aactgcgcga aattaacgcg 1740
cgcctggatg cggtgagcga agtgctgcat agcgaaagca gcgtgtttgg ccagattgaa 1800
aaccatctgc gcaaactgcc ggatattgaa cgcggcctgt gcagcattta tcataaaaaa 1860
tgcagcaccc aggaattttt tctgattgtg aaaaccctgt atcatctgaa aagcgaattt 1920
caggcgatta ttccggcggt gaacagccat gtgcagagcg atctgctgcg caccgtgatt 1980
ctggaaattc cggaactgct gagcccggtg gaacattatc tgaaaattct gaacgaacag 2040
gcggcgaaag tgggcgataa aaccgaactg tttaaagatc tgagcgattt tccgctgatt 2100
aaaaaacgca aagatgaaat tcagggcgtg agcgataaaa ttcgcatgca tctgcaggaa 2160
attcgcaaaa ttctgaaaaa cccgagcgcg cagtatgtga ccgtgagcgg ccaggaattt 2220
atgattgaaa ttaaaaacag cgcggtgagc tgcattccga ccgattgggt gaaagtgggc 2280
agcaccaaag cggtgagccg ctttcatagc ccgtttgtgg tggaaaacta tcgccatctg 2340
aaccagctgc gcgaacagct ggtgctggat tgcagcgcgg aatggctgga ttttctggaa 2400
aaatttagcg aacattatca ttatctgtgc aaagcggtgc atcatctggc gaccgtggat 2460
tgcattttta gcctggcgaa agtggcgaaa cagggcaact attgccgccc gaccgtgcag 2520
gaagaacgca aaattattat taaaaacggc cgccatccgg tgattgatgt gctgctgggc 2580
gaacaggatc agtatgtgcc gaacagcacc gatctgagcg aagatagcga acgcgtgatg 2640
attattaccg gcccgaacat gggcggcaaa agcagctata ttaaacaggt ggcgctgatt 2700
accattatgg cgcagattgg cagctatgtg ccggcggaag aagcgaccat tggcattgtg 2760
gatggcattt ttacccgcat gggcgcggcg gataacattt ataaaggccg cagcaccttt 2820
atggaagaac tgaccgatac cgcggaaatt attcgcaaag cgaccagcca gagcctggtg 2880
attctggatg aactgggccg cggcaccagc acccatgatg gcattgcgat tgcgtatgcg 2940
accctggaat attttattcg cgatgtgaaa agcctgaccc tgtttgtgac ccattatccg 3000
ccggtgtgcg aactggaaaa aaactatagc catcaggtgg gcaactatca tatgggcttt 3060
ctggtgagcg aagatgaaag caaactggat ccgggcgaag aacaggtgcc ggattttgtg 3120
acctttctgt atcagattac ccgcggcatt gcggcgcgca gctatggcct gaacgtggcg 3180
aaactggcgg atattccggg cgaaattctg aaaaaagcgg cgcataaaag caaagaactg 3240
gaaggcctga ttaacaccaa acgcaaacgc ctgaaatatt ttgcgaaact gtggaccatg 3300
cataacgcgc aggatctgca gaaatggacc gaagaatttg aaatggaaga aacccagacc 3360
agcctgccgc at 3372

<210> SEQ ID NO 390
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 390
ugcuagguga tgcactgcuu 20

<210> SEQ ID NO 391
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 391
ugcuagguga tgcactgcuu 20

<210> SEQ ID NO 392
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 392
ugctagguga tgcactgcuu 20

<210> SEQ ID NO 393
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 393
ugcuagguga tgcactgcuu 20

<210> SEQ ID NO 394
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 394
ugcuagguga tgcactgcuu 20

<210> SEQ ID NO 395
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 395
ugcuagguga tgcactgcuu 20

<210> SEQ ID NO 396
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 396
ugctaggtga tgcacugctu 20

<210> SEQ ID NO 397
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 397
ugctaggtga tgcacugcuu 20

<210> SEQ ID NO 398
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 398
ugctaggtga tgcacugcuu 20

<210> SEQ ID NO 399
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 399
ugctaggtga tgcactgcuu 20

<210> SEQ ID NO 400
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 400
ugctaggtga tgcacugcuu 20

<210> SEQ ID NO 401
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 401
ugctaggtga tgcacugcuu 20

<210> SEQ ID NO 402
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 402
ugcuaggtga tgcactgcuu 20

<210> SEQ ID NO 403
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 403
ugcuaggtga tgcactgcuu 20

<210> SEQ ID NO 404
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 404
ugctaggtga tgcactgcuu 20

<210> SEQ ID NO 405
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 405
ugcuaggtga tgcactgcuu 20

<210> SEQ ID NO 406
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 406
ugcuaggtga tgcactgcuu 20

<210> SEQ ID NO 407
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 407
ugctaggtga tgcacugctu 20

<210> SEQ ID NO 408
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 408
ugctaggtga tgcacugcuu 20

<210> SEQ ID NO 409
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 409
ugctaggtga tgcacugcuu 20

<210> SEQ ID NO 410
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 410
ugctaggtga tgcactgcuu 20

<210> SEQ ID NO 411
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 411
ugctaggtga tgcacugcuu 20

<210> SEQ ID NO 412
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 412
ugcuaggtga tgcactgcuu 20

<210> SEQ ID NO 413
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 413
ugcuaggtga tgcactgcuu 20

<210> SEQ ID NO 414
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 414
ugctaggtga tgcactgcuu 20

<210> SEQ ID NO 415
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 415
ugcuaggtga tgcactgcuu 20

<210> SEQ ID NO 416
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 416
ugcuaggtga tgcactgcuu 20

<210> SEQ ID NO 417
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 417
gctaggtgat gcacugctu 19

<210> SEQ ID NO 418

<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 418
gctaggtgat gcacugcuu 19

<210> SEQ ID NO 419
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 419
gctaggtgat gcacugcuu 19

<210> SEQ ID NO 420
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 420
gctaggtgat gcactgcuu 19

<210> SEQ ID NO 421
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 421
gctaggtgat gcacugcuu 19

<210> SEQ ID NO 422
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 422
ugcuaggtga tgcactgcuu 20

<210> SEQ ID NO 423
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 423
ugcuaggtga tgcactgcuu 20

<210> SEQ ID NO 424
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 424
ugctaggtga tgcactgcuu 20

<210> SEQ ID NO 425
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 425
ugcuaggtga tgcactgcuu 20

<210> SEQ ID NO 426
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 426
ugcuaggtga tgcacugctu 20

<210> SEQ ID NO 427
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 427
ugcuaggtga tgcacugcuu 20

<210> SEQ ID NO 428
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 428
ugcuaggtga tgcacugcuu 20

<210> SEQ ID NO 429
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 429
ugcuaggtga tgcactgcuu 20

<210> SEQ ID NO 430
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 430
ugcuaggtga tgcactgcu 19

<210> SEQ ID NO 431
<211> LENGTH: 19
<212> TYPE: DNA

<213> ORGANISM: Artificial Sequence
<220> FEATURE:
<223> OTHER INFORMATION: synthetic oligonucleotide

<400> SEQUENCE: 431
ugcuaggtga tgcactgcu 19

<210> SEQ ID NO 432
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 432
ugctaggtga tgcactgcu 19

<210> SEQ ID NO 433
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 433
ugcuaggtga tgcactgcu 19

<210> SEQ ID NO 434
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 434
gcuaggtgat gcacugctu 19

<210> SEQ ID NO 435
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 435
gcuaggtgat gcacugcuu 19

<210> SEQ ID NO 436
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 436
gcuaggtgat gcacugcuu 19

<210> SEQ ID NO 437
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 437
gcuaggtgat gcactgcuu 19

<210> SEQ ID NO 438
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 438
ugcuaggtga tgcactgc 18

<210> SEQ ID NO 439
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 439
ugcuaggtga tgcactgc 18

<210> SEQ ID NO 440
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 440
ugctaggtga tgcactgc 18

<210> SEQ ID NO 441
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 441
ugcuaggtga tgcactgc 18

<210> SEQ ID NO 442
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 442
cuaggtgatg cacugctu 18

<210> SEQ ID NO 443
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 443
cuaggtgatg cacugcuu 18

<210> SEQ ID NO 444
<211> LENGTH: 18
<212> TYPE: DNA
<213> ORGANISM: Artificial Sequence
<220> FEATURE:

```
<223> OTHER INFORMATION: synthetic oligonucleotide

<400> SEQUENCE: 444

cuaggtgatg cacugcuu                                                18


<210> SEQ ID NO 445
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 445

cuaggtgatg cactgcuu                                                18


<210> SEQ ID NO 446
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 446

ugcuaggtga tgcacugcuu                                              20


<210> SEQ ID NO 447
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 447

ugcuaggtga tgcacugcuu                                              20


<210> SEQ ID NO 448
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 448

ugctaggtga tgcacugcuu                                              20


<210> SEQ ID NO 449
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 449

ugcuaggtga tgcacugctu                                              20


<210> SEQ ID NO 450
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 450

ugcuaggtga tgcacugcuu                                              20
```

<210> SEQ ID NO 451
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 451
ugcuaggtga tgcacugcuu 20

<210> SEQ ID NO 452
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 452
ugcuaggtga tgcacugcu 19

<210> SEQ ID NO 453
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 453
ugcuaggtga tgcacugcu 19

<210> SEQ ID NO 454
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 454
ugctaggtga tgcacugcu 19

<210> SEQ ID NO 455
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 455
gcuaggtgat gcacugctu 19

<210> SEQ ID NO 456
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 456
gcuaggtgat gcacugcuu 19

<210> SEQ ID NO 457
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 457
gcuaggtgat gcacugcuu 19

<210> SEQ ID NO 458
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 458
ugcuaggtga tgcacugc 18

<210> SEQ ID NO 459
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 459
ugcuaggtga tgcacugc 18

<210> SEQ ID NO 460
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 460
ugctaggtga tgcacugc 18

<210> SEQ ID NO 461
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 461
cuaggtgatg cacugctu 18

<210> SEQ ID NO 462
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 462
cuaggtgatg cacugcuu 18

<210> SEQ ID NO 463
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 463
cuaggtgatg cacugcuu 18

<210> SEQ ID NO 464
<211> LENGTH: 17

<212> TYPE: DNA
<213> ORGANISM: Artificial Sequence
<220> FEATURE:
<223> OTHER INFORMATION: synthetic oligonucleotide

<400> SEQUENCE: 464
ugcuaggtga tgcacug 17

<210> SEQ ID NO 465
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 465
ugcuaggtga tgcacug 17

<210> SEQ ID NO 466
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 466
ugctaggtga tgcacug 17

<210> SEQ ID NO 467
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 467
uaggtgatgc acugctu 17

<210> SEQ ID NO 468
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 468
uaggtgatgc acugcuu 17

<210> SEQ ID NO 469
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 469
uaggtgatgc acugcuu 17

<210> SEQ ID NO 470
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 470
gcuaggtgat gcacugcuu 19

<210> SEQ ID NO 471
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 471
gctaggtgat gcacugcuu 19

<210> SEQ ID NO 472
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 472
ugcuaggtga tgcacugcu 19

<210> SEQ ID NO 473
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 473
ugcuaggtga tgcacugcu 19

<210> SEQ ID NO 474
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 474
gcuaggtgat gcacugcu 18

<210> SEQ ID NO 475
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 475
gctaggtgat gcacugcu 18

<210> SEQ ID NO 476
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 476
gcuaggtgat gcacugcu 18

<210> SEQ ID NO 477
<211> LENGTH: 18
<212> TYPE: DNA
<213> ORGANISM: Artificial Sequence

```
<220> FEATURE:
<223> OTHER INFORMATION: synthetic oligonucleotide

<400> SEQUENCE: 477

gcuaggtgat gcacugcu                                                18


<210> SEQ ID NO 478
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 478

gcuaggtgat gcacugc                                                 17


<210> SEQ ID NO 479
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 479

gctaggtgat gcacugc                                                 17


<210> SEQ ID NO 480
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 480

gcuaggtgat gcacugc                                                 17


<210> SEQ ID NO 481
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 481

ugcuagguga tgcactgcuu                                              20


<210> SEQ ID NO 482
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 482

ugctaggtga tgcacugcuu                                              20


<210> SEQ ID NO 483
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 483

ugcuaggtga tgcactgcuu                                              20
```

<210> SEQ ID NO 484
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 484
ugctaggtga tgcacugcuu 20

<210> SEQ ID NO 485
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 485
ugcuaggtga tgcactgcuu 20

<210> SEQ ID NO 486
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 486
gctaggtgat gcacugcuu 19

<210> SEQ ID NO 487
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 487
ugcuaggtga tgcactgcuu 20

<210> SEQ ID NO 488
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 488
ugcuaggtga tgcacugcuu 20

<210> SEQ ID NO 489
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 489
ugcuaggtga tgcactgcu 19

<210> SEQ ID NO 490
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 490
gcuaggtgat gcacugcuu 19

<210> SEQ ID NO 491
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 491
ugcuaggtga tgcactgc 18

<210> SEQ ID NO 492
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 492
cuaggtgatg cacugcuu 18

<210> SEQ ID NO 493
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 493
ugcuaggtga tgcacugcuu 20

<210> SEQ ID NO 494
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 494
ugcuaggtga tgcacugcu 19

<210> SEQ ID NO 495
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 495
ugcuaggtga tgcacugc 18

<210> SEQ ID NO 496
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 496
cuaggtgatg cacugcuu 18

<210> SEQ ID NO 497

<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 497
ugcuaggtga tgcacug 17

<210> SEQ ID NO 498
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 498
uaggtgatgc acugcuu 17

<210> SEQ ID NO 499
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 499
gcuaggtgat gcacugcuu 19

<210> SEQ ID NO 500
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 500
gcuaggtgat gcacugcu 18

<210> SEQ ID NO 501
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 501
gcuaggtgat gcacugc 17

<210> SEQ ID NO 502
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 502
utgauccugt tctcccagca 20

<210> SEQ ID NO 503
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 503
uugauccugt tctcccagca 20

<210> SEQ ID NO 504
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 504
uugauccugt tctcccagca 20

<210> SEQ ID NO 505
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 505
uugatccugt tctcccagca 20

<210> SEQ ID NO 506
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 506
uugauccugt tctcccagca 20

<210> SEQ ID NO 507
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 507
uugauccugt tctcccagca 20

<210> SEQ ID NO 508
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 508
uugatcctgt tcucccagca 20

<210> SEQ ID NO 509
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 509
uugatcctgt tcucccagca 20

<210> SEQ ID NO 510
<211> LENGTH: 20
<212> TYPE: DNA

<213> ORGANISM: Artificial Sequence
<220> FEATURE:
<223> OTHER INFORMATION: synthetic oligonucleotide

<400> SEQUENCE: 510
uugatcctgt tcucccagca 20

<210> SEQ ID NO 511
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 511
uugatcctgt tcucccagca 20

<210> SEQ ID NO 512
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 512
uugatcctgt tcucccagca 20

<210> SEQ ID NO 513
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 513
uugatcctgt tcucccagca 20

<210> SEQ ID NO 514
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 514
utgaucctgt tctcccagca 20

<210> SEQ ID NO 515
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 515
uugaucctgt tctcccagca 20

<210> SEQ ID NO 516
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 516
uugaucctgt tctcccagca 20

<210> SEQ ID NO 517
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 517
uugatcctgt tctcccagca 20

<210> SEQ ID NO 518
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 518
uugaucctgt tctcccagca 20

<210> SEQ ID NO 519
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 519
uugatcctgt tctcccagca 20

<210> SEQ ID NO 520
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 520
uugatcctgt tctcccagca 20

<210> SEQ ID NO 521
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 521
uugatcctgt tctcccagca 20

<210> SEQ ID NO 522
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 522
uugatcctgt tctcccagca 20

<210> SEQ ID NO 523
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 523
uugatcctgt tctcccagca 20

<210> SEQ ID NO 524
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 524
utgaucctgt tctcccagc 19

<210> SEQ ID NO 525
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 525
uugaucctgt tctcccagc 19

<210> SEQ ID NO 526
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 526
uugaucctgt tctcccagc 19

<210> SEQ ID NO 527
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 527
uugatcctgt tctcccagc 19

<210> SEQ ID NO 528
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 528
uugaucctgt tctcccagc 19

<210> SEQ ID NO 529
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 529
ugatcctgtt ctcccagca 19

<210> SEQ ID NO 530
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 530
ugatcctgtt ctcccagca 19

<210> SEQ ID NO 531
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 531
ugatcctgtt ctcccagca 19

<210> SEQ ID NO 532
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 532
ugatcctgtt ctcccagca 19

<210> SEQ ID NO 533
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 533
ugatcctgtt ctcccagca 19

<210> SEQ ID NO 534
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 534
utgaucctgt tctcccagca 20

<210> SEQ ID NO 535
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 535
uugaucctgt tctcccagca 20

<210> SEQ ID NO 536
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 536
uugaucctgt tctcccagca 20

<210> SEQ ID NO 537
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 537
uugatcctgt tctcccagca 20

<210> SEQ ID NO 538
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 538
uugatcctgt tctcccagca 20

<210> SEQ ID NO 539
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 539
uugatcctgt tctcccagca 20

<210> SEQ ID NO 540
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 540
uugatcctgt tctcccagca 20

<210> SEQ ID NO 541
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 541
uugatcctgt tctcccagca 20

<210> SEQ ID NO 542
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 542
utgaucctgt tctcccagc 19

<210> SEQ ID NO 543
<211> LENGTH: 19

<212> TYPE: DNA
<213> ORGANISM: Artificial Sequence
<220> FEATURE:
<223> OTHER INFORMATION: synthetic oligonucleotide

<400> SEQUENCE: 543
uugaucctgt tctcccagc 19

<210> SEQ ID NO 544
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 544
uugaucctgt tctcccagc 19

<210> SEQ ID NO 545
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 545
uugatcctgt tctcccagc 19

<210> SEQ ID NO 546
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 546
uugatcctgt tctcccagca 20

<210> SEQ ID NO 547
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 547
uugatcctgt tctcccagca 20

<210> SEQ ID NO 548
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 548
uugatcctgt tctcccagca 20

<210> SEQ ID NO 549
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 549
uugatcctgt tctcccagca 20

<210> SEQ ID NO 550
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 550
utgaucctgt tctcccag 18

<210> SEQ ID NO 551
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 551
uugaucctgt tctcccag 18

<210> SEQ ID NO 552
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 552
uugaucctgt tctcccag 18

<210> SEQ ID NO 553
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 553
uugatcctgt tctcccag 18

<210> SEQ ID NO 554
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 554
gatcctgttc tcccagca 18

<210> SEQ ID NO 555
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 555
gatcctgttc tcccagca 18

<210> SEQ ID NO 556
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 556
gatcctgttc tcccagca 18

<210> SEQ ID NO 557
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 557
gatcctgttc tcccagca 18

<210> SEQ ID NO 558
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 558
utgaucctgt tctcccagca 20

<210> SEQ ID NO 559
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 559
uugaucctgt tctcccagca 20

<210> SEQ ID NO 560
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 560
uugaucctgt tctcccagca 20

<210> SEQ ID NO 561
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 561
uugaucctgt tctcccagca 20

<210> SEQ ID NO 562
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 562
uugaucctgt tctcccagca 20

<210> SEQ ID NO 563
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 563
uugaucctgt tctcccagca 20

<210> SEQ ID NO 564
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 564
utgaucctgt tctcccagc 19

<210> SEQ ID NO 565
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 565
uugaucctgt tctcccagc 19

<210> SEQ ID NO 566
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 566
uugaucctgt tctcccagc 19

<210> SEQ ID NO 567
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 567
ugaucctgtt ctcccagca 19

<210> SEQ ID NO 568
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 568
ugaucctgtt ctcccagca 19

<210> SEQ ID NO 569
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 569
ugaucctgtt ctcccagca 19

<210> SEQ ID NO 570
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 570
utgaucctgt tctcccag 18

<210> SEQ ID NO 571
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 571
uugaucctgt tctcccag 18

<210> SEQ ID NO 572
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 572
uugaucctgt tctcccag 18

<210> SEQ ID NO 573
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 573
gaucctgttc tcccagca 18

<210> SEQ ID NO 574
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 574
gaucctgttc tcccagca 18

<210> SEQ ID NO 575
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 575
gaucctgttc tcccagca 18

<210> SEQ ID NO 576

<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 576
utgaucctgt tctccca 17

<210> SEQ ID NO 577
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 577
uugaucctgt tctccca 17

<210> SEQ ID NO 578
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 578
uugaucctgt tctccca 17

<210> SEQ ID NO 579
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 579
aucctgttct cccagca 17

<210> SEQ ID NO 580
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 580
aucctgttct cccagca 17

<210> SEQ ID NO 581
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 581
aucctgttct cccagca 17

<210> SEQ ID NO 582
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 582
ugauccugtt ctcccagca 19

<210> SEQ ID NO 583
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 583
ugauccugtt ctcccagca 19

<210> SEQ ID NO 584
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 584
uugauccugt tctcccagc 19

<210> SEQ ID NO 585
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 585
uugauccugt tctcccagc 19

<210> SEQ ID NO 586
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 586
ugauccugtt ctcccagc 18

<210> SEQ ID NO 587
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 587
ugauccugtt ctcccagc 18

<210> SEQ ID NO 588
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 588
ugauccugtt ctcccagc 18

<210> SEQ ID NO 589
<211> LENGTH: 18
<212> TYPE: DNA

<213> ORGANISM: Artificial Sequence
<220> FEATURE:
<223> OTHER INFORMATION: synthetic oligonucleotide

<400> SEQUENCE: 589
ugaucctgtt ctcccagc 18

<210> SEQ ID NO 590
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 590
ugaucctgtt ctcccag 17

<210> SEQ ID NO 591
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 591
ugaucctgtt ctcccag 17

<210> SEQ ID NO 592
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 592
ugaucctgtt ctcccag 17

<210> SEQ ID NO 593
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 593
uugauccugt tctcccagca 20

<210> SEQ ID NO 594
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 594
uugatcctgt tcucccagca 20

<210> SEQ ID NO 595
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 595
uugaucctgt tctcccagca 20

<210> SEQ ID NO 596
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 596
uugatcctgt tctcccagca 20

<210> SEQ ID NO 597
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 597
uugaucctgt tctcccagc 19

<210> SEQ ID NO 598
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 598
ugatcctgtt ctcccagca 19

<210> SEQ ID NO 599
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 599
uugaucctgt tctcccagca 20

<210> SEQ ID NO 600
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 600
uugatcctgt tctcccagca 20

<210> SEQ ID NO 601
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 601
uugaucctgt tctcccagc 19

<210> SEQ ID NO 602
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 602
uugatcctgt tctcccagca 20

<210> SEQ ID NO 603
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 603
uugaucctgt tctcccag 18

<210> SEQ ID NO 604
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 604
gatcctgttc tcccagca 18

<210> SEQ ID NO 605
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 605
uugaucctgt tctcccagca 20

<210> SEQ ID NO 606
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 606
uugaucctgt tctcccagc 19

<210> SEQ ID NO 607
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 607
uugaucctgt tctcccag 18

<210> SEQ ID NO 608
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 608
gaucctgttc tcccagca 18

<210> SEQ ID NO 609
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 609
uugaucctgt tctccca 17

<210> SEQ ID NO 610
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 610
aucctgttct cccagca 17

<210> SEQ ID NO 611
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 611
ugaucctgtt ctcccagca 19

<210> SEQ ID NO 612
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 612
ugaucctgtt ctcccagc 18

<210> SEQ ID NO 613
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 613
ugaucctgtt ctcccag 17

<210> SEQ ID NO 614
<211> LENGTH: 4472
<212> TYPE: DNA
<213> ORGANISM: Artificial Sequence
<220> FEATURE:
<223> OTHER INFORMATION: nucleotide sequence

<400> SEQUENCE: 614
ccgcagacgc ctgggaactg cggccgcggg ctcgcgctcc tcgccaggcc ctgccgccgg 60
gctgccatcc ttgccctgcc atgtctcgcc ggaagcctgc gtcgggcggc ctcgctgcct 120
ccagctcagc ccctgcgagg caagcggttt tgagccgatt cttccagtct acgggaagcc 180
tgaaatccac ctcctcctcc acaggtgcag ccgaccaggt ggaccctggc gctgcagcgg 240
ctgcagcggc cgcagcggcc gcagcgcccc cagcgccccc agctcccgcc ttcccgcccc 300

```
agctgccgcc gcacatagct acagaaattg acagaagaaa gaagagacca ttggaaaatg    360
atgggcctgt taaaaagaaa gtaaagaaag tccaacaaaa ggaaggagga agtgatctgg    420
gaatgtctgg caactctgag ccaaagaaat gtctgaggac caggaatgtt tcaaagtctc    480
tggaaaaatt gaaagaattc tgctgcgatt ctgcccttcc tcaaagtaga gtccagacag    540
aatctctgca ggagagattt gcagttctgc caaaatgtac tgattttgat gatatcagtc    600
ttctacacgc aaagaatgca gtttcttctg aagattcgaa acgtcaaatt aatcaaaagg    660
acacaacact tttgatctc agtcagtttg gatcatcaaa tacaagtcat gaaaatttac    720
agaaaactgc ttccaaatca gctaacaaac ggtccaaaag catctatacg ccgctagaat    780
tacaatacat agaaatgaag cagcagcaca aagatgcagt tttgtgtgtg gaatgtggat    840
ataagtatag attctttggg gaagatgcag agattgcagc ccgagagctc aatatttatt    900
gccatttaga tcacaacttt atgacagcaa gtatacctac tcacagactg tttgttcatg    960
tacgccgcct ggtggcaaaa ggatataagg tgggagttgt gaagcaaact gaaactgcag   1020
cattaaaggc cattggagac aacagaagtt cactcttttc ccggaaattg actgcccttt   1080
atacaaaatc tacacttatt ggagaagatg tgaatcccct aatcaagctg gatgatgctg   1140
taaatgttga tgagataatg actgatactt ctaccagcta tcttctgtgc atctctgaaa   1200
ataaggaaaa tgttagggac aaaaaaaagg gcaacatttt tattggcatt gtgggagtgc   1260
agcctgccac aggcgaggtt gtgtttgata gtttccagga ctctgcttct cgttcagagc   1320
tagaaacccg gatgtcaagc ctgcagccag tagagctgct gcttccttcg gccttgtccg   1380
agcaaacaga ggcgctcatc cacagagcca catctgttag tgtgcaggat gacagaattc   1440
gagtcgaaag gatggataac atttattttg aatacagcca tgctttccag gcagttacag   1500
agttttatgc aaaagataca gttgacatca aaggttctca aattatttct ggcattgtta   1560
acttagagaa gcctgtgatt tgctctttgg ctgccatcat aaaatacctc aaagaattca   1620
acttggaaaa gatgctctcc aaacctgaga attttaaaca gctatcaagt aaaatggaat   1680
ttatgacaat taatggaaca acattaagga atctggaaat cctacagaat cagactgata   1740
tgaaaaccaa aggaagtttg ctgtgggttt tagaccacac taaaacttca tttgggagac   1800
ggaagttaaa gaagtgggtg acccagccac tccttaaatt aagggaaata aatgcccggc   1860
ttgatgctgt atcggaagtt ctccattcag aatctagtgt gtttggtcag atagaaaatc   1920
atctacgtaa attgcccgac atagagaggg gactctgtag catttatcac aaaaaatgtt   1980
ctacccaaga gttcttcttg attgtcaaaa ctttatatca cctaaagtca gaatttcaag   2040
caataatacc tgctgttaat tcccacattc agtcagactt gctccggacc gttattttag   2100
aaattcctga actcctcagt ccagtggagc attacttaaa gatactcaat gaacaagctg   2160
ccaaagttgg ggataaaact gaattattta aagacctttc tgacttccct ttaataaaaa   2220
agaggaagga tgaaattcaa ggtgttattg acgagatccg aatgcatttg caagaaatac   2280
gaaaaatact aaaaaatcct tctgcacaat atgtgacagt atcaggacag gagtttatga   2340
tagaaataaa gaactctgct gtatcttgta taccaactga ttgggtaaag gttggaagca   2400
caaaagctgt gagccgcttt cactctcctt ttattgtaga aaattacaga catctgaatc   2460
agctccggga gcagctagtc cttgactgca gtgctgaatg gcttgatttt ctagagaaat   2520
tcagtgaaca ttatcactcc ttgtgtaaag cagtgcatca cctagcaact gttgactgca   2580
ttttctccct ggccaaggtc gctaagcaag gagattactg cagaccaact gtacaagaag   2640
aaagaaaaat tgtaataaaa aatggaaggc accctgtgat tgatgtgttg ctgggagaac   2700
```

```
aggatcaata tgtcccaaat aatacagatt tatcagagga ctcagagaga gtaatgataa   2760

ttaccggacc aaacatgggt ggaaagagct cctacataaa acaagttgca ttgattacca   2820

tcatggctca gattggctcc tatgttcctg cagaagaagc gacaattggg attgtggatg   2880

gcattttcac aaggatgggt gctgcagaca atatatataa aggacagagt acatttatgg   2940

aagaactgac tgacacagca gaaataatca gaaaagcaac atcacagtcc ttggttatct   3000

tggatgaact aggaagaggg acgagcactc atgatggaat tgccattgcc tatgctacac   3060

ttgagtattt catcagagat gtgaaatcct taaccctgtt tgtcacccat tatccgccag   3120

tttgtgaact agaaaaaaat tactcacacc aggtggggaa ttaccacatg ggattcttgg   3180

tcagtgagga tgaaagcaaa ctggatccag gcgcagcaga acaagtccct gattttgtca   3240

ccttccttta ccaaataact agaggaattg cagcaaggag ttatggatta aatgtggcta   3300

aactagcaga tgttcctgga gaaattttga agaaagcagc tcacaagtca aaagagctgg   3360

aaggattaat aaatacgaaa agaaagagac tcaagtattt tgcaaagtta tggacgatgc   3420

ataatgcaca agacctgcag aagtggacag aggagttcaa catggaagaa acacagactt   3480

ctcttcttca ttaaaatgaa gactacattt gtgaacaaaa aatggagaat taaaaatacc   3540

aactgtacaa aataactctc cagtaacagc ctatctttgt gtgacatgtg agcataaaat   3600

tatgaccatg gtatattcct attggaaaca gagaggtttt tctgaagaca gtctttttca   3660

agtttctgtc ttcctaactt ttctacgtat aaacactctt gaatagactt ccactttgta   3720

attagaaaat tttatggaca gtaagtccag taaagcctta agtggcagaa tataattccc   3780

aagcttttgg agggtgatat aaaaatttac ttgatatttt tatttgtttc agttcagata   3840

attggcaact gggtgaatct ggcaggaatc tatccattga actaaaataa ttttattatg   3900

caaccagttt atccaccaag aacataagaa ttttttataa gtagaaagaa ttggccaggc   3960

atggtggctc atgcctgtaa tcccagcact ttgggaggcc aaggtaggca gatcacctga   4020

ggtcaggagt tcaagaccag cctggccaac atggcaaaac cccatcttta ctaaaaatat   4080

aaagtacatc tctactaaaa atacgaaaaa attagctggg catggtggcg cacacctgta   4140

gtcccagcta ctccggaggc tgaggcagga gaatctcttg aacctgggag gcggaggttg   4200

caatgagccg agatcacgtc actgcactcc agcttgggca acagagcaag actccatctc   4260

aaaaaaaaaa aaagaaaaaa gaaaagaaat agaattatca agcttttaaa aactagagca   4320

cagaaggaat aaggtcatga aatttaaaag gttaaatatt gtcataggat taagcagttt   4380

aaagattgtt ggatgaaatt atttgtcatt cattcaagta ataaatattt aatgaatact   4440

tgctataaaa aaaaaaaaaa aaaaaaaaaa aa                                 4472
```

<210> SEQ ID NO 615
<211> LENGTH: 4
<212> TYPE: DNA
<213> ORGANISM: Artificial Sequence
<220> FEATURE:
<223> OTHER INFORMATION: Trinucleotide Repeat Expansion

<400> SEQUENCE: 615

```
cctg                                                                4
```

```
<210> SEQ ID NO 616
<211> LENGTH: 5
<212> TYPE: DNA
<213> ORGANISM: Artificial Sequence
<220> FEATURE:
<223> OTHER INFORMATION: Trinucleotide Repeat Expansion

<400> SEQUENCE: 616

attct                                                             5
```